United States Patent
Levinson (12)

(10) Patent No.: US 6,288,218 B1
(45) Date of Patent: Sep. 11, 2001

(54) COMPOSITIONS AND METHODS FOR THE TREATMENT AND DIAGNOSIS OF IMMUNE DISORDERS

(76) Inventor: Douglas Adam Levinson, 111 Maple St., Sherborn, MA (US) 01770

( * ) Notice: Subject to any disclaimer, the term of this patent is extended or adjusted under 35 U.S.C. 154(b) by 0 days.

(21) Appl. No.: 08/937,399

(22) Filed: Sep. 25, 1997

Related U.S. Application Data

(60) Division of application No. 08/609,583, filed on Mar. 1, 1996, which is a continuation-in-part of application No. 08/487,748, filed on Jun. 7, 1995, now Pat. No. 5,721,351, which is a continuation-in-part of application No. 08/398,633, filed on Mar. 3, 1995, now Pat. No. 6,066,332.

(51) Int. Cl.[7] ............ C07H 21/04; C07H 19/00; C12Q 1/68; C12Q 1/66
(52) U.S. Cl. ............ 536/23.4; 435/6; 435/8; 536/22.1; 536/23.1
(58) Field of Search ............ 435/6, 8; 536/22.1, 536/23.1, 23.4

(56) References Cited

U.S. PATENT DOCUMENTS 5,116,964   5/1992   Capon et al. .

FOREIGN PATENT DOCUMENTS 239400   8/1994   (EP) .

OTHER PUBLICATIONS

Seder and Gros, 1995, "The functional role of CD8+ T helper type 2 cells", J Exp Med 181:5–7.
Bergers et al., 1994, "Alternative promoter usage of the Fos–responsive gene Fit–1 generates mRNA isoforms coding for either secreted or membrane–bound proteins related to the IL–1 receptor", EMBO J 13(5):1176–1188.
Gavett et al., 1994, "Depletion of murine CD4+ T lymphocytes prevents antigen–induced airway hyperreactivity and pulmonary eosinophilia", Am J Respir Cell Mol Biol 10:587–593.
Kaneshima et al., 1994, "Human hematolymphoid cells in SCID mice", Curr Opin Immunol 6:327–333.
Lukacs et al., 1994, "Interleukin–4–dependent pulmonary eosinophil infiltration in a murine model of asthma", Am J Respir Cell Mol Biol 10:526–532.
Maggi et al., 1994, "Th2–like CD8+ T cells showing B cell helper function and reduced cytolytic activity in human immunodeficiency virus type 1 infection", J Exp Med 180:489–495.
Maggi et al., 1994, "Ability of HIV to promote a $T_H1$ to $T_H0$ shift and to replicate preferentially in $T_H2$ to $T_H0$ cells", Science 265:244–248.
Manetti et al., 1994, "CD30 expression by CD8+ T cells producing type 2 helper cytokines. Evidence for large numbers of CD8+ CD30+ T cells clones in human immunodeficiency virus infection", J Exp Med 180:2407–2411.

Marsh et al., 1994, "Linkage analysis of IL4 and other chromosome 5q31.1 markers and total serum immunoglobulin E concentrations", Science 264:1152–1156.
Chen et al., 1993, "RAG–2–deficient blastocyst complementation: An assay of gene function in lymphocyte development" Proc Natl Acad Sci USA 90:4528–4532.
Clerici et al., 1993, "Restoration of HIV–specific cell–mediated immune responses by interleukin–12 in vitro", Science 262:1721–1724.
Clerici et al., 1993, "Changes in interleukin–2 and interleukin–4 production in asymptomatic–human immunodeficiency virus–seropositive individuals", J Clin Invest 91:759–765.
Kanagawa et al., 1993, "Resistance of mice deficient in IL–4 to retrovirus–induced immunodeficiency syndrome (MAIDS)", Science 262:240–242.
Robinson et al., 1993, "Activation of CD4+ T cells, increased $T_{H2}$–type cytokine mRNA expression, eosinophil recruitment in bronchoalveolar lavage after allergen inhalation challenge in patients with atopic asthma", J Allergy Clin Immunol 92:313–324.
Yanagisawa et al., 1993, "Presence of a novel primary response gene ST2L, encoding a product highly similar to the interleukin 1 receptor type 1", FEBS Lett 318(1):83–87.
Liang and Pardee, 1992, "Differential display of eukaryotic messenger RNA by means of the polymerase chain reaction", Science 257:967–971.
Shinkai et al., 1992, "RAG–2–deficient mice lack mature lymphocytes owing to inability to initiate V(D)J rearrangement", Cell 68:855–867.

(List continued on next page.)

*Primary Examiner*—Rodney P. Swartz

(57) ABSTRACT

The present invention relates to methods and compositions for the treatment and diagnosis of immune disorders, especially T helper lymphocyte-related disorders. For example, genes which are differentially expressed within and among T helper (TH) cells and TH cell subpopulations, which include, but are not limited to TH0, TH1 and TH2 cell subpopulations are identified. Genes are also identified via the ability of their gene products to interact with gene products involved in the differentiation, maintenance and effector function of such TH cells and TH cell subpopulations. The genes identified can be used diagnostically or as targets for therapeutic intervention. In this regard, the present invention provides methods for the identification and therapeutic use of compounds as treatments of immune disorders, especially TH cell subpopulation-related disorders. Additionally, methods are provided for the diagnostic evaluation and prognosis of TH cell subpopulation-related disorders, for the identification of subjects exhibiting a predisposition to such conditions, for monitoring patients undergoing clinical evaluation for the treatment of such disorders, and for monitoring the efficacy of compounds used in clinical trials.

18 Claims, 37 Drawing Sheets

OTHER PUBLICATIONS

Figure 1:
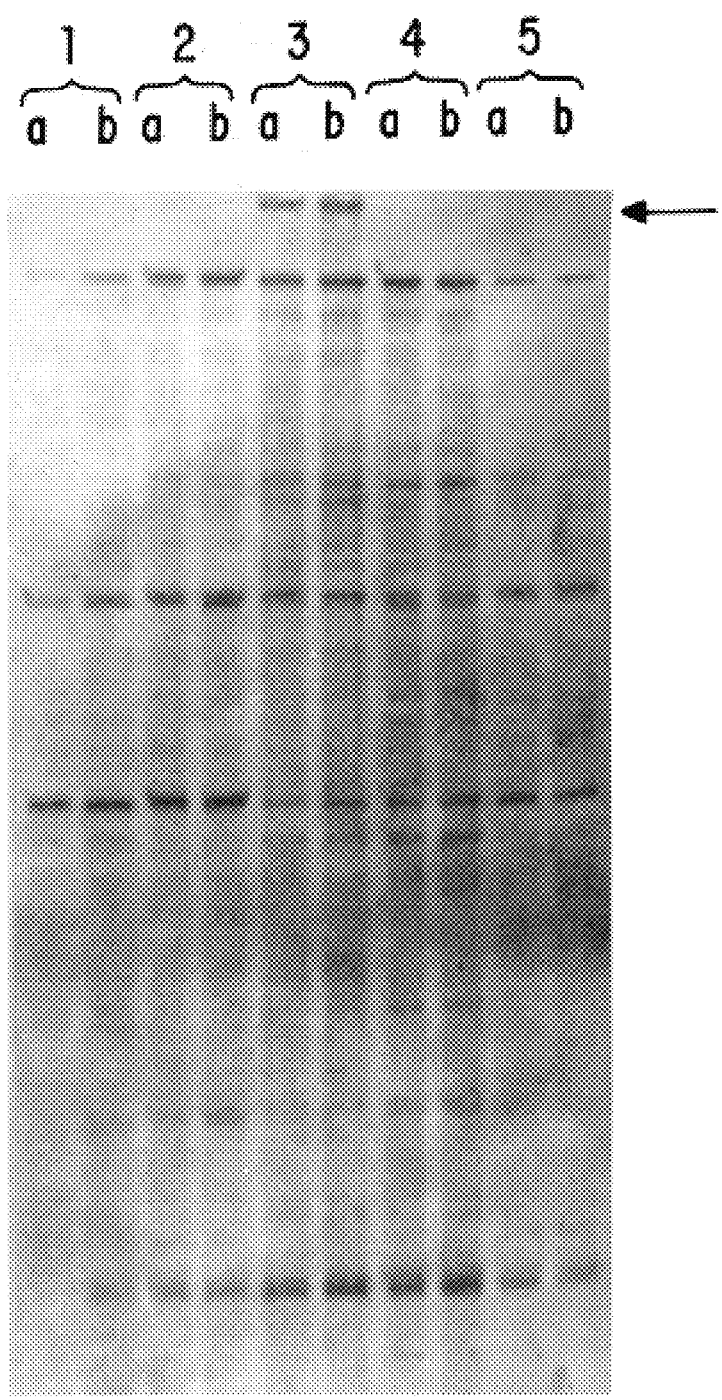

Tominaga et al., 1992, "Nucleotide sequence of a complementary DNA for human ST2", Biochim Biophys Acta 1171:215–218.

Werenskiold, 1992, "Characterization of a secreted glycoprotein of the immunoglobulin superfamily inducible by mitogen and oncogene", Eur J Biochem 204:1041–1047.

Young et al., 1992, "Expression of cytolytic mediators by synovial fluid lymphocytes in rheumatoid arthritis", Am J Path 140(5):1261–1268.

Del Prete et al., 1991, "Purified protein derivative of *mycobacterium tuberculosis* and excretory–secreted antigen(s) of *Toxocara canis* expand in vitro human T cells with stable and opposite (Type 1 T helper of Type 2 T helper) profile f cytokine production", J Clin Invest 88:346–350.

Ebnet et al., 1991, "In vivo primed mouse T cells selectively express T cell–specific serine proteinase–1 and the proteinase–like molecules granzyme B and C", Int Immunol 3(1):9–19.

McMahan et al., 1991, "A novel IL–1 receptor, cloned from B cells by mammalian expression, is expressed in many cell types", EMBO J 10(10):2821–2832.

Moll et al., 1991, "Expression of T–cell–associated serine proteinase 1 during murine *Leishmania major* infection correlates with susceptibility to disease", Infect Immun 59(12):4701–4705.

Mosmann and Moore, 1991, "The role of IL–10 in cross–regulation of $T_H1$ and $T_H2$ responses", Immunol Today 12:A49–A53.

Tominaga et al., 1991, "Molecular cloning of the murine ST2 gene. Characterization and chromosomal mapping", Biochim Biophys Acta 1090:1–8.

Yamamura et al., 1991, "Defining protective responses to pathogens: Cytokine profiles in leprosy lesions", Science 254:277–279.

Makino et al., 1990, "H–2–associated and background genes influence the development of a murine retrovirus–induced immunodeficiency syndrome", J Immunol 144(11):4347–4355.

Murphy et al., 1990, "Induction by antigen of intrathymic apoptosis od $CD4^+$ $CD8^+$ $TCR^{lo}$ thymocytes in vivo", Science 250:1720–1723.

Ojcius and Young, 1990, "Cell–mediated killing: Effector mechanisms and mediators", Cancer Cells 2:138–145.

Wiernenga et al., 1990, "Evidence for compartmentalization of functional subsets of $CD4^+$ T lymphocytes in atopic patients", J Immunol 144(12):4651–4656.

Cooper et al., 1989, "Analysis of naturally occurring delayed–type hypersensitivity reactions in leprosy by in situ hybridization", J Exp Med 169:1565–1581.

Firestein et al., 1989, "A new murine $CD4^+$ T cell subset with an unrestricted cytokine profile", J Immunol 143(2):518–525.

Klemenz et al., 1989, "Serum– and oncoprotein–mediated induction of a gene with sequence similarity to the gene encoding carcinoembryonic antigen", Proc Natl Acad Sci USA 86:5708–5712.

Liu et al., 1989, "Perforin and serine esterase gene expression in stimulated human T cells", J Exp Med 170:2105–2118.

Mosmann and Coffman, 1989, "TH1 and TH2 cells: Different patterns of lymphokine secretion lead to different functional properties", Ann Rev Immunol 7:145–173.

Tominaga, 1989, "A putative protein of a growth specific cDNA from BALB/c–3T3 cells is highly similar to the extracellular portion of mouse interleukin 1 receptor", FEBS Lett 258(2):301–304.

Werenskiold et al., 1989, "Induction of a mitogen–responsive gene after expression of the Ha–ras oncogene in NIH 3T3 fibroblasts", Mol Cell Biol 9(11):5207–5214.

Fruth et al., 1988, "Determination of frequency of T cells expressing the T cell–specific serine proteinase 1 (TSP–1) reveals two types of $L3T4^+$ T lymphocytes", Eur J Immunol 18:773–781.

Mueller et al., 1988, "A high proportion of T lymphocytes that infiltrate H–2–incompatible heart allografts in vivo express genes encoding cytotoxic cell–specific serine proteases, but do not express the MEL–14–defined lymph node homing receptor", J Exp Med 167:1124–1136.

Gershenfeld and Weissman, 1986, "Cloning of a cDNA for a T cell–specific serine protease from a cytotoxic T lymphocyte", Science 232:854–858.

Masson et al., 1986, "Identification of granzyme A isolated from cytotoxic T–lymphocytes–granules as one of the proteases encoded by CTL–specific genes", FEBS Lett 208(1):84–88.

Masson et al., 1986, "Granules of cytotoxic T–lymphocytes contain two serine esterases", EMBO J 5(7):1595–1600.

Gu et al., 1994, "Deletion of a DNA polymerase β gene segment in T cells using cell–type specific gene targeting", Science 265:103–106.

Larhammar et al., 1992, "Cloning and functional expression of a human neuropeptide Y/peptide YY receptor of the Y1 type", J Biol Chem 267:10935–10938.

Law et al., 1991, "Identification of the subunits of GTP–binding proteins coupled to somatostatin receptors", J Biol Chem 266:17885–17897.

Gershenfeld et al., 1988, "Cloning and chromosomal assignment of a human cDNA encoding a T cell– and natural killer cell– specific trypsin–like serine protease", Proc Natl Acad Sci USA 85:1184–1188.

Ishidoh et al., 1987, "Molecular cloning and sequencing of cDNA for rat cathepsin H", FEBS Lett 226:33–37.

Askew et al., 1989, "Molecular recognition with convergent functional groups. 6. Synthetic and structural studies with a mode receptor for nucleic acid components", J Am Chem Soc 111:1082–1090.

Lewis et al., 1989, "Automated site–directed drug design: the concept of spacer skeletons for primary structure generation", Proc R Soc Lond 236:125–140.

Lewis et al., 1989, "Automated site–directed drug design: the formation of molecular templates in primary structure generation", Proc R Soc Lond 236:141–162.

McKinlay et al., 1989, "Rational design of antiviral agents", Annu Rev Pharmacol Toxicol 29:111–22.

Perry et al., *QSAR: Quantitative structure–activity relationships in drug design*, pp. 189–193 (Alan R. Liss, Inc. 1989).

Ripka, Jun. 16, 1988, "Computers picture the perfect drug", New Scientist pp. 54–58.

Rotvinen et al., 1988, "Computer–aided drug design", Acta Pharmaceutica Fennica 97:159–166.

Liew, F., 1994, "Induction and Regulation of CD4+ T Cell Subsets", CIBA Foundation Symposium 87:170–178.

Volmer et al., 1994, "T Lymphocytes Derived From Skin Lesions of Patients with Psoriasis Vulgaris Express a Novel Cytokine Pattern that is Distinct from that of T Helper Type 2 Cells", Eur. J. Immunol. 24:2377–2382.

Houge, G., 1993, "Simplified Construction of a Subtracted cDNA Library Using Asymmetric PCR", PCR Methods and Applications 2(3):204–209.

Miller, A., 1992, "Human Gene Therapy Comes of Age", Nature 357:455–460.

Tepper, R. et al., 1990, "IL–4 induces Allergic–Like Inflammatory Disease and Alters T Cell Development in Transgenic Mice", Cell 62:457–467.

Aruffo, A. et al., 1990, "CD44 Is the Principal Cell Surface Receptor for Hyaluronate", Cell 61:1303–1313.

Chien, C. et al., 1991, "The Two–Hybrid System: A Method to Identify and Clone Genes for Proteins that Interact with a Protein of Interest", Proc. Natl. Acad. Sci. USA 88:9578–9582.

```
            10         20         30         40         50         60
    CTGGTGAGGG GGATCTACAA CTTGTTCGGT TAAAGAAAAA AGCAACAGCC AACAGAAATG  60
    TGGTTATCCT TCACCTACCT AAAAAGGGAG ATGATGTGAA ACCAGGAACC AGATGCCGAG 120
    TAGCAGGATG GGGGAGATTT GGCAATAAGT CAGCTCCCTC TGAAACTCTG AGAGAAGTCA 180
    ACATCACTGT CATAGACAGA AAAATCTGCA ATGATGAAAA ACACTATAAT TTTCATCCTG 240
    TAATTGGTCT AAACATGATT TGGGCAGGGG ACCTCCCCGG CGGAAAGGAC TCCTGCAATG 300
    GGGATTCTGG CAGCCCTCTC CTATGTGATT GGTATTTGGG AAGCATCACC TCCTTTT    357
```

FIG. 2

```
            10         20         30         40         50         60
    TTAGCGCCAT TGCCATAGAG AGACCTCAGC CATCAATCAC TAGCACATGA TTGACAGACA  60
    GAGAATGGGA CTTTGGGCTT TGGCAATTCT GACACTTCCC ATGTATTTGA CAGTTACGGA 120
    GGGCAGTAAA TCGTCCTGGG GTCTGGAAAA TGAGGCTTTA ATTGTGAGAT GCCCCAAAG 180
    AGGACGCTCG ACTTATCCTG TGGAATGGTA TTACTCAGAT ACAAATGAAA GTATTCCTAC 240
    CCAAAAAAAA AAAAA                                                  255
```

FIG. 4A

```
                                                                                            CC      2

GGGTCGACCCACGCGTCCGAGCCTCCTCAGTCAAGAGAAGCATCCCTCCAGAAACAGGAAACATGACACTTTGAAAG            81

AATGCCAAACGGCGTGAAAATAAAACAGAGCATTCCCATTTGCACCGACCAATCTCCAATCTCCTGTAAGATTCAAAA           160

GGGCAAGAGAGGCGGTGACCGTTCACGAAAGCTAAAATCCCATGCTATTGAACATGAAGACTTCTGATGCTTAAATC            239

TCATTAACTGCTTTAAGTCACTCCCAGGAGCTTGGATCCCAACTTCTAGCAGTAATAGTCTGTGTAAAAAAAAAAAAA          318

AATCAGTCTACAACCACTCTCTAAATGCATGGATGAACTCATCAGAACATCAAAACCCAAGGAAACCCTAAGAGAGAAG          397

AATTCTAATAAAAAGAATTTTACATTGAAAACTTACAAGGCAAGGTCCCTTCCCTGCTGACAGCCTAAGAAGTGATGT           476

M    A    M    N    S    M    C    I    E    E    Q    R    H    L    E      15
AACTGCCACTGTGAAGACC ATG GCG ATG AAC AGC ATG TGC ATT GAA GAG CAG CGC CAC CTC GAA          540

H    Y    L    F    P    V    V    Y    I    I    V    F    I    V    S    V    P    A    N    I   35
CAC TAT TTG TTC CCG GTG GTC TAC ATA ATT GTG TTT ATA GTC AGC GTC CCA GCC AAC ATC          600

G    S    L    C    V    S    F    L    Q    A    K    K    E    N    E    L    G    I    Y    L   55
GGA TCT TTA TGC GTA TCC TTT CTG CAA GCG AAG AAG GAA AAT GAG CTA GGG ATT TAC CTC          660

F    S    L    S    D    L    Y    A    L    T    L    P    L    W    I    N    Y        75
TTC AGT CTG TCC CTG TCA GAC CTG TAT GCG CTG ACT CTG CCC CTC TGG ATC AAT TAC              720
```

FIG. 9A

```
  T   W   N   K   D   N   W   T   F   S   P   T   L   C   K   G   S   V   F   F    95
ACT TGG AAT AAA GAC AAC TGG ACT TTC TCT CCC ACC TTG TGC AAA GGA AGC GTT TTC TTC   780

T   Y   M   N   F   Y   S   S   T   A   F   L   T   C   I   A   L   D   R   Y   115
ACC TAC ATG AAC TTT TAC AGC AGT ACG GCG TTC CTC ACT TGC ATT GCC CTG GAC CGC TAT   840

L   A   V   V   Y   P   L   K   F   S   F   L   R   T   R   R   F   A   F   I   135
TTA GCA GTC GTC TAC CCT CTG AAG TTC TCC TTC CTA AGA ACG AGA AGA TTC GCG TTT ATT   900

T   S   L   S   I   W   I   L   E   S   F   F   N   S   M   L   L   W   K   D   155
ACC AGC CTC TCC ATC TGG ATA TTA GAG TCC TTC TTT AAC TCT ATG CTT CTG TGG AAA GAT   960

E   T   S   V   E   Y   C   D   S   D   K   S   N   F   T   L   C   Y   D   K   175
GAA ACG AGT GTT GAA TAT TGT GAC TCG GAC AAA TCT AAT TTC ACT CTC TGC TAT GAC AAA  1020

Y   P   L   E   K   W   Q   I   N   L   N   L   F   R   T   C   M   G   Y   A   195
TAC CCT CTG GAG AAA TGG CAG ATA AAC CTC AAC CTG TTT CGG ACG TGC ATG GGC TAC GCA  1080

I   P   L   I   T   I   M   I   C   N   H   K   V   Y   R   A   V   R   H   N   215
ATA CCC TTG ATC ACC ATC ATG ATC TGC AAC CAT AAA GTC TAC CGA GCT GTG CGG CAC AAC  1140

Q   A   T   E   N   S   E   K   R   R   I   I   K   L   L   A   S   I   T   L   235
CAA GCC ACG GAA AAC AGC GAG AAG AGA AGG ATC ATA AAG TTG CTT GCT AGC ATC ACG TTG  1200

T   F   V   L   C   F   T   P   F   H   V   M   V   L   I   R   C   V   L   E   255
ACT TTC GTC CTA TGC TTT ACC CCC TTC CAC GTG ATG GTG CTC ATC CGC TGC GTT TTA GAG  1260
```

FIG. 9B

```
      R   D   M   N   V   N   D   K   S   G   W   Q   T   F   T   V   Y   R   V   T   275
     CGC GAC ATG AAC GTC AAT GAC AAG TCT GGA TGG CAG ACG TTT ACG GTG TAC AGA GTC ACA 1320

V   A   L   T   S   L   N   C   V   A   D   P   I   L   Y   C   F   V   T   E   295
     GTA GCC CTG ACG AGT CTA AAC TGT GTT GCC GAT CCC ATT CTG TAC TGC TTT GTG ACT GAG 1380

T   G   R   A   D   M   W   N   I   L   K   L   C   T   R   K   H   N   R   H   315
     ACG GGG AGA GCT GAT ATG TGG AAC ATA TTA AAA TTG TGT ACT AGG AAA CAC AAT AGA CAC 1440

Q   G   K   K   R   D   I   L   S   V   S   T   R   D   A   V   E   L   E   I   335
     CAA GGG AAA AAA AGG GAC ATA CTT TCT GTG TCC ACA AGA GAT GCT GTA GAA TTA GAG ATT 1500

I   D   *                                                                       338
     ATA GAC TAA GAGGTGGAGGCAGGTTAAGTTACATGGTATTATTTAATGAAACTTACATTTTGGAAAAGAAATCTGG  1576

CATAGTAGAACCCAGTGGAAATAGTTTGAAGGTACATTGTATGACTCCTATGTTGGCTTTATTAAGTAAGGTATAGAAA  1655

TGTATTATCTTGTATGTGTATTCTAATGACTAGGCATCATTGTTTAGTACCAATTCTCTTTGCCTCTATGTTATAACCCC 1734

TAAGAAGCACGCGGGACTGTTCGTCTTTAAATCAGTGGCCATTCTATCTGACTACTATGACTTTTGTTGTTCTGC      1813

TTTGGGTTTTCAGTCTGCCTGCATCAGTCTTCTCCCTCTGTATACGTCTGTCTTCAACAAATGTAAGGACTAAATACCCC 1892
```

FIG. 9C

TCCCGATCACACATCCATTATCAAGGATTTGAAGCCACTCCATGTACTGGGTTATAAAAGAAATGTTCTCATGAACTTTCA 1971

TGAAGTTTACATACCTTTGGGGATCTAGTCACCGAGTCACATAAAGTAAAAGTAAATGGAAAAAAAAAAAAAAAAAAAAA 2050

AGGGC 2055

FIG. 9D

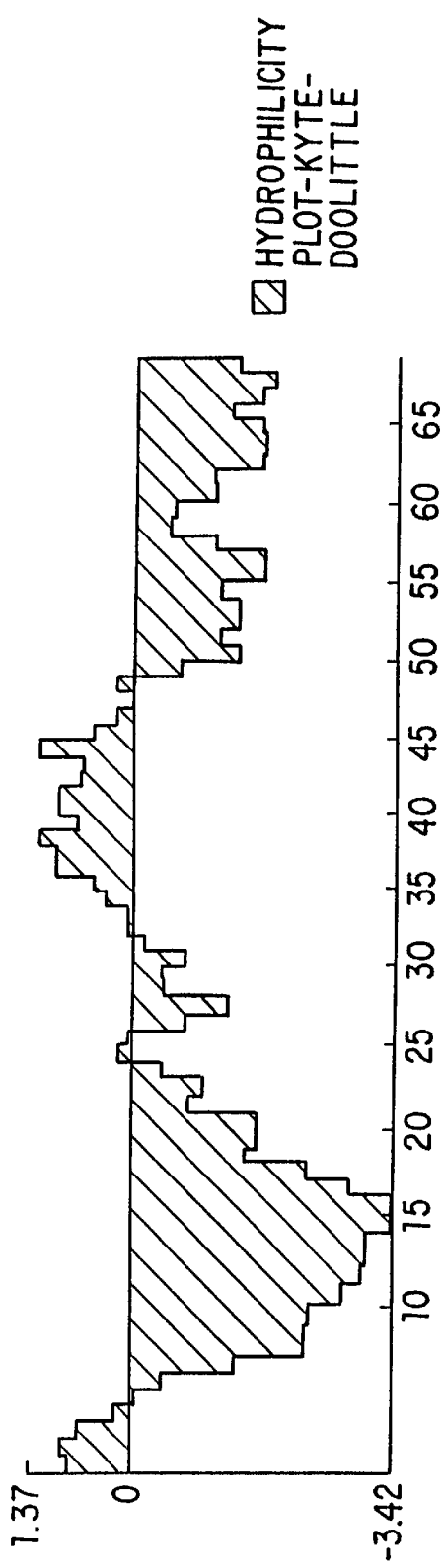
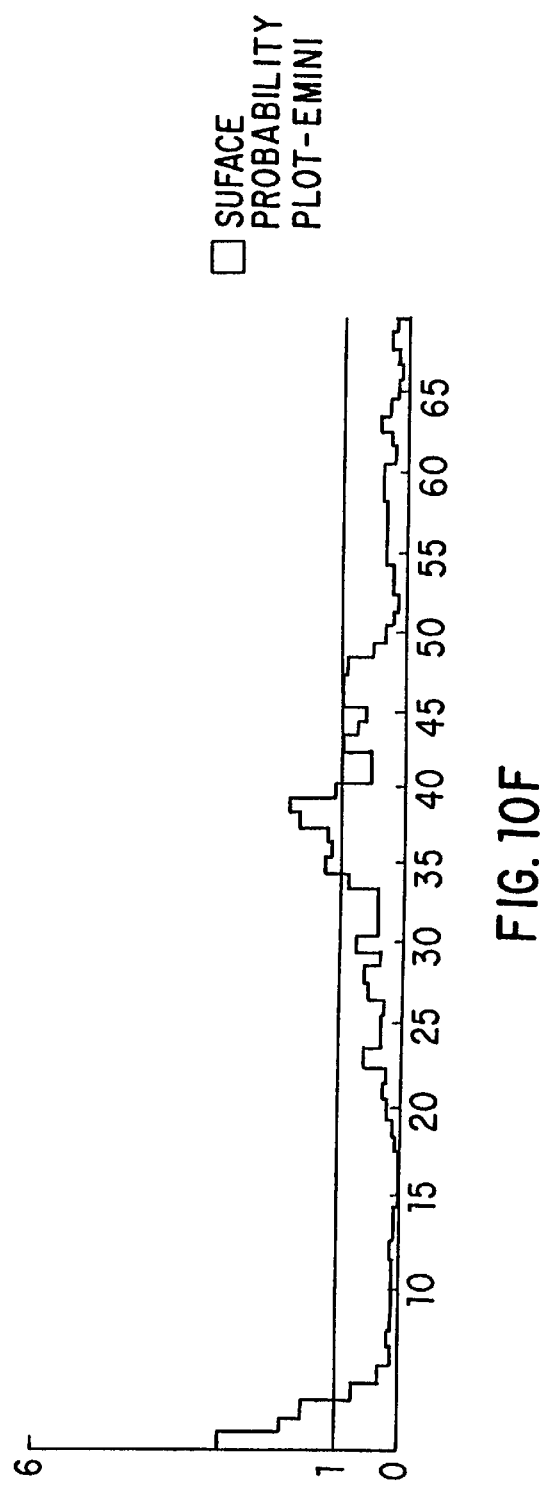

CGCCAGTGTGCTGGAATTCGGCTTAGAGCATTTCTTTCA
AACCACAGGTTAACACACACTTACTAAAAAGCAATGCTG
TTAGAGGAGAAGGGCTTGGGAGACTCGGCCATTTGAAAC
ANAAGCAAGGCACTCTCCAGGNNCAGCAAGTGGATTCCC
ATTTCCTGCTGAGGGCGGGTTCACACTGAGACTGCACTC
CAGTCAGCGGGAGGAATCACCTGCATTAATGCTTGTCCT
CTGCAGAGCTAGTGTGCCTTCCACTCTGGGTACACTTGG
GTGTCAACATTTCAAAATGATGACCTAAGAGGCTCTCAT
AGTTGGTGATAACTATGGNAGGACAGAAGAACACTGGCT
GTATTGTCTTTTTCTTTCAGCACTAGTGTCTTGGCCCTT
AACTAAAACGGGTTCCATCATCCTCCAAACCAGGAAGAT
AGATTGTTAGACAGGTCCTTTCCCCTCAACT

FIG. 12

TTTNNGGGACAGGGTTTCNCTGTGTATCTCTGGCTGTCC
TGGAACTNACTCTGTAGACCAGGTTGGCCTCGANCTCAG
AAATCTACCTGCCTCTCCCTCCANAGTGCTGGGATTAAN
GGTGTATGCCACCAATNCCCGGCCTTAATATATTNNTAA
ACAACTTCATTTGAATGANATATTGACACTACCCTTGGA
ATAAGAGTNCCCAGAATGANGTACAGGNTTCANGGAATC
ATTTAA

FIG. 14

CTTAGCAGGTGGAGTTGCAGCAGGAAGCCTGGTAGCCAC
ACTCCAATCAGCAGGGGTCCTTGGACTCTCCACATCAAC
AAATGCCATCCTAGGGGCTGCTGGGGCACTGTTGGAGCC
TTGCTCTGAGCTTAGGAGATGACACTTCTATCAGCTCAA
CTCAAAGCCTGTACAGACTACGCAGGAGATGAAGTTCCA
AAAGGCACCTTCAGAACCCTCA

FIG. 15

```
         10         20         30         40         50         60         70
TTTTTTTTTT TNGGGAGAGG CTAGCACTGA AATTACAGTT TCAGTGGAAT TTAGAGAAGT AATAACTGCA  70
AAAATTTATT TACACACACA CAGGGCATTT CTAAAGCTTT TACCTGTGTA AGTGCAGTTT AATCANCCCC 140
ATTACCTTAT GACCTTGGTT GGCAATGTCT CTAAAGCTTT AAAATTAAAA TAAAATTAAA AAGATGGTTT 210
TCCATCTCAT AAAATCCCCT TGGGAATGG  AAGACTTCCT CTTTGGGGTN TTTTTTAGAG GGAACAGGAG 280
GTAACTGTTA ATTATTTATA CATTCTAATA AACCATGAAT GCACCACATA AATACTGTA  CTCGGGGAGC 350
AAACACTGTN TGGGGGGGTT CTCTCTTACC AGAAGGAACA GGGGGCTTTT CAATGGCTGT GGGC        414

FIG. 13
```

```
remt161g0f  F--------------------------------------------------                    BAND 161
gi/218574/  MRQKAVSLFLCYLLLFTCSGVEAGKKKCSESSDSGSGF-WKALTFMAVGGGLAVAGLP--  CHIMP GENE
gi/32698/g  MRQKAVSVFLCYLLLFTCSGVEAGKKKCSESSDSGSGF-WKALTFMAVGGGLAVAGLP--  HUMAN 6-16
gi/32701/g  ------------VEAGKKKCSESSDSGSGF-WKALTFMAVGGGLAVAGLP--          HUMAN 6-16
gi/32702/g  ----------------GKKKCSESSDSGSGF-WKALTFMAVGGGLAVAGLP--         HUMAN 6-16
gi/35184/g  MEASAL---------TSSAVTSVAKVVRVASGSAVVLPLARIATVVIGGVVAMAAVPMV   HUMAN P27 remt161g0f  ---FVFLA--------------GGVAAGSLVATLQSAGVLGLSTSTNAILGAA        BAND 161
gi/218574/  --ALGFTGAGIAANSVAASLMSWSAILNGGGVPAGGLVATLQSLGAGG----SSVITGNI CHIMP GENE
gi/32698/g  --ALGFTGAGIAANSVAASLMSWSAILNGGGVPAGGLVATLQSLGAGG----SSVIGNI  HUMAN 6-16
gi/32701/g  --ALGFTGAGIAANSVAASLMSWSAILNGGGVPAGGLVATLQSLGAGG----SSVIGNI  HUMAN 6-16
gi/32702/g  --ALGFTGAGIAANSVAASLMSWSAILNGGGVPAGGLVATLQSLGAGG----SSVVIGNI HUMAN 6-16
gi/35184/g  LSAMGFTAAGIASSSIAAKMMSAAAIANGGGVASGSLVGTLQSLGATGLSGLTKFILGSI HUMAM P27
              ***.*. ** * . ..* remt161g0f  GALLEPCSELRR--------                             BAND 161
gi/218574/  GALMGYATHKYLDSEEDEE   CHIMP GENE (SEQ. ID NO: 13)
gi/32698/g  GALMRYATHKYLDSEEDEE   HUMAN 6-16 (SEQ. ID NO: 14)
gi/32701/g  GALMRYATHKYLDSEEDEE   HUMAN 6-16 (SEQ. ID NO: 15)
gi/32702/g  GALMRYATHKYLDSEEDEE   HUMAN 6-16 (SEQ. ID NO: 16)
gi/35184/g  GSAIAAVIARFY          HUMAN P27  (SEQ. ID NO: 17)
            *. .
```

FIG. 16

```
                                                           M   F   S   G   L   T   L      6
               NGTCGACCACGCGTCGGATTTCCCCTCCCAAGTACTC ATG TTT TCA GGT CTT ACC CTC         60

N   C   V   L   L   L   L   Q   L   A   R   S   L   E   D   G   Y   K                  26
AAC TGT GTC CTG CTG CTG CTA CAA CTA CTT GCA AGG TCA TTG GAA GAT GGT TAT AAG             120

V   E   V   G   K   N   A   Y   L   P   C   S   Y   T   L   P   T   S   G   T          46
GTT GAG GTT GGT AAA AAT GCC TAT CTG CCC TGC AGT TAC ACT CTA CCT ACA TCT GGG ACA         180

L   V   P   M   C   W   G   K   G   F   C   P   W   S   Q   C   T   N   E   L          66
CTT GTG CCT ATG TGC TGG GGC AAG GGA TTC TGT CCT TGG TCA CAG TGT ACC AAT GAG TTG         240

L   R   T   D   E   R   N   V   T   Y   Q   K   S   S   R   Y   Q   L   K   G          86
CTC AGA ACT GAT GAA AGA AAT GTG ACA TAT CAG AAA TCC AGC AGA TAC CAG CTA AAG GGC         300

D   L   N   K   G   D   V   S   L   I   I   K   N   V   T   L   D   D   H   G         106
GAT CTC AAC AAA GGA GAT GTG TCT CTG ATC ATA AAG AAT GTG ACT CTG GAT GAC CAT GGG         360

T   Y   C   C   R   I   Q   F   P   G   L   M   N   D   K   L   E   L   K             126
ACC TAC TGC TGC AGG ATA CAG TTC CCT GGT CTT ATG AAT GAT AAA AAA TTA GAA CTG AAA         420

L   D   I   K   A   A   K   V   T   P   A   Q   T   A   H   G   D   S   T   T         146
TTA GAC ATC AAA GCA GCA AAG GTC ACT CCA GCT CAG ACT GCC CAT GGG GAC TCT ACT ACA         480

A   S   P   R   T   L   T   T   E   R   N   G   S   E   T   Q   T   L   V   T         166
GCT TCT CCA AGA ACC CTA ACC ACG GAG AGA AAT GGT TCA GAG ACA CAG ACA CTG GTG ACC         540
```

FIG. 17A

```
 L   H   N   N   G   T   K   I   S   T   W   A   D   E   I   K   D   S   G       186
CTC CAT AAT AAC AAT GGA ACA AAA ATT TCC ACA TGG GCT GAT GAA ATT AAG GAC TCT GGA   600

E   T   I   R   T   A   I   H   I   G   V   G   V   S   A   G   L   L   A       206
GAA ACG ATC AGA ACT GCT ATC CAC ATT GGA GTG GGA GTC TCT GCT GGG TTG ACC CTG GCA   660

L   I   I   G   V   L   L   K   W   Y   S   C   K   K   K   K   L   S   S       226
CTT ATC ATT GGT GTC TTA ATC CTT AAA TGG TAT TCC TGT AAG AAA AAG AAG TTA TCG AGT   720

L   S   L   I   T   L   A   N   L   P   P   G   G   L   A   N   A   G   A   V   246
TTG AGC CTT ATT ACA CTG GCC AAC TTG CCT CCA GGA GGG TTG GCA AAT GCA GGA GCA GTC   780

R   I   R   S   E   E   N   I   Y   T   I   E   E   N   V   Y   E   V   E   N   266
AGG ATT CGC TCT GAG GAA AAT ATC TAC ACC ATC GAG GAG AAC GTA TAT GAA GTG GAG AAT   840

S   N   E   Y   Y   C   Y   V   N   S   Q   Q   P   S   *                       280
TCA AAT GAG TAC TAC TGC TAC GTC AAC AGC CAG CAG CCA TCC TGA CCGCCTCTGGACTGCCACT   903

TTTAAAGGCTCGCCTTCATTTCTGACTTGGTATTCCCTTTkTGGAAAACTATGTGATATGTCACTTGGCAACCTCAT    982

TGGAGGTTCTGACCAGCCACTGAGAAAGAGTTCCAGTTTTCTGGGGATAATTAACTCACAAGGGGATTCGACTGTA    1061

ACTCATGCTACACATTGAAATGCTCCATTTTATCCCTGAGTTTCAGGGATCGGATCTCCCACTCCAGAGACTTCAATCATG 1140

CGTGTTGAAGCTCACTCGTGCTTTCATACATTAGGAATGGTTAGTGTGATGTCTTTGAGACATAGAGGTTTGTGGTATA  1219
```

FIG. 17B

```
TCCGCAAAGCTCCTGAACAGGTAGGGGAATAAAGGGCTAAGATAGGAAGGTGCGGYTCTTTGTTGATGTTGGAAAATC  1298

TTAAGAAGTTGGTAGCTTTTCT AGAGATTTCTGACCTTGAAAGATTAAGAAAAAGCCAGGTGGCATATGCTTAACAC  1376

GATATAACTTGGGAACCTTAGGCAGGAGGGTGATAAGTTCAAGGTCAGCCAGGGCTATGCTGGTAAGACTGTCTCAMCA  1455

TCCAAAGACGAAAATAAACATAGAGACAGCAGGCTGGAGATGAGGCTCGGACAGTGAGGTGCATTGTGTACAAGCA  1534

CGAGGAATCTATATTTGATCGTAGACCCCACATGAAAAAGCTAGGCCTGGTAGAGACATGCTTGTAGACTCAAGAGATGG  1613

AGAGGTAAAGGCACAACAGATCCCCGGGGCTTGCGTGCAGTCAGCTTAGCCTAGGTGCTGAGTTCCAAGTCCACAAGAG  1692

TCCCTGTCTCAMGTAAGATGGRCTGAGTATCTGGGCATGTCCATGGGGTTGTCCTCTCCTCTCAGAGAGACATGC  1771

ACATGACCCTGCACACACACACACACACACACACACACACACATGAAATGAAGGTTCTCTCTG  1850

TGCCTGCTACCTCTCTATAACATGTATCTCTACAGGACTCTCCTGCCTCTGTTAAGACATGAGTGGGAGCATGGCAG  1929

AGCAGTCCAGTAATTTATTCCAGCACTCAGAAAGGCTGGAGCAGAAGCGTGGAGAGTTCAGGAGCACTGTGCCAACACT  2008

GCCAGACTCTTCTTACACAAGAAAAAGGTTACCCGCAAGCAGCTGACTCAGAGACAACTTCTCCATTCCTGGAGGAAACCCTGCGAAAGGCAAA  2087

CTTTGACTGTTGTGTGCTCAAGGGGAACTGACTCAGACAACTTCTCCATTCCTGGAGGAAACTGAGCTGTTTCTGACA  2166

GAAGAACAACCGGTGACTGGGACATACGAGAAGGCAGAGCTCTTGCAGCAATCTATATAGTCAGCAAATATTCTTTGGGA  2245
```

FIG. 17C

```
GGACAGTGTCACCAAATTGATTTCCAAGCCGGGTGGACCTCAGTTTCATCTGGCTTACAGCTGCTGCCCAGTGCCCTT  2324
GATCTGTGCTGGCTCCCATCTATAACAGAATCAAATTAAATAGACCCCGAGTGAAAATATTAAGTGAGCAGAAAGGTAG  2403
CTTTGTTCAAAGATTTTTTGCATTGGGGAGCAACTGTGTACATCAGAGGACACTCTGTTAGTGAGGACACCAAAACCTG  2482
TGGTACCGTTTTTTCATGTATGAATTTGTTGTTTAGGTTGCTTCTAGCTAGAGGTCCTGGCTTTCTTAGGTG  2561
GGTATGGAAGGGAGACCATCTAACAAAATCCATTAGAGATAACAGCTCTCATGCAGAAGGAAACTAATCTCAAATGT  2640
TTTAAAGTAATAAAACTGTACTGGCAAAGTACTTTGAGCATAAAAAAAAAAAAAAAAGGGGCCGC  2710
```

FIG. 17D

```
                      M   T   L   T   A   H   L   S   Y   F   L   V   L                        13
C CGGGTCGACC CACGCGTCCG ATG ACA CTG ACT GCC CAC CTC TCC TAC TTT CTG GTC CTG                    60

L   L   A   G   Q   G   L   S   D   S   L   L   T   K   D   A   G   P   R   P                33
TTG TTA GCG GGC CAA GGC CTC AGT GAC TCC CTC ACC AAG GAT GCA GGT CCC CGC CCA                   120

L   E   L   K   E   V   F   K   L   F   Q   I   R   F   N   R   S   Y   W   N                53
CTG GAG CTG AAG GAA GTC TTC AAG CTG TTC CAG ATC CGG TTC AAC CGG AGT TAC TGG AAC               180

P   A   E   Y   T   R   L   S   I   F   A   H   N   L   A   Q   A   Q   R                    73
CCA GCA GAG TAC ACT CGC CTG AGC ATC TTT GCC CAC AAT CTG GCT CAG GCT CAA AGG                   240

L   Q   Q   E   D   L   G   T   A   E   F   G   E   T   P   F   S   D   L   T                93
CTA CAG CAA GAA GAC TTG GGT ACA GCT GAG TTT GGA GAG ACT CCA TTC AGT GAC CTC ACA               300

E   E   F   G   Q   L   Y   G   Q   E   R   S   P   E   R   T   P   N   M                   113
GAG GAG TTT GGC CAG CTG TAC GGG CAG GAG AGG TCA CCA GAA AGG ACC CCC AAC ATG                   360

T   K   K   V   E   S   N   T   W   G   E   S   V   P   R   T   C   D   W   R               133
ACC AAA AAG GTA GAG TCT AAC ACG TGG GGG GAA TCT GTG CCC CGC ACC TGT GAC TGG CGT               420

K   A   K   N   I   I   S   V   K   N   Q   G   S   C   K   C   W   A                       153
AAA GCA AAG AAC ATC ATC TCG GTC AAG AAC CAG GGA AGC TGC AAA TGC TGG GCC                       480

M   A   A   D   N   I   Q   A   L   W   R   I   K   H   Q   Q   F   V   D                   173
ATG GCA GCT GCC GAC AAC ATC CAG GCT CTG TGG CGC ATC AAA CAC CAG CAG TTT GTG GAC               540
```

FIG. 22A

FIG. 22B

```
V   S   V   Q   E   L   L   D   C   E   R   C   G   N   G   C   N   G   G   F   193
GTC TCT GTG CAG GAG CTG CTG GAC TGC GAA CGC TGT GGA AAT GGT TGC AAT GGT GGC TTC 600

V   V   D   A   Y   L   T   V   L   N   N   S   G   L   A   S   E   K   D   Y   213
GTG TGG GAC GCA TAT CTA ACT GTC CTC AAC AAC AGT GGC CTG GCC AGT GAA AAG GAT TAT 660

P   F   Q   G   D   R   K   P   H   R   C   L   A   K   Y   K   K   V   A   233
CCA TTC CAG GGG GAC AGA AAG CCT CAC AGA TGC CTA GCC AAG TAC AAG AAG GTG GCC 720

W   I   Q   D   F   T   M   L   S   N   N   I   N   E   Q   A   I   A   H   Y   A   253
TGG ATC CAG GAT TTC ACC ATG TTG TCC AAT AAT ATT GAG CAG GCA ATT GCC CAC TAC CTG GCC 780

V   H   G   P   I   T   V   T   S   C   D   P   R   Q   L   L   Q   H   Y   Q   273
GTG CAT GGA CCT ATC ACC GTG ACC TCC TGT GAC CCT CGG CAA CTA CTC CAG CAT TAC CAG 840

V   I   K   A   T   P   K   E   K   E   G   M   Q   T   G   Q   V   D   H   S   293
GTC ATC AAG GCT ACA CCC AAG GAG AAA GAG GGC ATG CAG ACA GGG CAA GTG GAC CAC TCT 900

V   G   F   G   H   S   S   P   Y   W   I   L   K   N   S   W   G   A   H   W   G   313
GTG GGC TTT GGC CAC TCC TCC CCA TAC TGG ATC CTG AAG AAC TCC TGG GGA GCT CAC TGG GGC 960

K   R   H   R   S   F   R   L   Y   R   G   N   T   C   G   L   S   R   333
AAA CGT CGC AGT TTC AGG CTG TAT CGG GGA AAC ACC TGT GGC CTG TCT CGA 1020

E   K   G   Y   F   R   L   Y   R   G   N   T   C   G   V   T   K   Y   P   353
GAG AAG GGT TAC TTC AGG CTG TAT CGG GGA AAC ACC TGT GGA GTC ACC AAG TAT CCC 1080
```

```
F   T   A   Q   V   D   S   P   V   K   K   A   R   T   S   C   P   P   *      371
TTC ACA GCT CAA GTG GAC TCA CCA GTA AAG AAG GCA CGG ACC TCT TGT CCT CCC TGA AGG 1140

CAGCAGVCAC TCTTCTGCTT CTCCCACATG GCCACTGCCC CTTGTCAGCC CTGCCCACAT CCTCTCTGTA 1210
TGGCTTCATA AACCAAGACT GCTCCGTGAA AAAAAAAAAAAAAA                               1257
```

FIG. 22C

```
                    M   T   L   T   A   H   L   S   Y   F   L   V   L      13
  C CGGGTCGACC CACGCGTCCG ATG ACA CTG ACT GCC CAC CTC TCC TAC TTT CTG GTC CTG   60

L   L   A   G   Q   G   L   S   D   S   L   L   T   K   D   A   G   P   R   P     33
 TTG TTA GCG GGC CAA GGC CTC AGT GAC TCC CTC CTC ACC AAG GAT GCA GGT CCC CGC CCA   120

L   E   L   K   E   V   F   K   L   F   Q   I   R   F   N   R   S   Y   W   N     53
 CTG GAG CTG AAG GAA GTC TTC AAG CTG TTC CAG ATC CGG TTC AAC CGG AGT TAC TGG AAC   180

P   A  (E)  Y   T   R (R)  L   S (I) (F)  A   H (N)  L   A (A)  Q   R     73
 CCA GCA GAG TAC ACT CGC CGT CTC AGC ATC TTT GCC CAC AAT CTG GCT CAG CAA AGG   240

L   Q   Q   E   D   L   G   T   A   E   F   G   E   T   P   F   S   D   L   T     93
 CTA CAG CAA GAA GAC TTG GGT ACA GCT GAG TTT GGA GAG ACT CCA TTC AGT GAC CTC ACA   300

E   E   F   G   Q   L   Y   G   Q   E   R   S   P   E   R   T   P   N   M    113
 GAG GAG TTT GGC CAG TTA TAC GGG CAG GAG AGG TCA CCA GAA AGG ACC CCC AAC ATG   360

T   K   K   V   E   S   N   T   W   G   E   S   V   P   R   T   C   D   W   R    133
 ACC AAA AAG GTA GAG TCT AAC ACG TGG GGG GAA TCT GTG CCC CGC ACC TGT GAC TGG CGT   420

K   A   K   N   I   I   S   S   V   K   N   Q   G   S   C   K  [C]  W   A    153
 AAA GCA AAG AAC ATC ATC TCG TCG GTC AAG AAC CAG GGA AGC TGC AAA TGC TGG GCC   480

M   A   A   D   N   I   Q   A   L   W   R   I   K   H   Q   Q   F   V   D    173
 ATG GCA GCT GAC AAC ATC CAG GCT CTG TGG CGC ATC AAA CAC CAG CAG TTT GTG GAC   540
```

FIG.23A

```
   V   S   V   Q   E   L   L   D   C   E   R   C   G   N   G   C   N   G   G   F   193
   GTC TCT GTG CAG GAG CTG CTG GAC TGC GAA CGC TGT GGA AAT GGT TGC AAT GGT GGC TTC   600

V   W   D   A   Y   L   T   V   L   N   N   S   G   L   A   S   E   K   D   Y   213
   GTG TGG GAC GCA TAT CTA ACT GTC CTC AAC AGT GGC CTG GCC AGT GAA AAG GAT TAT   660

P   F   Q   G   D   R   K   P   H   R   C   L   A   K   K   Y   K   K   V   A   233
   CCA TTC CAG GGG GAC AGA AAG CCT CAC AGA TGC CTA GCC AAG AAG TAC AAG AAG GTG GCC   720

W   I   Q   D   F   T   M   L   S   N   N   E   Q   A   I   A   H   Y   L   A   253
   TGG ATC CAG GAT TTC ACC ATG TTG TCC AAT AAT GAG CAG GCA ATT GCC CAC TAC CTG GCC   780

V   H   G   P   I   T   V   T   S   C   D   P   R   Q   V   D   H   Y   Q   G   273
   GTG CAT GGA CCT ATC ACC GTG ACC TCC TGT GAC CCT CGG CAA GTG GAC CAT TAC CAG GGT   840

V   I   K   A   T   P   S   S   C   D   E   K   E   G   M   Q   T   V   L   L   293
   GTC ATC AAG GCT ACA CCC AGC TCC TGT GAC GAG AAA GAG GGG ATG CAG ACA GTC TTG CTG   900

V   G   F   G   K   H   S   S   P   Y   W   I   L   K   N   S   A   H   S   R   313
   GTG GGC TTT GGC AAG CAC TCC TCC CCA TAC TGG ATC CTG AAG AAC TCC GCT CAC TCT CGA   960

K   R   H   S               G   A   H   W   G   333
   AAA CGT CAC                 GGA GCT CAC TGG GGC   1020
```

MATURE

FIG.23B

```
        E   K   G   Y   F   R   L   Y   R   G   N   N   T   C   G   V   T   K   Y   P       353
        GAG AAG GGT TAC TTC AGG CTG TAT CGG GGA AAC AAC ACC TGT GGA GTC ACC AAG TAT CCC      1080

F   T   A   Q   V   D   S   P   V   K   K   A   R   T   S   C   P   P   *           371
        TTC ACA GCT CAA GTG GAC TCA CCA GTA AAG AAG GCA CGG ACC TCT TGT CCT CCT TGA AGG      1140

CAGCAGVCAC TCTTCTGCTT CTCCCACATG GCCACTGCCC CTTGTCAGCC CTGCCCACAT CCTCTCTGTA          1210

TGGCTTCATA AACCAAGACT GCTCCGTGAA AAAAAAAAAAAAAAA                                     1257
```

FIG. 23C

```
                                                                    M  F  S  H  L  P    6
CGCTAACAGAGGTGTCCTCTGACTTTTCTTCTGCAAGCTCC ATG TTT TCA CAT CTT CCC  18

F  D  C  V  L  L  L  L  L  T  R  S  S  E  V  E  Y    26
TTT GAC TGT GTC CTG CTG CTG CTA CTT ACA AGG TCC TCA GAA GTG GAA TAC  78

R  A  E  V  G  Q  N  A  Y  L  P  C  F  Y  T  P  A  A  P  G    46
AGA GCG GAG GTC GGT CAG AAT GCC TAT CTG CCC TGC TTC TAC ACC CCA GCC GCC CCA GGG 138

N  L  V  P  V  C  W  G  K  G  A  C  P  V  F  E  C  G  N  V    66
AAC CTC GTG CCC GTC TGC TGG GGC AAA GGA GCC TGT CCT GTG TTT GAA TGT GGC AAC GTG 198

V  L  R  T  D  E  R  D  V  N  Y  W  T  S  R  Y  W  L  N  G    86
GTG CTC AGG ACT GAT GAA AGG GAT GTG AAT TAT TGG ACA TCC AGA TAC TGG CTA AAT GGG 258

D  F  R  K  G  D  V  S  L  T  I  E  N  V  T  L  A  D  S  G   106
GAT TTC CGC AAA GGA GAT GTG TCC CTG ACC ATA GAG AAT GTG ACT CTA GCA GAC AGT GGG 318

I  Y  C  C  R  I  Q  P  G  I  M  N  D  E  K  F  N  L  K   126
ATC TAC TGC TGC CGG ATC CAA ATC CCA GGC ATA ATG AAT GAT GAA AAA TTT AAC CTG AAG 378

L  V  I  K  P  A  K  V  T  P  A  P  T  L  Q  R  D  F  T  A   146
TTG GTC ATC AAA CCA GCC AAG GTC ACC CCT GCA CCG ACT CTG CAG AGA GAC TTC ACT GCA 438

A  F  P  R  M  L  T  T  R  G  H  G  P  A  E  T  Q  T  L  G   166
GCC TTT CCA AGG ATG CTT ACC ACC AGG GGA CAT GGC CCA GCA GAG ACA CAG ACA CTG GGG 498
```

FIG. 24A

```
  S   L   P   D   I   N   L   T   Q   I   S   T   L   A   N   E   L   R   D   S    186
AGC CTC CCT GAT ATA AAT CTA ACA CAA ATA TCC ACA TTG GCC AAT GAG TTA CGG GAC TCT    558

R   L   A   N   D   L   R   D   S   G   A   T   I   R   I   G   I   Y   I   G    206
AGA TTG GCC AAT GAC TTA CGG GAC TCT GGA GCA ACC ATC AGA ATA GGC ATC TAC ATC GGA    618

A   G   I   C   A   G   L   L   A   L   I   F   F   G   A   L   I   F   K   W    226
GCA GGG ATC TGT GCT GGG CTG CTG GCT CTT ATC TTC TTC GGC GCT TTA ATT TTC AAA TGG    678

Y   S   H   S   K   E   K   I   Q   N   L   S   L   I   S   L   R   S   E   E    246
TAT TCT CAT AGC AAA GAG AAG ATA CAG AAT TTA AGC CTC ATC TCT TTG AGC TCA GAA GAA    738

P   S   G   L   A   N   V   A   E   G   I   R   S   E   E   N   I   Y   T   T    266
CCC TCA GGA TTG GCA AAT GTA GCA GAG GGA ATT CGC TCA GAA GAA AAC ATC TAT ACC        798

I   E   N   V   Y   E   V   E   E   P   N   E   Y   Y   C   Y   V   S   S        286
ATT GAA GAG AAC GTA TAT GAA GTG GAG GAG CCC AAT GAG TAT TAT TGC TAT GTC AGC AGC    858

R   Q   Q   P   S   Q   P   L   G   C   R   F   A   M   P                        301
AGG CAG CAG CCT TCA CAA CCT TTG GGT TGT CGC TTT GCA ATG CCA TAGATCAACCACCTTATT     903

TTTGAGCTTGGTGTTTGTCTTTTCAGAAACTATGAGCTGTCACCTGACTGGTTTTGGAGGTTCTGTCCACTGCTA

TGGAGCAGAGTTTTCCCATTTTCAGAAGATAATGACTCACACATGGGAATTGAACTGGGACCTGCACTGAACTTAAACAGG
```

FIG. 24B

CATGTCATTGCCTCTGTATTTAAGCCAACAGAGTTACCCAACCAGAGACTGTTAATCATGGATGTTAGAGCTCAAACG

GGCTTTTATATACACTAGGAATTCTTGACGTGGGGTCTCTGGAGCTCCAGGAAATTCGGG CACATCATATGTCCATGA

AACTTCAGATAAACTAGGRAAAACTGGGTGCTGAGGTGAAAGCATAACTTTTTGGCACAGAAAGTCTAAAGGGGCCAC

TGATTTTCAAAGAGATCTGTGATCCCTTTTGTTTTTGTTTTTGAGATGGAGTCTTGCTCTGTTGCCAGGCTGGAGT

GCAATGGCACAATCTCGGCTCACTGCAAGCTCCGCCTCCTGGGTTCAAGCGATTCCTCCTGCCTCAGCCTCCTGAGTGGC

TGGGATTACAGGCATGCACCACCATGCCCAGCTAATTTGTTGTATTTTAGTAGAGACAGGGTTTCACCATGTTGGCCA

GTGTGGTCTCAAACTCCTGACCTCATGATTTGCCTGCCTCGGCCTCCCAAAGCACTGGGATTACAGGGTGAGCCACCA

CATCCAGCCAGTGATCCTTAAAAGATTAAGAGATGACTAGGTCTACCTTGATCTTGAAGATTCCCTTGGAATGT

TGAGATTTAGGCTTATTTGAGCACTACCTGCCAACTGTCAGTGCCAGTGCATAGCCCTTCTTTTGTCTCCCTTATGAA

GACTGCCCTGCAGGGCTGAGATGTGGCAGGAGCTCCCAGGGAAAAAGGAAGTGCATTTGATTGGTGTGTATTGGCCAAG

TTTTGCTTGTGTGTGCTTGAAAGAAAATATCTCTGACCAACTTCTGTATTCGTGGACCAAACTGAAGCTATATTTTC

ACAGAAGAAGAAGCAGTGACGGGGACACAAATTCTGTTGCCTGGTGGAAAGAAAGGCAAAGGCCTTCAGCAATCTATATT

FIG. 24C

ACCAGGCGCTGGATCCTTTGACAGAGAGTGGTCCCTAAACTTAAATTTCAAGACGGTATAGGCTTGATCTGTCTTGCTTA

TTGTTGCCCCCTGCGCCTAGCACAATTCTGACACACAATTGGAACTTACTAAAAATTTTTTTACTGTTAAAAAAAAA

AAAAAAAAA

FIG. 24D

COMPOSITIONS AND METHODS FOR THE TREATMENT AND DIAGNOSIS OF IMMUNE DISORDERS

This is a divisional of U.S. patent application Ser. No. 08/609,583, filed on Mar. 1, 1996, which is a continuation-in-part of U.S. patent application Ser. No. 08/487,748, filed Jun. 7, 1995, now issued as U.S. Pat. No. 5,721,351, which is a continuation-in-part of U.S. patent application Ser. No. 08/398,633, filed Mar. 3, 1995, now issued as U.S. Pat. No. 6,066,332, each of which is incorporated herein by reference in its entirety.

1. INTRODUCTION

The present invention relates to methods and compositions for the treatment and diagnosis of immune disorders, especially T lymphocyte-related disorders, including, but not limited to, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy. For example, genes which are differentially expressed within and among T helper (TH) cells and TH cell subpopulations, which include, but are not limited to TH0, TH1 and TH2 cell subpopulations are identified. Genes are also identified via the ability of their gene products to interact with gene products involved in the differentiation, maintenance and effector function of such TH cells and TH cell subpopulations. The genes identified can be used diagnostically or as targets for therapeutic intervention. In this regard, the present invention provides methods for the identification and therapeutic use of compounds as treatments of immune disorders, especially TH cell subpopulation-related disorders. Additionally, methods are provided for the diagnostic evaluation and prognosis of TH cell subpopulation-related disorders, for the identification of subjects exhibiting a predisposition to such conditions, for monitoring patients undergoing clinical evaluation for the treatment of such disorders, and for monitoring the efficacy of compounds used in clinical trials.

2. BACKGROUND OF THE INVENTION

Two distinct types of T lymphocytes are recognized: $CD8^+$ cytotoxic T lymphocytes (CTLs) and $CD4^+$ helper T lymphocytes (TH cells). CTLs recognize and kill cells which display foreign antigens of their surfaces. CTL precursors display T cell receptors that recognize processed peptides derived from foreign proteins, in conjunction with class I MHC molecules, on other cell surfaces. This recognition process triggers the activation, maturation and proliferation of the precursor CTLs, resulting in CTL clones capable of destroying the cells exhibiting the antigens recognized as foreign.

TH cells are involved in both humoral and cell-mediated forms of effector immune responses. With respect to the humoral, or antibody, immune response, antibodies are produced by B lymphocytes through interactions with TH cells. Specifically, extracellular antigens are endocytosed by antigen-presenting cells (APCs), processed, and presented preferentially in association with class II major histocompatibility complex (MHC) molecules to $CD4^+$ class II MHC-restricted TH cells. These TH cells in turn activate B lymphocytes, resulting in antibody production.

The cell-mediated, or cellular, immune response, functions to neutralize microbes which inhabit intracellular locations. Foreign antigens, such as, for example, viral antigens, are synthesized within infected cells and presented on the surfaces of such cells in association with class I MHC molecules. This, then, leads to the stimulation of the $CD8^+$ class I MHC-restricted CTLs.

Some agents, such as mycobacteria, which cause tuberculosis and leprosy, are engulfed by macrophages and processed in vacuoles containing proteolytic enzymes and other toxic substances. While these macrophage components are capable of killing and digesting most microbes, agents such as mycobacteria survive and multiply. The agents' antigens are processed, though, by the macrophages and presented preferentially in association with class II MHC molecules to $CD4^+$ class II MHC-restricted TH cells, which become stimulated to secrete interferon-γ, which, in turn, activates macrophages. Such activation results in the cells' exhibiting increased bacteriocidal ability.

TH cells are composed of at least two distinct subpopulations, termed TH1 and TH2 cell subpopulations. Evidence suggests that TH1 and TH2 subtypes represent extremely polarized populations of TH cells. While such subpopulations were originally discovered in murine systems (reviewed in Mosmann, T. R. and Coffman, R. L., 1989, Ann. Rev. Immunol. 7:145), the existence of TH1- and TH2-like subpopulations has also been established in humans (Del Prete, A. F. et al., 1991, J. Clin. Invest. 88:346; Wiernenga, E. A. et al., 1990, J. Imm. 144:4651; Yamamura, M. et al., 1991, Science 254:277; Robinson, D. et al., 1993, J. Allergy Clin. Imm. 92:313). While TH1-like and TH2-like cells can represent the most extremely polarized TH cell subpopulations, other TH cell subpopulations, such as TH1 cells (Firestein, G. S. et al., 1989, J. Imm. 143:518), which represent TH cells which have characteristics of TH1 and TH2 cell subpopulations.

TH1-like and TH2-like cells appear to function as part of the different effector functions of the immune system (Mosmann, T. R. and Coffmann, R. L., 1989, Ann. Rev. Imm. 7:145). Specifically, TH1-like cells direct the development of cell-mediated immunity, triggering phagocyte-mediated host defenses, and are associated with delayed hypersensitivity. Accordingly, infections with intracellular microbes tend to induce TH1-type responses. TH2 cells drive humoral immune responses, which are associated with, for example, defenses against certain helminthic parasites, and are involved in antibody and allergic responses.

It has been noted that the ability of the different TH cell types to drive different immune effector responses is due to the exclusive combinations of cytokines which are expressed within a particular TH cell subpopulation. For example, TH1 cells are known to secrete interleukin-2 (IL-2), interferon-γ (IFN-γ), and lymphotoxin, while TH2 cells secrete interleukin-4 (IL-4), interleukin-5 (IL-5), and interleukin-10 (IL-10).

It is thought that TH1 and TH2 subpopulations arise from a common naive precursor (referred to as THP). For example, naive $CD4^+$ cells from mice which express a single transgenic T cell receptor can be induced to develop into either the TH1 or TH2 cell type. The conditions of antigen stimulation, including the nature and amount of antigen involved, the type of antigen-presenting cells, and the type of hormone and cytokine molecules present seem to all represent determinants of the pattern of TH1 versus TH2 differentiation, with, perhaps, the decisive role belonging to the cytokines present. With such a complex series of possible determinants, a full accounting of the exact factors important in driving TH1 or TH2 differentiation are, as yet largely unknown.

Further, it has recently been noted that, in addition to $CD4^+$ TH cells, $CD8^+$ CTLs can, under certain conditions, also exhibit TH1-like or TH2-like cytokine profiles (Seder, R. A. et al., 1995, J. Exp. Med. 181:5–7; Manetti, R. et al., 1994, J. Exp. Med. 180:2407–2411; Maggi, E. et al., 1994, J. Exp. Med. 180:489–495). While the precise functional role of such $CD8^+$ TH-like cells is currently unknown, these cell subpopulations appear to have great relevance to immune responses against infectious agents such as viruses and intracellular parasites.

Once TH1 and TH2 subpopulations are expanded, the cell types tend to negatively regulate one another through the actions of cytokines unique to each. For example, TH1-produced IFN-γ negatively regulates TH2 cells, while TH2-produced IL-10 negatively regulates TH1 cells. Moreover, cytokines produced by TH1 and TH2 antagonize the effector functions of one another (Mosmann, T. R. and Moore, 1991, Immunol. Today 12:49).

Failure to control or resolve an infectious process often results from an inappropriate, rather than an insufficient immune response, and can underlie a variety of distinct immunological disorders. Such disorders can include, for example, atopic conditions (i.e., IgE-mediated allergic conditions) such as asthma, allergy, including allergic rhinitis, dermatitis, including psoriasis, pathogen susceptibilities, chronic inflammatory disease, organ-specific autoimmunity, graft rejection and graft versus host disease. For example, nonhealing forms of human and murine leishmaniasis result from strong but counterproductive TH2-like-dominated immune responses. Lepromatous leprosy also appears to feature a prevalent, but inappropriate, TH2-like response.

It is possible that another example can be HIV infection. Here, it has been suggested that a drop in the ratio of TH1-like cells to other TH cell subpopulations can play a critical role in the progression toward disease symptoms. Further, it has been noted that, at least in vitro, TH2-like clones appear to be more efficient supporters of HIV viral replication than TH1-like clones.

Further, while TH1-mediated inflammatory responses to many pathogenic microorganisms are beneficial, such responses to self antigens are usually deleterious. It has been suggested that the preferential activation of TH1-like responses is central to the pathogenesis of such human inflammatory autoimmune diseases as multiple sclerosis and insulin-dependent diabetes. For example, TH1-type cytokines predominate in the cerebrospinal fluid of patients with multiple sclerosis, pancreases of insulin-dependent diabetes patients, thyroid glands of Hashimoto's thyroiditis, and gut of Crohn's disease patients, suggesting that such patients mount a TH1-like, not a TH2-like, response to the antigen(s) involved in the etiopathogenesis of such disorders.

A primary goal, for both diagnostic and therapeutic reasons, therefore, would be the ability to identify, isolate and/or target members of a particular TH cell subpopulation. The ability to identify those genes which are differentially expressed within and/or among such TH cell subpopulations is required to achieve such a goal. To date, investigations have focused on the expression of a limited number of specific known cytokines and cytokine receptors in the TH cell population. Cytokines, however, exert effects on cell types in addition to specific TH cell subpopulations, i.e., exhibit a variety of pleiotropic effects. It would be beneficial, therefore, to identify reliable markers (e.g., gene sequences) of TH cell subpopulations whose effects are TH cell subpopulation specific, e.g., which, unlike secreted cytokines, are TH cell subpopulation specific.

3. SUMMARY OF THE INVENTION

The present invention relates to methods and compositions for the treatment of immune disorders, especially T helper (TH) cell and TH cell-like related disorders. First, genes are identified and described which are differentially expressed within and among TH cells and TH cell subpopulations. Second, genes are identified and described which are differentially expressed within TH cell subpopulations in TH cell subpopulation-related disorders. The modulation of the expression of the identified genes and/or the activity of the identified gene products can be utilized therapeutically to ameliorate immune disorder symptoms and to modulate TH cell responsiveness, for example, responsiveness to antigen. Further, the identified genes and/or gene products can be used to diagnose individuals exhibiting or predisposed to such immune disorders. Still further, the identified genes and/or gene products can be used to detect TH cell responsiveness, for example, responsiveness to antigen.

"Differential expression," as used herein, refers to both quantitative as well as qualitative differences in the genes' temporal and/or cellular expression patterns within and among the TH cell subpopulations. Differentially expressed genes can represent "fingerprint genes" and/or "target genes".

"Fingerprint gene," as used herein, refers to a differentially expressed gene whose expression pattern can be utilized as part of a prognostic or diagnostic evaluation of immune disorders, e.g., TH cell-related disorders, or which, alternatively, can be used in methods for identifying compounds useful in the treatment of such disorders. For example, the effect of the compound on the fingerprint gene expression normally displayed in connection with the disorder can be used to evaluate the efficacy of the compound as a treatment for such a disorder, or may, additionally, be used to monitor patients undergoing clinical evaluation for the treatment of such disorders.

"Fingerprint pattern," as used herein, refers to the pattern generated when the expression pattern of a series (which can range from two up to all the fingerprint genes which exist for a given state) of fingerprint genes is determined. A fingerprint pattern can be used in the same diagnostic, prognostic, and compound identification methods as the expression of a single fingerprint gene.

"Target gene," as used herein, refers to a differentially expressed gene involved in immune disorders, e.g., TH cell related disorders, such that modulation of the level of target gene expression or of a target gene product activity can act to ameliorate the immune disorder. Compounds that modulate target gene expression or activity of the target gene product can be used in the treatment of immune disorders.

Further, "pathway genes" are defined via the ability of their gene products to interact with gene products involved in TH cell subpopulation-related disorders and/or to interact with gene products which are involved in the differentiation and effector function of the TH cell subpopulations. Pathway genes can also exhibit target gene and/or fingerprint gene characteristics.

Although the target, fingerprint and/or pathway genes described herein can be differentially expressed within and/or among TH cell subpopulations, and/or can interact with TH cell subpopulation gene products, the genes can also be involved in mechanisms important to additional immune processes.

The invention encompasses the following nucleotides, host cells expressing such nucleotides and the expression products of such nucleotides: (a) nucleotides that encode a mammalian differentially expressed and/or pathway gene product including, but not limited to a human and murine 10, 54, 57, 105, 106, 161 and 200 gene product; (b) nucleotides that encode portions of a differentially expressed and/or pathway gene product that corresponds to its functional domains, and the polypeptide products encoded by such nucleotide sequences, and in which, in the case of receptor-type gene products, such domains include, but are not limited to extracellular domains (ECD), transmembrane domains (TM) and cytoplasmic domains (CD); (c) nucleotides that encode mutants of a differentially expressed and/or pathway gene product, in which all or part of one of its domains is deleted or altered, and which, in the case of receptor-type gene products, such mutants include, but are not limited to, soluble receptors in which all or a portion of the TM is deleted, and nonfunctional receptors in which all or a portion of CD is deleted; and (d) nucleotides that encode fusion proteins containing a differentially expressed and/or pathway gene product or one of its domains fused to another polypeptide.

The present invention also includes the products of such fingerprint, target, and pathway genes, as well as antibodies to such gene products. Furthermore, the engineering and use of cell- and animal-based models of TH cell subpopulation-related disorders to which such gene products can contribute, are also described.

The present invention also relates to methods for prognostic and diagnostic evaluation of various TH cell subpopulation-related disorders, and for the identification of subjects who are predisposed to such disorders. Furthermore, the invention provides methods for evaluating the efficacy of drugs for immune disorders, and monitoring the progress of patients involved in clinical trials for the treatment of such disorders.

The TH cell subpopulation-related disorders described herein can include, for example, TH1 or TH1-like related disorders or can, alternatively, include TH2 or TH2-like related disorders. Examples of TH1 or TH1-like related disorders include chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease and sarcoidosis. Examples of TH2 or TH2-like related disorders include atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

It is further contemplated that the methods and compositions described herein can be utilized in the prognostic and diagnostic evaluation of disorders involving other immune cells, including CD8$^+$ CTLs, exhibiting TH-like cell subpopulation gene expression patterns and/or activity. It is still further contemplated that the methods and compositions described herein can be utilized in the amelioration of symptoms stemming from disorders involving such immune cells, especially such CD8$^+$ CTLs, which exhibit TH-like cell subpopulation gene expression patterns and/or activity.

The invention further provides methods for the identification of compounds which modulate the expression of genes or the activity of gene products involved in TH cell subpopulation-related disorders and processes relevant to the differentiation, maintenance and/or effector function of the subpopulations. Still further, the present invention provides methods for the treatment of TH cell subpopulation-related disorders which can, for example, involve the administration of such modulatory compounds to individuals exhibiting TH cell subpopulation-related disorder symptoms or tendencies. Additionally, treatment can result in the stimulation or depletion of one or more of the TH cell subpopulations.

"Stimulation", as used herein, can refer to an effective increase in the number of cells belonging to a TH cell subpopulation, via, for example, the proliferation of such TH cell subpopulation cells. The term can also refer to an increase in the activity of cells belonging to a TH cell subpopulation, as would be evidenced, for example, by a per cell increase in the expression of the TH cell subpopulation-specific cytokine pattern.

"Depletion", as used herein, can refer to an effective reduction in the number of cells belonging to a TH cell subpopulation, via, for example, a reduction in the proliferation of such TH cell subpopulation cells. The term can also refer to a decrease in the activity of cells belonging to a TH cell subpopulation, as would be evidenced, for example, by a per cell decrease in the expression of the TH cell subpopulation-specific cytokine pattern.

The invention is based, in part on systematic search strategies involving paradigms which utilize TH0, TH1, TH2, TH1-like and TH2-like cells, in systems which mimic the activity of the immune system or immune disorders, coupled with sensitive and high-throughput gene expression assays, to identify genes differentially expressed within and/or among TH cell subpopulations. In contrast to approaches that merely evaluate the expression of a single known gene product presumed to play a role in some immune cell-related process or disorder, the search strategies and assays used herein permit the identification of all genes, whether known or novel, which are differentially expressed within and among TH cell subpopulations, as well as making possible the characterization of their temporal regulation and function in the TH cell response and/or in TH cell mediated disorders. This comprehensive approach and evaluation permits the discovery of novel genes and gene products, as well as the identification of a constellation of genes and gene products (whether novel or known) involved in novel pathways (e.g., modulation pathways) that play a major role in the TH-cell mediated immune responses and TH cell subpopulation-related disorders. Thus, the present invention makes possible the identification and characterization of targets useful for prognosis, diagnosis, monitoring, rational drug design, and/or therapeutic intervention of immune system disorders.

The Examples described in Sections 6 through 8, below, demonstrate the successful use of the search strategies of the invention to identify genes which are differentially expressed among and/or within TH cell subpopulations. Section 9 describes the successful cloning of a human homolog of one of the identified genes (the 200 gene).

The 102 and 103 genes represent genes which, while previously known, are shown here to be differentially expressed among TH cell subpopulations. Specifically, the 102 gene corresponds to the Granzyme A, or Hanukah factor, gene, which encodes a trypsin-like serine protease. While this gene had previously been reported to be expressed in natural killer cells and a fraction of CD4+ cells, the results described herein reveal, for the first time, that the gene is differentially expressed within the TH2 cell subpopulation. Specifically, the 102 gene is expressed at a level many-fold higher in the TH2 cell subpopulation than in the TH1 cell subpopulation.

The 103 gene corresponds to a gene known as the T1, ST-2 or Fit-1 gene, which encodes, possibly via alternative splicing, both transmembrane and soluble gene products. The gene 103 products belong to the immunoglobulin superfamily, and bear a high resemblance to the interleukin-1 (IL-1) receptor. The results presented herein demonstrate, for the first time, that this gene is expressed, in vivo, in a tightly controlled TH2-specific fashion. Thus, given its status as both a TH2 cell subpopulation-specific marker and a cell surface protein, the gene 103 products can be utilized in a variety of methods to diagnose and/or modulate immune system disorders, in particular TH2 cell subpopulation-related disorders.

In addition to these known genes, the systematic search strategies described herein were used to identify several novel genes which are differentially expressed within and/or among TH cell subpopulations. Specifically, these include the 10, 54, 57, 105, 106, 161 and 200 genes.

The 54, 105, 106 and murine 200 genes are each shown to be differentially expressed within the TH1 cell subpopulation. Specifically, these genes are expressed at levels many-fold higher in TH1 cell subpopulations than in TH2 cell subpopulations.

The novel 54 gene product is a 371 amino acid cysteine protease, as evidenced by the presence of three thiol protease domains at approximately amino acid residue 145 to 156 (CYS domain), approximately amino acid residue 287 to 297 (HIS domain) and approximately amino acid residue 321 to 340 (ASN domain) of the 54 gene product amino acid sequence.

The 10 and 57 genes represent TH inducible gene sequences. That is, the expression of such genes in unstimulated TH cells is either undetectable or barely detectable, but is significantly upregulated in both stimulated TH1 and stimulated TH2 cells. Thus, the 10 and 57 genes and/or their gene products can represent new targets for therapeutic treatment as part of a non-TH cell subpopulation dependent intervention program.

The 10 gene product is a 338 amino acid receptor molecule which is a particularly suitable target for such a program in that the 10 gene product belongs to a class of proteins having a seven transmembrane domain sequence motif, which tend to represent G protein-coupled receptor molecules. The 10 gene product structure, therefore, indicates that it ay be involved in signal transduction events which may be important to T cell responses in general, and further indicates that modulation of 10 gene product may effectively ameliorate a wide range of T cell-related disorders.

Specifically, because the 10 gene product is a transmembrane product, its activity, via either a physical change in the number of 10 gene-expressing cells or by a change in the functional level of 10 gene product activity, can be particularly amenable to modulation. For example, natural ligands, derivatives of natural ligands and antibodies which bind to the 10 gene product can be utilized to reduce the number of induced T cells present by either physically separating such cells away from other cells in a population, or, alternatively, by targeting the specific destruction of the induced T cells or inhibiting the proliferation of such T cells.

Additionally, compounds such as 10 gene sequences or gene products such as, for example, soluble 10 gene products, can be utilized to reduce the level of induced T cell activity, and, ultimately, bring about the amelioration of a wide range of T cell-related disorders. For example, in the case of soluble gene 10 gene products, the compounds can compete with the endogenous (i.e., natural) ligand for the 10 gene product, leading to a modulation of induced T cell activity. Soluble proteins or peptides, such as peptides comprising one or more of the extracellular domains, or portions and/or analogs thereof, of the 10 gene product, including, for example, soluble fusion proteins such as Ig-tailed fusion proteins, can be particularly useful for this purpose. Additionally, antibodies directed against one or more of the extracellular portions of the 10 gene product may either reduce 10 gene product function by, for example, blocking ligand binding. Additionally, antibodies directed against the 10 gene product can, in certain instances, serve to increase the level of 10 gene product activity.

The receptor nature of the 10 gene product makes possible useful methods for the identification of compounds which modulate the receptor's functional activity and which can act as therapeutic agents in the amelioration of a wide range of T cell-related disorders. For example, functional assays which measure intracellular calcium release levels may be utilized to identify compounds which act as either agonists or antagonists of 10 gene product activity. Such assays may, additionally, be utilized to identify the natural 10 gene product ligand. Still further, any of these modulatory compounds can be utilized as therapeutic agents for the amelioration of a wide range of T cell-related disorders.

Finally, the 161 gene is shown to be an additional new and potentially interesting target for a therapeutic method aimed at the amelioration of immune disorder related symptoms. In fact, it is possible that 161 gene expression may be indicative of the presence of yet another TH cell subpopulation, in addition to TH1, TH2 and TH0 cell subpopulations.

The identification of TH cell subpopulation specific markers can be utilized in the treatment of a number of immune disorders, especially TH cell subpopulation-related disorders. For example, markers for the TH2 subpopulation can be used to ameliorate conditions involving an inappropriate IgE immune response, including but not limited to the symptoms which accompany atopic conditions such as allergy and/or asthma. IgE-type antibodies are produced by stimulated B cells which require, at least in part, IL-4 produced by the TH2 cell subpopulation. Therefore, a treatment which reduces the effective concentration of secreted IL-4, e.g., by reducing the activity or number of TH2 cells, will bring about a reduction in the level of circulating IgE, leading, in turn, to the amelioration or elimination of atopic conditions. Any of the TH2-specific gene products described herein can, therefore, be used as a target to reduce or deplete the number and/or activity of TH2 cell subpopulation cells for the treatment of such conditions.

The 103 gene can be particularly suitable for this purpose since one of its gene products is a membrane-bound TH2 cell subpopulation molecule. Accordingly, natural ligands, derivatives of natural ligands and antibodies which bind to this 103 gene product, can be utilized to reduce the number of TH2 cells present by either physically separating such cells away from other cells in a population, or, alternatively, by targeting the specific destruction of TH2 cells or inhibiting the proliferation of such TH2 cells. Additionally, compounds such as 103 gene sequences or gene products can be utilized to reduce the level of TH2 cell activity, cause a reduction in IL-4 production, and, ultimately, bring about the amelioration of IgE related disorders. For example, the compounds can compete with the endogenous (i.e., natural) ligand for the 103 gene product. The resulting reduction in the amount of ligand-bound 103 gene transmembrane protein will modulate TH2 cellular activity. Soluble proteins or peptides, such as peptides comprising the extracellular domain, or portions and/or analogs thereof, of the 103 gene product, including, for example, soluble fusion proteins such as Ig-tailed fusion proteins, can be particularly useful for this purpose.

The identification of TH cell subpopulation specific markers can additionally be utilized in the treatment of a TH1 cell subpopulation-related disorders. For example, markers for the TH1 cell subpopulation can be used to ameliorate conditions involving an inappropriate cell-mediated immune response, including, but not limited to chronic inflammatory and autoimmune disorders. Further, transgenic animals overexpressing or misexpressing such gene sequences and/ or transgenic "knockout" animals exhibiting little or no expression of such sequences can be utilized as animal models for TH cell subpopulation-related disorders. The Example presented in Section 11, below, describes the production of 200 and 103 transgenic animals.

TH1 cell subpopulation specific gene sequences and/or gene products such as the 54 (which encodes a 371 amino acid cysteine protease gene product), 105, 106 and 200 (the murine homolog of which encodes a 280 amino acid transmembrane gene product, the human homolog of which encodes a 301 amino acid transmembrane gene product, both of which are members of the Ig superfamily) genes can, therefore, be suitable for ameliorating such TH1 cell subpopulation-related disorders. The 200 gene product can be particularly suitable for such a purpose in that it is not only TH1 cell subpopulation-restricted, but the Ig superfamily 200 gene product is, additionally, membrane-bound. Therefore, natural ligands, derivatives of natural ligands and antibodies which bind to the 200 gene product can be utilized to reduce the number of TH1 cells present by either physically separating such cells away from other cells in a population, or, alternatively, by targeting the specific destruction of TH1 cells or inhibiting the proliferation of such TH1 cells. Additionally, compounds such as 200 gene sequences or gene products such as soluble 200 gene products, can be utilized to reduce the level of TH2 cell activity, thus bringing about the amelioration of TH1 cell subpopulation-related disorders. For example, the compounds can compete with the endogenous (i.e., natural) ligand for the 200 gene product. The resulting reduction in the amount of ligand-bound 200 gene transmembrane protein will modulate TH2 cellular activity. Soluble proteins or peptides, such as peptides comprising the extracellular domain, or portions (such as, for example, the Ig portion) and/or analogs thereof, of the 200 gene product, including, for example, soluble fusion proteins such as Ig-tailed fusion proteins, can be particularly useful for this purpose. The Example presented in Section 10, below, describes the construction and expression of 200 gene product and 103 gene product Ig fusion constructs and proteins.

3.1 Definitions

The term "TH cell subpopulation", as used herein, refers to a population of TH cells exhibiting a gene expression pattern (e.g., a discrete pattern of cytokines and/or receptor or other cell surface molecules) and activity which are distinct from the expression pattern and activity of other TH cells. Such TH cell subpopulations can include, but are not limited to, TH0, TH1 and TH2 subpopulations, which will, for clarity and example, and not by way of limitation, be frequently used herein as representative TH cell subpopulations.

The term "TH-like cell subpopulation", (e.g., "TH1-like" or "TH2-like"), as used herein is intended to refer not only to a population of $CD4^+$ TH cells having the properties described, above, for a TH cell subpopulation, but also refers to $CD4^-$ cells, including $CD8^+$ CTLs, which exhibit TH-like cytokine expression patterns.

"Differential expression", as used herein, refers to both quantitative as well as qualitative differences in the genes' temporal and/or cellular expression patterns.

"Target gene", as used herein, refers to a differentially expressed gene involved in immune disorders and/or in the differentiation, maintenance and/or effector function of TH cell subpopulations, such that modulation of the level of target gene expression or of target gene product presence and/or activity can, for example, act to result in the specific depletion or repression, or, alternatively, the stimulation or augmentation of one or more TH cell subpopulation, bringing about, in turn, the amelioration of symptoms of immune disorders, e.g., TH cell subpopulation-related disorders. A target gene can also exhibit fingerprint and/or pathway gene characteristics.

"Fingerprint gene," as used herein, refers to a differentially expressed gene whose mRNA expression pattern, protein level and/or activity can be utilized as part of a prognostic or diagnostic in the evaluation of immune disorders, e.g., TH cell subpopulation-related disorders, or which, alternatively, can be used in methods for identifying compounds useful for the treatment of such disorders, by, for example, evaluating the effect of the compound on the fingerprint gene expression normally displayed in connection with the disease. A fingerprint gene can also exhibit target and/or pathway gene characteristics.

"Fingerprint pattern," as used herein, refers to the pattern generated when the mRNA expression pattern, protein level and/or activity of a series (which can range from two up to all the fingerprint genes which exist for a given state) of fingerprint genes is determined. A fingerprint pattern can be a part of the same methods described, above, for the expression of a single fingerprint gene.

"Pathway genes", as used herein, refers to a gene whose product exhibits an ability to interact with gene products involved in immune disorders, e.g., TH cell subpopulation-related disorders and/or to interact with gene products which are involved in the differentiation and effector function of TH cell subpopulations. Pathway genes can also exhibit target gene and/or fingerprint gene characteristics.

"Negative modulation", as used herein, refers to a reduction in the level and/or activity of target gene product relative to the level and/or activity of the target gene product in the absence of the modulatory treatment. Alternatively, the term, as used herein, refers to a reduction in the number and/or activity of cells belonging to the TH cell subpopulation relative to the number and/or activity of the TH cell subpopulation in the absence of the modulatory treatment.

"Positive modulation", as used herein, refers to an increase in the level and/or activity of target gene product relative to the level and/or activity of the gene product in the absence of the modulatory treatment. Alternatively, the term, as used herein, refers to an increase in the number and/or activity of cells belonging to the TH cell subpopulation, relative to the number and/or activity of the TH cell subpopulation in the absence of the modulatory treatment.

4. DESCRIPTION OF THE FIGURES

FIG. 1. Differential display analysis of RNA from murine TH cell subsets. Splenic T cells derived from T cell receptor transgenic mice were differentiated in vitro to become polarized populations of TH1 or TH2 subtypes. Lane 1: TH2 population 24 hours after tertiary stimulation; lane 2: TH1 population 24 hours after tertiary stimulation; lane 3: TH2 population 1 week after secondary stimulation; lane 4: TH1 population 1 week after secondary stimulation; lane 5: TA3 cell line, which was used as antigen presenting cell (APC) for in vitro stimulation. (This sample was used as a negative control.) Each set of lanes consists of duplicates (a and b), in which cDNAs were independently generated from the same source of RNA. Arrow points to differentially expressed sequence, which is referred to herein as band 102. Further, the gene corresponding to band 102 is referred to herein as the 102 gene. All lanes are products of a polymerase chain reaction (PCR) in which $T_{11}GG$ was used as the 3' oligonucleotide and a random 10 mer oligonucleotide (Oligo #4, OP-D kit, Operon, Inc.) was used as the 5' oligonucleotide.

FIG. 2. Nucleotide sequence of clone 102.1 of band 102 (SEQ. ID NO: 1). The gene corresponding to band 102 is referred to herein as the 102 gene.

Figure 3:
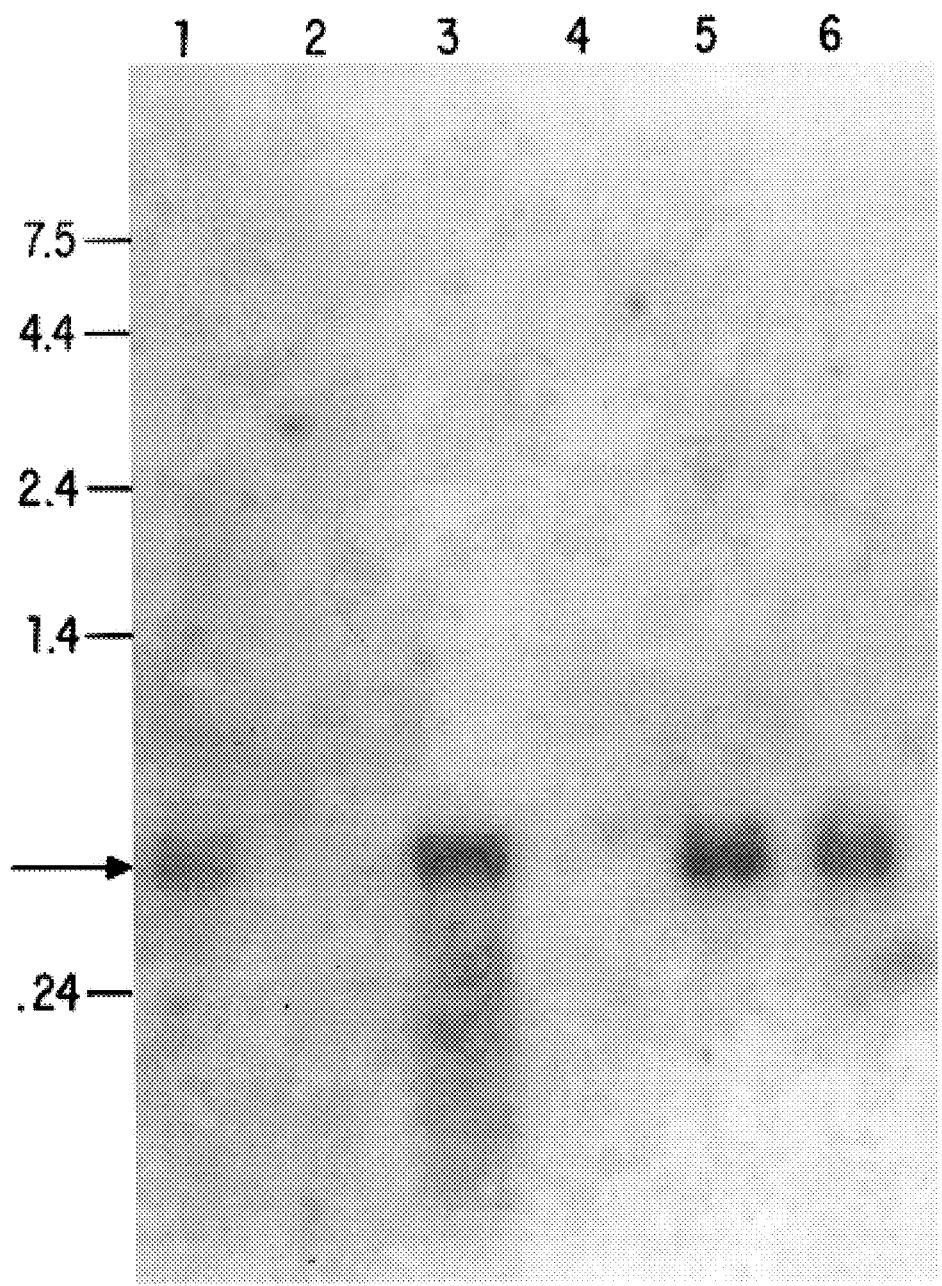

FIG. 3. Northern blot analysis of confirming differential regulation of the 102 gene within primary TH1/TH2 cultures and murine tissues. RNA was harvested from T cell lines derived from a T cell receptor transgenic strain stimulated in vitro. Lane 1, TH2, 40 hours after second stimulation; lane 2, TH1, 40 hours after second stimulation; lane 3, TH2 population 24 hours after tertiary stimulation; lane 4, TH1, 24 hours after tertiary stimulation; lane 5, murine thymus; lane 6, murine spleen. Five micrograms of total RNA was used per lane. The cloned band 102 sequence was used as a probe.

FIG. 4A. Nucleotide sequence clone 103.1 of band 103 (SEQ ID NO:2). The gene corresponding to band 103 is referred to herein as gene 103.

Figure 4B:
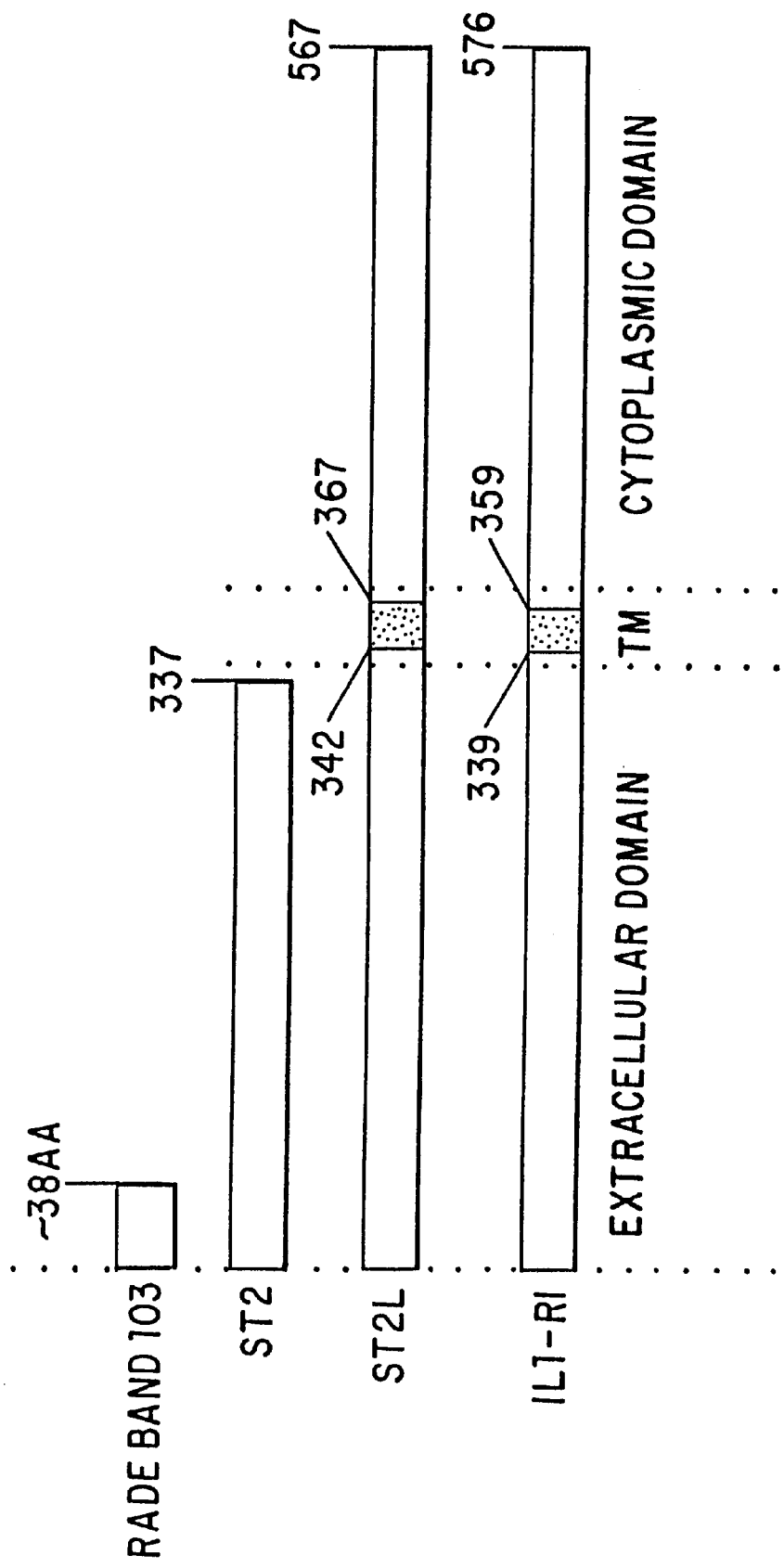

FIG. 4B. 103 gene products. This diagram illustrates the relationship between band 103, 103 gene (also known as ST-2, T1 and Fit-1) products and the IL-1 receptor polypeptide structure. The extracellular, transmembrane and cytoplasmic domains of the proteins are noted, along with the amino acid residues marking the boundaries of these domains. (Adapted from Yanagisawa et al., 1993, FEBS 318:83–87.)

Figure 5:
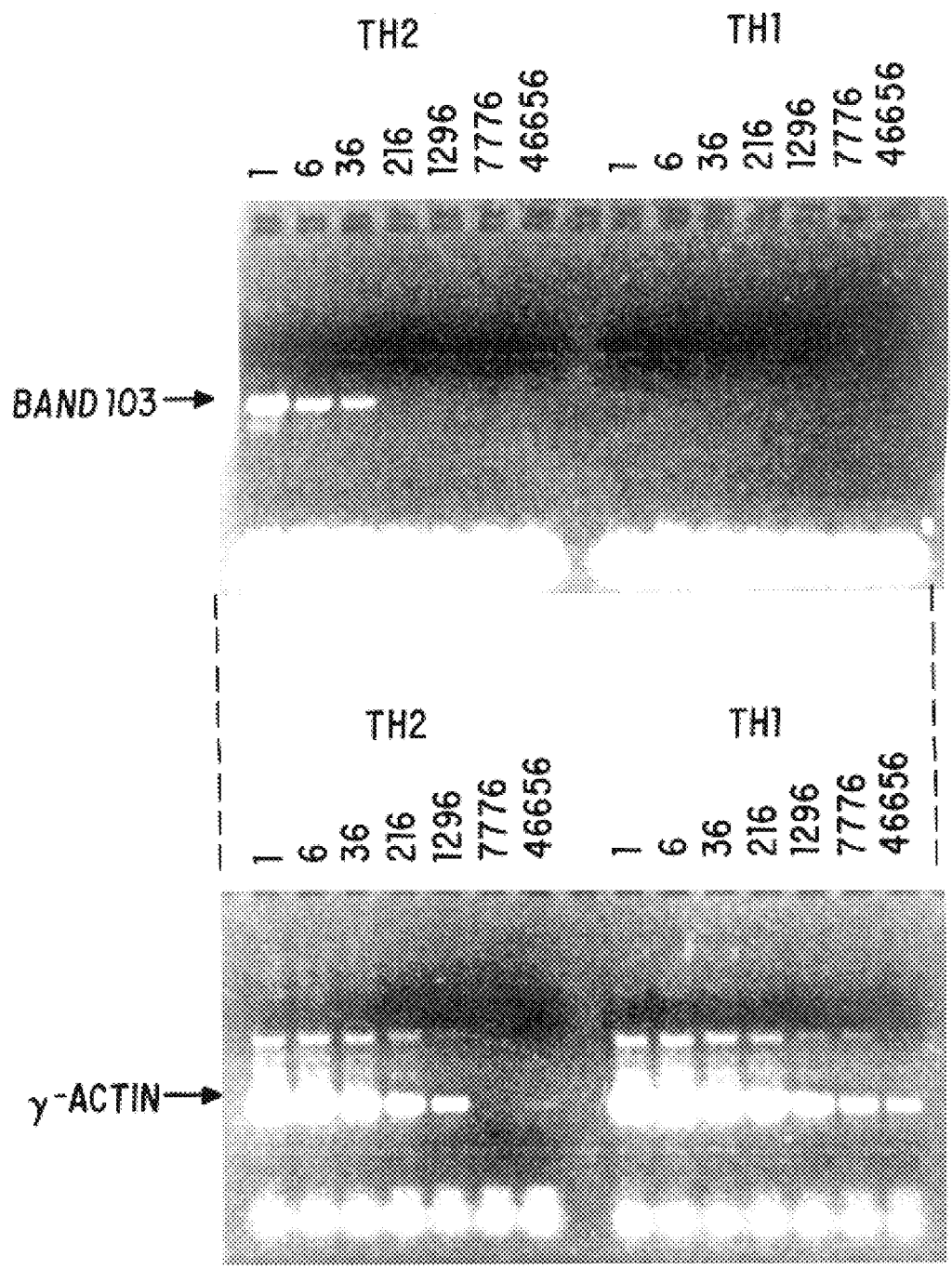

FIG. 5. Quantitative RT-PCR analysis of 103 gene expression in polarized populations of murine TH cells. RNA samples were harvested from cultured T cell populations 24 hours after tertiary stimulation with antigen. cDNA samples were PCR amplified and the products of those reactions were electrophoresed on a 1% agarose gel and visualized by ethidium bromide staining. 103 gene expression is shown in the upper panel. γ-actin data, bottom panel, was included as a control for differences in sample quality. The numbers above each lane represent the dilution factors of each cDNA. The same cDNA samples were used for both the 103 gene and the γ-actin amplifications.

Figure 6:
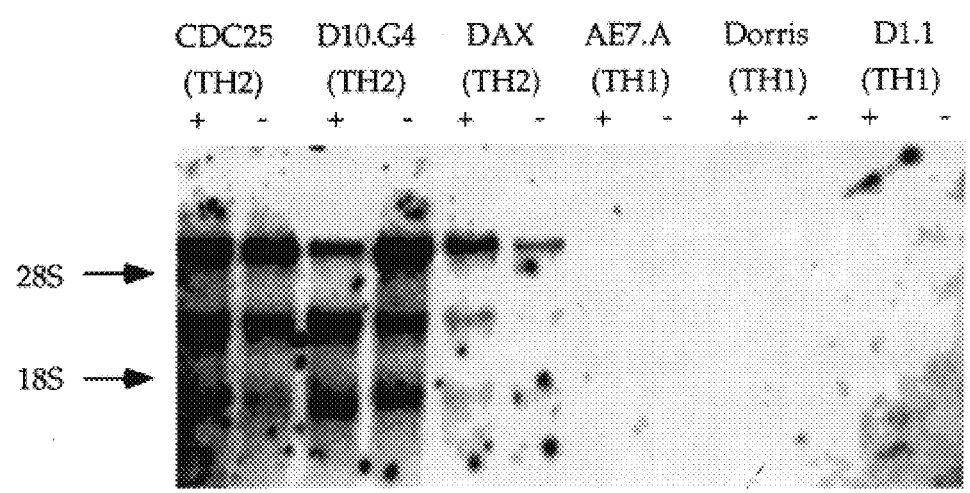

FIG. 6. Northern blot analysis of 103 gene expression in representative murine TH cell lines (TH2: CDC25, D10.G4, DAX; TH1: AE7.A, Dorris, D1.1). Clones were either unstimulated (−) or stimulated (+) for 6 hours with plate-bound anti-CD3 antibody. Ten micrograms of total RNA were loaded per lane. The positions of 18s and 28s ribosomal RNA are shown as reference markers.

Figure 7:
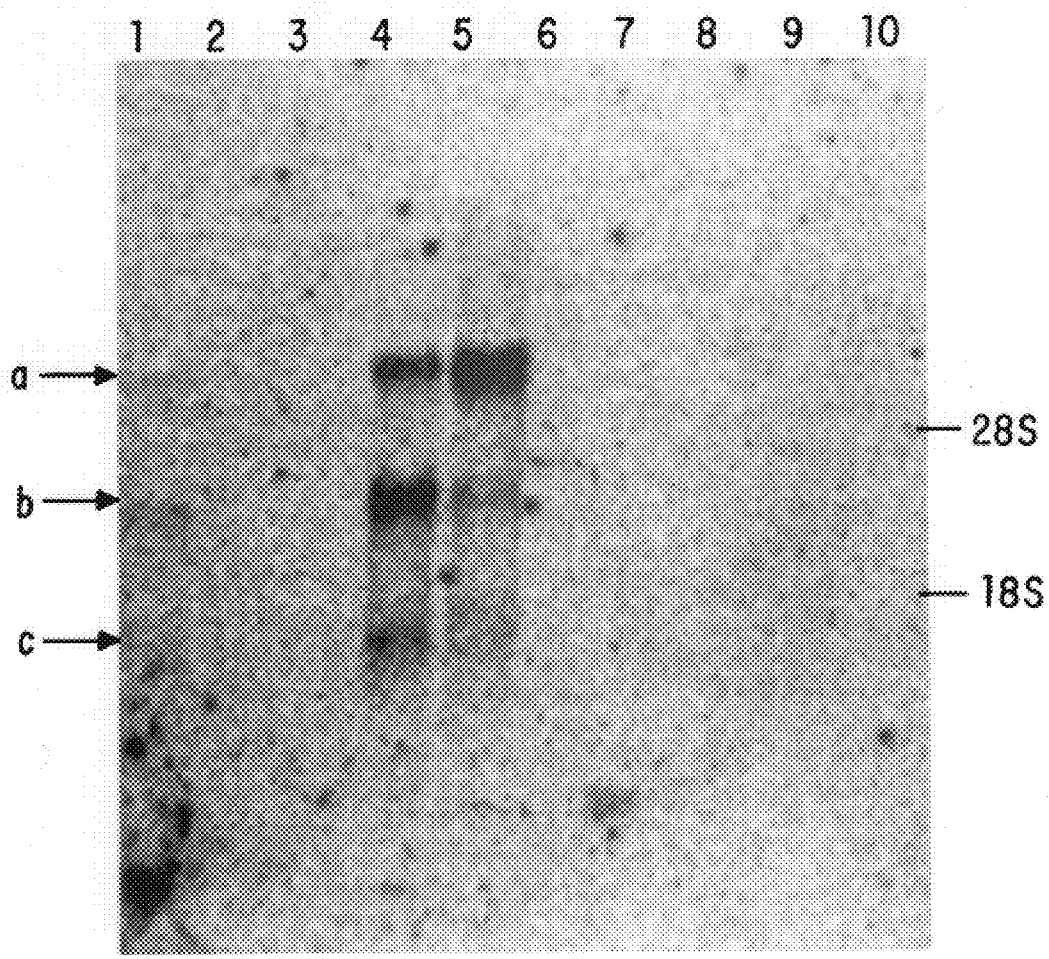

FIG. 7. Northern blot analysis of 103 gene expression in T cell clones and murine tissues. Lane 1: DAX cells, no stimulation; lane 2, AE7 cells, stimulation; lane 3, AE7 cells, no stimulation; lane 4, D10.G4 cells, stimulation; lane 5, D10.G4 cells, no stimulation; lane 6, brain; lane 7, heart; lane 8, lung; lane 9, spleen; lane 10, liver. Clones were stimulated with plate-bound anti-CD3 antibody for 6 hours. 7.5 and 10 micrograms total RNA was used for each cell line and each tissue, respectively. a, b, and c arrows refer to RNA encoding full length (a) and truncated (b,c) forms of the 103 gene. The positions of 18s and 28s ribosomal RNA markers are shown.

Figure 8:
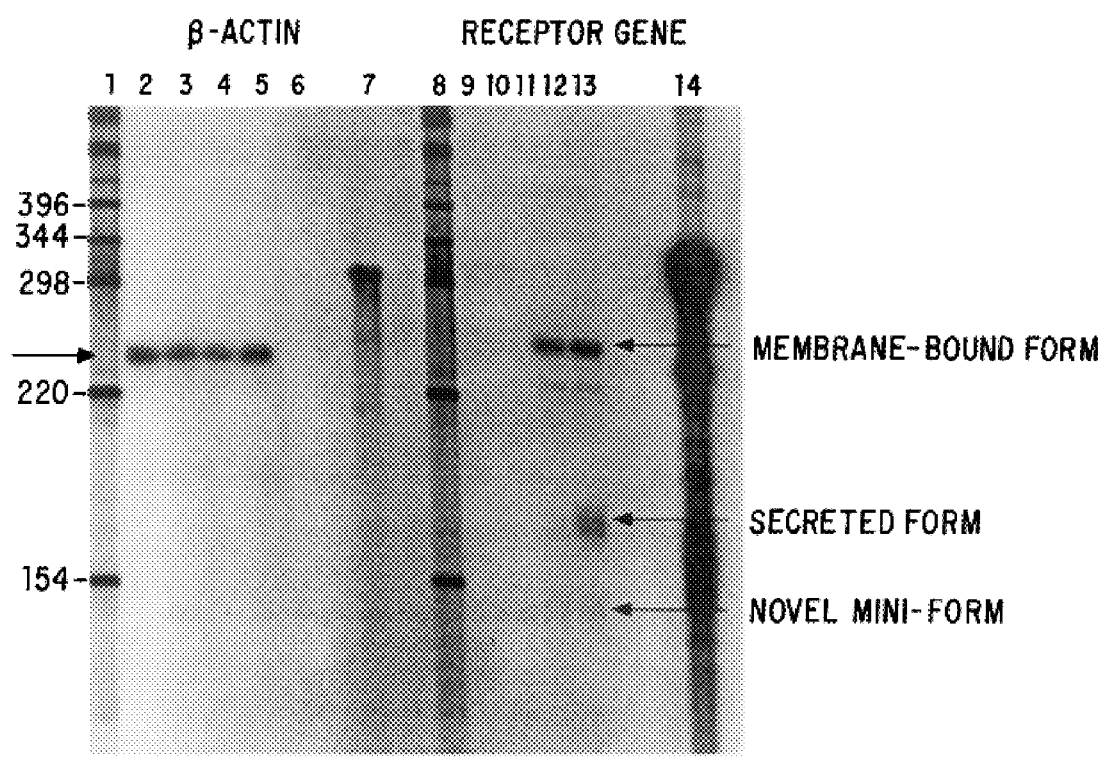
Figure 10A:
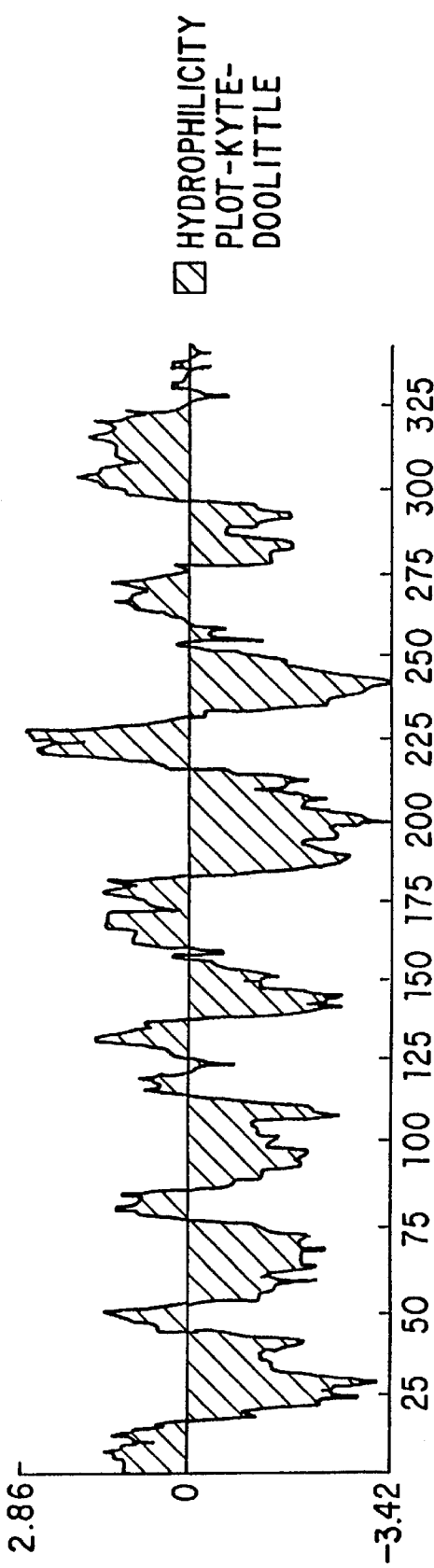
Figure 10B:
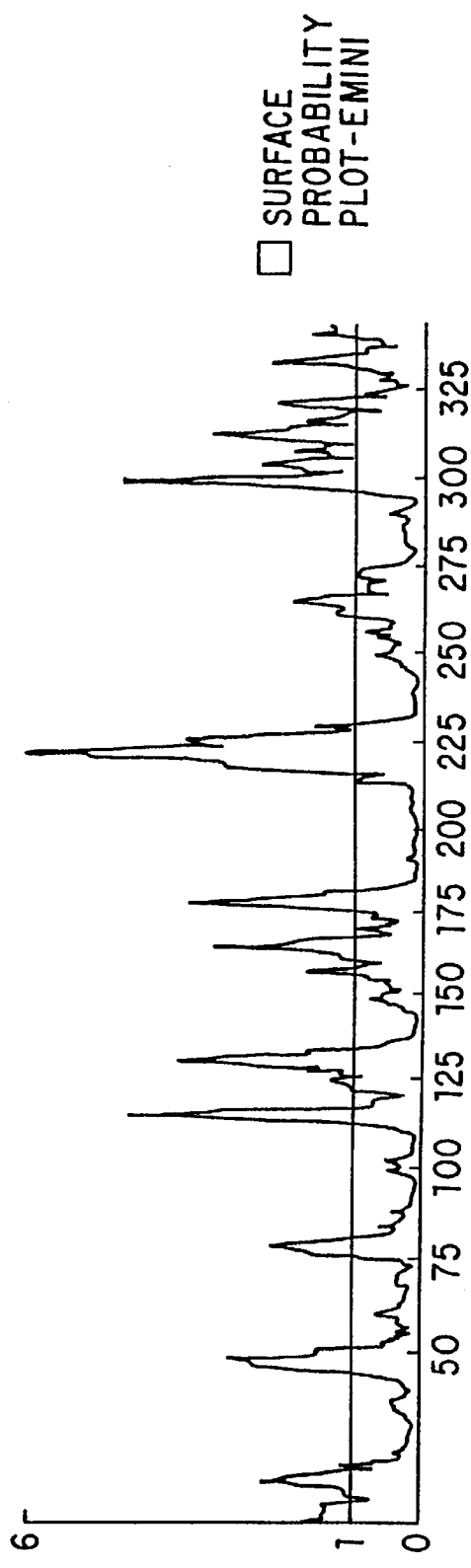
Figure 10C:
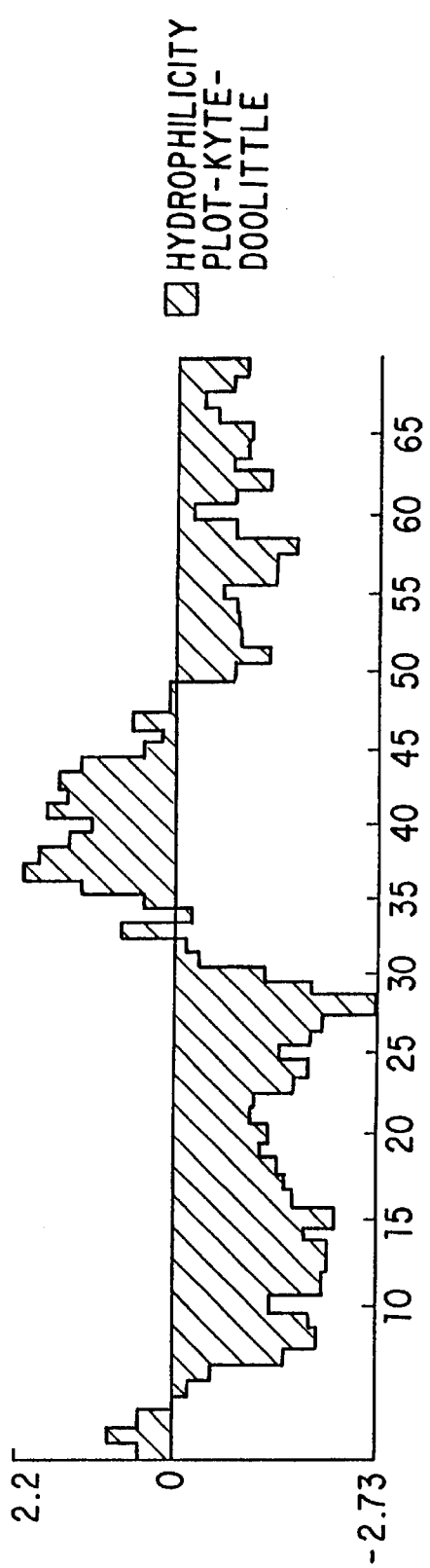
Figure 10D:
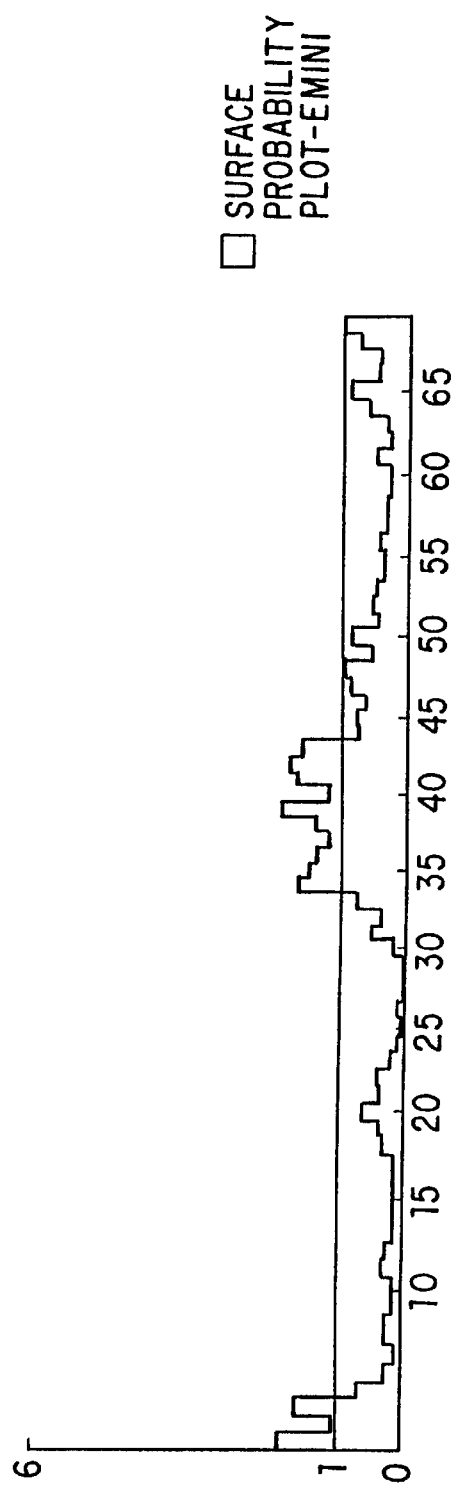

FIG. 8. RNAse protection analysis of 103 gene mRNA, illustrating regulation of 103 gene expression in murine TH cell clones. Lanes 2–6: β-actin protection; lanes 9–13: 103 gene protection; lanes 1 and 8: markers; lanes 2 and 9: unstimulated TH1 clones; lanes 3 and 10: stimulated TH1 clones; lanes 4 and 11: unstimulated TH2 clones; lanes 5 and 12: stimulated TH2 clones; lanes 6 and 13: fully RNAse A digested unprotected probe; lanes 7 and 14: probe alone, in absence of added RNAse.

Expected fragment sizes:

β-actin protected probe: 250 nucleotides;
β-actin full length probe: 330 nucleotides;
103 gene long form fragment: 257 nucleotides;
103 gene short form fragment: 173 nucleotides;
103 gene full length probe: 329 nucleotides.

FIGS. 9A–9D. The full length 10 gene nucleotide sequence (SEQ ID NO: 3) is shown on the top line, while the derived amino acid sequence of the 10 gene product (SEQ ID NO: 9) is shown on the bottom line. The underlined portion of the nucleotide sequence corresponds to the band 10 nucleotide sequence. The data shown in FIGS. 10A–F was obtained through the use of the portion of the 10 gene product which is encoded by the band 10 nucleotide sequence.

FIGS. 10A–10F. 10 gene hydrophilicity data, indicating that the 10 gene-derived amino acid sequence predicts the presence of a seven transmembrane domain structural motif. 10A–10B) platelet activating factor receptor hydrophilicity plot illustrating the protein's seven transmembrane domain structural motif; 10C–10D) 10 gene hydrophilicity plot illustrating a portion of the protein's putative seven transmembrane domain structural motif; 10E–10F) platelet activating factor receptor hydrophilicity plot illustrating part of the protein's seven transmembrane structural motif.

Figure 11:
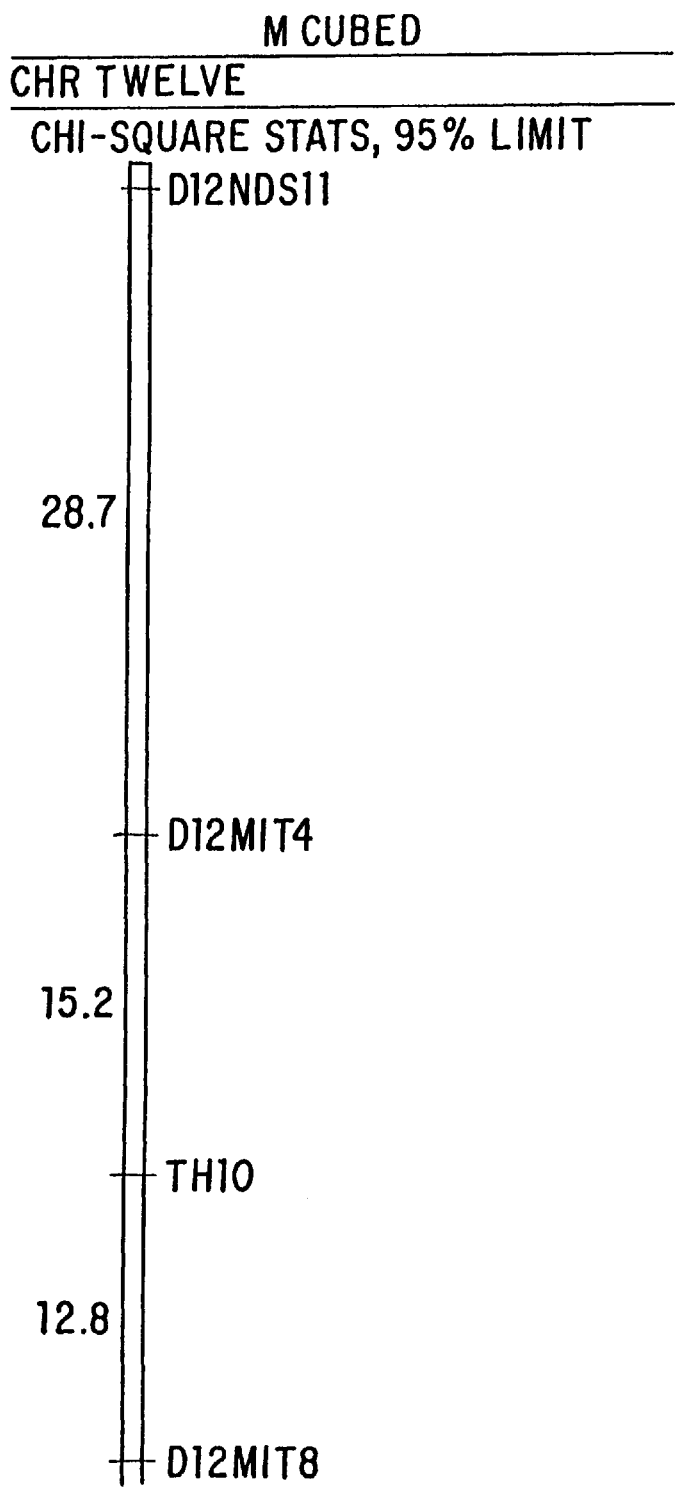

FIG. 11. Chromosomal mapping of locus containing the 10 gene sequence. A map of a portion of mouse chromosome 12 is shown. Numbers to left of chromosome are in centi-Morgans; D12NDS11, D12MIT4, and D12MIT8 represent mouse microsatellite markers; TH10 represents 10 gene.

FIG. 12. Nucleotide sequence of clone 7 of band 57 (SEQ ID NO:4). The gene corresponding to band 57 is referred to herein as the 57 gene.

FIG. 13. Consensus nucleotide sequence of band 105 (SEQ ID NO:5). "N" signifies "any nucleotide". The gene corresponding to band 105 is referred to herein as the 105 gene.

FIG. 14. Nucleotide sequence obtained from clone H of band 106 (SEQ ID NO:6). "N" signifies "any nucleotide". The gene corresponding to band 106 is referred to herein as the 106 gene.

FIG. 15. Nucleotide sequence of clone G of band 161 (SEQ ID NO:7). The gene corresponding to band 161 is referred to herein as the 161 gene.

FIG. 16. Multiple sequence alignment of 161 clone G with amino acid sequences identified in a BLAST search. Asterisks signify positions that are identical; dots indicate conserved positions.

FIGS. 17A–17D. Nucleotide and amino acid sequence of the full length murine 200 gene. Bottom line: murine 200 gene nucleotide sequence (SEQ ID NO:8); top line: murine 200 gene product derived amino acid sequence (SEQ ID NO: 10).

Figure 18:
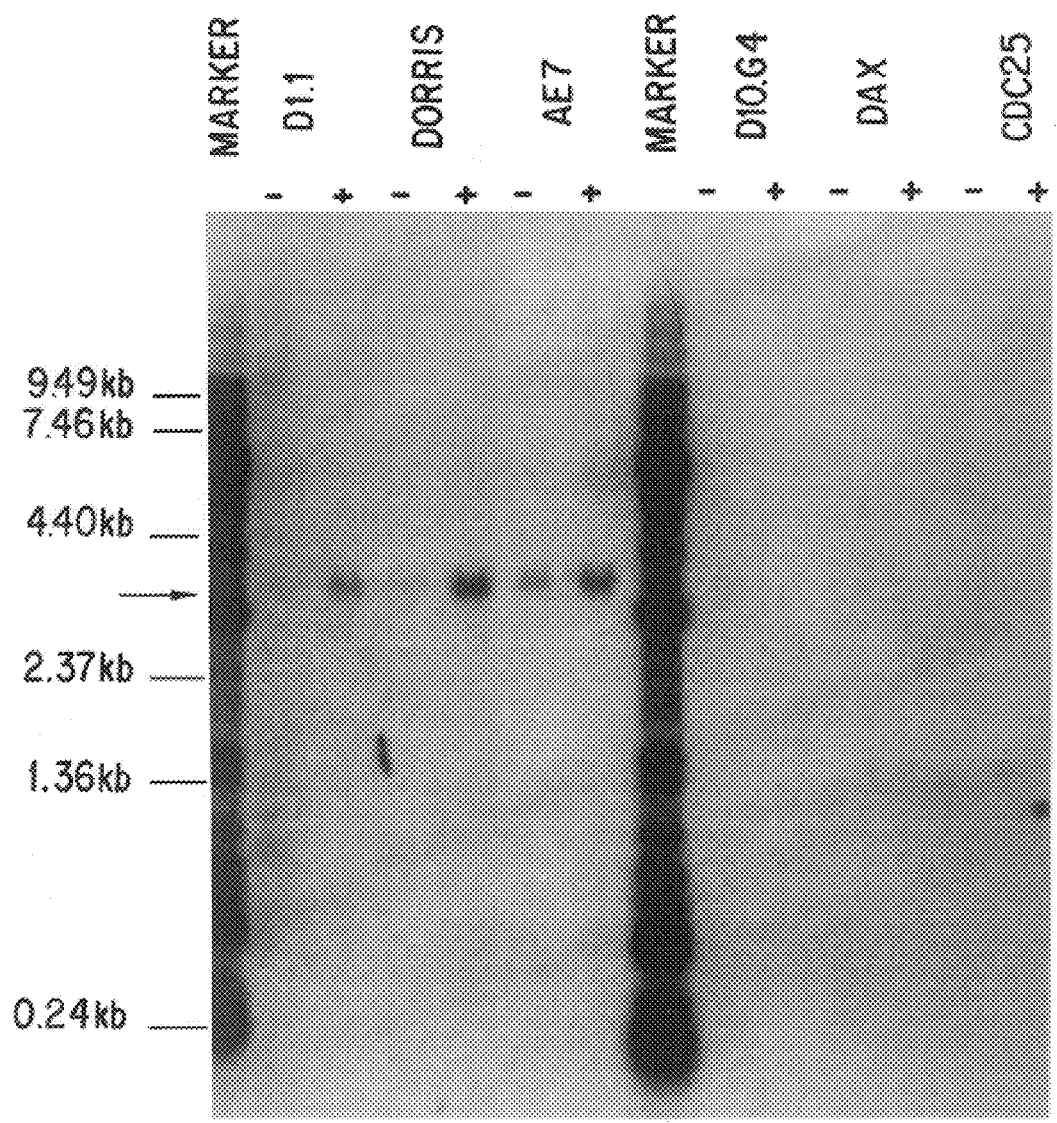

FIG. 18. Northern blot analysis of murine 200 gene expression in representative murine TH cell lines (TH2: CDC25, D10.G4, DAX; TH1: AE7.A, Dorris, D1.1). Clones were either unstimulated (−) or stimulated (+) for 6 hours with plate-bound anti-CD3 antibody. The positions of RNA markers, in kilobases, are shown for reference. The arrow marks the position of 200 gene mRNA.

Figure 19:
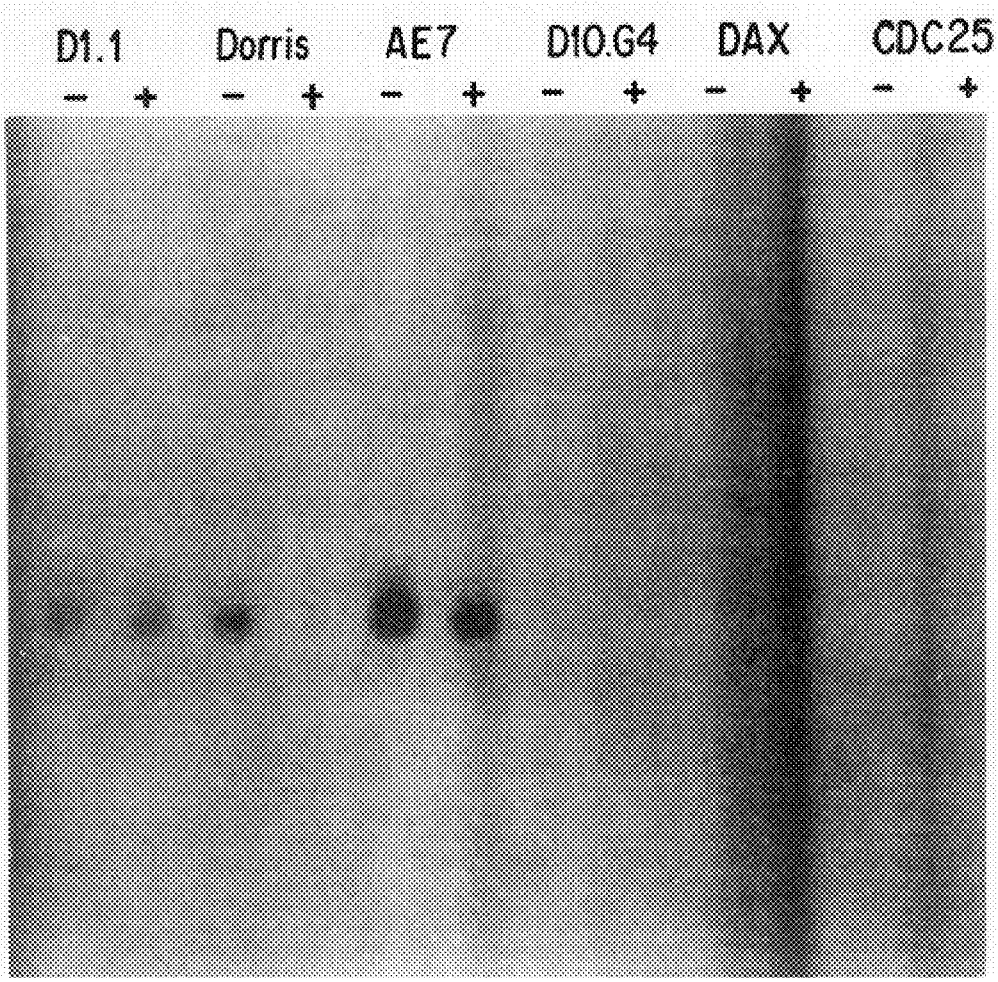

FIG. 19. Northern blot analysis of 54 gene expression within TH1 (D1.1, Dorris, AE7) cell lines and TH2 (D10.G4, DAX, CDC25) cell lines, either stimulated (+) or unstimulated (−) with anti-CD3 antibodies. 15 micrograms of total RNA were loaded per lane. Cells were stimulated between 6 and 7 hours with anti-CD3 antibodies, as described, below, in Section 8.1. The Northern blots were hybridized with a probe made from the entire band 54 nucleotide sequence.

Figure 20:
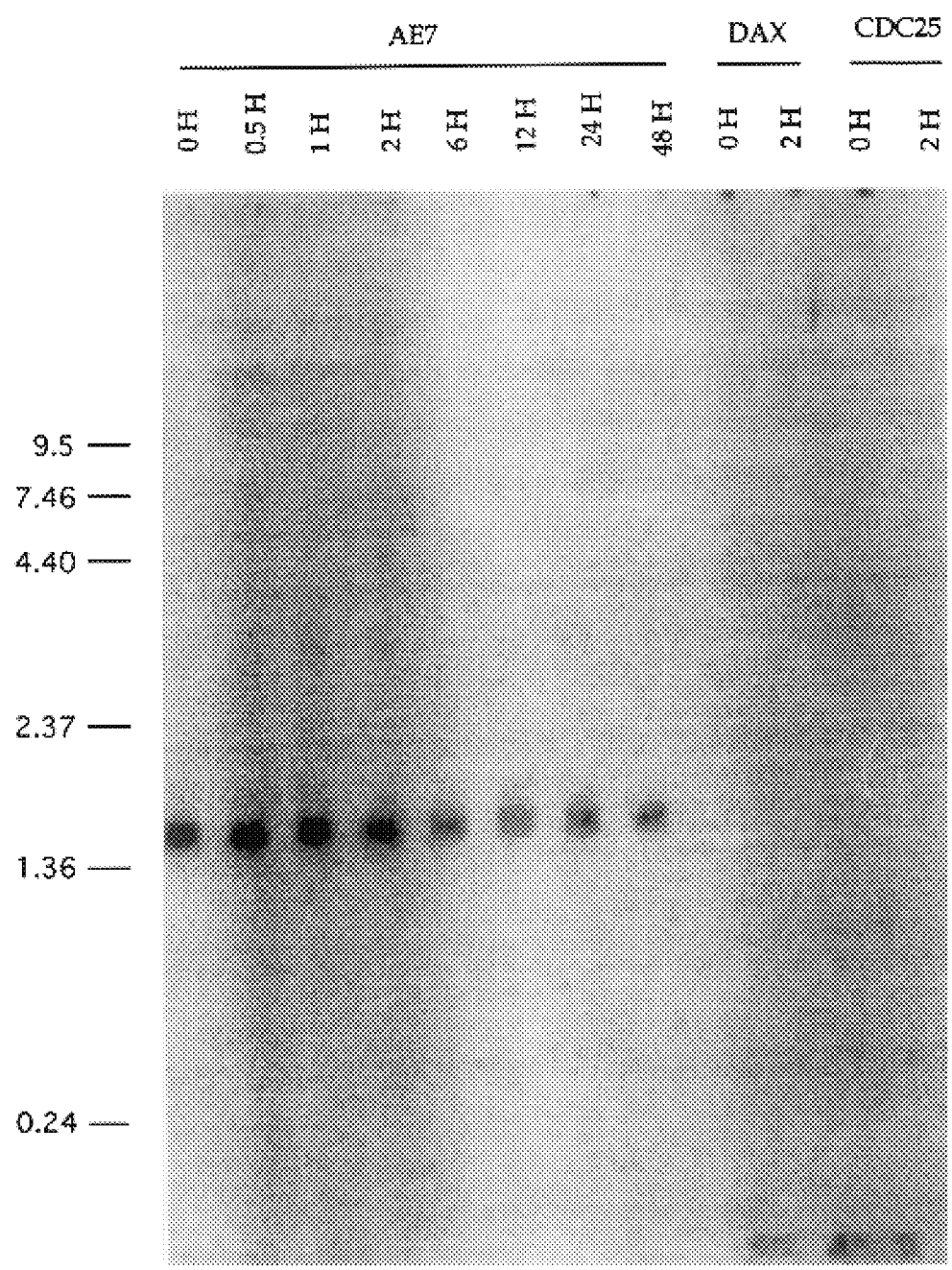

FIG. 20. Northern blot analysis of gene 54 time course study. RNA from TH1 cell line AE7 cells was isolated, either unstimulated or stimulated for varying periods of time, as indicated. Second, RNA from two TH2 cell lines (DAX, CDC25) was isolated from either unstimulated cells or from cells which had been stimulated for two hours with anti-CD3 antibodies. 15 micrograms total RNA were loaded per lane. A band 54 DNA probe was used for hybridization.

Figure 21:
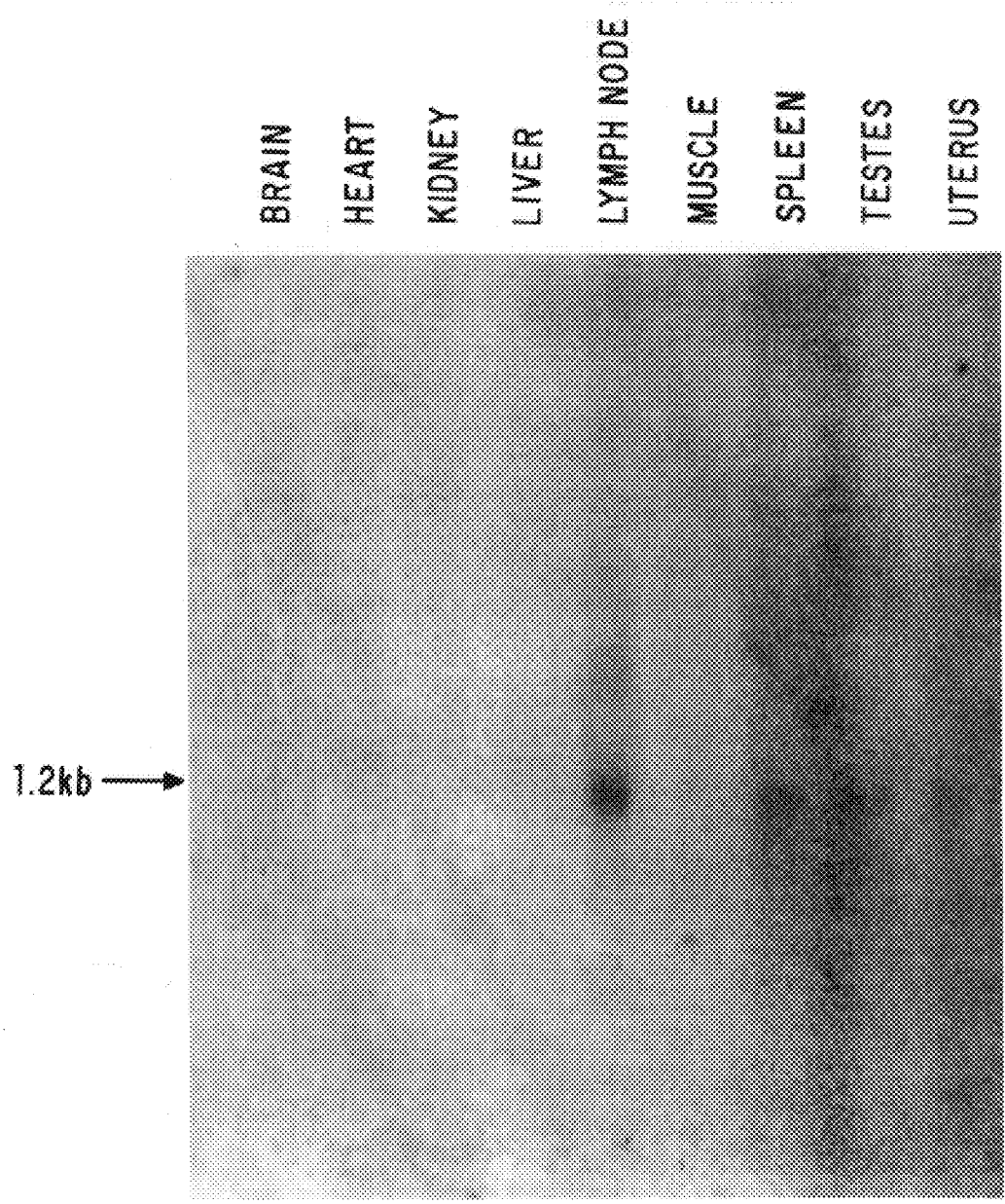

FIG. 21. Northern blot analysis of 54 gene expression in various tissues. 15 micrograms of total RNA were loaded per lane. A band 54 DNA probe was used for hybridization.

FIGS. 22A–22C. Nucleotide and amino acid sequence of the full length 54 gene. Bottom line: 54 gene nucleotide sequence (SEQ ID NO:11). Top line: 54 gene derived amino acid sequence (SEQ ID NO:12).

FIGS. 23A–23C. The 54 gene product bears a high level of homology to the cysteine protease class of proteins. The 54 gene product amino acid is depicted with its predicted pre-pro sequence and mature cysteine protease polypeptide sequence identified. The individual boxed amino acid residues represent residues thought to lie within the cysteine protease active site and the stretch of amino acid residues which are boxed represent a region with homology to a stretch of amino acid residues normally seen within the preproenzyme portion of cysteine protease molecules. The circled amino acid residues within this stretch represent conserved amino acids. The arrow indicates the putative post-translational cleavage site.

FIGS. 24A–24D. Nucleotide and amino acid sequence of the full length human 200 gene. Bottom line: human 200 gene nucleotide sequence (SEQ ID NO: 23); top line: human 200 gene product derived amino acid sequence (SEQ ID NO:24).

5. DETAILED DESCRIPTION OF THE INVENTION

Methods and compositions for the treatment and diagnosis of immune disorders, especially TH cell subpopulation-related disorders, including, but not limited to, atopic conditions, such as asthma and allergy, including allergic rhinitis, psoriasis, the effects of pathogen infection, chronic inflammatory diseases, organ-specific autoimmunity, graft rejection and graft versus host disease, are described. The invention is based, in part, on the evaluation of the expression and role of all genes that are differentially expressed within and/or among TH cell subpopulations in paradigms that are physiologically relevant to TH-mediated immune response and/or TH-subpopulation related disorders. This permits the definition of disease pathways that are useful both diagnostically and therapeutically.

Genes, termed "target genes" and/or "fingerprint genes", which are differentially expressed within and among TH cells and TH cell subpopulations in normal and/or disease states, and/or during the differentiation into such mature subpopulations are described in Section 5.4. Additionally, genes, termed "pathway genes", whose gene products exhibit an ability to interact with gene products involved in TH cell subpopulation-related disorders and/or with gene products which are involved in the differentiation and effector function of the subpopulations are described in Section 5.4. Pathway genes can additionally have fingerprint and/or target gene characteristics. Methods for the identification of such fingerprint, target, and pathway genes are also described in Sections 5.1 and 5.2.

Further, the gene products of such fingerprint, target, and pathway genes are described in Section 5.5, antibodies to such gene products are described in Section 5.6, as are cell- and animal-based models of TH cell subpopulation differentiation and TH cell subpopulation-related disorders to which such gene products can contribute in Section 5.7.

Methods for prognostic and diagnostic evaluation of various TH cell subpopulation-related disorders, for the identification of subjects exhibiting a predisposition to such disorders, and for monitoring the efficacy of compounds used in clinical trials are described in Section 5.11.

Methods for the identification of compounds which modulate the expression of genes or the activity of gene products involved in TH cell subpopulation-related disorders and to the differentiation and effector function of TH cell subpopulations are described in Section 5.8, and methods for the treatment of immune disorders are described in Section 5.9.

5.1 Identification of Differentially Expressed Genes

Described herein are methods for the identification of differentially expressed genes which are involved in immune disorders, e.g., TH cell subpopulation-related disorders, and/ or which are involved in the differentiation, maintenance and effector function of the subpopulations. There exist a number of levels at which the differential expression of such genes can be exhibited. For example, differential expression can occur in undifferentiated TH cells versus differentiated or differentiating TH cells (although not necessarily within one TH cell subpopulation versus another), in naive TH cells versus memory TH cells, within one TH cell subpopulation versus another (e.g., TH1 versus TH2 subpopulations), in mature, stimulated cells versus mature, unstimulated cells of a given TH cell subpopulation or in TH cell subpopulation-related disorder states relative to their expression in normal, or non-TH cell subpopulation-related disorder states. Such differentially expressed genes can represent target and/or fingerprint genes.

Methods for the identification of such differentially expressed genes are described, below, in Section 5.1.1. Methods for the further characterization of such differentially expressed genes, and for their categorization as target and/or fingerprint genes, are presented, below, in Section 5.3.

"Differential expression" as used herein refers to both quantitative as well as qualitative differences in the genes' temporal and/or cell type expression patterns. Thus, a differentially expressed gene can qualitatively have its expression activated or completely inactivated in, for example, normal versus TH cell subpopulation-related disorder states, in one TH cell subpopulation versus another (e.g., TH1 versus TH2), in antigen stimulated versus unstimulated sets of TH cells, or in undifferentiated versus differentiated or differentiating TH cells. Such a qualitatively regulated gene will exhibit an expression pattern within a state or cell type which is detectable by standard techniques in one such state or cell type, but is not detectable in both.

Alternatively, a differentially expressed gene can exhibit an expression level which differs, i.e., is quantitatively increased or decreased, in normal versus TH cell subpopulation-related disorder states, in antigen stimulated versus unstimulated sets of TH cells, in one TH cell subpopulation versus another, or in undifferentiated versus differentiated or differentiating TH cells. Because differentiation is a multistage event, genes which are differentially expressed can also be identified at any such intermediate differentiative stage.

The degree to which expression differs need only be large enough to be visualized via standard characterization techniques, such as, for example, the differential display technique described below. Other such standard characterization techniques by which expression differences can be visualized include, but are not limited to, quantitative RT (reverse transcriptase) PCR and Northern analyses and RNase protection techniques.

Differentially expressed genes can be further described as target genes and/or fingerprint genes. "Fingerprint gene," as used herein, refers to a differentially expressed gene whose expression pattern can be utilized as part of a prognostic or diagnostic TH cell subpopulation-related disorder evaluation, or which, alternatively, can be used in methods for identifying compounds useful for the treatment of TH cell subpopulation-related disorders. A fingerprint gene can also have the characteristics of a target gene or a pathway gene (see below, in Section 5.2).

"Fingerprint pattern," as used herein, refers to the pattern generated when the expression pattern of a series (which can range from two up to all the fingerprint genes which exist for a given state) of fingerprint genes is determined. A fingerprint pattern can also be used in methods for identifying compounds useful in the treatment of immune disorders, e.g., by evaluating the effect of the compound on the fingerprint pattern normally displayed in connection with the disease.

"Target gene", as used herein, refers to a differentially expressed gene involved in TH cell subpopulation-related disorders and/or in differentiation, maintenance and/or effector function of the subpopulations in a manner by which modulation of the level of target gene expression or of target gene product activity can act to ameliorate symptoms of TH cell subpopulation-related disorders. For example, such modulation can result either the depletion or stimulation of one or more TH cell subpopulation, which, in turn, brings about the amelioration of immune disorder, e.g., TH cell subpopulation disorder, symptoms.

"Stimulation", as used herein, can refer to an effective increase in the number of cells belonging to a T cell population, such as a TH cell subpopulation, via, for example, the proliferation of such TH cell subpopulation cells. The term can also refer to an increase in the activity of cells belonging to a TH cell subpopulation, as would by evidenced, for example, by a per cell increase in the expression of the TH cell subpopulation-specific cytokine pattern.

"Depletion", as used herein, can refer to an effective reduction in the number of cells belonging to a T cell population, such as a TH cell subpopulation, via, for example, a reduction in the proliferation of such TH cell subpopulation cells. The term can also refer to a decrease in the activity of cells belonging to a TH cell subpopulation, as would be evidenced, for example, by a per cell decrease in the expression of the TH cell subpopulation-specific cytokine pattern.

TH cell subpopulation-related disorders include, for example, atopic conditions, such as asthma and allergy, including allergic rhinitis, the effects of pathogen, including viral, infection, chronic inflammatory diseases, psoriasis, glomerular nephritis, organ-specific autoimmunity, graft rejection and graft versus host disease. A target gene can also have the characteristics of a fingerprint gene and/or a pathway gene (as described, below, in Section 5.2).

5.1.1 Methods for the Identification of Differentially Expressed Genes

A variety of methods can be utilized for the identification of genes which are involved in immune disorder states, e.g., TH cell subpopulation-related disorder states, and/or which are involved in differentiation, maintenance and/or effector function of the subpopulations. Described in Section 5.1.1.1 are experimental paradigms which can be utilized for the generation of subjects and samples which can be used for the identification of such genes. Material generated in paradigm categories can be characterized for the presence of differentially expressed gene sequences as discussed, below, in Section 5.1.1.2.

5.1.1.1 Paradigms for the Identification of Differentially Expressed Genes

Paradigms which represent models of normal and abnormal immune responses are described herein. These paradigms can be utilized for the identification of genes which are differentially expressed within and among TH cell subpopulations, including but not limited to TH1 and TH2 subpopulations. Such genes can be involved in, for example, TH cell subpopulation differentiation, maintenance, and/or effector function, and in TH cell subpopulation-related disorders. For example, TH cells can be induced to differentiate into either TH1 or TH2 states, can be stimulated with, for example, a foreign antigen, and can be collected at various points during the procedure for analysis of differential gene expression.

In one embodiment of such a paradigm, referred to herein as the "transgenic T cell paradigm", transgenic animals, preferably mice, are utilized which have been engineered to express a particular T cell receptor, such that the predominant T cell population of the immune system of such a transgenic animal recognizes only one antigen. Such a system is preferred in that it provides a source for a large population of identical T cells whose naivete can be assured, and whose response to the single antigen it recognizes is also assured. T helper cells isolated from such a transgenic animal are induced, in vitro, to differentiate into TH cell subpopulations such as TH1, TH2, or TH0 cell subpopulations. In a specific embodiment, one T helper cell group (the TH1 group) is exposed to IL-12, a cytokine known to induce differentiation into the TH1 state, a second T helper cell group (the TH2 group) is exposed to IL-4, a cytokine known to induce differentiation into the TH2 state, and a third group is allowed, by a lack of cytokine-mediated induction, to enter a TH-undirected state.

A second paradigm, referred to herein as a "T cell line paradigm", can be utilized which uses mature TH cell clones, such as TH1 and TH2 and TH1-like and TH2-like cell lines, preferably human cell lines. Such TH cell lines can include, but are not limited to the following well known murine cell lines: Doris, AE7, D10.G4, DAX, D1.1 and CDC25. Such T cell lines can be derived from normal individuals as well as individuals exhibiting TH cell subpopulation-related disorders, such as, for example, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease, sarcoidosis, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

The TH cell clones can be stimulated in a variety of ways. Such stimulation methods include, but are not limited to, pharmacological methods, such as exposure to phorbol esters, calcium ionophores, or lectins (e.g., Concanavalin A), by treatment with antibodies directed against T-cell receptor epitopes (e.g., anti-CD3 antibodies) or exposure, in the presence of an appropriate antigen presenting cell (APC), to an antigen that the particular TH cells are known to recognize. Following such primary stimulation, the cells can be maintained in culture without stimulation and, for example, in the presence of IL-2, utilizing standard techniques well known to those of skill in the art. The cells can then be exposed to one or more additional cycles of stimulation and maintenance.

A third paradigm, referred to herein as an "in vivo paradigm", can also be utilized to discover differentially expressed gene sequences. In vivo stimulation of animal models forms the basis for this paradigm. The in vivo nature of the stimulation can prove to be especially predictive of the analogous responses in living patients. Stimulation can be accomplished via a variety of methods. For example, animals, such as transgenic animals described earlier in this Section, can be injected with appropriate antigen and appropriate cytokine to drive the desired TH cell differentiation. Draining lymph nodes can then be harvested at various time points after stimulation. Lymph nodes from, for example, TH1-directed animals can be compared to those of TH2-directed animals.

A wide range of animal models, representing both models of normal immune differentiation and function as well as those representing immune disorders can be utilized for this in vivo paradigm. For example, any of the animal models, both recombinant and non-recombinant, described, below, in Section 5.7.1, can be used.

Cell samples can be collected during any point of such a procedure. For example, cells can be obtained following any stimulation period and/or any maintenance period. Additionally, cells can be collected during various points during the TH cell differentiation process. RNA collected from such samples can be compared and analyzed according to, for example, methods described, below, in Section 5.1.1.2. For example, RNA from TH0, TH1 and TH2 groups isolated at a given time point can then be analyzed and compared. Additionally, RNA from stimulated and non-stimulated cells within a given TH cell group can also be compared and analyzed. Further, RNA collected from undifferentiated TH cells can be compared to RNA collected from cells at various stages during the differentiative process which ultimately yields TH cell subpopulations.

5.1.1.2 Analysis of Paradigm Material

In order to identify differentially expressed genes, RNA, either total or mRNA, can be isolated from the TH cells utilized in paradigms such as those described in Section 5.1.1.1. Any RNA isolation technique which does not select against the isolation of mRNA can be utilized for the purification of such RNA samples. See, for example, Ausubel, F. M. et al., eds., 1987–1993, *Current Protocols in Molecular Biology*, John Wiley & Sons, Inc. New York, which is incorporated herein by reference in its entirety. Additionally, large numbers of cell samples can readily be processed using techniques well known to those of skill in the art, such as, for example, the single-step RNA isolation process of Chomczynski, P. (1989, U.S. Pat. No. 4,843,155), which is incorporated herein by reference in its entirety.

Transcripts within the collected RNA samples which represent RNA produced by differentially expressed genes can be identified by utilizing a variety of methods which are well known to those of skill in the art. For example, differential screening (Tedder, T. F. et al., 1988, Proc. Natl. Acad. Sci. U.S.A. 85:208–212), subtractive hybridization (Hedrick, S. M. et al., 1984, Nature 308:149–153; Lee, S. W. et al., 1984, Proc. Natl. Acad. Sci. U.S.A. 88:2825), and, preferably, differential display (Liang, P. and Pardee, A. B., 1992, Science 257:967–971; U.S. Pat. No. 5,262,311, which are incorporated herein by reference in their entirety), can be utilized to identify nucleic acid sequences derived from genes that are differentially expressed.

Differential screening involves the duplicate screening of a cDNA library in which one copy of the library is screened with a total cell cDNA probe corresponding to the mRNA population of one cell type while a duplicate copy of the cDNA library is screened with a total cDNA probe corresponding to the mRNA population of a second cell type. For example, one cDNA probe can correspond to a total cell cDNA probe of a cell type or tissue derived from a control subject, while the second cDNA probe can correspond to a total cell cDNA probe of the same cell type or tissue derived from an experimental subject. Those clones which hybridize to one probe but not to the other potentially represent clones derived from genes differentially expressed in the cell type of interest in control versus experimental subjects.

Subtractive hybridization techniques generally involve the isolation of mRNA taken from two different sources, the hybridization of the mRNA or single-stranded cDNA reverse-transcribed from the isolated mRNA, and the removal of all hybridized, and therefore double-stranded, sequences. The remaining non-hybridized, single-stranded cDNAs, potentially represent clones derived from genes that are differentially expressed among the two mRNA sources. Such single-stranded cDNAs are then used as the starting material for the construction of a library comprising clones derived from differentially expressed genes.

The differential display technique is a procedure, utilizing the well-known polymerase chain reaction (PCR; the experimental embodiment set forth in Mullis, K. B., 1987, U.S. Pat. No. 4,683,202), which allows for the identification of sequences derived from genes which are differentially expressed. First, isolated RNA is reverse-transcribed into single-stranded cDNA, utilizing standard techniques which are well known to those of skill in the art. Primers for the reverse transcriptase reaction can include, but are not limited to, oligo dT-containing primers, preferably of the 3' primer type of oligonucleotide described below.

Next, this technique uses pairs of PCR primers, as described below, which allow for the amplification of clones representing a reproducible subset of the RNA transcripts present within any given cell. Utilizing different pairs of primers allows each of the primed mRNA transcripts present in a cell to be amplified. Among such amplified transcripts can be identified those which have been produced from differentially expressed genes.

The 3' oligonucleotide primer of the primer pairs can contain an oligo dT stretch of 10–13, preferably 11, dT nucleotides at its 5' end, which hybridizes to the poly(A) tail of mRNA or to the complement of a cDNA reverse transcribed from an mRNA poly(A) tail. In order to increase the specificity of the 3' primer, the primer can contain one or more, preferably two, additional nucleotides at its 3' end. Because, statistically, only a subset of the mRNA derived sequences present in the sample of interest will hybridize to such primers, the additional nucleotides allow the primers to amplify only a subset of the mRNA derived sequences present in the sample of interest. This is preferred in that it allows more accurate and complete visualization and characterization of each of the bands representing amplified sequences.

The 5' primer can contain a nucleotide sequence expected, statistically, to have the ability to hybridize to cDNA sequences derived from the cells or tissues of interest. The nucleotide sequence can be an arbitrary one, and the length of the 5' oligonucleotide primer can range from about 9 to about 15 nucleotides, with about 13 nucleotides being preferred.

Arbitrary primer sequences cause the lengths of the amplified partial cDNAs produced to be variable, thus allowing different clones to be separated by using standard denaturing sequencing gel electrophoresis.

PCR reaction conditions should be chosen which optimize amplified product yield and specificity, and, additionally, produce amplified products of lengths which can be resolved utilizing standard gel electrophoresis techniques. Such reaction conditions are well known to those of skill in the art, and important reaction parameters include, for example, length and nucleotide sequence of oligonucleotide primers as discussed above, and annealing and elongation step temperatures and reaction times.

The pattern of clones resulting from the reverse transcription and amplification of the mRNA of two different cell types is displayed via sequencing gel electrophoresis and compared. Differentially expressed genes are indicated by differences in the two banding patterns.

Once potentially differentially expressed gene sequences have been identified via bulk techniques such as, for example, those described above, the differential expression of such putatively differentially expressed genes should be corroborated. Corroboration can be accomplished via, for example, such well known techniques as Northern analysis, quantitative RT/PCR, or RNAse protection.

Upon corroboration, the differentially expressed genes can be further characterized, and can be identified as target and/or fingerprint genes, as discussed, below, in Section 5.3.

The amplified sequences of differentially expressed genes obtained through, for example, differential display can be used to isolate full length clones of the corresponding gene. The full length coding portion of the gene can readily be isolated, without undue experimentation, by molecular biological techniques well known in the art. For example, the isolated differentially expressed amplified fragment can be labeled and used to screen a cDNA library. Alternatively, the labeled fragment can be used to screen a genomic library.

PCR technology can also be utilized to isolate full length cDNA sequences. As described, above, in this Section, the isolated, amplified gene fragments obtained through differential display have 5' terminal ends at some random point within the gene and usually have 3' terminal ends at a position corresponding to the 3' end of the transcribed portion of the gene. Once nucleotide sequence information from an amplified fragment is obtained, the remainder of the gene (i.e., the 5' end of the gene, when utilizing differential display) can be obtained using, for example, RT-PCR.

In one embodiment of such a procedure for the identification and cloning of full length gene sequences, RNA can be isolated, following standard procedures, from an appropriate tissue or cellular source. A reverse transcription reaction can then be performed on the RNA using an oligonucleotide primer complimentary to the mRNA that corresponds to the amplified fragment, for the priming of first strand synthesis. Because the primer is anti-parallel to the mRNA, extension will proceed toward the 5' end of the mRNA. The resulting RNA/DNA hybrid can then be "tailed" with guanines using a standard terminal transferase reaction, the hybrid can be digested with RNAase H, and second strand synthesis can then be primed with a poly-C primer. Using the two primers, the 5' portion of the gene is amplified using PCR. Sequences obtained can then be isolated and recombined with previously isolated sequences to generate a full-length cDNA of the differentially expressed genes of the invention. For a review of cloning strategies and recombinant DNA techniques, see e.g., Sambrook et al., 1989, Molecular Cloning, A Laboratory Manual, (Volumes 1–3) Cold Spring Harbor Press, New York; and Ausubel et al., 1989, Current Protocols in Molecular Biology, Green Publishing Associates and Wiley Interscience, New York.

5.2 Methods for the Identification of Pathway Genes

Methods are described herein for the identification of pathway genes. "Pathway gene", as used herein, refers to a gene whose gene product exhibits the ability to interact with gene products involved in TH cell subpopulation-related disorders and/or to interact with gene products which are involved in differentiation, maintenance and/or effector function of TH cell subpopulations. A pathway gene can be differentially expressed and, therefore, can have the characteristics of a target and/or fingerprint gene, as described, above, in Section 5.1.

Any method suitable for detecting protein-protein interactions can be employed for identifying pathway gene products by identifying interactions between gene products and gene products known to be involved in TH cell subpopulation-related disorders and/or involved in differentiation, maintenance, and/or effector function of the subpopulations. Such known gene products can be cellular or extracellular proteins. Those gene products which interact with such known gene products represent pathway gene products and the genes which encode them represent pathway genes.

Among the traditional methods which can be employed are co-immunoprecipitation, crosslinking and co-purification through gradients or chromatographic columns. Utilizing procedures such as these allows for the identification of pathway gene products. Once identified, a pathway gene product can be used, in conjunction with standard techniques., to identify its corresponding pathway gene. For example, at least a portion of the amino acid sequence of the pathway gene product can be ascertained using techniques well known to those of skill in the art, such as via the Edman degradation technique (see, e.g., Creighton, 1983, "Proteins: Structures and Molecular Principles", W.H. Freeman & Co., New York, pp.34–49). The amino acid sequence obtained can be used as a guide for the generation of oligonucleotide mixtures that can be used to screen for pathway gene sequences. Screening can be accomplished, for example, by standard hybridization or PCR techniques. Techniques for the generation of oligonucleotide mixtures and for screening are well-known. (See, e.g., Ausubel, supra., and PCR Protocols: A Guide to Methods and Applications, 1990, Innis, M. et al., eds. Academic Press, Inc., New York).

Additionally, methods can be employed which result in the simultaneous identification of pathway genes which encode proteins interacting with a protein involved in TH cell subpopulation-related disorder states and/or differentiation, maintenance, and/or effector function of the subpopulations. These methods include, for example, probing expression libraries with labeled protein known or suggested to be involved in the disorders and/or the differentiation, maintenance, and/or effector function of the subpopulations, using this protein in a manner similar to the well known technique of antibody probing of λgt11 libraries.

One method which detects protein interactions in vivo, the two-hybrid system, is described in detail for illustration purposes only and not by way of limitation. One version of this system has been described (Chien et al., 1991, Proc. Natl. Acad. Sci. U.S.A., 88:9578–9582) and is commercially available from Clontech (Palo Alto, Calif.).

Briefly, utilizing such a system, plasmids are constructed that encode two hybrid proteins: one consists of the DNA-binding domain of a transcription activator protein fused to a known protein, in this case, a protein known to be involved in TH cell subpopulation differentiation or effector function, or in TH cell subpopulation-related disorders, and the other consists of the activator protein's activation domain fused to an unknown protein that is encoded by a cDNA which has been recombined into this plasmid as part of a cDNA library. The plasmids are transformed into a strain of the yeast *Saccharomyces cerevisiae* that contains a reporter gene (e.g., lacZ) whose regulatory region contains the transcription activator's binding sites. Either hybrid protein alone cannot activate transcription of the reporter gene, the DNA-binding domain hybrid cannot because it does not provide activation function, and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with a known "bait" gene product. By way of example, and not by way of limitation, gene products known to be involved in TH cell subpopulation-related disorders and/or differentiation, maintenance, and/or effector function of the subpopulations can be used as the bait gene products.

Total genomic or cDNA sequences are fused to the DNA encoding an activation domain. This library and a plasmid encoding a hybrid of the bait gene product fused to the DNA-binding domain are cotransformed into a yeast reporter strain, and the resulting transformants are screened for those that express the reporter gene. For example, and not by way of limitation, the bait gene can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait gene product are to be detected can be made using methods routinely practiced in the art. According to the particular system described herein, for example, the cDNA fragments can be inserted into a vector such that they are translationally fused to the activation domain of GAL4. This library can be co-transformed along with the bait gene-GAL4 fusion plasmid into a yeast strain which contains a lacZ gene driven by a promoter which contains GAL4 activation sequence. A cDNA encoded protein, fused to GAL4 activation domain, that interacts with bait gene product will reconstitute an active GAL4 protein and thereby drive expression of the lacZ gene. Colonies which express lacZ can be detected by their blue color in the presence of X-gal. The cDNA can then be purified from these strains, and used to produce and isolate the bait gene-interacting protein using techniques routinely practiced in the art.

Once a pathway gene has been identified and isolated, it can be further characterized as, for example, discussed below, in Section 5.3.

5.3 Characterization of Differentially Expressed and Pathway Genes

Differentially expressed genes, such as those identified via the methods discussed, above, in Section 5.1, and pathway genes, such as those identified via the methods discussed, above, in Section 5.2, above, as well as genes identified by alternative means, can be further characterized by utilizing, for example, methods such as those discussed herein. Such genes will be referred to herein as "identified genes".

Analyses such as those described herein yield information regarding the biological function of the identified genes. An assessment of the biological function of the differentially expressed genes, in addition, will allow for their designation as target and/or fingerprint genes.

Specifically, any of the differentially expressed genes whose further characterization indicates that a modulation of the gene's expression or a modulation of the gene product's activity can ameliorate any of the TH cell subpopulation-related disorders of interest will be designated "target genes", as defined, above, in Section 5.1. Such target genes and target gene products, along with those discussed below, will constitute the focus of the compound discovery strategies discussed, below, in Section 5.8. Further, such target genes, target gene products and/or modulating compounds can be used as part of the TH cell subpopulation-disorder treatment methods described, below, in Section 5.9. Such methods can include, for example, methods whereby the TH cell subpopulation of interest is selectively depleted or repressed, or, alternatively, stimulated or augmented.

Any of the differentially expressed genes whose further characterization indicates that such modulations can not positively affect TH cell subpopulation-related disorders of interest, but whose expression pattern contributes to a gene expression "fingerprint" pattern correlative of, for example, a TH1/TH2-related disorder state, will be designated a "fingerprint gene". "Fingerprint patterns" will be more fully discussed, below, in Section 5.11.1. It should be noted that each of the target genes can also function as fingerprint genes, as well as can all or a portion of the pathway genes.

It should further be noted that the pathway genes can also be characterized according to techniques such as those described herein. Those pathway genes which yield information indicating that modulation of the gene's expression or a modulation of the gene product's activity can ameliorate any a TH cell subpopulation-related disorder will be also be designated "target genes". Such target genes and target gene products, along with those discussed above, will constitute the focus of the compound discovery strategies discussed, below, in Section 5.8 and can be used as part of the treatment methods described in Section 5.9, below.

In instances wherein a pathway gene's characterization indicates that modulation of gene expression or gene product activity can not positively affect TH cell subpopulation-related disorders of interest, but whose expression is differentially expressed and contributes to a gene expression fingerprint pattern correlative of, for example, a TH1/TH2-related disorder state, such pathway genes can additionally be designated as fingerprint genes.

A variety of techniques can be utilized to further characterize the identified genes. First, the nucleotide sequence of the identified genes, which can be obtained by utilizing standard techniques well known to those of skill in the art, can, for example, be used to reveal homologies to one or more known sequence motifs which can yield information regarding the biological function of the identified gene product.

Second, an analysis of the tissue and/or cell type distribution of the mRNA produced by the identified genes can be conducted, utilizing standard techniques well known to those of skill in the art. Such techniques can include, for example, Northern, RNAse protection, and RT-PCR analyses. Such analyses provide information as to, for example, whether the identified genes are expressed in cell types expected to contribute to the specific TH cell subpopulation-related disorders of interest. Such analyses can also provide quantitative information regarding steady state mRNA regulation, yielding data concerning which of the identified genes exhibits a high level of regulation in cell types which can be expected to contribute to the TH cell subpopulation-related disorders of interest. Additionally, standard in situ hybridization techniques can be utilized to provide information regarding which cells within a given tissue or population of cells express the identified gene. Such an analysis can provide information regarding the biological function of an identified gene relative to a given TH cell subpopulation-related disorder in instances wherein only a subset of the cells within a tissue or a population of cells is thought to be relevant to the disorder.

Third, the sequences of the identified genes can be used, utilizing standard techniques, to place the genes onto genetic maps, e.g., mouse (Copeland, N. G. and Jenkins, N. A., 1991, Trends in Genetics 7:113–118) and human genetic maps (Cohen, D., et al., 1993, Nature 366:698–701). Such mapping information can yield information regarding the genes' importance to human disease by, for example, identifying genes which map within genetic regions to which known genetic TH cell subpopulation-related disorders map.

Such regions include, for example, the mouse Scl-1 locus, which is suspected to be involved in Leishmaniasis, or the human 5q31.1 chromosomal region which contains one or more loci thought to regulate IgE production in a nonantigen-specific fashion, and can, therefore, be involved in allergy, a TH2-like-related disorder (Marsh, D. et al., 1994, Science 264:1152–1156).

Fourth, the biological function of the identified genes can be more directly assessed by utilizing relevant in vivo and in vitro systems. In vivo systems can include, but are not limited to, animal systems which naturally exhibit the symptoms of immune disorders, or ones which have been engineered to exhibit such symptoms. Further, such systems can include systems for the further characterization of the cell type differentiation and effector function, and can include, but are not limited to transgenic animal systems such as those described, above, in Section 5.1.1.1, and Section 5.7.1, below. In vitro systems can include, but are not limited to, cell-based systems comprising, for example, TH1 or TH2 cell types. The TH subpopulation cells can be wild type cells, or can be non-wild type cells containing modifications known or suspected of contributing to the TH cell subpopulation-related disorder of interest. Such systems are discussed in detail, below, in Section 5.7.2.

In further characterizing the biological function of the identified genes, the expression of these genes can be modulated within the in vivo and/or in vitro systems, i.e., either overexpressed or underexpressed in, for example, transgenic animals and/or cell lines, and its subsequent effect on the system can then be assayed. Alternatively, the activity of the product of the identified gene can be modulated by either increasing or decreasing the level of activity in the in vivo and/or in vitro system of interest, and its subsequent effect then assayed.

The information obtained through such characterizations can suggest relevant methods for the treatment or control of immune disorders, such as TH cell subpopulation-related disorders, involving the gene of interest. For example, relevant treatment can include not only a modulation of gene expression and/or gene product activity, but can also include a selective depletion or stimulation of the TH cell subpopulation of interest. Characterization procedures such as those described herein can indicate where such modulation should be positive or negative. As used herein, "positive modulation" refers to an increase in gene expression or activity of the gene or gene product of interest, or to a stimulation of a TH cell subpopulation, relative to that observed in the absence of the modulatory treatment. "Negative modulation", as used herein, refers to a decrease in gene expression or activity, or a depletion of a TH cell subpopulation, relative to that observed in the absence of the modulatory treatment. "Stimulation" and "depletion" are as defined, above, in Section 3. Methods of treatment are discussed, below, in Section 5.9.

5.4 Differentially Expressed and Pathway Genes

Differentially expressed genes such as those identified in Section 5.1.1, above, and pathway genes, such as those identified in Section 5.2, above, are described herein.

The differentially expressed and pathway genes of the invention are listed below, in Table 1. Differentially expressed gene sequences are shown in FIGS. 2, 4A, 9A–9D, 12–15, 17A–17D, 22A–22C and 24A–24D. The nucleotide sequences identified via differential display analysis are referred to herein as band 10, 54, 57, 102, 103, 105, 106, 161 and 200. The genes corresponding to these sequences are referred to herein as the 10, 54, 57, 102, 103, 106, 161 and 200 genes, respectively. Table 1 lists differentially expressed genes identified through, for example, the paradigms discussed, above, in Section 5.1.1.1, and below, in the Examples presented in Sections 6–8.

Table 1 summarizes information regarding the further characterization of such genes. Table 2 lists *E. coli* clones, deposited with the Agricultural Research Service Culture Collection (NRRL) or the American Type Culture Collection (ATCC), which contain sequences found within the genes of Table 1.

In Table 1, the column headed "Diff. Exp." details the differential expression characteristic by which the sequence has been identified. Under this column, "TH Inducible", refers to those cases where differential expression arises upon exposure of the cell type of interest to an agent capable of bringing about TH cell stimulation or activation. These sequences, therefore, are differentially expressed in undifferentiated, partially or fully differentiated TH cells, and the genes corresponding to these sequences are expressed in both TH1 and TH2 cell subpopulations.

"TH1", under this column, refers to a sequence corresponding to a gene expressed preferentially in mature, fully differentiated TH1 cells relative to TH2 cells. "TH2", under this column, refers to a sequence corresponding to a gene preferentially expressed in mature, fully differentiated TH2 cell subpopulations relative to TH1 cell subpopulations. Preferential expression can be qualitative or quantitative, as described, above, in Section 5.1.

Tissue expression patterns are also summarized in Table 1. The column headed "Tissue/Cell Dist." lists tissues and/or cell types in which expression of the gene has been tested and whether expression of the gene within a given tissue or cell type has been observed. Specifically, "+" indicates detectable mRNA from the gene of interest, while "−" refers to no detectable mRNA from the gene of interest. Unless otherwise noted, "+" and "−" refer to all samples of a given tissue or cell type tested. "Detectable", as used herein, is as described, above, in Section 5.1.

Additionally, the physical locus to which the gene maps on the human and/or mouse chromosome map is indicated in the column headed "Locus". Further, in instances wherein the genes correspond to genes known to be found in nucleic acid databases, references (i.e., citations and/or gene names) to such known genes are listed in the column headed "Ref.".

The genes listed in Table 1 can be obtained using cloning methods well known to those of skill in the art, and include but are not limited to the use of appropriate probes to detect the genes within an appropriate cDNA or gDNA (genomic DNA) library. (See, for example, Sambrook et al., 1989, Molecular Cloning: A Laboratory Manual, Cold Spring Harbor Laboratories, which is incorporated herein by reference in its entirety.) Probes for the sequences reported herein can be obtained directly from the isolated clones deposited with the NRRL, as indicated in Table 2, below. Alternatively, oligonucleotide probes for the genes can be synthesized based on the DNA sequences disclosed herein in FIGS. 2, 4A, 9A–9D, 12–15, 17A–17D, 22A–22C and 24A–24D. With respect to the previously reported genes, synthetic oligonucleotides can be synthesized or produced based on the sequences provided for the previously known genes described in the following references: granzyme A, Hanukah factor: Masson, D. et al., 1986, FEBS Lett. 208:84–88; Masson, D. et al., 1986, EMBO J. 5:1595–1600; Gershenfeld, H. K. and Weissman, I. L., 1986, Science 232:854–858; ST-2, T1, Fit-1: Klemenz, R. et al., 1989, Proc. Natl. Acad. Sci. U.S.A. 86:5708–5712; Tominaga, S., 1989, FEBS Lett. 258:301–301; Werenskiold, A. K. et al., 1989, Mol. Cell. Biol. 9:5207–5214; Tominaga, S. et al., 1992, Biochem. Biophys. Acta. 1171:215–218; Werenskiold, A. K., 1992, Eur. J. Biochem. 204:1041–1047; Yanagisawa, K. et al., 1993, FEBS Lett. 318:83–87; and Bergers, G. et al., 1994, EMBO J. 13:1176–1188.

The probes can be used to screen cDNA libraries prepared from an appropriate cell or cell line in which the gene is transcribed. Appropriate cell lines can include, for example, Dorris, AE7, D10.G4, DAX, D1.1 and CDC25 cell lines. In addition, purified primary naive T cells derived from either transgenic or non-transgenic strains can be used. Alternatively, the genes described herein can be cloned from a cDNA library constructed from, for example, NIH 3T3 cell lines stably transfected with the Ha-ras(EJ) gene, 5C10 cells, and peripheral blood lymphocytes.

TABLE 1

DIFFERENTIALLY EXPRESSED AND PATHWAY GENES

| Gene | Diff. Exp. | Tissue/Cell Dist. | Locus | Ref |
|---|---|---|---|---|
| 102 | TH2 | TH2 Specific | | ref1 |
| 103 | TH2 | (+) TH2 (−) Lymph Node; Spleen; Thymus; Brain; Lung; Bone Marrow; Heart; Spleen. | | ref2 |
| 10 | TH Inducible | (+) Spleen; TH1; TH2. (−) Liver; Brain; Thymus; Bone Marrow; Heart; Lymph Node. | See FIG. 11 | |
| 57 | TH Inducible | (+) TH1; TH2; Spleen | | |
| 105 | TH1 | (+) TH1; Spleen | | |
| 106 | TH1 | (+) TH1; Thymus; Spleen | | |
| 161 | Subset Specific[3] | (+) Spleen (−) Thymus | | |
| 200 | TH1 | (+) TH1 | | |
| 54 | TH1 | (+) TH1; spleen; testis; uterus (−) brain; heart; kidney; liver; muscle | | |

[1]Masson, D. et al., 1986, FEBS Lett. 208: 84–88; Masson, D. et al., 1986, EMBO J. 5: 1595–1600; Gershenfeld, H. K. and Weissman, I. L., 1986, Science 232: 854–858.

TABLE 1-continued

DIFFERENTIALLY EXPRESSED AND PATHWAY GENES

| Gene | Diff. Exp. | Tissue/Cell Dist. | Locus | Ref |
|---|---|---|---|---|

[2]Klemenz, R. et al., 1989, Proc. Natl. Acad. Sci. USA 86: 5708–5712; Tominaga, S., 1989, FEBS Lett. 258: 301–301; Werenskiold, A. K. et al., 1989, Mol. Cell. Biol. 9: 5207–5214; Tominaga, S. et al., 1992, Biochem. Biophys. Acta. 1171: 215–218; Werenskiold, A. K., 1992, Eur. J. Biochem. 204: 1041–1047; Yanagisawa, K. et al., 1993, FEBS Lett. 318: 83–87; Bergers, G. et al., 1994, EMBO J. 13: 1176–1188.
[3]Band 161 expression has been observed in either TH1 or TH2 cell subpopulations, but has not been found, simultaneously, in both TH1 and TH2 cell subpopulations.

Table 2, below, lists isolated *E. coli* clones which contain sequences within the novel genes listed in Table 1.

TABLE 2

| GENE | CLONE |
|---|---|
| 10 | 10-C |
| 10 | 10-X |
| 57 | 57-E |
| 105 | 105-A |
| 106 | 106-H |
| 161 | 161-G |
| 200 (murine) | 200-O |
| 200 (murine) | DH10B (ZIP) ™ containing 200-P |
| 200 (murine) | 200-AF |
| 200 (human) | feht 200-C |
| 54 | 54-C |
| 200 (human) | feht 200-C |

As used herein, "differentially expressed gene" (i.e. target and fingerprint gene) or "pathway gene" refers to (a) a gene containing: at least one of the DNA sequences disclosed herein (as shown in FIGS. 2, 4A, 9A–9D, 12–15, 17A–17D, 22A–22C and 24A–24D), or contained in the clones listed in Table 2, as deposited with the NRRL or ATCC; (b) any DNA sequence that encodes the amino acid sequence encoded by: the DNA sequences disclosed herein (as shown in FIGS. 2, 4A, 9A–9D, 12–15, 17A–17D, 22A–22C and 24A–24D), contained in the clones, listed in Table 2, as deposited with the NRRL or ATCC contained within the coding region of the gene to which the DNA sequences disclosed herein (as shown in FIGS. 2, 4A, 9A–9D, 12–15, 17A–17D, 22A–22C and 24A–24D) belong or contained in the clones listed in Table 2, as deposited with the NRRL or ATCC, belong; (c) any DNA sequence that hybridizes to the complement of: the coding sequences disclosed herein (as shown in FIGS. 2, 4A, 9A–9D, 12–15, 17A–17D, 22A–22C and 24A–24D), contained in clones listed in Table 2, as deposited with the NRRL or ATCC, or contained within the coding region of the gene to which the DNA sequences disclosed herein (as shown in FIGS. 2, 4A, 9A–9D, 12–15, 17A–17D, 22A–22C and 24A–24D) belong or contained in the clones listed in Table 2, as deposited with the NRRL or ATCC, under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3), and encodes a gene product functionally equivalent to a gene product encoded by a gene of (a), above; and/or (d) any DNA sequence that hybridizes to the complement of: the coding sequences disclosed herein, (as shown in FIGS. 2, 4A, 9A–9D, 12–15, 17A–17D, 22A–22C and 24A–24D) belong or contained in the clones listed in Table 2, as deposited with the NRRL or contained within the coding region of the gene to which DNA sequences disclosed herein (as shown in FIGS. 2, 4A, 9A–9D, 12–15, 17A–17D, 22A–22C and 24A–24D) belong or contained in the clones, listed in Table 2, as deposited with the NRRL or ATCC, under less stringent conditions, such as moderately stringent conditions, e.g., washing in 0.2×SSC/0.1% SDS at 42° C. (Ausubel et al., 1989, supra), yet which still encodes a gene product functionally equivalent to a gene product encoded by a gene of (a), above. The invention also includes degenerate variants of sequences (a) through (d).

The invention encompasses the following nucleotides, host cells expressing such nucleotides and the expression products of such nucleotides: (a) nucleotides that encode a mammalian differentially expressed and/or pathway gene product including, but not limited to a human and murine 10, 54, 57, 105, 106, 161 and 200 gene product; (b) nucleotides that encode portions of differentially expressed and/or pathway gene product that corresponds to its functional domains, and the polypeptide products encoded by such nucleotide sequences, and in which, in the case of receptor-type gene products, such domains include, but are not limited to extracellular domains (ECD), transmembrane domains (TM) and cytoplasmic domains (CD); (c) nucleotides that encode mutants of a differentially expressed and/or pathway gene, product, in which all or part of one of its domains is deleted or altered, and which, in the case of receptor-type gene products, such mutants include, but are not limited to, soluble receptors in which all or a portion of the TM is deleted, and nonfunctional receptors in which all or a portion of CD is deleted; and (d) nucleotides that encode fusion proteins containing a differentially expressed and/or pathway gene product or one of its domains fused to another polypeptide.

The invention also includes nucleic acid molecules, preferably DNA molecules, that hybridize to, and are therefore the complements of, the DNA sequences (a) through (d), in the preceding paragraph. Such hybridization conditions can be highly stringent or less highly stringent, as described above. In instances wherein the nucleic acid molecules are deoxyoligonucleotides ("oligos"), highly stringent conditions can refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules can act as target gene antisense molecules, useful, for example, in target gene regulation and/or as antisense primers in amplification reactions of target, fingerprint, and/or pathway gene nucleic acid sequences. Further, such sequences can be used as part of ribozyme and/or triple helix sequences, also useful for target gene regulation. Still further, such molecules can be used as components of diagnostic methods whereby the presence of, or predisposition to, an immune disorder, e.g., TH cell subpopulation-related disorder, can be detected.

The invention also encompasses (a) DNA vectors that contain any of the foregoing coding sequences and/or their complements (i.e., antisense); (b) DNA expression vectors that contain any of the foregoing coding sequences operatively associated with a regulatory element that directs the expression of the coding sequences; and (c) genetically engineered host cells that contain any of the foregoing coding sequences operatively associated with a regulatory element that directs the expression of the coding sequences in the host cell. As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid phosphatase, and the promoters of the yeast α-mating factors. The invention includes fragments of any of the DNA sequences disclosed herein.

In addition to the gene sequences described above, homologs of these gene sequences and/or full length coding sequences of these genes, as can be present in the same or other species, can be identified and isolated, without undue experimentation, by molecular biological techniques well known in the art. Further, there can exist genes at other genetic loci within the genome of the same species that encode proteins which have extensive homology to one or more domains of such gene products. These genes can also be identified via similar techniques.

For example, the isolated differentially expressed gene sequence can be labeled and used to screen a cDNA library constructed from mRNA obtained from the organism of interest. Hybridization conditions should be of a lower stringency when the cDNA library was derived from an organism different from the type of organism from which the labeled sequence was derived. cDNA screening can also identify clones derived from alternatively spliced transcripts in the same or different species. Alternatively, the labeled fragment can be used to screen a genomic library derived from the organism of interest, again, using appropriately stringent conditions. Low stringency conditions will be well known to those of skill in the art, and will vary predictably depending on the specific organisms from which the library and the labeled sequences are derived. For guidance regarding such conditions see, for example, Sambrook et al., 1989, Molecular Cloning, A Laboratory Manual, Cold Springs Harbor Press, New York; and Ausubel et al., 1989, Current Protocols in Molecular Biology, (Green Publishing Associates and Wiley Interscience, New York).

Further, a previously unknown differentially expressed or pathway gene-type sequence can be isolated by performing PCR using two degenerate oligonucleotide primer pools designed on the basis of amino acid sequences within the gene of interest. The template for the reaction can be cDNA obtained by reverse transcription of mRNA prepared from human or non-human cell lines or tissue known or suspected to express a differentially expressed or pathway gene allele. The PCR product can be subcloned and sequenced to insure that the amplified sequences represent the sequences of a differentially expressed or pathway gene-like nucleic acid sequence.

The PCR fragment can then be used to isolate a full length cDNA clone by a variety of methods. For example, the amplified fragment can be used to screen a bacteriophage cDNA library. Alternatively, the labeled fragment can be used to screen a genomic library.

PCR technology can also be utilized to isolate full length cDNA sequences. For example, RNA can be isolated, following standard procedures, from an appropriate cellular or tissue source. A reverse transcription reaction can be performed on the RNA using an oligonucleotide primer specific for the most 5' end of the amplified fragment for the priming of first strand synthesis. The resulting RNA/DNA hybrid can then be "tailed" with guanines using a standard terminal transferase reaction, the hybrid can be digested with RNAase H, and second strand synthesis can then be primed with a poly-C primer. Thus, cDNA sequences upstream of the amplified fragment can easily be isolated. For a review of cloning strategies which can be used, see e.g., Sambrook et al., 1989, Molecular Cloning, A Laboratory Manual, Cold Springs Harbor Press, New York; and Ausubel et al., 1989, Current Protocols in Molecular Biology, (Green Publishing Associates and Wiley Interscience, New York).

In cases where the differentially expressed or pathway gene identified is the normal, or wild type, gene, this gene can be used to isolate mutant alleles of the gene. Such an isolation is preferable in processes and disorders which are known or suspected to have a genetic basis. Mutant alleles can be isolated from individuals either known or suspected to have a genotype which contributes to TH cell subpopulation-disorder related symptoms. Mutant alleles and mutant allele products can then be utilized in the therapeutic and diagnostic assay systems described below.

A cDNA of a mutant gene can be isolated, for example, by using PCR, a technique which is well known to those of skill in the art. In this case, the first cDNA strand can be synthesized by hybridizing a oligo-dT oligonucleotide to mRNA isolated from tissue known to, or suspected of, being expressed in an individual putatively carrying the mutant allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant gene to that of the normal gene, the mutation(s) responsible for the loss or alteration of function of the mutant gene product can be ascertained.

Alternatively, a genomic or cDNA library can be constructed and screened using DNA or RNA, respectively, from a tissue known to or suspected of expressing the gene of interest in an individual suspected of or known to carry the mutant allele. The normal gene or any suitable fragment thereof can then be labeled and used as a probed to identify the corresponding mutant allele in the library. The clone containing this gene can then be purified through methods routinely practiced in the art, and subjected to sequence analysis as described, above, in this Section.

Additionally, an expression library can be constructed utilizing DNA isolated from or cDNA synthesized from a tissue known to or suspected of expressing the gene of interest in an individual suspected of or known to carry the mutant allele. In this manner, gene products made by the putatively mutant tissue can be expressed and screened using standard antibody screening techniques in conjunction with antibodies raised against the normal gene product, as described, below, in Section 5.6. (For screening techniques, see, for example, Harlow, E. and Lane, eds., 1988, "Antibodies: A Laboratory Manual", Cold Spring Harbor Press, Cold Spring Harbor.) In cases where the mutation results in an expressed gene product with altered function (e.g., as a result of a missense mutation), a polyclonal set of antibodies are likely to cross-react with the mutant gene product. Library clones detected via their reaction with such labeled antibodies can be purified and subjected to sequence analysis as described in this Section, above.

5.5 Differentially Expressed and Pathway Gene Products

Differentially expressed and pathway gene products include those proteins encoded by the differentially expressed and pathway genes corresponding to the gene sequences described in Section 5.4, above, as, for example, the peptides listed in FIGS. 9A–9D, 17A–17D, 22A–22C and 24A–24D.

In addition, differentially expressed and pathway gene products can include proteins that represent functionally equivalent gene products. Such gene products include, but are not limited to natural variants of the peptides listed in FIGS. 9A–9D, 17A–17D, 22A–22C and 24A–24D. Such an equivalent differentially expressed or pathway gene product can contain deletions, additions or substitutions of amino acid residues within the amino acid sequence encoded by the differentially expressed or pathway gene sequences described, above, in Section 5.4, but which result in a silent change, thus producing a functionally equivalent differentially expressed or pathway gene product. Amino acid substitutions can be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid. "Functionally equivalent", as utilized herein, refers to a protein capable of exhibiting a substantially similar in vivo activity as the endogenous differentially expressed or pathway gene products encoded by the differentially expressed or pathway gene sequences described in Section 5.4, above. Alternatively, when utilized as part of assays such as those described, below, in Section 5.3, "functionally equivalent" can refer to peptides capable of interacting with other cellular or extracellular molecules in a manner substantially similar to the way in which the corresponding portion of the endogenous differentially expressed or pathway gene product would.

Peptides corresponding to one or more domains of the differentially expressed or pathway gene products (e.g., TM, ECD or CD), truncated or deleted differentially expressed or pathway gene products (e.g., in the case of receptor-type gene products, proteins in which the full length differentially expressed or pathway gene products, a differentially expressed or pathway gene peptide or truncated differentially expressed or pathway gene product is fused to an unrelated protein are also within the scope of the invention and can be designed on the basis of the differentially expressed or pathway gene nucleotide and amino acid sequences disclosed in this Section and in Section 5.4, above. Such fusion proteins include but are not limited to IgFC fusions which stabilize the differentially expressed or pathway gene and prolong half-life in vivo; or fusions to any amino acid sequence that allows the fusion protein to be anchored to the cell membrane, allowing peptides to be exhibited on the cell surface; or fusions to an enzyme, fluorescent protein, or luminescent protein which provide a marker function.

Other mutations to the differentially expressed or pathway gene product coding sequence can be made to generate polypeptides that are better suited for expression, scale up, etc. in the host cells chosen. For example, cysteine residues can be deleted or substituted with another amino acid in order to eliminate disulfide bridges; in the case of secreted or transmembrane proteins, N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions of any one or more of the glycosylation recognition sequences (N-X-S or N-X-T), and/or an amino acid deletion at the second position of any one or more such recognition sequences will prevent glycosylation of the protein at the modified tripeptide sequence. (See, e.g., Miyajima et al., 1986, EMBO J. 5(6):1193–1197).

The differentially expressed or pathway gene products can be produced by synthetic techniques or via recombinant DNA technology using techniques well known in the art. Thus, methods for preparing the differentially expressed or pathway gene polypeptides and peptides of the invention are described herein. First, the polypeptides and peptides of the invention can be synthesized or prepared by techniques well known in the art. See, for example, Creighton, 1983, "Proteins: Structures and Molecular Principles", W.H. Freeman and Co., New York, which is incorporated herein by reference in its entirety. Peptides can, for example, be synthesized on a solid support or in solution.

Alternatively, recombinant DNA methods which are well known to those skilled in the art can be used to construct expression vectors containing differentially expressed or pathway gene protein coding sequences and appropriate transcriptional/translational control signals. These methods include, for example, in vitro recombinant DNA techniques, synthetic techniques and in vivo recombination/genetic recombination. See, for example, the techniques described in Sambrook et al., 1989, Molecular Cloning: A Laboratory Manual, Cold Spring Harbor Press, Cold Spring Harbor, N.Y. which is incorporated by reference herein in their entirety, and Ausubel, 1989, supra. Alternatively, RNA capable of encoding differentially expressed or pathway gene protein sequences can be chemically synthesized using, for example, synthesizers. See, for example, the techniques described in "Oligonucleotide Synthesis", 1984, Gait, M. J. ed., IRL Press, Oxford, which is incorporated by reference herein in its entirety.

A variety of host-expression vector systems can be utilized to express the differentially expressed or pathway gene coding sequences of the invention. Such host-expression systems represent vehicles by which the coding sequences of interest can be produced and subsequently purified, but also represent cells which can, when transformed or transfected with the appropriate nucleotide coding sequences, exhibit the differentially expressed or pathway gene protein of the invention in situ. These include but are not limited to microorganisms such as bacteria (e.g., *E. coli, B. subtilis*) transformed with recombinant bacteriophage DNA, plasmid DNA or cosmid DNA expression vectors containing differentially expressed or pathway gene protein coding sequences; yeast (e.g., Saccharomyces, Pichia) transformed with recombinant yeast expression vectors containing the differentially expressed or pathway gene protein coding sequences; insect cell systems infected with recombinant virus expression vectors (e.g., baculovirus) containing the differentially expressed or pathway gene protein coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing differentially expressed or pathway gene protein coding sequences; or mammalian cell systems (e.g. COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors can be advantageously selected depending upon the use intended for the differentially expressed or pathway gene protein being expressed. For example, when a large quantity of such a protein is to be produced, for the generation of antibodies or to screen peptide libraries, for example, vectors which direct the expression of high levels of fusion protein products that are readily purified can be desirable. Such vectors include, but are not limited, to the E. coli expression vector pUR278 (Ruther et al., 1983, EMBO J. 2:1791), in which the differentially expressed or pathway gene protein coding sequence can be ligated individually into the vector in frame with the lacZ coding region so that a fusion protein is produced; pIN vectors (Inouye & Inouye, 1985, Nucleic Acids Res. 13:3101–3109; Van Heeke & Schuster, 1989, J. Biol. Chem. 264:5503–5509); and the like. pGEX vectors can also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene protein can be released from the GST moiety.

In an insect system, Autographa californica nuclear polyhedrosis virus (AcNPV) is used as a vector to express foreign genes. The virus grows in Spodoptera frugiperda cells. The differentially expressed or pathway gene coding sequence can be cloned individually into non-essential regions (for example the polyhedrin gene) of the virus and placed under control of an AcNPV promoter (for example the polyhedrin promoter). Successful insertion of differentially expressed or pathway gene coding sequence will result in inactivation of the polyhedrin gene and production of non-occluded recombinant virus (i.e., virus lacking the proteinaceous coat coded for by the polyhedrin gene). These recombinant viruses are then used to infect Spodoptera frugiperda cells in which the inserted gene is expressed, (e.g., see Smith et al., 1983, J. Viol. 46:584; Smith, U.S. Pat. No. 4,215,051).

In mammalian host cells, a number of viral-based expression systems can be utilized. In cases where an adenovirus is used as an expression vector, the differentially expressed or pathway gene coding sequence of interest can be ligated to an adenovirus transcription/translation control complex, e.g., the late promoter and tripartite leader sequence. This chimeric gene can then be inserted in the adenovirus genome by in vitro or in vivo recombination. Insertion in a non-essential region of the viral genome (e.g., region E1 or E3) will result in a recombinant virus that is viable and capable of expressing differentially expressed or pathway gene protein in infected hosts, (e.g., See Logan & Shenk, 1984, Proc. Natl. Acad. Sci. U.S.A. 81:3655–3659). Specific initiation signals can also be required for efficient translation of inserted differentially expressed or pathway gene coding sequences. These signals include the ATG initiation codon and adjacent sequences. In cases where an entire differentially expressed or pathway gene, including its own initiation codon and adjacent sequences, is inserted into the appropriate expression vector, no additional translational control signals can be needed. However, in cases where only a portion of the differentially expressed or pathway gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression can be enhanced by the inclusion of appropriate transcription enhancer elements, transcription terminators, etc. (see Bittner et al., 1987, Methods in Enzymol. 153:516–544).

In addition, a host cell strain can be chosen which modulates the expression of the inserted sequences, or modifies and processes the gene product in the specific fashion desired. Such modifications (e.g., glycosylation) and processing (e.g., cleavage) of protein products can be important for the function of the protein. Different host cells have characteristic and specific mechanisms for the post-translational processing and modification of proteins. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product can be used. Such mammalian host cells include but are not limited to CHO, VERO, BHK, HeLa, COS, MDCK, 293, 3T3, WI38, etc.

For long-term, high-yield production of recombinant proteins, stable expression is preferred. For example, cell lines which stably express the differentially expressed or pathway gene protein can be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells can be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method can advantageously be used to engineer cell lines which express the differentially expressed or pathway gene protein. Such engineered cell lines can be particularly useful in screening and evaluation of compounds that affect the endogenous activity of the differentially expressed or pathway gene protein.

A number of selection systems can be used, including but not limited to the herpes simplex virus thymidine kinase (Wigler, et al., 1977, Cell 11:223), hypoxanthine-guanine phosphoribosyltransferase (Szybalska & Szybalski, 1962, Proc. Natl. Acad. Sci. U.S.A. 48:2026), and adenine phosphoribosyltransferase (Lowy, et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler, et al., 1980, Natl. Acad. Sci. U.S.A. 77:3567; O'Hare, et al., 1981, Proc. Natl. Acad. Sci. U.S.A. 78:1527); gpt, which confers resistance to mycophenolic acid (Mulligan & Berg, 1981, Proc. Natl. Acad. Sci. U.S.A. 78:2072); neo, which confers resistance to the aminoglycoside G-418 (Colberre-Garapin, et al., 1981, J. Mol. Biol. 150:1); and hygro, which confers resistance to hygromycin (Santerre, et al., 1984, Gene 30:147) genes.

Alternatively, any fusion protein may be readily purified by utilizing an antibody specific for the fusion protein being expressed. For example, a system described by Janknecht et al. allows for the ready purification of non-denatured fusion proteins expressed in human cells lines (Janknecht, et al., 1991, Proc. Natl. Acad. Sci. U.S.A. 88: 8972–8976). In this system, the gene of interest is subcloned into a vaccinia recombination plasmid such that the gene's open reading fram eis translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

When used as a component in assay systems such as those described herein, the differentially expressed or pathway gene protein can be labeled, either directly or indirectly, to facilitate detection of a complex formed between the differentially expressed or pathway gene protein and a test substance. Any of a variety of suitable labeling systems can be used including but not limited to radioisotopes such as $^{125}I$; enzyme labelling systems that generate a detectable colorimetric signal or light when exposed to substrate; and fluorescent labels.

Indirect labeling involves the use of a protein, such as a labeled antibody, which specifically binds to either a differentially expressed or pathway gene product. Such antibodies include but are not limited to polyclonal, monoclonal, chimeric, single chain, Fab fragments and fragments produced by an Fab expression library.

Where recombinant DNA technology is used to produce the differentially expressed or pathway gene protein for such assay systems, it can be advantageous to engineer fusion proteins that can facilitate labeling (either direct or indirect), immobilization, solubility and/or detection.

Fusion proteins, which can facilitate solubility and/or expression, and can increase the blood half-life of the protein, can include, but are not limited to soluble Ig-tailed fusion proteins. Methods for engineering such soluble Ig-tailed fusion proteins are well known to those of skill in the art. See, for example U.S. Pat. No. 5,116,964, which is incorporated herein by reference in its entirety. Further, in addition to the Ig-region encoded by the IgG1 vector, the Fc portion of the Ig region utilized can be modified, by amino acid substitutions, to reduce complement activation and Fc binding. (See, e.g., European Patent No. 239400 B1, Aug. 3, 1994).

Among the soluble Ig-tailed fusion proteins which can be produced are soluble Ig-tailed fusion proteins containing 103 gene products, 200 gene products or 10 gene products. The 103 gene product or 200 gene contained within such fusion proteins can comprise, respectively, for example, the 103 gene extracellular domain or portions, preferably ligand-binding portions, thereof, or the 200 gene extracellular domain or portions, preferably ligand-binding portions, thereof. The 10 gene product contained within such fusion proteins can comprise, for example, one or more of the extracellular domains or portions, preferably ligand-binding portions, of the seven transmembrane domain sequence motif.

The amino acid sequences of the 103 gene products are known. (See, for example, Klemenz, R. et al., 1989, Proc. Natl. Acad. Sci. U.S.A. 86:5708–5712; Tominaga, S., 1989, FEBS Lett. 258:301–301; Werenskiold, A. K. et al., 1989, Mol. Cell. Biol.9:5207–5214; Tominaga, S. et al., 1992, Biochem. Biophys. Acta. 1171:215–218; Werenskiold, A. K., 1992, Eur. J. Biochem. 204:1041–1047; Yanagisawa, K. et al., 1993, FEBS Lett. 318:83–87; Bergers, G. et al., 1994, EMBO J. 13:1176–1188.) Further, as indicated in FIG. 4B, the amino acid residues which delineate the extracellular, transmembrane and cytoplasmic domains of the 103 gene products are also known. Therefore, by utilizing well known techniques, one of skill in the art would readily be capable of producing such soluble Ig-tailed 103 gene product fusion proteins. The Example presented below, in Section 10, below, describes the construction of a 103 gene product-Ig fusion protein.

The signal sequence, extracellular, transmembrane and cytoplasmic domains of both the murine and human 200 gene products have been elucidated and can be utilized in, for example, the construction of 200 gene product-Ig fusion proteins. Specifically, the 280 amino acid murine 200 gene product (FIGS. 17A–17D; SEQ ID NO:10) contains a signal sequence from approximately amino acid residue 1 to approximately amino acid residue 20, an extracellular domain from approximately amino acid residue 21 to approximately amino acid residue 192, a transmembrane domain from approximately amino acid residue 193 to amino acid residue 214, and a cytoplasmic domain from approximately amino acid residue 215 to amino acid residue 280. Further, the 301 amino acid human 200 gene product (FIGS. 24A–24D; SEQ. ID. NO: 24) contains a signal sequence from amino acid residue 1 to approximately 20, a mature extracellular domain from approximately amino acid residue 21 to 200, a transmembrane domain from approximately amino acid residue 201–224 and a cytoplasmic domain from approximately amino acid residue 225 to 301. Given the elucidation of these domains, one of skill in the art would readily be capable of producing soluble Ig-tailed 200 gene product fusion proteins. The Example presented, below, in Section 10 describes the construction of murine and human 200 gene product-Ig fusion proteins.

The 338 amino acid residue 10 gene product (FIGS. 9A–9D; SEQ ID NO:9) extracellular domains include 10 gene product amino acid residues from approximately amino acid residue 1 to 19, approximately amino acid residue 74 to 87, approximately amino acid residue 153 to 187 and approximately amino acid residue 254 to 272. Thus, such 10 gene product domain information can be used, in conjunction with well-known techniques, such that one of skill in the art can readily be capable of producing soluble Ig-tailed 10 gene fusion proteins comprising one or more 10 gene product extra-cellular domain regions and an Ig tail.

5.6. Antibodies Specific for Differentially Expressed or Pathway Gene Products Described herein are methods for the production of antibodies capable of specifically recognizing one or more differentially expressed or pathway gene product epitopes. Such antibodies can include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. The Ig tails of such antibodies can be modified to reduce complement activation and Fc binding. (See, for example, European Patent No. 239400 B1, Aug. 3, 1994).

Such antibodies can be used, for example, in the detection of a fingerprint, target, or pathway gene product in a biological sample, and can be used as part of diagnostic techniques. Alternatively, such antibodies can be utilized as part of an immune disorder treatment method, as described, below, in Section 5.9. For example, the antibodies can be used to modulate target gene activity, can be used to modulate TH cell subpopulation differentiation, maintenance and/ or effector function, or, in the case of antibodies directed to cell surface epitopes, can be used to isolate a TH cell subpopulation of interest, for either depletion or augmentation purposes.

For the production of antibodies to a differentially expressed or pathway gene, various host animals can be immunized by injection with a differentially expressed or pathway gene protein, or a portion thereof. Such host animals can include but are not limited to rabbits, mice, and rats, to name but a few. Various adjuvants can be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as target gene product, or an antigenic functional derivative thereof. For the production of polyclonal antibodies, host animals such as those described above, can be immunized by injection with differentially expressed or pathway gene product supplemented with adjuvants as also described above.

Monoclonal antibodies, which are homogeneous populations of antibodies to a particular antigen, can be obtained by any technique which provides for the production of antibody molecules by continuous cell lines in culture. These include, but are not limited to the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. U.S.A. 80:2026–2030), and the EBV-hybridoma technique (Cole et al., 1985, Monoclonal Antibodies And Cancer Therapy, Alan R. Liss, Inc., pp. 77–96). Such antibodies can be of any immunoglobulin class including IgG, IgM, IgE, IgA, IgD and any subclass thereof. The hybridoma producing the mAb of this invention can be cultivated in vitro or in vivo. Production of high titers of mAbs in vivo makes this the presently preferred method of production.

In addition, techniques developed for the production of "chimeric antibodies" (Morrison et al., 1984, Proc. Natl. Acad. Sci., 81:6851–6855; Neuberger et al., 1984, Nature, 312:604–608; Takeda et al., 1985, Nature, 314:452–454; U.S. Pat. No. 4,816,567) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region.

Alternatively, techniques described for the production of single chain antibodies (U.S. Pat. No. 4,946,778; Bird, 1988, Science 242:423–426; Huston et al., 1988, Proc. Natl. Acad. Sci. U.S.A. 85:5879–5883; and Ward et al., 1989, Nature 334:544–546) and for making humanized monoclonal antibodies (U.S. Pat. No. 5,225,539, which is incorporated herein by reference in its entirety) can be utilized to produce anti-differentially expressed or anti-pathway gene product antibodies.

Antibody fragments which recognize specific epitopes can be generated by known techniques. For example, such fragments include but are not limited to: the $F(ab')_2$ fragments which can be produced by pepsin digestion of the antibody molecule and the Fab fragments which can be generated by reducing the disulfide bridges of the $F(ab')_2$ fragments. Alternatively, Fab expression libraries can be constructed (Huse et al., 1989, Science, 246:1275–1281) to allow rapid and easy identification of monoclonal Fab fragments with the desired specificity.

Antibodies to the differentially expressed or pathway gene products can, in turn, be utilized to generate anti-idiotype antibodies that "mimic" such gene products, using techniques well known to those skilled in the art. (See, e.g., Greenspan & Bona, 1993, FASEB J 7(5):437–444; and Nissinoff, 1991, J. Immunol. 147(8):2429–2438). For example, in the case of receptor-type molecules (e.g., 10, 103 and 200 gene products) antibodies which bind to the ECD and competitively inhibit the binding of ligand to the receptor can be used to generate anti-idiotypes that "mimic" the ECD and, therefore, bind and neutralize the ligand. Such neutralizing anti-idiotypes or Fab fragments of such anti-idiotypes can be used in therapeutic regimens of TH cell subpopulation-related disorders.

5.7. Cell- and Animal-Based Model Systems

Described herein are cell- and animal-based systems which act as models for immune disorders and for models of TH cell subpopulation differentiation, maintenance, and/or effector function. These systems can be used in a variety of applications. For example, the animal-based model systems can be utilized to identify differentially expressed genes via the in vivo paradigm described, above, in Section 5.1.1.1. Cell- and animal-based model systems can also be used to further characterize differentially expressed and path way genes, as described, above, in Section 5.3. Such, further characterization can, for example, indicate that a differentially expressed gene is a target gene. Second, such assays can be utilized as part of screening strategies designed to identify compounds which are capable of ameliorating TH cell subpopulation-related disorder symptoms, a s described, below. Thus, the animal- and cell-based models can be used to identify drugs, pharmaceuticals, therapies and interventions which can be effective in treating immune disorders such as TH cell subpopulation-related disorders. In addition, as described in detail, below, in Section 5.10.1, such animal models can be used to determine the $LD_{50}$ and the $ED_{50}$ in animal subjects, and such data can be used to determine the in vivo efficacy of potential immune disorder treatments.

5.7.1 Animal-Based Systems

Animal-based model systems of TH cell subpopulation-related disorders can include both non-recombinant animals as well as recombinantly engineered transgenic animals.

Animal models for TH cell subpopulation-related disorders can include, for example, genetic models. For example, such animal models can include Leishmania resistance models experimental allergic encephalomyelitis models and (BALB/c Cr×DBA/2Cr) F1 mice. These latter mice develop a fatal disseminated disease by systemic infection with virulent *Candida albicans* associated with strong TH2-like responses. Additionally, well known mouse models for asthma can be utilized to study the amelioration of symptoms caused by a TH2-like response. (See, for example, Lukacs, N. W. et al., 1994, Am. J. Resp. Cell Mol. Biol. 10:526–532; Gavett, S. H. et al., 1994, Am. J. Cell Mol. Biol. 10:587–593.) Further, the animal model, murine acquired immunodeficiency syndrome (MAIDS; Kanagawa, B. et al., 1993, Science 262:240; Makino, M. et al., 1990, J. Imm. 144:4347) can be used for such studies.

Alternatively, such well known animal models as SCIDhu mice (see for example, Kenshima, H. et al., 1994, Curr. Opin. Imm. 6327–333) which represents an in vivo model of the human hematolymphoid system, can be utilized. Further, the RAG-2-deficient blastocyst complementation technique (Chen, J. et al., 1993, Proc. Natl. Acad. Sci. U.S.A. 90:4528–4532; Shinkai, Y. et al., 1992, Cell 68:855–867) can be utilized to produce mice containing, for example, humanized lymphocytes and/or which express target gene sequences. Still further, targeting techniques directed specifically to T cells, for example, the technique of Gu et al. (Gu, H. et al., 1994, Science 265:103–106) can be utilized to produce animals containing transgenes in only T cell populations.

Animal models exhibiting TH cell subpopulation-related disorder-like symptoms can be engineered by utilizing, for example, target gene sequences such as those described, above, in Section 5.4, in conjunction with techniques for producing transgenic animals that are well known to those of skill in the art. For example, target gene sequences can be introduced into, and overexpressed and/or misexpressed in, the genome of the animal of interest, or, if endogenous target gene sequences are present, they can either be overexpressed, misexpressed, or, alternatively, can be disrupted in order to underexpress or inactivate target gene expression. The construction and characterization of 200 gene and 103 gene transgenic animals is described in Section 11, below.

In order to overexpress or misexpress a target gene sequence, the coding portion of the target gene sequence can be ligated to a regulatory sequence which is capable of driving high level gene expression or expression in a cell type in which the gene is not normally expressed in the animal and/or cell type of interest. Such regulatory regions will be well known to those of skill in the art, and can be utilized in the absence of undue experimentation.

For underexpression of an endogenous target gene sequence, such a sequence can be isolated and engineered such that when reintroduced into the genome of the animal of interest, the endogenous target gene alleles will be inactivated. Preferably, the engineered target gene sequence is introduced via gene targeting such that the endogenous target sequence is disrupted upon integration of the engineered target gene sequence into the animal's genome. Gene targeting is discussed, below, in this Section.

Animals of any species, including, but not limited to, mice, rats, rabbits, guinea pigs, pigs, micro-pigs, goats, and non-human primates, e.g., baboons, squirrels, monkeys, and chimpanzees can be used to generate animal models of TH cell subpopulation-related disorders.

Any technique known in the art can be used to introduce a target gene transgene into animals to produce the founder lines of transgenic animals. Such techniques include, but are not limited to pronuclear microinjection (Hoppe, P. C. and Wagner, T. E., 1989, U.S. Pat. No. 4,873,191); retrovirus mediated gene transfer into germ lines (Van der Putten et al., 1985, Proc. Natl. Acad. Sci., U.S.A. 82:6148–6152); gene targeting in embryonic stem cells (Thompson et al., 1989, Cell 56:313–321); electroporation of embryos (Lo, 1983, Mol Cell. Biol. 3:1803–1814); and sperm-mediated gene transfer (Lavitrano et al., 1989, Cell 57:717–723); etc. For a review of such techniques, see Gordon, 1989, Transgenic Animals, Intl. Rev. Cytol. 115:171–229, which is incorporated by reference herein in its entirety.

The present invention provides for transgenic animals that carry the transgene in all their cells, as well as animals which carry the transgene in some, but not all their cells, i.e., mosaic animals. (See, for example, techniques described by Jakobovits, 1994, Curr. Biol. 4:761–763.) The transgene can be integrated as a single transgene or in concatamers, e.g., head-to-head tandems or head-to-tail tandems. The transgene can also be selectively introduced into and activated in a particular cell type by following, for example, the teaching of Lasko et al. (Lasko, M. et al., 1992, Proc. Natl. Acad. Sci. U.S.A. 89:6232–6236). The regulatory sequences required for such a cell-type specific activation will depend upon the particular cell type of interest, and will be apparent to those of skill in the art.

When it is desired that the target gene transgene be integrated into the chromosomal site of the endogenous target gene, gene targeting is preferred. Briefly, when such a technique is to be utilized, vectors containing some nucleotide sequences homologous to the endogenous target gene of interest are designed for the purpose of integrating, via homologous recombination with chromosomal sequences, into and disrupting the function of, the nucleotide sequence of the endogenous target gene. The transgene can also be selectively introduced into a particular cell type, thus inactivating the endogenous gene of interest in only that cell type, by following, for example, the teaching of Gu et al. (Gu, H. et al., 1994, Science 265:103–106). The regulatory sequences required for such a cell-type specific inactivation will depend upon the particular cell type of interest, and will be apparent to those of skill in the art.

Once transgenic animals have been generated, the expression of the recombinant target gene and protein can be assayed utilizing standard techniques. Initial screening can be accomplished by Southern blot analysis or PCR techniques to analyze animal tissues to assay whether integration of the transgene has taken place. The level of mRNA expression of the transgene in the tissues of the transgenic animals can also be assessed using techniques which include but are not limited to Northern blot analysis of tissue samples obtained from the animal, in situ hybridization analysis, and RT-PCR. Samples of target gene-expressing tissue, can also be evaluated immunocytochemically using antibodies specific for the target gene transgene gene product of interest.

The target gene transgenic animals that express target gene mRNA or target gene transgene peptide (detected immunocytochemically, using antibodies directed against target gene product epitopes) at easily detectable levels can then be further evaluated to identify those animals which display characteristic TH cell subpopulation-related disorder-like symptoms, or exhibit characteristic TH cell subpopulation differentiation phenotypes. TH1-like-related disorder symptoms can include, for example, those associated with chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease and sarcoidosis. TH2-like-related disorder symptoms can include, those associated with atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

Additionally, specific cell types within the transgenic animals can be analyzed and assayed for cellular phenotypes characteristic of TH cell subpopulation-related disorders. Such cellular phenotypes can include, for example, differential cytokine expression characteristic of the TH cell subpopulation of interest. Further, such cellular phenotypes can include an assessment of a particular cell type's fingerprint pattern of expression and its comparison to known fingerprint expression profiles of the particular cell type in animals exhibiting specific TH cell subpopulation-related disorders. Such transgenic animals serve as suitable model systems for TH cell-related disorders.

Once target gene transgenic founder animals are produced (i.e., those animals which express target gene proteins in cells or tissues of interest, and which, preferably, exhibit symptoms of TH cell subpopulation-related disorders), they can be bred, inbred, outbred, or crossbred to produce colonies of the particular animal. Examples of such breeding strategies include but are not limited to: outbreeding of founder animals with more than one integration site in order to establish separate lines; inbreeding of separate lines in order to produce compound target gene transgenics that express the target gene transgene of interest at higher levels because of the effects of additive expression of each target gene transgene; crossing of heterozygous transgenic animals to produce animals homozygous for a given integration site in order to both augment expression and eliminate the possible need for screening of animals by DNA analysis; crossing of separate homozygous lines to produce compound heterozygous or homozygous lines; breeding animals to different inbred genetic backgrounds so as to examine effects of modifying alleles on expression of the target gene transgene and the development of TH cell subpopulation-related disorder-like symptoms. One such approach is to cross the target gene transgenic founder animals with a wild type strain to produce an F1 generation that exhibits TH cell subpopulation-related disorder-like symptoms, such as those described above. The F1 generation can then be inbred in order to develop a homozygous line, if it is found that homozygous target gene transgenic animals are viable.

5.7.2. Cell-Based Assays

Cells that contain and express target gene sequences which encode target gene protein, and, further, exhibit cellular phenotypes associated with a TH cell subpopulation-related disorder of interest, can be utilized to identify compounds that exhibit an ability to ameliorate TH cell subpopulation-related disorder symptoms. Cellular phenotypes which can indicate an ability to ameliorate TH cell subpopulation-related disorder symptoms can include, for example, an inhibition or potentiation of cytokine or cell surface marker expression associated with the TH cell subpopulation of interest, or, alternatively, an inhibition or potentiation of specific TH cell subpopulations.

Further, the fingerprint pattern of gene expression of cells of interest can be analyzed and compared to the normal, non-TH cell subpopulation-related disorder fingerprint pattern. Those compounds which cause cells exhibiting TH cell subpopulation-related disorder-like cellular phenotypes to produce a fingerprint pattern more closely resembling a normal fingerprint pattern for the cell of interest can be considered candidates for further testing regarding an ability to ameliorate TH cell subpopulation-related disorder symptoms.

Cells which can be utilized for such assays can, for example, include non-recombinant cell lines, such as Dorris, AE7, D10.G4, DAX, D1.1 and CDC25 cell lines. In addition, purified primary naive T cells derived from either transgenic or non-transgenic strains can also be used.

Further, cells which can be used for such assays can also include recombinant, transgenic cell lines. For example, the TH cell subpopulation-related disorder animal models of the invention, discussed, above, in Section 5.7.1, can be used to generate, for example, TH1-like and/or TH2-like cell lines that can be used as cell culture models for the disorder of interest. While primary cultures derived from TH cell subpopulation-related disorder transgenic animals can be utilized, the generation of continuous cell lines is preferred. For examples of techniques which can be used to derive a continuous cell line from the transgenic animals, see Small et al., 1985, Mol. Cell Biol. 5:642–648.

Alternatively, cells of a cell type known to be involved in TH cell subpopulation-related disorders can be transfected with sequences capable of increasing or decreasing the amount of target gene expression within the cell. For example, target gene sequences can be introduced into, and overexpressed in, the genome of the cell of interest, or, if endogenous target gene sequences are present, they can either be overexpressed or, alternatively, can be disrupted in order to underexpress or inactivate target gene expression.

In order to overexpress a target gene sequence, the coding portion of the target gene sequence can be ligated to a regulatory sequence which is capable of driving gene expression in the cell type of interest. Such regulatory regions will be well known to those of skill in the art, and can be utilized in the absence of undue experimentation.

For underexpression of an endogenous target gene sequence, such a sequence can be isolated and engineered such that when reintroduced into the genome of the cell type of interest, the endogenous target gene alleles will be inactivated. Preferably, the engineered target gene sequence is introduced via gene targeting such that the endogenous target sequence is disrupted upon integration of the engineered target gene sequence into the cell's genome. Gene targeting is discussed, above, in Section 5.7.1.

Transfection of target gene sequence nucleic acid can be accomplished by utilizing standard techniques. See, for example, Ausubel, 1989, supra. Transfected cells should be evaluated for the presence of the recombinant target gene sequences, for expression and accumulation of target gene mRNA, and for the presence of recombinant target gene protein production. In instances wherein a decrease in target gene expression is desired, standard techniques can be used to demonstrate whether a decrease in endogenous target gene expression and/or in target gene product production is achieved.

5.8. Screening Assays for Compounds That Interact With the Target Gene Product The following assays are designed to identify compounds that bind to target gene products, bind to other cellular proteins that interact with a target gene product, and to compounds that interfere with the interaction of the target gene product with other cellular proteins. For example, in the cases of 10, 103 and 200 gene products, which are or are predicted to be transmembrane receptor-type proteins, such techniques can identify ligands for such receptors. A 103 gene product ligand can, for example, act as the basis for amelioration of such TH2-like-specific disorders as asthma or allergy, given that gene 103 expression is TH2-specific. A 200 gene product ligand can, for example, act as the basis for amelioration of TH1-like-specific disorders. A 10 gene product ligand can, for example, act as the basis for amelioratoin of a wide range of T cell disorders, given the TH inducible nature of it gene expression pattern.

Compounds can include, but are not limited to, other cellular proteins. Further, such compounds can include, but are not limited to, peptides such as, for example, soluble peptides, including, but not limited to, Ig-tailed fusion peptides, comprising extracellular portions of target gene product transmembrane receptors, and members of random peptide libraries (see, e.g., Lam, K. S. et al., 1991, Nature 354:82–84; Houghten, R. et al., 1991, Nature 354:84–86) made of D-and/or L-configuration amino acids, phosphopeptides (including but not limited to members of random or partially degenerate, directed phosphopeptide libraries; see, e.g., Songyang, Z. et al., 1993, Cell 72:767–778), antibodies (including, but not limited to polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules. In the case of receptor-type target molecules, such compounds can include organic molecules (e.g., peptidomimetics) that bind to the ECD and either mimic the activity triggered by the natural ligand (i.e., agonists); as well as peptides, antibodies or fragments thereof, and other organic compounds that mimic the ECD (or a portion thereof) and bind to a "neutralize" natural ligand.

Computer modelling and searching technologies permit identification of compounds, or the improvement of already identified compounds, that can modulate target or pathway gene expression or activity. Having identified such a compound or composition, the active sites or regions are identified.

In the case of compounds affecting receptor molecules, such active sites might typically be ligand binding sites, such as the interaction domains of ligand with receptor itself. The active site can be identified using methods known in the art including, for example, from the amino acid sequences of peptides, from the nucleotide sequences of nucleic acids, or from study of complexes of the relevant compound or composition with its natural ligand. In the latter case, chemical or X-ray crystallographic methods can be used to find the active site by finding where on the factor the complexed ligand is found.

Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures may be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site, either experimentally, by modeling, or by a combination, candidate modulating compounds can be identified by searching databases containing compounds along with information on their molecular structure. Such a search seeks compounds having structures that match the determined active site structure and that interact with the groups defining the active site. Such a search can be manual, but is preferably computer assisted. These compounds found from this search are potential target or pathway gene product modulating compounds.

Alternatively, these methods can be used to identify improved modulating compounds from an already known modulating compound or ligand. The composition of the known compound can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

Further experimental and computer modeling methods useful to identify modulating compounds based upon identification of the active sites of target or pathway gene or gene products and related transduction and transcription factors will be apparent to those of skill in the art.

Examples of molecular modelling systems are the CHARMm and QUANTA programs (Polygen Corporation, Waltham, Mass.). CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modelling of drugs interactive with specific proteins, such as Rotivinen, et al., 1988, *Acta Pharmaceutical Fennica* 97:159–166; Ripka, *New Scientist* 54–57 (Jun. 16, 1988); McKinaly and Rossmann, 1989, *Annu. Rev. Pharmacol. Toxiciol.* 29:111–122; Perry and Davies, *OSAR: Quantitative Structure-Activity Relationships in Drug Design* pp. 189–193 (Alan R. Liss, Inc. 1989); Lewis and Dean, 1989 *Proc. R. Soc. Lond.* 236:125–140 and 141–162; and, with respect to a model receptor for nucleic acid components, Askew, et al., 1989, *J. Am. Chem. Soc.* 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to regions of DNA or RNA, once that region is identified.

Although generally described above with reference to design and generation of compounds which could alter binding, one could also screen libraries of known compounds, including natural products or synthetic chemicals, and biologically active materials, including proteins, for compounds which are inhibitors or activators.

Compounds identified via assays such as those described herein can be useful, for example, in elaborating the biological function of the target gene product, and for ameliorating the symptoms of immune disorders. In instances, for example, in which a TH cell subpopulation-related disorder situation results from a lower overall level of target gene expression, target gene product, and/or target gene product activity in a cell or tissue involved in such a disorder, compounds that interact with the target gene product can include ones which accentuate or amplify the activity of the bound target gene protein. Such compounds would bring about an effective increase in the level of target gene activity, thus ameliorating symptoms. In instances whereby mutations within the target gene cause aberrant target gene proteins to be made which have a deleterious effect that leads to a TH cell subpopulation-related disorder, or, alternatively, in instances whereby normal target gene activity is necessary for a TH cell subpopulation-related disorder to occur, compounds that bind target gene protein can be identified that inhibit the activity of the bound target gene protein. Assays for identifying additional compounds as well as for testing the effectiveness of compounds, identified by, for example, techniques, such as those described in Section 5.8.1–5.8.3, are discussed, below, in Section 5.8.4.

5.8.1. In Vitro Screening Assays for Compounds That Bind to a Target Gene Product In vitro systems can be designed to identify compounds capable of binding the target gene products of the invention. Compounds identified can be useful, for example, in modulating the activity of wild type and/or mutant target gene products, can be useful in elaborating the biological function of target gene products, can be utilized in screens for identifying compounds that disrupt normal target gene product interactions, or can in themselves disrupt such interactions.

The principle of the assays used to identify compounds that bind to the target gene product involves preparing a reaction mixture of the target gene product and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring target gene product or the test substance onto a solid phase and detecting target gene product/test compound complexes anchored on the solid phase at the end of the reaction. In one embodiment of such a method, the target gene product can be anchored onto a solid surface, and the test compound, which is not anchored, can be labeled, either directly or indirectly.

In practice, microtiter plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously nonimmobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the previously nonimmobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for target gene product or the test compound to anchor any complexes formed in solution, and a labeled antibody specific for the other component of the possible complex to detect anchored complexes.

5.8.2. Assays for Cellular Proteins That Interact With the Target Gene Protein Any method suitable for detecting protein-protein interactions can be employed for identifying novel target protein-cellular or extracellular protein interactions. These methods are outlined in Section 5.2., above, for the identification of pathway genes, and can be utilized herein with respect to the identification of proteins which interact with identified target proteins.

5.8.3. Assays for Compounds That Interfere With Target Gene Product/Cellular Macromolecule Interaction The target gene products of the invention can, in vivo, interact with one or more cellular or extracellular macromolecules, such as proteins. Such macromolecules can include, but are not limited to, nucleic acid molecules and those proteins identified via methods such as those described, above, in Section 5.8.2. For purposes of this discussion, such cellular and extracellular macromolecules are referred to herein as "binding partners". Compounds that disrupt such interactions can be useful in regulating the activity of the target gene protein, especially mutant target gene proteins. Such compounds can include, but are not limited to molecules such as antibodies, peptides, and the like, as described, for example, in Section 5.8.1. above.

The basic principle of the assay systems used to identify compounds that interfere with the interaction between the target gene product and its cellular or extracellular binding partner or partners involves preparing a reaction mixture containing the target gene product and the binding partner under conditions and for a time sufficient to allow the two to interact and bind, thus form a complex. In order to test a compound for inhibitory activity, the reaction mixture is prepared in the presence and absence of the test compound. The test compound can be initially included in the reaction mixture, or can be added at a time subsequent to the addition of target gene product and its cellular or extracellular binding partner. Control reaction mixtures are incubated without the test compound or with a placebo. The formation of any complexes between the target gene protein and the cellular or extracellular binding partner is then detected. The formation of a complex in the control reaction, but not in the reaction mixture containing the test compound, indicates that the compound interferes with the interaction of the target gene protein and the interactive binding partner. Additionally, complex formation within reaction mixtures containing the test compound and normal target gene protein can also be compared to complex formation within reaction mixtures containing the test compound and a mutant target gene protein. This comparison can be important in those cases wherein it is desirable to identify compounds that disrupt interactions of mutant but not normal target gene proteins.

The assay for compounds that interfere with the interaction of the target gene products and binding partners can be conducted in a heterogeneous or homogeneous format. Heterogeneous assays involve anchoring either the target gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the target gene products and the binding partners, e.g., by competition, can be identified by conducting the reaction in the presence of the test substance; i.e., by adding the test substance to the reaction mixture prior to or simultaneously with the target gene protein and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the target gene protein or the interactive cellular or extracellular binding partner, is anchored onto a solid surface, while the non-anchored species is labeled, either directly or indirectly. In practice, microtiter plates are conveniently utilized. The anchored species can be immobilized by non-covalent or covalent attachments. Non-covalent attachment can be accomplished simply by coating the solid surface with a solution of the target gene product or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the target gene protein and the interactive cellular or extracellular binding partner is prepared in which either the target gene product or its binding partner is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt target gene protein/cellular or extracellular binding partner interaction can be identified.

In a particular embodiment, the target gene product can be prepared for immobilization using recombinant DNA techniques described in Section 5.5, above. For example, the target gene coding region can be fused to a glutathione-S-transferase (GST) gene using a fusion vector, such as pGEX-5X-1, in such a manner that its binding activity is maintained in the resulting fusion protein. The interactive cellular or extracellular binding partner can be purified and used to raise a monoclonal antibody, using methods routinely practiced in the art and described above, in Section 5.6. This antibody can be labeled with the radioactive isotope $^{125}$I, for example, by methods routinely practiced in the art. In a heterogeneous assay, e.g., the GST-target gene fusion protein can be anchored to glutathione-agarose beads. The interactive cellular or extracellular binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the target gene protein and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST-target gene fusion protein and the interactive cellular or extracellular binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the target gene product/binding partner interaction can be detected by adding the labeled antibody and measuring the radioactivity associated with the beads.

In another embodiment of the invention, these same techniques can be employed using peptide fragments that correspond to the binding domains of the target gene product and/or the interactive cellular or extracellular binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner is obtained, short gene segments can be engineered to express peptide fragments of the protein, which can then be tested for binding activity and purified or synthesized.

For example, and not by way of limitation, a target gene product can be anchored to a solid material as described, above, in this Section, by making a GST-target gene fusion protein and allowing it to bind to glutathione agarose beads. The interactive cellular or extracellular binding partner can be labeled with a radioactive isotope, such as $^{35}$S, and cleaved with a proteolytic enzyme such as trypsin. Cleavage products can then be added to the anchored GST-target gene fusion protein and allowed to bind. After washing away unbound peptides, labeled bound material, representing the cellular or extracellular binding partner binding domain, can be eluted, purified, and analyzed for amino acid sequence by well known methods. Peptides so identified can be produced synthetically or fused to appropriate facilitative proteins using well known recombinant DNA technology.

5.8.4 Assays for Amelioration of Immune Disorder Symptoms and/or the Modulation of Target Gene Product Function Any of the binding compounds, including but not limited to, compounds such as those identified in the foregoing assay systems, can be tested for the ability to ameliorate symptoms of immune disorders e.g., TH cell subpopulation-related disorders. Cell-based and animal model-based assays for the identification of compounds exhibiting such an ability to ameliorate immune disorder symptoms are described below. Further, cell-based assays for the identification of compounds which modulate target gene product function, in instances where the target gene product is a receptor having a seven transmembrane domain sequence, such as, for example, that of the 10 gene product, are described, below, in Section 5.8.4.1.

First, cell-based systems such as those described, above, in Section 5.7.2, can be used to identify compounds which can act to ameliorate TH cell subpopulation-related disorder symptoms. For example, such cell systems can be exposed to a compound, suspected of exhibiting an ability to ameliorate the disorder symptoms, at a sufficient concentration and for a time sufficient to elicit such an amelioration in the exposed cells. After exposure, the cells are examined to determine whether one or more of the TH cell subpopulation-related disorder-like cellular phenotypes has been altered to resemble a phenotype more likely to produce a lower incidence or severity of disorder symptoms. Additional cell-based assays are discussed, below, in Section 5.8.4.1.

Taking the TH cell subpopulation-related disorder asthma, which is, specifically, a TH2-like-related disorder, any TH2 or TH2-like cell system can be utilized. Upon exposure to such cell systems, compounds can be assayed for their ability to modulate the TH2-like phenotype of such cells, such that the cells exhibit loss of a TH2-like phenotype. Compounds with such TH2 modulatory capability represent ones which can potentially exhibit the ability to ameliorate asthma-related symptoms in vivo.

In addition, animal-based systems, such as those described, above, in Section 5.7.1, can be used to identify compounds capable of ameliorating TH cell subpopulation-related disorder-like symptoms. Such animal models can be used as test substrates for the identification of drugs, pharmaceuticals, therapies, and interventions which can be effective in treating such disorders. For example, animal models can be exposed to a compound, suspected of exhibiting an ability to ameliorate TH cell subpopulation-related disorder symptoms, at a sufficient concentration and for a time sufficient to elicit such an amelioration of the symptoms in the exposed animals. The response of the animals to the exposure, and thus the efficacy of the compound in question, can be monitored by assessing the reversal of disorders associated with TH cell subpopulation-related disorders of interest. With regard to intervention, any treatments which reverse any aspect of TH cell subpopulation-related disorder-like symptoms should be considered as candidates for corresponding human TH cell subpopulation-related disorder therapeutic intervention. Dosages of test agents can be determined by deriving dose-response curves, as discussed in Section 5.10, below.

Gene expression patterns can be utilized in conjunction with either cell-based or animal-based systems, to assess the ability of a compound to ameliorate TH cell subpopulation-related disorder-like symptoms. For example, the expression pattern of one or more fingerprint genes can form part of a fingerprint profile which can be then be used in such an assessment. Fingerprint profiles are described, below, in Section 5.11. Fingerprint profiles can be characterized for known states, either TH cell subpopulation-related disorder states, or normal TH cell differentiative states, within the cell- and/or animal-based model systems.

5.8.4.1. Methods for the Identification of Compounds Which Modulate Target Gene Product Function In this Section, methods are described for the identification of compounds which act as either agonists or antagonists of receptor target gene products. The 10 gene product (FIGS. 9A–9D; SEQ ID NO:9) is an example of a seven transmembrane domain target gene product. For ease of explanation, and not by way of limitation, therefore, the 10 gene product will be used to illustrate the methods described in this Section.

The compounds tested may be, for example, compounds such as those identified via the assays described, above, in Sections 5.8.1 to 5.8.3. Such compounds may include, but are not limited to peptides such as, for example, soluble peptides, including, but not limited to, Ig-tailed fusion peptides, comprising extracellular portions of target gene product transmembrane receptors, and members of random peptide libraries (see, e.g., Lam, K. S. et al., 1991, Nature 354:82–84; Houghten, R. et al., 1991, Nature 354:84–86) made of D- and/or L-configuration amino acids, phosphopeptides (including but not limited to members of random or partially degenerate, directed phosphopeptide libraries; see, e.g., Songyang, Z. et al., 1993, Cell 72:767–778), antibodies (including, but not limited to polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

The assays described herein are functional assays which identify compounds that affect the receptor target gene's activity by affecting the level of intracellular calcium release within cells expressing such seven transmembrane domain receptor target protein (e.g., the 10 gene product). Intracellular calcium release is measured because such seven transmembrane domain receptors tend to be G protein-coupled receptors and because activation of these receptors leads to a G protein-mediated intracellular calcium release. Modulation (i.e., agonization or antagonization) of the receptor target gene product function, then, would result in a difference in intracellular calcium levels.

The assays comprise contacting a seven transmembrane domain receptor target gene-expressing cell with a test compound and measuring the level of intracellular calcium. Those compounds which produce an intracellular calcium profile which differs from that which the cell would exhibit in the absence of the compound represent either agonists or antagonists. An agonist compound would cause an increase in intracellular calcium levels relative to control cells while an antagonist would result in a decrease in intracellular calcium levels relative to control cells.

While any cell expressing a seven transmembrane receptor target gene product may be used herein, it is preferred that cells be used whose intracellular calcium levels may readily measured. Xenopus oocytes, due to their large size, are among such preferred cells because they can easily be injected with intracellular calcium reporter compounds. Additionally, myeloma cells may be utilized. Such reporter compounds include, but are not limited to, calcium-binding agents such as the well known FURA-2 and INDO-2. FURA-2/calcium complexes and INDO-2/calcium complexes fluoresce, making possible the measurement of differences in intracellular calcium levels.

For the purposes of the assays described herein, the Xenopus oocytes should be transfected with nucleotide sequences encoding the target protein of interest (e.g., the 10 gene product). The cells can be transfected and express the sequence of interest via techniques which are well known to those of skill in the art and which may include, for example, techniques such as those described, above, in Section 5.5. Xenopus oocytes can be injected with RNA encoding the target gene product of interest such that the injected oocytes will express the gene product.

The assays described in this Section may, first, be used to identify compounds which act as agonists of the target gene product of interest, e.g., the 10 gene product. "Agonist", as used herein, refers to a compound which modulates target gene product activity by increasing the target gene product's activity, as evaluated by the compound's ability to bring about an increase in calcium influx, leading to an increase intracellular calcium levels. Among such agonists can be, for example, the natural ligand for the receptor target gene product, e.g., the natural ligand for the 10 gene product.

Agonists identified via such assays may act as useful therapeutic agents for the amelioration of a wide range of T cell-related disorders, including, for example, TH cell subpopulation-related disorders, in instances whereby such disorders are caused by a reduced or absent level of target gene product activity. Any of the agonist compounds identified herein can be used, for example, as part of the treatment methods described in Section 5.9.2, below. Further, such agonists can be used to identify antagonists of the receptor target gene product of interest, e.g., as described, below.

"Antagonist", as used herein, refers to a compound which modulates target gene product activity by decreasing the target gene product's activity, as evaluated by the compound's ability to bring about a decrease in calcium influx. Antagonists identified via such assays may act as useful therapeutic agents for the amelioration of a wide range of T cell-related disorders, including, for example, TH cell subpopulation-related disorders, in instances whereby the disorder is caused by an increased or inappropriate level of target gene product activity.

An antagonist screen may be performed utilizing target gene product-expressing cells as described, above, and which include, but are not limited to, such cells as 10 gene-expressing cells, for example, 10 gene-expressing Xenopus oocytes. In those instances whereby the T cell-related disorder is caused by a mutant target gene product, the cells utilized in the antagonist assay can be cells which express the mutant receptor target gene product involved in causing the T cell-related disorder.

To conduct an antagonist screen, a target gene-expressing cell is contacted with 1) an agonist of the target gene product and 2) a test compound for a given period of time. The level of intracellular calcium is then measured in the cells and in cells which have been contacted with agonist alone. A test compound is considered to be an antagonist if the level of intracellular calcium release in the presence of the test compound is lower than the level of intracellular calcium release in the absence of the test compound.

Any of the antagonist compounds identified herein can be used, for example, as part of the treatment methods described, below, in Section 5.9.1.

Among the potential antagonist compounds of the seven transmembrane domain receptor target gene products described herein are peptides which contain one or more of the receptor target gene product's extracellular domains, preferably those domains are domains which are responsible for ligand-binding such that the peptides act to compete with the endogenous receptor for ligand. In the case of the 10 gene product, for example, such extracellular domains include from approximately 10 gene product amino acid residue 1 to 19, amino acid residue 74 to 87, amino acid residue 153–187 and amino acid residue 254 to 272. Such extracellular domain antagonist compounds may comprise soluble Ig-tailed fusion proteins which may be produced by utilizing techniques such as those described, above, in Section 5.5. Additionally, antibodies directed against the extracellular portion of the 10 gene product may reduce 10 gene product function by, for example, blocking ligand binding.

5.9. Compounds and Methods for Treatment of Immune Disorders and for Modulation of TH Cell Responsiveness Described below are methods and compositions which can be used to ameliorate immune disorder symptoms via, for example, a modulation of the TH cell subpopulation of interest. Such modulation can be of a positive or negative nature, depending on the specific situation involved, but each modulatory event yields a net result in which symptoms of the immune disorder are ameliorated. Further, described below are methods for the modulation of TH cell responsiveness to antigen.

"Negative modulation", as used herein, refers to a reduction in the level and/or activity of target gene product relative to the level and/or activity of the target gene product in the absence of the modulatory treatment. Alternatively, the term, as used herein, refers to a depletion of the T cell subpopulation (e.g., via a reduction in the number of cells belonging to the TH cell subpopulation) relative to the number present in the absence of the modulatory treatment. "Depletion," as used herein, is as defined, above, in Section 3.

"Positive modulation", as used herein, refers to an increase in the level and/or activity of target gene product relative to the level and/or activity of the gene product in the absence of the modulatory treatment. Alternatively, the term, as used herein, refers to a stimulation of the T cell subpopulation (e.g., via an increase in the number of cells belonging to the TH cell subpopulation), relative to the number present in the absence of the modulatory treatment. "Stimulation," as used herein, is as defined, above, in Section 3.

It is possible that a TH cell subpopulation-related disorder or other immune disorder, can occur as a result of normal target gene activity during the course of, for example, exposure to a certain antigen which elicits an immune response that leads to the development of the disorder. For example, the TH2-like-related disorders, asthma and allergy, are likely candidates of disorders having such a mechanism. Additionally, a disorder can be brought about, at least in part, by an abnormally high level of target gene product, or by the presence of a target gene product exhibiting an abnormal activity. As such, a technique which elicits a negative modulatory effect, i.e., brings about a reduction in the level and/or activity of target gene product, or alternatively, brings about a depletion of the TH cell subpopulation (e.g., via a physical reduction in the number of cells belonging to the TH cell subpopulation), would effect an amelioration of TH cell subpopulation-related disorder symptoms in either of the above scenarios.

Negative modulatory techniques for the reduction of target gene expression levels or target gene product activity levels, (either normal or abnormal), and for the reduction in the number of specific TH cell subpopulation cells are discussed in Section 5.9.1, below.

Alternatively, it is possible that a TH cell subpopulation-related disorder or other immune disorders can be brought about, at least in part, by the absence or reduction of the level of target gene expression, a reduction in the level of a target gene product's activity, or a reduction in the overall number of cells belonging to a specific TH cell subpopulation. As such, a technique which elicits a positive modulatory effect, i.e., brings about an increase in the level of target gene expression and/or the activity of such gene products, or, alternatively, a stimulation of the TH cell subpopulation (e.g., via a physical increase in the number of cells belonging to a TH cell subpopulation), would effect an amelioration of immune disorder symptoms.

For example, a reduction in the overall number of TH1-like cells relative to TH2-like cells within a HIV-infected individual can correlate with the progression to AIDS (Clerci, M. et al., 1993, J. Clin. Invest. 91:759; Clerci, M. et al., 1993, Science 262:1721; Maggi, E. et al., 1994, Science 265:244). A treatment capable of increasing the number of TH1-like cells relative to TH2-like cells within an HIV-infected individual may, therefore, serve to prevent or slow the progression to disease.

Positive modulatory techniques for increasing target gene expression levels or target gene product activity levels, and for increasing the level of specific TH cell subpopulation cells are discussed, below, in Section 5.9.2.

Among the immune disorders whose symptoms can be ameliorated are TH1 or TH1-like related immune disorders and TH2 or TH2-like related immune disorders. Examples of TH1 or TH1-like related disorders include chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease and sarcoidosis. Examples of TH2 or TH2-like related disorders include atopic conditions, such as asthma and allergy, including allergic rhinitis, gastrotestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

The methods described herein can additionally be utilized the modulate the level of responsiveness, for example, responsiveness to antigen, of a TH cell subpopulation. Such methods are important in that many immune disorders involve inappropriate rather than insufficient immune responses. For example, disorders such as atopic, IgE-mediated allergic conditions, including asthma, pathogen susceptibilities and chronic inflammatory disease, involve strong but counterproductive TH2-mediated immune responses. Further, inappropriate TH1-mediated immune responses to self-antigens is central to the development of such disorders as multiple sclerosis, psoriasis, insulin dependent diabetes, Hashimoto's thyroiditis and Crohn's disease.

Methods for modulating TH cell responsiveness can comprise, for example, contacting a compound to a TH cell so that the responsiveness of the T helper cell is modulated relative to the responsiveness of the T helper cell in the absence of the compound. The modulation can increase or decrease the responsiveness of the TH cell. Any of the techniques described, below, in Sections 5.9.1–5.9.3.2 can be utilized to effect an appropriate modulation of TH cell responsiveness.

5.9.1 Negative Modulatory Techniques

As discussed, above, successful treatment of certain immune disorders can be brought about by techniques which serve to inhibit the expression or activity of target gene products, or which, alternatively, serve to reduce the overall number of cells belonging to a specific TH cell subpopulation.

For example, compounds such as those identified through assays described, above, in Section 5.8, which exhibit negative modulatory activity, can be used in accordance with the invention to ameliorate certain TH cell subpopulation-related disorder symptoms. As discussed in Section 5.8, above, such molecules can include, but are not limited to peptides (such as, for example, peptides representing soluble extracellular portions of target gene product transmembrane receptors), phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof). Techniques for the determination of effective doses and administration of such compounds are described, below, in Section 5.10.

Further, antisense and ribozyme molecules which inhibit expression of the target gene can also be used in accordance with the invention to reduce the level of target gene expression, thus effectively reducing the level of target gene activity. Still further, triple helix molecules can be utilized in reducing the level of target gene activity. Such techniques are described, below, in Section 5.9.1.1.

Additionally, techniques for the depletion of specific TH cell subpopulations are discussed, below, in Section 5.9.3. Such techniques can take advantage of, for example, novel cell surface markers which are specific to the TH cell subpopulation to be depleted, and can include in vivo or in vitro targeted destruction, or, alternatively, selective purification away, of the TH cell subpopulation of interest.

Among the TH cell subpopulation-related sequences identified by the methods described by the present invention is a gene designated herein as the 103 gene, as discussed in the Example presented in Section 7, below. The 103 gene is demonstrated herein to represent a TH2-specific gene in that 103 gene expression is found to be absent TH1 cells as well as all other tissues tested. Further, at least one of the proteins produced by the 103 gene is a transmembrane protein.

The 103 gene and its products can, therefore, be utilized in the treatment of TH2 cell subpopulation-related disorders. For example, a 103 gene product or portions thereof can be utilized, either directly or indirectly, to ameliorate conditions involving inappropriate IgE immune responses, including, but not limited to the symptoms which accompany atopic conditions such as allergy and/or asthma. IgE-type antibodies are produced by stimulated B cells which require, at least in part, IL-4 produced by the TH2 cell subpopulation. Therefore, any treatment, including, for example, the use of a gene 103 product or portion thereof, which reduces the effective concentration of secreted IL-4, e.g., by reducing the number or activity of TH2 cells, can bring about a reduction in the level of circulating IgE, leading, in turn, to the amelioration of the conditions stemming from an inappropriate IgE immune response.

There exist a variety of ways in which the TH2 specific 103 gene products can be used to effect such a reduction in the activity and/or effective concentration of TH2 cells. For example, natural ligands, derivatives of natural ligands and antibodies which bind to the 103 gene product can be utilized to reduce the number of TH2 cells present by either physically separating such cells away from other cells in a population, thereby deleting the TH2 cell subpopulation, or, alternatively, by targeting the specific destruction of TH2 cells. Such techniques are discussed, below, in Section 5.9.3. Further, such compounds can be used to inhibit the proliferation of TH2 cells.

Additionally, compounds such as 103 gene sequences or gene products can be utilized to reduce the level of TH2 cell activity, cause a reduction in IL-4 production, and, ultimately, bring about the amelioration of IgE related disorders.

For example, compounds can be administered which compete with endogenous ligand for the 103 gene product. The resulting reduction in the amount of ligand-bound 103 gene transmembrane protein will modulate TH2 cellular activity. Compounds which can be particularly useful for this purpose include, for example, soluble proteins or peptides, such as peptides comprising the extracellular domain, or portions and/or analogs thereof, of the gene 103 product, including, for example, soluble fusion proteins such as Ig-tailed fusion proteins. (For a discussion of the production of Ig-tailed fusion proteins see, for example, U.S. Pat. No. 5,116,964.)

The novel 200 gene, which encodes a receptor target gene product that is a member of the Ig superfamily, exhibits a TH1-specific pattern of gene expression. The 200 gene, especially the human 200 gene, and its products can, therefore, be utilized in the treatment of TH1 cell subpopulation-related disorders such as, for example, chronic inflammatory diseases, psoriasis, graft rejection and graft versus host disease.

The treatment of such disorder may require a reduction in the activity and/or effective concentration of the TH1 cell subpopulation involved in the disorder of interest. As such, a number of methods exist whereby the TH1 specific 200 gene products can be used to effect such a reduction in the activity and/or effective concentration of TH1 cells. For example, natural ligands, derivatives of natural ligands and antibodies which bind to the 200 gene product can be utilized to reduce the number of TH1 cells present by either physically separating such cells away from other cells in a population, thereby deleting the TH1 cell subpopulation, or, alternatively, by targeting the specific destruction of TH1 cells. Such techniques are discussed, below, in Section 5.9.3. Further, such compounds can be used to inhibit the proliferation of TH1 cells.

Additionally, compounds can be administered which compete with endogenous ligand for the 200 gene product. Such compounds would bind to and "neutralize" circulating ligand. The resulting reduction in the amount of ligand-bound 200 gene transmembrane protein will modulate TH1 cellular activity. Compounds which can be particularly useful for this purpose include, for example, soluble proteins or peptides, such as peptides comprising the extracellular domain, or portions and/or analogs thereof, of the gene 200 product, including, for example, soluble fusion proteins such as Ig-tailed fusion proteins or antibodies. (For a discussion of the production of Ig-tailed fusion proteins see, for example, U.S. Pat. No. 5,116,964.)

To this end, peptides corresponding to the ECD of the 200 gene product, soluble deletion mutants of 200 gene product, or either of these 200 gene product domains or mutants fused to another polypeptide (e.g., an IgFc polypeptide) can be utilized. Alternatively, anti-idiotypic antibodies or Fab fragments of antiidiotypic antibodies that mimic the 200 gene product ECD and neutralize 200 gene product ligand can be used. Such 200 gene product peptides, proteins, fusion proteins, anti-idiotypic antibodies or Fabs are administered to a subject in amounts sufficient to neutralize Ob and to effectuate an amelioration of a T cell subpopulation-related disorder.

200 gene product peptides corresponding to the ECD having the amino acid sequence shown in FIGS. 17A–17D from about amino acid residue number 21 to about 192 can be used. Human 200 gene product peptides corresponding to the ECD having the amino acid sequence shown in FIGS. 24A–24D from approximately amino acid reside number 21 to about 200. Mutants in which all or part of the hydrophobic anchor sequence (e.g., about amino acid residue number 193 to 214 in FIGS. 17A–17D, or about 201 to about 224 in FIGS. 24A–24D) could also be used. Fusion of these peptides to an IgFc polypeptide should not only increase the stability of the preparation, but will increase the half-life and activity of the fusion protein in vivo. The Fc region of the Ig portion of the fusion protein may be further modified to reduce immunoglobulin effector function. For example, nucleotide sequences encoding the fusion protein may be modified to encode fusion proteins which replace cysteine residues in the hinge region with serine residues and/or amino acids within the CH2 domain believed to be required for IgC binding to FC receptors and complement activation.

In an alternative embodiment for neutralizing circulating 200 gene product ligand, cells that are genetically engineered to express such soluble or secreted forms of 200 gene product may be administered to a patient, whereupon they will serve as "bioreactors" in vivo to provide a continuous supply of the 200 gene product ligand neutralizing protein. Such cells may be obtained from the patient or an MHC compatible donor and can include, but are not limited to fibroblasts, blood cells (e.g., lymphocytes), adipocytes, muscle cells, endothelial cells etc. The cells are genetically engineered in vitro using recombinant DNA techniques to introduce the coding sequence for the 200 gene product peptide, or 200 gene product fusion proteins (discussed above) into the cells, e.g., by transduction (using viral vectors, and preferably vectors that integrate the transgene into the cell genome) or transfection procedures, including but not limited to the use of plasmids, cosmids, YACs, electroporation, liposomes, etc. The 200 gene product coding sequence can be placed under the control of a strong constitutive or inducible promoter or promoter/enhancer to achieve expression and secretion of the 200 gene peptide or fusion protein. The engineered cells which express and secrete the desired 200 gene product can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

It is to be understood that, while such approaches and techniques are described, for sake of clarity, using the 200 gene product as an example, they may be applied to any of the target and/or pathway gene products having such receptor-type structures.

The 10 gene product is identified herein as a receptor target gene product having a seven transmembrane domain sequence motif. Further, the 10 gene is shown to exhibit a TH inducible pattern of expression, meaning that 10 gene expression increases in both TH1 and TH2 cell subpopulations in response to stimulation and can important to T cell responses in general. The 10 gene and its products can, therefore, be utilized in the treatment of a wide T cell-related disorders. Techniques such as those described, above, for the 103 and the 200 genes and gene products can also be utilized for the amelioration of disorders in which 10 gene expression is involved.

5.9.1.1. Negative Modulatory Antisense, Ribozyme and Triple Helix Approaches Among the compounds which can exhibit the ability to ameliorate TH cell subpopulation-related disorder symptoms are antisense, ribozyme, and triple helix molecules. Such molecules can be designed to reduce or inhibit either wild type, or if appropriate, mutant target gene activity. Techniques for the production and use of such molecules are well known to those of skill in the art.

Antisense approaches involve the design of oligonucleotides (either DNA or RNA) that are complementary to target or pathway gene mRNA. The antisense oligonucleotides will bind to the complementary target or pathway gene mRNA transcripts and prevent translation. Absolute complementarity, although preferred, is not required. A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have recently shown to be effective at inhibiting translation of mRNAs as well. See generally, Wagner, R., 1994, Nature 372:333–335. Thus, oligonucleotides complementary to either the 5'- or 3'-non-translated, non-coding regions of target or pathway genes, as shown, for example, in FIGS. 9A–9D, 17A–17D, 22A–22C, 23A–23C, and 24A–24D, could be used in an antisense approach to inhibit translation of endogenous target or pathway gene mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of target or pathway gene mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., 1989, Proc.

Natl. Acad. Sci. U.S.A. 86:6553–6556; Lemaitre et al., 1987, Proc. Natl. Acad. Sci. 84:648–652; PCT Publication No. WO88/09810, published Dec. 15, 1988) or the blood-brainbarrier (see, e.g., PCT Publication No. WO89/10134, published Apr. 25, 1988), hybridization-triggered cleavage agents. (See, e.g., Krol et al., 1988, BioTechniques 6:958–976) or intercalating agents. (See, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier et al., 1987, Nucl. Acids Res. 15:6625–6641). The oligonucleotide is a 2'-O-methylribonucleotide (Inoue et al., 1987, Nucl. Acids Res. 15:6131–6148), or a chimeric RNA-DNA analogue (Inoue et al., 1987, FEBS Lett. 215:327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448–7451), etc.

The antisense molecules should be delivered to cells which express the target or pathway gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target or pathway gene transcripts and thereby prevent translation of the target or pathway gene mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290:304–310), the promoter contained in the 3' long terminal repeat of Rous sarcoma virus (Yamamoto et al., 1980, Cell 22:787–797), the herpes thymidine kinase promoter (Wagner et al., 1981, Proc. Natl. Acad. Sci. U.S.A. 78:1441–1445), the regulatory sequences of the metallothionein gene (Brinster et al., 1982, Nature 296:39–42), etc. Any type of plasmid, cosmid, YAC or viral vector can be used to prepare the recombinant DNA construct which can be introduced directly into the tissue site. Alternatively, viral vectors can be used which selectively infect the desired tissue.

Ribozymes are enzymatic RNA molecules capable of catalyzing the specific cleavage of RNA (For a review see, for example Rossi, J., 1994, Current Biology 4:469–471). The mechanism of ribozyme action involves sequence specific hybridization of the ribozyme molecule to complementary target RNA, followed by a endonucleolytic cleavage. The composition of ribozyme molecules must include one or more sequences complementary to the target gene mRNA, and must include the well known catalytic sequence responsible for mRNA cleavage. For this sequence, see U.S. Pat. No. 5,093,246, which is incorporated by reference herein in its entirety. As such, within the scope of the invention are engineered hammerhead motif ribozyme molecules that specifically and efficiently catalyze endonucleolytic cleavage of RNA sequences encoding target gene proteins.

Ribozyme molecules designed to catalytically cleave target or pathway gene mRNA transcripts can also be used to prevent translation of target or pathway gene mRNA and expression of target or pathway gene. (See, e.g., PCT International Publication WO90/11364, published Oct. 4, 1990; Sarver et al., 1990, Science 247:1222–1225). While ribozymes that cleave mRNA at site specific recognition sequences can be used to destroy target or pathway gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, 1988, Nature, 334:585–591. Preferably the ribozyme is engineered so that the cleavage recognition site is located near the 5' end of the target or pathway gene mRNA; i.e., to increase efficiency and minimize the intracellular accumulation of non-functional mRNA transcripts.

The ribozymes of the present invention also include RNA endoribonucleases (hereinafter "Cech-type ribozymes") such as the one which occurs naturally in Tetrahymena Thermophila (known as the IVS, or L-19 IVS RNA) and which has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in target or pathway gene.

As in the antisense approach, the ribozymes can be composed of modified oligonucleotides (e.g. for improved stability, targeting, etc.) and should be delivered to cells which express the target or pathway gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target or pathway gene messages and inhibit translation. Because ribozymes unlike antisense molecules, are catalytic, a lower intracellular concentration is required for efficiency.

In instances wherein the antisense, ribozyme, and/or triple helix molecules described herein are utilized to inhibit mutant gene expression, it is possible that the technique can also efficiently reduce or inhibit the transcription (triple helix) and/or translation (antisense, ribozyme) of mRNA produced by normal target gene alleles that the possibility can arise wherein the concentration of normal target gene product present can be lower than is necessary for a normal phenotype. In such cases, to ensure that substantially normal levels of target gene activity are maintained, therefore, nucleic acid molecules that encode and express target gene polypeptides exhibiting normal target gene activity can be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it can be preferable to coadminister normal target gene protein in order to maintain the requisite level of target gene activity.

Anti-sense RNA and DNA, ribozyme, and triple helix molecules of the invention can be prepared by any method known in the art for the synthesis of DNA and RNA molecules. These include techniques for chemically synthesizing oligodeoxyribonucleotides and oligoribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences can be incorporated into a wide variety of vectors which incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone.

Endogenous target and/or pathway gene expression can also be reduced by inactivating or "knocking out" the target and/or pathway gene or its promoter using targeted homologous recombination. (E.g., see Smithies et al., 1985, Nature 317:230–234; Thomas & Capecchi, 1987, Cell 51:503–512; Thompson et al., 1989 Cell 5:313–321; each of which is incorporated by reference herein in its entirety). For example, a mutant, non-functional target and/or pathway gene (or a completely unrelated DNA sequence) flanked by DNA homologous to the endogenous target and/or pathway gene (either the coding regions or regulatory regions of the target and/or pathway gene) can be used, with or without a selectable marker and/or a negative selectable marker, to transfect cells that express target and/or pathway gene in vivo. Insertion of the DNA construct, via targeted homologous recombination, results in inactivation of the target and/or pathway gene. Such approaches are particularly suited in the agricultural field where modifications to ES (embryonic stem) cells can be used to generate animal offspring with an inactive target and/or pathway gene (e.g., see Thomas & Capecchi 1987 and Thompson 1989, supra). Such techniques can also be utilized to generate T cell subpopulation-related disorder animal models. It should be noted that this approach can be adapted for use in humans provided the recombinant DNA constructs are directly administered or targeted to the required site in vivo using appropriate viral vectors, e.g., herpes virus vectors.

Alternatively, endogenous target and/or pathway gene expression can be reduced by targeting deoxyribonucleotide sequences complementary to the regulatory region of the target and/or pathway gene (i.e., the target and/or pathway gene promoter and/or enhancers) to form triple helical structures that prevent transcription of the target or pathway gene in target cells in the body. (See generally, Helene, C. 1991, Anticancer Drug Des., 6(6):569–84; Helene, C., et al., 1992, Ann, N. Y. Accad. Sci., 660:27–36; and Maher, L. J., 1992, Bioassays 14(12):807–15). In yet another embodiment of the invention, the activity of target and/or pathway gene can be reduced using a "dominant negative" approach. To this end, constructs which encode defective target and/or pathway gene products can be used in gene therapy approaches to diminish the activity of the target and/or pathway gene product in appropriate target cells.

5.9.2. Positive Modulatory Techniques

As discussed above, successful treatment of certain immune disorders can be brought about by techniques which serve to increase the level of target gene expression or to increase the activity of target gene product, or which, or alternatively, serve to effectively increase the overall number of cells belonging to a specific TH cell subpopulation.

For example, compounds such as those identified through assays described, above, in Section 5.8, which exhibit positive modulatory activity can be used in accordance with the invention to ameliorate certain TH cell subpopulation-related disorder symptoms. As discussed in Section 5.8, above, such molecules can include, but are not limited to peptides representing soluble extracellular portions of target gene product transmembrane proteins, phosphopeptides, small organic or inorganic molecules, or antibodies (including, for example, polyclonal, monoclonal, humanized, anti-idiotypic, chimeric or single chain antibodies, and FAb, F(ab')$_2$ and FAb expression library fragments, and epitope-binding fragments thereof).

For example, a compound, such as a target gene protein, can, at a level sufficient to ameliorate immune disorder symptoms, be administered to a patient exhibiting such symptoms. Any of the techniques discussed, below, in Section 5.10, can be utilized for such administration. One of skill in the art will readily know how to determine the concentration of effective, non-toxic doses of the compound, utilizing techniques such as those described, below, in Section 5.10.1.

In instances wherein the compound to be administered is a peptide compound, DNA sequences encoding the peptide compound can be directly administered to a patient exhibiting immune disorder symptoms, at a concentration sufficient to produce a level of peptide compound sufficient to ameliorate the disorder symptoms. Any of the techniques discussed, below, in Section 5.10, which achieve intracellular administration of compounds, such as, for example, liposome administration, can be utilized for the administration of such DNA molecules. The DNA molecules can be produced, for example, by well known recombinant techniques.

In the case of peptides compounds which act extracellularly, the DNA molecules encoding such peptides can be taken up and expressed by any cell type, so long as a sufficient circulating concentration of peptide results for the elicitation of a reduction in the immune disorder symptoms. In the case of compounds which act intracellularly, the DNA molecules encoding such peptides must be taken up and expressed by the TH cell subpopulation of interest at a sufficient level to bring about the reduction of immune disorders.

Any technique which serves to selectively administer DNA molecules to the TH cell subpopulation of interest is, therefore, preferred, for the DNA molecules encoding intracellularly acting peptides. In the case of asthma, for example, techniques for the selective administration of the molecules to TH cell subpopulations residing within lung tissue are preferred.

Further, in instances wherein the TH cell subpopulation-related disorder involves an aberrant gene, patients can be treated by gene replacement therapy. One or more copies of a normal target gene or a portion of the gene that directs the production of a normal target gene protein with target gene function, can be inserted into cells, using vectors which include, but are not limited to adenovirus, adeno-associated virus, and retrovirus vectors, in addition to other particles that introduce DNA into cells, such as liposomes.

Such gene replacement techniques can be accomplished either in vivo or in vitro. As above, for genes encoding extracellular molecules, the cell type expressing the target gene is less important than achieving a sufficient circulating concentration of the extracellular molecule for the amelioration of immune disorders. Further, as above, when the gene encodes a cell which acts intracellularly or as a transmembrane molecule, the gene must be expressed with the TH cell subpopulation cell type of interest. Techniques which select for expression within the cell type of interest are, therefore, preferred for this latter class of target genes. In vivo, such techniques can, for example, include appropriate local administration of target gene sequences.

Additional methods which may be utilized to increase the overall level of target and/or pathway gene expression and/or target and/or pathway gene activity include the introduction of appropriate target and/or pathway gene-expressing cells, preferably autologous cells, into a patient at positions and in numbers which are sufficient to ameliorate the symptoms of T cell subpopulation related disorders. Such cells may be either recombinant or non-recombinant. Among the cells which can be administered to increase the overall level of target and/or pathway gene expression in a patient are normal cells, which express the target and/or pathway gene. The cells can be administered at the anatomical site of expression, or as part of a tissue graft located at a different site in the body. Such cell-based gene therapy techniques are well known to those skilled in the art, see, e.g., Anderson, et al., U.S. Pat. No. 5,399,349; Mulligan & Wilson, U.S. Pat. No. 5,460,959.

In vitro, target gene sequences can be introduced into autologous cells. These cells expressing the target gene sequence of interest can then be reintroduced, preferably by intravenous administration, into the patient such that there results an amelioration of the symptoms of the disorder.

Alternatively, TH cells belonging to a specific TH cell subpopulation can be administered to a patient such that the overall number of cells belonging to that TH cell subpopulation relative to other TH cell subpopulation cells is increased, which results in an amelioration of a TH cell subpopulation-related disorder. Techniques for such TH cell subpopulation augmentation are described, below, in Section 5.9.3.2.

5.9.3 Negative or Positive Modulatory Techniques

Described herein are modulatory techniques which, depending on the specific application for which they are utilized, can yield either positive or negative responses leading to the amelioration of immune disorders, including TH cell subpopulation-related disorders. Thus, in appropriate instances, the procedures of this Section can be used in conjunction with the negative modulatory techniques described, above, in Section 5.9.1 or, alternatively, in conjunction with the positive modulatory techniques described, above, in Section 5.9.2.

5.9.3.1. Antibody Techniques

Antibodies exhibiting modulatory capability can be utilized to ameliorate immune disorders such as TH cell subpopulation-related disorders. Depending on the specific antibody, the modulatory effect can be negative and can, therefore, by utilized as part of the techniques described, above, in Section 5.9.1, or can be positive, and can, therefore, be used in conjunction with the techniques described, above, in Section 5.9.2.

An antibody having negative modulatory capability refers to an antibody which specifically binds to and interferes with the action of a protein. In the case of an extracellular receptor, for example, such an antibody would specifically bind the extracellular domain of the receptor in a manner which does not activate the receptor but which disrupts the ability of the receptor to bind its natural ligand. For example, antibodies directed against the extracellular domains of genes 103 or 200 can function as such negative modulators.

Additionally, antibodies directed against one or more of the 10 gene product extracellular domains can function in a negative modulatory manner. Such antibodies can be generated using standard techniques described in Section 5.6, above, against full length wild type or mutant proteins, or against peptides corresponding to portions of the proteins. The antibodies include but are not limited to polyclonal, monoclonal, FAb fragments, single chain antibodies, chimeric antibodies, and the like.

An antibody having positive modulatory capability refers to an antibody which specifically binds to a protein and, by binding, serves to, either directly or indirectly, activate the function of the protein which it recognizes. For example, an antibody can bind to the extracellular portion of a transmembrane protein in a manner which causes the transmembrane protein to function as though its endogenous ligand was binding, thus activating, for example, a signal transduction pathway. antibodies can be generated using standard techniques described in Section 5.6, above, against full length wild type or mutant proteins, or against peptides corresponding to portions of the proteins. The antibodies include but are not limited to polyclonal, monoclonal, FAb fragments, single chain antibodies, chimeric antibodies, and the like.

In instances where the protein, such as a target gene protein, to which the antibody is directed is intracellular and whole antibodies are used, internalizing antibodies can be preferred. However, lipofectin or liposomes can be used to deliver the antibody or a fragment of the Fab region which binds to the gene product epitope into cells. Where fragments of the antibody are used, the smallest inhibitory fragment which binds to the protein's binding domain is preferred. For example, peptides having an amino acid sequence corresponding to the domain of the variable region of the antibody that binds to the protein can be used. Such peptides can be synthesized chemically or produced via recombinant DNA technology using methods well known in the art (e.g., see Creighton, 1983, supra; and Sambrook et al., 1989, above). Alternatively, single chain antibodies, such as neutralizing antibodies, which bind to intracellular epitopes can also be administered. Such single chain antibodies can be administered, for example, by expressing nucleotide sequences encoding single-chain antibodies within the target cell population by utilizing, for example, techniques such as those described in Marasco et al. (Marasco, W. et al., 1993, Proc. Natl. Acad. Sci. U.S.A. 90:7889–7893).

In instances where the protein to which the antibody is directed is extracellular, or is a transmembrane protein, any of the administration techniques described, below in Section 5.10 which are appropriate for peptide administration can be utilized to effectively administer the antibodies to their site of action.

5.9.3.2 Methods for Increasing or Decreasing Specific TH Cell Subpopulation Concentrations Techniques described herein can be utilized to either deplete or augment the total number of cells belonging to a given TH cell subpopulation, thus effectively increasing or decreasing the ratio of the TH cell subpopulation of interest to other TH cell subpopulations. Specifically, separation techniques are described which can be used to either deplete or augment the total number of cells present within a TH cell subpopulation, and, further, targeting techniques are described which can be utilized to deplete specific TH cell subpopulations.

Depending on the particular application, changing the number of cells belonging to a TH cell subpopulation can yield either stimulatory or inhibitory responses leading to the amelioration of TH cell subpopulation disorders. Thus, in appropriate instances, the procedures of this Section can be used in conjunction with the inhibitory techniques described, above, in Section 5.9.1. or, alternatively, in conjunction with the stimulatory techniques described, above, in Section 5.9.2.

The separation techniques described herein are based on the presence or absence of specific cell surface markers, preferably transmembrane markers. Such markers can include, but are not limited to, the TH2-specific 103 gene product extracellular domain markers, the TH1-specific 200 gene product extracellular domain markers and the TH inducible 10 gene product extracellular domain markers.

In instances wherein the goal of the separation is to increase or augment the number of cells belonging to a specific TH cell subpopulation, the antibodies used can also be specific to surface markers present on undifferentiated or partially undifferentiated TH cells. After separation, and purification of such undifferentiated or partially differentiated TH cells, the cells can be cultured in physiological buffer or culture medium and induced to differentiate by culturing in the presence of appropriate factors. For example, IL-4 can be added to induce the TH cells to differentiate into TH2 cells, while the cytokine IL-12 can be added to induce the TH cells to differentiate into TH1 cells. After differentiation, cells can be washed, resuspended in, for example, buffered saline, and reintroduced into a patient via, preferably, intravenous administration.

Separation techniques can be utilized which separate and purify cells, in vitro, from a population of cells, such as hematopoietic cells autologous to the patient being treated. An initial TH cell subpopulation-containing population of cells, such as hematopoietic cells, can be obtained using standard procedures well known to those of skill in the art. Peripheral blood can be utilized as one potential starting source for such techniques, and can, for example, be obtained via venipuncture and collection into heparinized tubes.

Once the starting source of autologous cells is obtained, the T cells, such as TH1 or TH2 cells, can be removed, and thus selectively separated and purified, by various methods which utilize antibodies which bind specific markers present on the T cell population of interest, while absent on other cells within the starting source. These techniques can include, for example, flow cytometry using a fluorescence activated cell sorter (FACS) and specific fluorochromes, biotin-avidin or biotin-streptavidin separations using biotin conjugated to cell surface marker-specific antibodies and avidin or streptavidin bound to a solid support such as affinity column matrix or plastic surfaces or magnetic separations using antibody-coated magnetic beads.

Separation via antibodies for specific markers can be by negative or positive selection procedures. In negative separation, antibodies are used which are specific for markers present on undesired cells. For example, in the case of a TH1 cell subpopulation-related disorder wherein it would be desirable to deplete the number of TH1 cells, such antibodies could be directed to the extracellular domain of the 200 gene product. Alternatively, in the case of TH2 cell subpopulation-related disorders wherein it would be desirable to deplete the number of TH1 cells, such antibodies could be directed to the extracellular domain of the 103 gene product. Cells bound by an antibody to such a cell surface marker can be removed or lysed and the remaining desired mixture retained.

In positive separation, antibodies specific for markers present on the desired cells of interest. For example, in the case of a TH1 cell subpopulation-related disorder wherein it would be desirable to increase the number of TH1 cells, such antibodies could be directed to the extracellular domain of the 200 gene product. Alternatively, in the case of TH2 cell subpopulation-related disorders wherein it would be desirable to increase the number of TH1 cells, such antibodies could be directed to the extracellular domain of the 103 gene product. Cells bound by the antibody are separated and retained. It will be understood that positive and negative separations can be used substantially simultaneously or in a sequential manner.

A common technique for antibody based separation is the use of flow cytometry such as by a florescence activated cell sorter (FACS). Typically, separation by flow cytometry is performed as follows. The suspended mixture of cells are centrifuged and resuspended in media. Antibodies which are conjugated to fluorochrome are added to allow the binding of the antibodies to specific cell surface markers. The cell mixture is then washed by one or more centrifugation and resuspension steps. The mixture is run through a FACS which separates the cells based on different fluorescence characteristics. FACS systems are available in varying levels of performance and ability, including multi-color analysis. The facilitating cell can be identified by a characteristic profile of forward and side scatter which is influenced by size and granularity, as well as by positive and/or negative expression of certain cell surface markers.

Other separation techniques besides flow cytometry can also provide fast separations. One such method is biotin-avidin based separation by affinity chromatography. Typically, such a technique is performed by incubating cells with biotin-coupled antibodies to specific markers, such as, for example, the transmembrane protein encoded by the 103 gene described herein, followed by passage through an avidin column. Biotin-antibody-cell complexes bind to the column via the biotin-avidin interaction, while other cells pass through the column. The specificity of the biotin-avidin system is well suited for rapid positive separation. Multiple passages can ensure separation of a sufficient level of the TH cell subpopulation of interest.

In instances whereby the goal of the separation technique is to deplete the overall number of cells belonging to a TH cell subpopulation, the cells derived from the starting source of cells which has now been effectively depleted of TH cell subpopulation cells can be reintroduced into the patient. Such a depletion of the TH cell subpopulation results in the amelioration of TH cell subpopulation-related disorders associated with the activity or overactivity of the TH cell subpopulation. Reintroduction of the TH cell subpopulation-depleted cells can be accomplished by washing the cells, resuspending in, for example, buffered saline, and intravenously administering the cells into the patient.

If cell viability and recovery are sufficient, TH cell subpopulation-depleted cells can be reintroduced into patients immediately subsequent to separation. Alternatively, TH cell subpopulation-depleted cells can be cultured and expanded ex vivo prior to administration to a patient. Expansion can be accomplished via well known techniques utilizing physiological buffers or culture media in the presence of appropriate expansion factors such as interleukins and other well known growth factors.

In instances whereby the goal of the separation technique is to augment or increase the overall number of cells belonging to a TH cell subpopulation, cells derived from the purified TH cell subpopulation cells can be reintroduced into the patient, thus resulting in the amelioration of TH cell subpopulation-related disorders associated with an under activity of the TH cell subpopulation.

The cells to be reintroduced will be cultured and expanded ex vivo prior to reintroduction. Purified TH cell subpopulation cells can be washed, suspended in, for example, buffered saline, and reintroduced into the patient via intravenous administration.

Cells to be expanded can be cultured, using standard procedures, in the presence of an appropriate expansion agent which induces proliferation of the purified TH cell subpopulation. Such an expansion agent can, for example, be any appropriate cytokine, antigen, or antibody. In the case of TH2 cells, for example, the expansion agent can be IL-4, while for TH1 cells, the expansion agent can, for example, be IL-12.

Prior to being reintroduced into a patient, the purified cells can be modified by, for example, transformation with gene sequences encoding gene products of interest. Such gene products should represent products which enhance the activity of the purified TH cell subpopulation or, alternatively, represent products which repress the activity of one or more of the other TH cell subpopulations. Cell transformation and gene expression procedures are well known to those of skill in the art, and can be as those described, above, in Section 5.5.

Well known targeting methods can, additionally, be utilized in instances wherein the goal is to deplete the number of cells belonging to a specific TH cell subpopulation. Such targeting methods can be in vivo or in vitro, and can involve the introduction of targeting agents into a population of cells such that the targeting agents selectively destroy a specific subset of the cells within the population. In vivo administration techniques which can be followed for such targeting agents are described, below, in Section 5.10.

Targeting agents generally comprise, first, a targeting moiety which, in the current instance, causes the targeting agent to selectively associate with a specific TH cell subpopulation. The targeting agents generally comprise, second, a moiety capable of destroying a cell with which the targeting agent has become associated.

Targeting moieties can include, but are not limited to, antibodies directed to cell surface markers found specifically on the TH cell subpopulation being targeted, or, alternatively, to ligands, such as growth factors, which bind receptor-type molecules found exclusively on the targeted TH cell subpopulation.

In the case of TH2 cells, for example, such a targeting moiety can represent an antibody directed against the extracellular portion of the 103 gene product described herein, or can, alternatively, represent a ligand specific for this receptor-type TH2 specific molecule. In the case of TH1 cells, for example, such a targeting moiety can represent an antibody directed against the extracellular portion of the 200 gene product described herein, or can, alternatively, represent a ligand specific for this receptor-type TH1 specific molecule.

Destructive moieties include any moiety capable of inactivating or destroying a cell to which the targeting agent has become bound. For example, a destructive moiety can include, but it is not limited to cytotoxins or radioactive agents. Cytotoxins include, for example, plant-, fungus-, or bacteria-derived toxins, with deglycosylated Ricin A chain toxins being generally preferred due to their potency and lengthy half-lives.

5.10. Pharmaceutical Preparations and Methods of Administration

The compounds, nucleic acid sequences and TH cell subpopulation cell described herein can be administered to a patient at therapeutically effective doses to treat or ameliorate immune disorders, e.g., TH cell subpopulation-related disorders. A therapeutically effective dose refers to that amount of a compound or TH cell subpopulation sufficient to result in amelioration of the immune disorder symptoms of the immune disorder symptoms, or alternatively, to that amount of a nucleic acid sequence sufficient to express a concentration of gene product which results in the amelioration of the TH cell subpopulation-related disorders or of other immune disorders.

5.10.1. Effective Dose

Toxicity and therapeutic efficacy of compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

5.10.2. Formulations and Use

Pharmaceutical compositions for use in accordance with the present invention can be formulated in conventional manner using one or more physiologically acceptable carriers or excipients.

Thus, the compounds and their physiologically acceptable salts and solvents can be formulated for administration by inhalation or insufflation (either through the mouth or the nose) or oral, buccal, parenteral or rectal administration.

For oral administration, the pharmaceutical compositions can take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets can be coated by methods well known in the art. Liquid preparations for oral administration can take the form of, for example, solutions, syrups or suspensions, or they can be presented as a dry product for constitution with water or other suitable vehicle before use. Such liquid preparations can be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations can also contain buffer salts, flavoring, coloring and sweetening agents as appropriate.

Preparations for oral administration can be suitably formulated to give controlled release of the active compound.

For buccal administration the compositions can take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator can be formulated containing a powder mix of the compound and a suitable powder base such as lactose or starch.

The compounds can be formulated for parenteral administration (i.e., intravenous or intramuscular) by injection, via, for example, bolus injection or continuous infusion. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use. It is preferred that the TH cell subpopulation cells be introduced into patients via intravenous administration.

The compounds can also be formulated in rectal compositions such as suppositories or retention enemas, e.g., containing conventional suppository bases such as cocoa butter or other glycerides.

In addition to the formulations described previously, the compounds can also be formulated as a depot preparation. Such long acting formulations can be administered by implantation (for example subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device which can contain one or more unit dosage forms containing the active ingredient. The pack can for example comprise metal or plastic foil, such as a blister pack. The pack or dispenser device can be accompanied by instructions for administration.

5.11. Diagnostic and Monitoring Techniques

A variety of methods can be employed for the diagnosis of immune disorders, e.g., TH cell subpopulation-related disorders, predisposition to such immune disorders, for monitoring the efficacy of anti-immune disorder compounds during, for example, clinical trials and for monitoring patients undergoing clinical evaluation for the treatment of such disorders. Further, a number of methods can be utilized for the detection of activated immune cells, e.g., activated members of TH cell subpopulations.

Such methods can, for example, utilize reagents such as the fingerprint gene nucleotide sequences described in Sections 5.1, and antibodies directed against differentially expressed and pathway gene peptides, as described, above, in Sections 5.5 (peptides) and 5.6 (antibodies). Specifically, such reagents can be used, for example, for: 1) the detection of the presence of target gene expression, target gene mutations, the detection of either over- or under-expression of target gene mRNA relative to the non-immune disorder state or relative to an unactivated TH cell subpopulation; 2) the detection of either an over- or an underabundance of target gene product relative to the non-immune disorder state or relative to the unactivated TH cell subpopulation state; and 3) the identification of specific TH cell subpopulation cells (e.g., TH cells involved in an immune disorder, or activated TH cells) within a mixed population of cells.

The methods described herein can be performed, for example, by utilizing pre-packaged diagnostic kits comprising at least one specific fingerprint gene nucleic acid or anti-fingerprint gene antibody reagent described herein, which can be conveniently used, e.g., in clinical settings, to diagnose patients exhibiting TH1- or TH2-related abnormalities.

Any cell type or tissue, preferably TH cells, in which the fingerprint gene is expressed can be utilized in the diagnostics described below.

Among the methods which can be utilized herein are methods for monitoring the efficacy of compounds in clinical trials for the treatment of immune disorders. Such compounds can, for example, be compounds such as those described, above, in Section 5.9. Such a method comprises detecting, in a patient sample, a gene transcript or gene product which is differentially expressed in a TH cell subpopulation in an immune disorder state relative to its expression in the TH cell subpopulation when the cell subpopulation is in a normal, or non-immune disorder, state.

Any of the nucleic acid detection techniques described, below, in Section 5.11.1 or any of the peptide detection techniques described, below, in Section 5.11.2 can be used to detect the gene transcript or gene product which is differentially expressed in the immune disorder TH cell subpopulation relative to its expression in the normal, or non-immune disorder, state.

During clinical trials, for example, the expression of a single fingerprint gene, or alternatively, the fingerprint pattern of a TH cell subpopulation, can be determined for the TH cell subpopulation in the presence or absence of the compound being tested. The efficacy of the compound can be followed by comparing the expression data obtained to the corresponding known expression patterns for the TH cell subpopulation in a normal, non-immune disorder state. Compounds exhibiting efficacy are those which alter the single fingerprint gene expression and/or the fingerprint pattern of the immune disorder TH cell subpopulation to more closely resemble that of the normal, non-immune disorder TH cell subpopulation.

The detection of the product or products of genes differentially expressed in a TH cell subpopulation in an immune disorder state relative to their expression in the TH cell subpopulation when the cell subpopulation is in a normal, or non-immune disorder, state can also be used for monitoring the efficacy of potential anti-immune disorder compounds during clinical trials. During clinical trials, for example, the level and/or activity of the products of one or more such differentially expressed genes can be determined for the TH cell subpopulation in the presence or absence of the compound being tested. The efficacy of the compound can be followed by comparing the protein level and/or activity data obtained to the corresponding known levels/activities for the TH cell subpopulation in a normal, non-immune disorder state. Compounds exhibiting efficacy are those which alter the pattern of the immune disorder TH cell subpopulation to more closely resemble that of the normal, non-immune disorder TH cell subpopulation.

Given the TH2-specific nature of the 103 gene, the detection of 103 gene transcripts and/or products can be particularly suitable for monitoring the efficacy of compounds in clinical trials for the treatment of TH2 cell subpopulation-related immune disorders such as, for example, asthma or allergy.

The expression patterns of the 105, 106 and 200 genes in TH1 cell subpopulations relative to TH2 cell subpopulations can make the detection of transcripts and/or products of these genes particularly suitable for monitoring the efficacy of compounds in clinical trials for the treatment of TH1 cell subpopulation-related immune disorders such as, for example, multiple sclerosis, psoriasis or insulin dependent diabetes.

Among the additional methods which can be utilized herein are methods for detecting TH cell responsiveness, for example, responsiveness to antigen, and for detecting activated immune cells, e.g., activated members of TH cell subpopulations. Detection methods such as these are important in that many immune disorders involve inappropriate rather than insufficient immune responses. Such detection methods can be used, for example, to detect a predisposition to an immune disorder.

Methods for detecting TH cell responsiveness and/or activation can comprise, for example, detecting in a TH cell sample a gene transcript or product which is differentially expressed in TH cell subpopulation which is in an activated or responsive state (e.g., a state in which the TH cell subpopulation has been exposed to antigen), relative to a TH cell subpopulation which is in an unactivated or nonresponsive state.

Any of the nucleic acid detection techniques described, below, in Section 5.11.1 or any of the peptide detection techniques described, below, in Section 5.11.2 can be used to detect such a differentially expressed gene transcript or gene product.

The TH2-specific nature of the 103 gene can make the detection of its gene transcripts and/or products particularly suitable for detecting activation and/or responsiveness of TH2 cells. Further, the TH1-specific nature of the 105, 106 and 200 genes can make the detection of transcripts and/or products of these genes particularly suitable for the detection of TH1 activation and/or responsiveness.

5.11.1 Detection of Fingerprint Gene Nucleic Acids

DNA or RNA from the cell type or tissue to be analyzed can easily be isolated using procedures which are well known to those in the art. Diagnostic procedures can also be performed "in situ" directly upon, for example tissue sections (fixed and/or frozen) of patient tissue obtained from biopsies or resections, such that no nucleic acid purification is necessary. Nucleic acid reagents such as those described in Section 5.4 can be used as probes and/or primers for such in situ procedures (see, for example, Nuovo, G. J., 1992, "PCR In Situ Hybridization: Protocols and Applications", Raven Press, New York). Expression of specific cells within a population of cells can also be determined, via, for example, in situ techniques such as those described above, or by standard flow cytometric techniques.

Fingerprint gene nucleotide sequences, either RNA or DNA, can, for example, be used in hybridization or amplification assays of biological samples to detect TH cell subpopulation-related disorder gene structures and expression. Such assays can include, but are not limited to, Southern or Northern analyses, single stranded conformational polymorphism analyses, in situ hybridization assays, and polymerase chain reaction analyses. Such analyses can reveal both quantitative aspects of the expression pattern of the fingerprint gene, and qualitative aspects of the fingerprint gene expression and/or gene composition. That is, such techniques can detect not only the presence of gene expression, but can also detect the amount of expression, particularly which specific cells are expressing the gene of interest, and can, further, for example, detect point mutations, insertions, deletions, chromosomal rearrangements, and/or activation or inactivation of gene expression.

Diagnostic methods for the detection of fingerprint gene-specific nucleic acid molecules can involve for example, contacting and incubating nucleic acids, derived from the cell type or tissue being analyzed, with one or more labeled nucleic acid reagents as are described in Section 5.4, under conditions favorable for the specific annealing of these reagents to their complementary sequences within the nucleic acid molecule of interest. Preferably, the lengths of these nucleic acid reagents are at least 15 to 30 nucleotides. After incubation, all non-annealed nucleic acids are removed from the nucleic acid:fingerprint molecule hybrid. The presence of nucleic acids from the cell type or tissue which have hybridized, if any such molecules exist, is then detected. Using such a detection scheme, the nucleic acid from the tissue or cell type of interest can be immobilized, for example, to a solid support such as a membrane, or a plastic surface such as that on a microtiter plate or polystyrene beads. In this case, after incubation, non-annealed, labeled nucleic acid reagents of the type described in Section 5.4 are easily removed. Detection of the remaining, annealed, labeled fingerprint nucleic acid reagents is accomplished using standard techniques well-known to those in the art.

Alternative diagnostic methods for the detection of fingerprint gene specific nucleic acid molecules can involve their amplification, e.g., by PCR (the experimental embodiment set forth in Mullis, K. B., 1987, U.S. Pat. No. 4,683, 202), ligase chain reaction (Barany, F., 1991, Proc. Natl. Acad. Sci. U.S.A. 88:189–193), self sustained sequence replication (Guatelli, J. C. et al., 1990, Proc. Natl. Acad. Sci. U.S.A. 87:1874–1878), transcriptional amplification system (Kwoh, D. Y et al., 1989, Proc. Natl. Acad. Sci. U.S.A. 86:1173–1177), Q-Beta Replicase (Lizardi, P. M. et al., 1988, Bio/Technology 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In one embodiment of such a detection scheme, a cDNA molecule is obtained from an RNA molecule of interest (e.g., by reverse transcription of the RNA molecule into cDNA). Cell types or tissues from which such RNA can be isolated include any tissue in which wild type fingerprint gene is known to be expressed, including, but not limited, to TH0, TH1 and/or TH2 cell type-containing tissues. A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the fingerprint gene nucleic acid reagents described in Section 5.4. The preferred lengths of such nucleic acid reagents are at least 9–30 nucleotides. For detection of the amplified product, the nucleic acid amplification can be performed using radioactively or non-radioactively labeled nucleotides. Alternatively, enough amplified product can be made such that the product can be visualized by standard ethidium bromide staining or by utilizing any other suitable nucleic acid staining method.

In addition to methods which focus primarily on the detection of one fingerprint nucleic acid sequence, fingerprint patterns can also be assessed in such detection schemes. Fingerprint patterns, in this context, contain the pattern of mRNA expression of a series (i.e., at least two and up to the total number present) of fingerprint genes obtained for a given tissue or cell type under a given set of conditions. Such conditions can include, for example, TH cell subpopulation-related disorders, and conditions relevant to processes involved in the differentiation, maintenance and effector function of TH cell subpopulations.

TH1-related disorders can include, for example, chronic inflammatory diseases and disorders, such as Crohn's disease, reactive arthritis, including Lyme disease, insulin-dependent diabetes, organ-specific autoimmunity, including multiple sclerosis, Hashimoto's thyroiditis and Grave's disease, contact dermatitis, psoriasis, graft rejection, graft versus host disease and sarcoidosis. TH2-related disorders can include, for example, atopic conditions, such as asthma and allergy, including allergic rhinitis, gastrointestinal allergies, including food allergies, eosinophilia, conjunctivitis, glomerular nephritis, certain pathogen susceptibilities such as helminthic (e.g., leishmaniasis) and certain viral infections, including HIV, and bacterial infections, including tuberculosis and lepromatous leprosy.

Fingerprint patterns can be generated, for example, by utilizing a differential display procedure, as discussed, above, in Section 5.1.1.2, Northern analysis and/or RT-PCR. Any of the gene sequences described, above, in Section 3.2.1 can be used as probes and/or RT-PCR primers for the generation and corroboration of such fingerprint patterns.

5.11.2 Detection of Target Gene Peptides

Antibodies directed against wild type or mutant fingerprint gene peptides, which are discussed, above, in Section 5.6, can also be used as TH cell subpopulation-related disorder diagnostics and prognostics, as described, for example, herein. Such diagnostic methods, can be used to detect fingerprint gene product, abnormalities in the level of fingerprint gene protein expression, or abnormalities in the structure and/or temporal, tissue, cellular, or subcellular location of fingerprint gene protein. Structural differences can include, for example, differences in the size, electronegativity, or antigenicity of the mutant fingerprint gene protein relative to the normal fingerprint gene protein.

Protein from the tissue or cell type to be analyzed can easily be isolated using techniques which are well known to those of skill in the art. The protein isolation methods employed herein can, for example, be such as those described in Harlow and Lane (Harlow, E. and Lane, D., 1988, "Antibodies: A Laboratory Manual", Cold Spring Harbor Laboratory Press, Cold Spring Harbor, N.Y.), which is incorporated herein by reference in its entirety.

Preferred diagnostic methods for the detection of wild type or mutant fingerprint gene peptide molecules can involve, for example, immunoassays wherein fingerprint gene peptides are detected by their interaction with an anti-fingerprint gene product-specific antibody.

For example, antibodies, or fragments of antibodies, such as those described, above, in Section 5.6, useful in the present invention can be used to quantitatively or qualitatively detect the presence of wild type or mutant fingerprint gene peptides. This can be accomplished, for example, by immunofluorescence techniques employing a fluorescently labeled antibody (see below, this Section,) coupled with light microscopic, flow cytometric, or fluorimetric detection. Such techniques are especially preferred if the fingerprint gene peptides are expressed on the cell surface, such as, for example, is the case with the 10 gene product, the 200 gene product and the transmembrane form of 103 gene product. Thus, the techniques described herein can be used to detect specific cells, within a population of cells, which express the fingerprint gene product of interest.

The antibodies (or fragments thereof) useful in the present invention can, additionally, be employed histologically, as in immunofluorescence or immunoelectron microscopy, for in situ detection of fingerprint gene peptides. In situ detection can be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fingerprint gene peptides, but also their distribution in the examined tissue. Using the present invention, those of ordinary skill will readily perceive that any of a wide variety of histological methods (such as staining procedures) can be modified in order to achieve such in situ detection.

Immunoassays for wild type or mutant fingerprint gene peptides typically comprise incubating a biological sample, such as a biological fluid, a tissue extract, freshly harvested cells, or cells which have been incubated in tissue culture, in the presence of a detectably labeled antibody capable of identifying fingerprint gene peptides, and detecting the bound antibody by any of a number of techniques well-known in the art.

The biological sample can be brought in contact with and immobilized onto a solid phase support or carrier such as nitrocellulose, or other solid support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on solid support can then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-wild type or mutant fingerprint gene product antibody can be determined according to well known methods. Those skilled in the art will be able to determine operative and optimal assay conditions for each determination by employing routine experimentation.

One of the ways in which the fingerprint gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1–7, Microbiological Associates Quarterly Publication, Walkersville, Md.); Voller, A. et al., 1978, J. Clin. Pathol. 31:507–520; Butler, J. E., 1981, Meth. Enzymol. 73:482–523; Maggio, E. (ed.), 1980, ENZYME IMMUNOASSAY, CRC Press, Boca Raton, Fla.; Ishikawa, E. et al., (eds.), 1981, ENZYME IMMUNOASSAY, Kgaku Shoin, Tokyo). The enzyme which is bound to the antibody will react with an appropriate substrate, preferably a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect fingerprint gene wild type or mutant peptides through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

6. EXAMPLE

Identification and Characterization of a TH2-Enriched Gene

In the Example presented in this Section, the transgenic T cell paradigm described, above, in Section 5.1.1.1, , was utilized to identify a gene, designated herein as the 102 gene, which is expressed in TH2 cells. The identified gene is present in TH2 cells at a much higher level than in TH1 cells. Thus, the Example presented herein demonstrates the usefulness of the paradigm approach of the invention for the identification of genes that are differentially expressed in TH cell subpopulations.

6.1 Materials and Methods

Transgenic mice: Naive CD4$^+$ cells were obtained from the spleens and/or lymph nodes of unprimed transgenic mouse strains harboring a T cell receptor (TCR) recognizing ovalbumin (Murphy et al., 1990, Science 250:1720).

Ova-specific transgenic T cells: Suspensions of ova-specific T cells were co-cultured with stimulatory peptide antigen and antigen presenting cells essentially as described in Murphy et al. (Murphy et al., 1990, Science 250:1720). Briefly, 2–4×10$^6$ T cells were incubated with approximately twice as many TA3 antigen presenting cells in the presence of 0.3 μM Ova peptide. TH1 cultures contained approximately 10 ng/ml recombinant mIL-12. Conversely, TH2 cells received IL-4 (1000 u/ml). Cultures were harvested at various time points after initiation of culture. T cells were purified of TA3 cells using anti-CD4 coated magnetic beads (Dynal, Inc.). T cells were pelleted by gentle centrifugation and lysed in the appropriate volume of RNAzol™ (Tel-Test, Friendswood, Tex.).

Tissue collection and RNA isolation: Cells were quick frozen on dry ice. Samples were then homogenized together with a mortar and pestle under liquid nitrogen.

Total cellular RNA was extracted from tissue with either RNAzol™ or RNAzolB™ (Tel-Test, Friendswood, Tex.), according to the manufacturer's instructions. Briefly, the tissue was solubilized in an appropriate amount of RNAzol™ or RNAzolB™, and RNA was extracted by the addition of 1/10 v/v chloroform to the solubilized sample followed by vigorous shaking for approximately 15 seconds. The mixture was then centrifuged for 15 minutes at 12,000 g and the aqueous phase was removed to a fresh tube. RNA was precipitated with isopropanol. The resultant RNA pellet was dissolved in water and re-extracted with an equal volume of chloroform to remove any remaining phenol. The extracted volume was precipitated with 2 volumes of ethanol in the presence of 150 mM sodium acetate. The precipitated RNA was dissolved in water and the concentration determined spectroscopically ($A_{260}$).

Differential display: Total cellular RNA (10–50 μg) was treated with 20 Units DNase I (Boehringer Mannheim, Germany) in the presence of 40 Units ribonuclease inhibitor (Boehringer Mannheim, Germany). After extraction with phenol/chloroform and ethanol precipitation, the RNA was dissolved in DEPC (diethyl pyrocarbonate)-treated water.

Differential mRNA display was carried out as described, above, in Section 5.1.1.2. RNA (0.4–2 μg) was reverse-transcribed using Superscript reverse transcriptase (GIBCO/BRL). The cDNAs were then amplified by PCR on a Perkin-Elmer 9600 thermal cycler. The reaction mixtures (20 μl) included arbitrary decanucleotides and one of twelve possible $T_{11}$VN sequences, wherein V represents either dG, dC, or dA, and N represents either dG, dT, dA, or dC. Parameters for the 40 cycle PCR were as follows: Hold 94° C. 2 minutes; Cycle 94° C. 15 seconds, 40° C. 2 minutes; Ramp to 72° 30 seconds; Hold 72° C. 5 minutes; Hold 4° C.

Radiolabelled PCR amplification products were analyzed by electrophoresis on 6% denaturing polyacrylamide gels.

Reamplification and subcloning: PCR bands of interest were recovered from sequencing gels and reamplified.

Briefly, autoradiograms were aligned with the dried gel, and the region containing the bands of interest was excised with a scalpel. The excised gel fragment was eluted by soaking in 100 μl TE (Tris-EDTA) buffer at approximately 100° C. for 15 minutes. The gel slice was then pelleted by brief centrifugation and the supernatant was transferred to a new microcentrifuge tube. DNA was combined with ethanol in the presence of 100 mM Sodium acetate and 30 μg glycogen (Boerhinger Mannhein, Germany) and precipitated on dry ice for approximately 10 minutes. Samples were centrifuged for 10 minutes and pellets were washed with 80% ethanol. Pellets were resuspended in 10 μl distilled water.

5 μl of the eluted DNA were reamplified in a 100 μl reaction containing: standard Cetus Taq polymerase buffer, 20 μM dNTPs, 1 μM of each of the oligonucleotide primers used in the initial generation of the amplified DNA. Cycling conditions used were the same as the initial conditions used to generate the amplified band, as described above. One-half of the amplification reaction was run on a 2% agarose gel and eluted using DE-81 paper (Whatman Paper, Ltd., England) as described in Sambrook et al., supra. Recovered fragments were ligated into the cloning vector pCR$^{\mathit{tm}}$II (Invitrogen, Inc., San Diego Calif.) and transformed into competent E. coli strain DH5α (Gibco/BRL, Gaithersburg, Md.). Colonies were grown on LB-agar plates containing ampicillin (100 μg/ml) and X-gal (40 μg/ml) to permit blue/white selection.

Sequence analysis: After subcloning, reamplified cDNA fragments were sequenced on an Applied Biosystems Automated Sequencer (Applied Biosystems, Inc. Seattle, Wash.). Sequence was obtained from four or more independent transformants containing the same insert. The nucleotide sequence shown herein represents either the consensus of the information obtained from the four sequences, or the sequence obtained from a representative clone, as indicated.

Such primary sequence data was edited and trimmed of vector sequences and highly repetitive sequences and used to search Genbank databases using the BLAST (Altschul, S. F. et al., 1990, J. Mol. Biol. 215:403–410) program.

Northern analysis: RNA samples were electrophoresed in a denaturing agarose gel containing 1–1.5% agarose (SeaKem™ LE, FMC BioProducts, Rockland, Me.) containing 6.3% formaldehyde. Samples containing 5–20 μg of total RNA were mixed with denaturing loading solution (72% deionized formamide and bromophenol blue) and heated to 70° C. for 5 minutes. Samples were placed on ice and immediately loaded onto gels. Gels were run in 1× MOPS buffer (100 mM MOPS, 25 mM sodium acetate, 5 mM EDTA). After electrophoresis, the gels were stained with ethidium bromide and visualized with ultraviolet light.

After completion of electrophoresis, gels were soaked in 50 mM sodium hydroxide with gentle agitation for approximately 30 minutes to lightly cleave RNA. Gels were rinsed twice in water and then neutralized by soaking in 0.1M Tris-HCl (pH 7.5) for approximately 30 minutes. Gels were briefly equilibrated with 20× SSC (3M sodium chloride, 0.3M sodium citrate) and then transferred to nylon membranes such as Hybond™,-N, (Amersham, Inc., Arlington Heights, Ill.) or Zeta-Probe (Bio-Rad, Inc., Hercules, Calif.) overnight in 20× SSC. Membranes containing transferred RNA were baked at 80° C. for 2 hours to immobilize the RNA.

DNA fragments to be used as probes were of various sizes and were labeled using a random hexamer labeling technique. Briefly, 25 ng of a purified DNA fragment was used to generate each probe. Fragments were added to a 20 μl random hexanucleotide labeling reaction (Boehringer Mannhein, Inc., Indianapolis, Ind.) containing random hexamers and a mix of the nucleotides dCTP, dGTP, and dTTP (at a final concentration of 25 μM each). The reaction mix was heat-denatured at 100° C. for 10 minutes and then chilled on ice. 5 μl of α-$^{32}$P-dATP (50 μCi; Amersham, Inc., Arlington Heights, Ill.) and Klenow DNA polymerase (2 units; Boehringer Mannheim, Inc., Indianapolis, Ind.) were added. Reactions were incubated at 37° for 30 minutes. Following incubation, 30 μl water was added to the labeling reaction and unincorporated nucleotides were removed by passing the reactions through a BioSpin-6™ chromatography column (Bio-Rad, Inc., Hercules, Calif.). Specific incorporation was determined using a scintillation counter. 1–5× $10^6$ cpm were used per ml hybridization mixture.

Nylon membranes containing immobilized RNA were prehybridized according to manufacturer's instructions. Radiolabelled probes were heat denatured at 70° C. in 50% deionized formamide for 10 minutes and ten added to the hybridization mixture (containing 50% formamide, 10% dextran sulfate, 0.1% SDS, 100 μg/ml sheared salmon sperm DNA, 5× SSC, 5× Denhardt's solution, 30 mM Tris-HCl (pH 8.5), 50 mM NaPO$_4$ (pH 6.5). Hybridizations were carried out at 42° C. overnight. Nylon membranes were then bathed for 2 minutes in a wash solution of 0.2× SSC and 0.1% SDS at room temperature to remove most of the remaining hybridization solution. The membranes were then bathed twice in fresh 42° C. preheated wash solution for 20 minutes. Filters were covered in plastic wrap and exposed to autoradiographic film to visualize results.

6.2 Results

A transgenic T cell paradigm (as described, above, in Section 6.1) was utilized to identify genes which are differentially expressed between TH1 and TH2 cells.

RNA samples were isolated from TH1 and TH2 cell populations after either secondary or tertiary antigen stimulation. The samples were then analyzed via differential display techniques. FIG. 1 shows amplified fragments obtained from these samples, with the arrow indicating a PCR product, designated band 102, which was judged to represent a cDNA derived from RNA produced by a gene which is expressed at a higher level in TH2 cell subpopulations, relative to TH1 cell subpopulations. The gene corresponding to band 102 is referred to herein as the 102 gene.

The amplified band 102 cDNA was recovered, reamplified, subcloned into a cloning vector and sequenced, as described, above, in Section 6.1. The nucleotide sequence (SEQ ID NO:1) of a representative band 102 clone, specifically, clone 102.1, is shown in FIG. 2.

A BLAST (Altschul, S. F. et al., 1990, J. Mol. Biol. 215:403–410) database search with this consensus sequence resulted in an alignment with 98% identity to the mouse Granzyme A, or Hanukah factor, gene, (Masson, D. et al., 1986, FEBS Lett. 208:84–88; Masson, D. et al., 1986, EMBO J. 5:1595–1600; Gershenfeld, H. K. and Weissman, I. L., 1986, Science 232:854–858), which encodes a trypsin-like serine protease. The human homolog of this gene is also known (Gershenfeld, H. K. et al., 1988, Proc. Natl. Acad. Sci. U.S.A. 85:1184–1188).

To confirm the gene's putative differential regulation, amplified band 102 cDNA was used to probe Northern RNA blots containing RNA samples from TH1 and TH2 cell lines, and from spleen and thymus tissue. FIG. 3 shows the results of one such Northern blot analysis, in which the steady state level of message for 102 gene mRNA are significantly increased in RNA samples derived from stimulated TH2 versus TH1 samples. Further, the positive signals in both thymus and spleen RNA samples supports the indication that the 102 gene product is involved in some aspect of T cell function. Thus, the Northern analysis confirmed the putative differential TH2 regulation which had been suggested by the differential display result.

Therefore, by utilizing the transgenic T cell paradigm described in this Section and in Section 5.1.1.1, above, a TH2 differentially regulated gene, designated here the 102 gene, and corresponding to the mouse Granzyme A/Hanukah factor gene, has been identified, thereby corroborating the usefulness of such paradigms in identifying genes expressed preferentially in T helper cell subpopulations such as TH1 or TH2 cell populations.

Further, while the gene identified here had previously been found to be expressed in natural killer T cells and, further, had been reported to be expressed in a fraction of CD4$^+$ cells (Fruth, U. et a;., 1988, Eur. J. Imm. 18:773–781; Liu, C. C. et al., 1989, J. Exp. Med. 170:2105–2118), the results described herein represent the first instance in which a TH cell subpopulation role for this gene has been found. Prior to this study, the gene had been reported to be expressed in T cells in a variety of situations, including TH1 cell subpopulation- and TH2 cell subpopulation-related disorders. For example, Granzyme A/Hanukah factor expression has been reported in allograft rejection (Muller, C. et al., 1988, J. Exp. Med. 167:1124–1136) and autoimmune diseases (Ojcius, D. M. and Young, D. E., 1990, Cancer Cells 2:138–145; Young, L. H. Y. et al., 1992, Am. J. Path. 140:1261–1268), which are TH1 cell subpopulation-related disorders, and also in Leishmania infection susceptible mice (Moll, H. et al., 1991, Inf. and Imm. 59:4701–4705) and in leprosy lesions (Ebnet, K. et al., 1991, Int. Imm. 3:9–19;

Cooper, C. L. et al., 1989, J. Exp. Med. 169:1565–1581), which are both TH2 cell subpopulation-related disorders.

The differential TH2-like expression demonstrated here represents, therefore, the first molecular evidence clearly indicating a more primary role for the gene product in TH2 versus TH1 cell subpopulations.

7. EXAMPLE

Identification and Characterization of a TH2-Specific Gene

In the Example presented in this Section, the transgenic T cell paradigm, described, above, in Sections 5.1.1.1 and 6, was utilized to identify a gene which is differentially expressed in TH2 cells. Specifically, this gene is present in TH2 cells while being completely absent from TH1 cells. The gene, which corresponds to a gene known, alternatively, as ST-2, T1 and Fit-1, does not appear to be expressed in any other assayed cell type or tissue, and is demonstrated here for the first time to encode a marker which is, in vivo, completely TH2-specific. The 103 gene encodes a cell surface protein, the potential significance of which is discussed herein.

7.1 Materials and Methods

RT-PCR analysis: Quantitative RT-PCR was performed as follows. 1–2 μg of total RNA, prepared as described, above, in Section 6.1, was reverse transcribed with oligo $dT_{(12-18)}$ primers and Superscript™ RNAase H⁻ reverse transcriptase (Gibco-BRL, Gaithersburg, Md.). Briefly, RNA was combined with 1 μl oligo dT (500 μg/ml) in a total volume of 11 μl. The mixture was heated to 70° C. for 10 minutes and chilled on ice. After a brief centrifugation, RNA was reverse transcribed for 1 hour. Aliquots of the first strand cDNA were stored at −20° C. until just prior to use.

Expression levels were determined by PCR amplification of serial dilutions of first strand cDNA. In this procedure, cDNA is serially diluted in water. The dilutions are then batch amplified by PCR using sequence-specific primers. All PCR reactions are amplified under identical conditions. Therefore, the amount of product generated should reflect the amount of sequence template which was initially present. 5–10 fold dilutions of cDNA were used and enough dilutions were used such that the amount of product subsequently produced ranged from clearly visible, by UV illumination of ethidium bromide-stained gels, to below detection levels. The method described herein can distinguish 10-fold differences in expression levels.

Primers were designed for the amplification of the sequenced amplified bands, which were chosen using the program OLIGO (National Biosciences, Plymouth, Minn.). Primer sequences used in this assay were as follows: and 103 sense primer, 5'-TTGCCATAGAGAGACCTC-3' (SEQ ID NO:18); band 103 antisense primer, 5'-TGCTGTCCAATTATACAGG-3' (SEQ ID NO:19); murine gamma actin sense primer, 5'-GAACACGGCATTGTCACTAACT-3' (SEQ ID NO:20); murine gamma actin antisense primer, 5'-CCTCATAGATGGGCACTGTGT-3' (SEQ ID NO:21).

All quantitative PCR reactions were carried out in a 9600 Perkin-Elmer PCR machine (Perkin-Elmer). Generally, amplification conditions were as follows: 30–40 cycles consisting of a 95° C. denaturation for 30 seconds, 50–60° C. annealing for 30 seconds, and 72° C. extension for 1 minute. Following cycling, reactions were extended for 10 minutes at 72° C.

RNase Protection Assays: RNAse protection assays were performed according to manufacturer's instructions, using a kit purchased from Ambion, Inc. RNA probes derived from GenBank Accession No. Y07519 were utilized in the RNAse protection assays. These probes were also generated according to manufacturer's instructions, using a kit purchased from Ambion, Inc. The sequence of these RNA probes corresponds to the 5' end of the gene, and includes both coding and 5' untranslated sequences.

Anti CD-3 stimulation: Conditions were as described, below, in Section 8.1.

Other Procedures: All other cell sample collection, RNA isolation, differential display, sequence analysis, and Northern procedures performed in the experiments described in this Example were as described, above, in Section 6.1.

7.2 Results

A differential display analysis of RNA isolated from TH1 and TH2 cell samples obtained from a transgenic T cell paradigm study as described, above, in Section 6.1. Specifically, TH cells were obtained from transgenic mice harboring a T cell receptor recognizing ovalbumin (Murphy et al., 1990, Science 250:1720) were stimulated three times, and RNA was obtained from TH1 and TH2 cells. Differential display analysis of the RNA samples resulted in the identification of a TH2 differentially expressed band, designated and referred to herein as band 103. The gene corresponding to band 103 is referred to herein as the 103 gene.

103 gene cDNA was isolated, amplified and subcloned, and nucleotide sequence (SEQ ID NO:2) was obtained, as shown in FIG. 4A. A database search revealed that the nucleotide sequence of band 103 resulted in an alignment with 98% identity to the mouse form of a gene known, alternatively, as the ST-2, T1 or Fit-1 gene (Klemenz, R. et al., 1989, Proc. Natl. Acad. Sci. U.S.A. 86:5708–5712; Tominaga, S., 1989, FEBS Lett. 258:301–301; Werenskiold, A. K. et al., 1989, Mol. Cell. Biol.9:5207–5214; Werenskiold, A. K., 1992, Eur. J. Biochem. 204:1041–1047; Yanagisawa, K. et al., 1993, FEBS Lett. 318:83–87; Bergers, G. et al., 1994, EMBO J. 13:1176–1188).

The 103 gene encodes, possibly via alternatively spliced transcripts, transmembrane and soluble forms of proteins which belong to the immunoglobulin superfamily. The soluble form of the protein shows a high level of similarity to the extracellular portion of the mouse interleukin-1 receptor type 1 (IL-1R1) and interleukin-1 receptor type 2 (IL-1R2; which lacks a cytoplasmic domain), while the transmembrane portion (termed ST2L) bears a high resemblance to the entire IL-1R1 sequence and to the extracellular IL-1R2 sequences. Further, the 103 gene appears to be tightly linked to the interleukin 1 receptor-type 1 locus (McMahon, C. J. et al., 1991, EMBO J. 10:2821–2832; Tominaga, S. et al., 1991, Biochem. Biophys. Acta. 1090:1–8). Additionally, the human 103 gene homolog has also been reported (Tominaga, S. et al., 1992, Biochem. Biophys. Acta. 1171:215–218). FIG. 4B illustrates the 103 gene transmembrane and soluble forms of protein, and shows their relationship to the IL-1R1 protein sequence.

A quantitative RT-PCR analysis (FIG. 5) of RNA obtained from cells of a TH1 and TH2 cells, generated as described above, 24 hours after tertiary antigen stimulation not only confirmed the putative TH2 differential expression of the gene, but, revealed that the expression of the 103 gene appears to be TH2 specific, i.e., the sensitive RT-PCR study detected no 103 gene message in the TH1 RNA sample.

The TH2 specificity of the 103 gene was further confirmed by a Northern analysis of several representative TH cell lines. Specifically, three TH2 clones (CDC25, D10.G4, DAX) and three TH1 clones (AE7.A, Dorris, D1.1) were utilized and RNA samples were isolated from either unstimulated cells or from cells which had been stimulated for 6 hours with plate-bound anti-CD3 antibody. The samples were probed with band 103 sequences, as shown in FIG. 6. While 103 gene RNA is present in RNA obtained from both unstimulated and stimulated cells of each of the TH2 cell lines, 103 gene RNA is completely absent from all of the samples obtained from either stimulated or unstimulated TH1 cells. As the RT-PCR analysis described above first demonstrated, the 103 gene appears to be TH2 specific, with no detectable TH1-derived signal being present.

The data presented in FIG. 7 represent an additional Northern analysis in which 103 gene expression was assayed in TH cell clones (lanes 1–5) and in murine tissues (lanes 6–10). In addition to corroborating the expression of 103 gene RNA in both stimulated and unstimulated TH2 cells, the data presented here demonstrate that 103 gene expression appears to be negative in each of the tissues (i.e., brain, heart, lung, spleen, and liver) tested.

FIG. 8 illustrates an RNAse protection assay which demonstrates two points regarding 103 gene regulation. First, this analysis of TH cell clones confirms the TH2-specific results described, above. Specifically, the results of this study demonstrate by RNase protection, that 103 gene mRNA is absent from the TH1 clone AE7, but is present in the TH2 clone D10.G4.

Second, RNAse protection revealed that alternate forms of 103 gene transcripts are produced upon stimulation of TH2 clones. Specifically, within 6 hours of anti-CD3 stimulation, two additional forms of 103 gene transcript appear in TH2 clones. These additional 103 gene transcript forms represent, one, a transcript encoding a shortened, secreted, soluble form of the band 103 gene product, and, two, a smaller, termed mini, transcript which encodes a yet shorter form of the gene product. Thus, it appears that, while the 103 gene transcript encoding the transmembrane gene product is expressed in both unstimulated and stimulated TH2 cells, the two shorter forms of transcript are expressed in a TH2-specific inducible manner. Further, while the 103 gene transcript encoding the transmembrane product are expressed in both unstimulated and stimulated TH2 cells, the level of this transcript present in stimulated is lower, i.e., is downregulated. Thus, the lower level of transmembrane product and higher level of secreted 103 gene product can act synergistically to dampen some stimulation-induced signal transduction event.

Additionally, it should be noted that the results presented herein represent the first time the mini form of 103 gene transcript, which can encode a shorter version of the soluble form of 103 gene product, has been observed.

To summarize, while 103 gene expression in T helper cell lines had previously been reported (Tominaga, S. et al., 1992, Biochem. Biophys. Acta. 1171:215–218), the TH paradigm/differential display techniques utilized here have demonstrated, for the first time, that the 103 gene encodes a TH2 cell subpopulation-specific surface marker. In fact, the results described in this Example demonstrate that the first identification of any in vivo TH cell subpopulation-specific cellular marker.

Given its status as both a TH2 cell subpopulation-specific marker and cell surface protein, the full length 103 gene product can be utilized in a variety of methods to modulate TH cell subpopulation-related disorders and/or to identify compounds which exhibit such modulatory capability. The truncated forms of the 103 gene products can, additionally, be used as part of these methods. Modulatory methods are described, above, in Section 5.9, while strategies for the identification of modulatory compounds are described, above, in Section 5.8.

8. EXAMPLE

Identification of Novel TH Cell Subpopulation Differentially Expressed Genes In the Example presented in this Section, novel gene sequences representing genes which are differentially expressed in TH cell subpopulations and/or during the differentiation of such subpopulations are described.

8.1 Materials and Methods

T cell clone paradigm: T cell clone paradigm searches were conducted as described, above, in Section 5.1.1.1. Specifically, the TH cell clone paradigms used three different clones: D10.G4 (TH2), AE7 (TH1) and D1.1 (TH1). Prior to stimulation, cell cultures were enriched for live cells by centrifugation through a Ficoll gradient. Recovered cells were counted and their viability was examined using trypan blue exclusion. Cells were replated into either T25 or T75 flasks at approximately $5 \times 10^6$ cells in 5 mls or $1.5 \times 10^6$ cells in 10 mls of culture medium, respectively.

Coating was performed, generally, according to Current Protocols in Immunology, 1992, Coligan, J. E. et al., John Wiley & Sons, New York, pp 3.12.4–3.12.6). Specifically, prior to plating, the flasks were coated with anti-CD3-$\epsilon$ antibodies (hybridoma supernatant from the 145-C11 hybridoma; Parmingen, Inc., San Diego Calif.). For coating, antibodies were resuspended in PBS at 1–2 $\mu$g/ml at a volume sufficient to coat the bottom of the flasks. Coating solution was incubated on the flasks for at least one hour at 37° C.

After incubation, the antibody coating solution was removed by aspiration and cells were immediately added. Flasks were placed in a 37° C. incubator for 6 hours. Cells were harvested by, for example, removal of supernatant from the culture, followed by direct lysing of cells by addition of RNAzol™ solution. cDNA was produced as described below.

cDNA isolation: RNA was harvested from cells using techniques described, above, in Section 6.1. mRNA was purified directly, using a QuickPrep™ mRNA Purification Kit (Pharmacia) according to manufacturer's instructions.

The TH1 cDNA library was constructed using a Gibco BRL SuperScript™ Lambda System Kit, according to manufacturer's instructions. Briefly, 4.5 $\mu$g of purified mRNA was used as starting material for the synthesis of poly A-primed first strand cDNA containing a Not-1 cloning site. Second strand cDNA synthesis was performed with RNAse H treatment followed by random priming. Sal-1 adaptors were ligated to the 5' end of the resulting double-stranded cDNA. The ligated cDNA was digested with Not-1 and size fractionated. Fractions containing cDNAs within the size range of 0.5 to 8.0 kb in length were cloned into Sal-1/Not-1 λZipLox™ arms. Recombinant phage was then packaged using the Stratagene Gigapack™ II Packaging Extracts Kit, according to manufacturer's instructions. *E. coli* strain Y 1090(ZL)™ (Gibco BRL) cells were transformed with packaged recombinant phage and plated at a density of 50,000 pfu per 150 mm dish. Plaques were screened by hybridization to a radiolabelled probe generated from a subcloned band 200 cDNA fragment. Excision of cDNA inserts from lambda clones and introduction of the recombinant plasmid DNA into *E. coli* DH10B(ZIP)™ (Gibco BRL) was performed according to manufacturer's instructions.

For isolation of 200 gene cDNAs, the cDNA library was screened with a probe generated by labeling the entire sequence of the band 200 subclone O, which was constructed using amplified DNA obtained from the differential display analysis. The band 200 sequence was excised from the pCRII Cloning Vector™ (Invitrogen) by digestion with EcoRI. Approximately 1/100,000 cDNA library plaques were scored as positive when screened with this probe. Several clones, including 200-P and 200AF, were chosen for further study.

The cDNA library described above was also used to isolate 54 gene cDNA clones. For screening, the entire excised band 54 insert was used as a probe.

Other procedures: All transgenic T cell manipulations, cell sample collection, additional RNA isolation, differential display, sequence analysis, and Northern procedures performed in the experiments described in this Example were as described, above, in Section 6.1.

8.2 Results

Transgenic T cell paradigm and T cell clone paradigm searches were conducted to identify gene sequences which represent genes differentially expressed within and/or among TH cell subpopulations and/or during the differentiation of such subpopulations. Described herein are several novel genes which have been identified via these paradigm searches. Specifically, the genes described herein have been designated the 10, 54, 57, 105, 106, 161 and 200 genes. A summary of the differential expression characteristics of the novel gene sequences described herein is presented in Table 1, above.

The band 10 and 57 have been identified as TH inducible gene sequences. That is, the expression of such genes in unstimulated TH cells is either undetectable or is detectable at extremely low levels, but is upregulated in both stimulated TH1 and TH2 cells. In fact, the 10 gene expression is detectable as early as 6 hours post stimulation. Thus, such gene products can be involved in the activation of TH cells and/or can be involved in the maintenance of mature TH cell function, in a non-TH cell subpopulation-specific manner.

FIGS. 9A–9D depicts the nucleotide sequence (SEQ ID NO:3) of the 10 gene coding region and the derived amino acid sequence of the 10 gene product (SEQ ID NO:10). While database searches reveal that the 10 gene sequence is novel, that is, has not previously been reported in the databases, an analysis of the portion of the 10 gene corresponding to the band 10 nucleotide sequence (the underlined portion of the nucleotide sequence of FIGS. 9A–9D) shows, as depicted in FIGS. 10A–10F, a high similarity to a specific class of known gene products. Specifically, as the hydrophilicity plots of FIGS. 10A–10F show, the 10 gene product appears to encode a protein having a seven transmembrane domain sequence motif. Interestingly, the gene products belonging to this class of protein tend to represent G protein-coupled receptor molecules. (See, e.g., Larhammar, D. et al., 1992, J. Biol. Chem. 267: 10935–10938; Law, S. F. et al., 1991, J. Biol. Chem. 266: 17885–17991.) Thus, the TH inducible expression of the 10 gene coupled with the predicted protein structure of its gene product, suggests that the 10 gene product is involved in a signal transduction event important to the differentiation of mature TH cells.

Additionally, as the map shown in FIG. 11 indicates, the chromosomal location of the murine 10 gene has been identified. The 10 gene locus is located on Chromosome 12, is closely linked to a class of genes encoding T cell autoantigens, and additionally, maps near the Ig heavy chain gene locus.

The nucleotide sequence (SEQ ID NO:4) of a representative band 57 clone is depicted in FIG. 12. The gene corresponding to band 57 is the 57 gene. The 57 gene appears to be a novel gene sequence in that it does not appear within the published databases. No homology to known peptide domains has, thus far, been identified.

As shown in Table 1, above, the genes 105, 106 and 200 are each expressed at a higher level within the TH1 cell subpopulation, as revealed by the TH1 differential appearance of amplified bands 105, 106 and 200. Nucleotide sequences contained within bands 105 and 106 are depicted in FIGS. 13 (SEQ ID NO:5) and 14 (SEQ ID NO:6), respectively. As discussed below, the sequence of the murine 200 gene is depicted in FIGS. 17A–17D (SEQ ID NO:8). None of these sequences appear within published databases. Given the TH1-specific expression pattern each of these sequences exhibits, the genes and their gene products can potentially be used as treatments for TH1-related disorders, as diagnostics for such disorders, and/or as part of methods for the identification of compounds capable of ameliorating TH1-related disorders.

The 161 gene appears to be TH cell subset specific. That is, 161 gene expression has been observed in either TH1 cells or in TH2 cells, but its expression has never been observed, simultaneously, in both TH1 and TH2 cell subpopulations. The details of the 161 gene differential expression pattern are currently being elucidated. It is possible that 161 gene expression is indicative of the presence of yet another TH cell subpopulation, in addition to TH1, TH2 and TH0 cell subpopulations.

FIG. 15 presents the band 161 nucleotide sequence. While the 161 gene appears to be a novel sequence, it bears a distinct level of similarity to a set of gene sequences (SEQ ID NOS:13–17) in published databases, as shown in FIG. 16. Interestingly, the genes within this group each contain alpha-interferon responsive promoters.

Band 200 was utilized as a probe to identify and isolate murine 200 gene cDNA clones, including clones designated 200-P, 200-AF and 200-O, which have been deposited with the NRRL, as summarized in Section 10, below. The cDNA clones were characterized, yielding the full length nucleotide sequence (SEQ ID NO:8) of the murine 200 gene coding region, as shown in FIGS. 17A–17D. FIGS. 17A–17D also depicts the murine 200 gene product derived amino acid sequence (SEQ ID NO:10). Database searches reveal that the 200 gene product is a novel receptor which contains an extracellular Ig domain, thus placing it within the Ig receptor superfamily. The cloning and characterization of the 200 gene human homolog is described in the Example presented in Section 9, below.

The results of a murine 200 gene mRNA Northern blot analysis are shown in FIG. 18. The data depicted in FIG. 18 demonstrates, first, that the 200 gene produces a transcript of approximately 1.2 kb in length, and, second, illustrates the TH1 specificity of 200 gene expression For the study, three TH1 clones (D1.1, Dorris, AE7) and three TH2 clones (D10G.4, DAX, CDC25) were utilized, and RNA samples were isolated from either unstimulated cells (−) or cells which had been stimulated for 6 hours with plate-bound anti-CD3 antibody (+). The samples were probed with 200 gene sequences, and, as shown in FIG. 18, RNA from both stimulated and unstimulated TH1 cells contained 200 gene mRNA, while none of the samples obtained from TH2 cells contained 200 gene mRNA. It should also be noted that 200 gene expression was higher in each of the stimulated TH1 cells relative to the corresponding unstimulated TH1 cells.

As shown in Table 1, above, the 54 gene is expressed in a TH1-restricted manner. The 54 gene was identified via T cell paradigm searches in which the expression pattern of a TH1 cell clone, AE7, was compared to that of a TH2 cell clone, D10.G4. The initial differential expression analysis was performed using differential display techniques, as described, above, in Section 6.1.

The TH1-restricted pattern of the 54 gene expression was corroborated through Northern analysis of RNA isolated from TH1 cell lines (AE7, D1.1, Dorris) and TH2 cell lines (D10.G4, DAX, CDC25), as shown in FIG. 19. The TH1/TH2 Northern blot data depicted in FIG. 19 additionally illustrates 54 gene expression within cell clones either stimulated or unstimulated with anti-CD3 antibodies, and demonstrates that 54 gene expression goes down within stimulated TH1 cells.

To further characterize the 54 gene expression, a detailed time course study was conducted using RNA isolated from AE7 clones. Specifically, RNA was isolated from unstimulated AE7 clones as well as from AE7 clones which had been stimulated with anti-CD3 antibodies for varying lengths of time, as noted in FIG. 20. As illustrated in FIG. 20, 54 gene expression decreased slightly by 2–6 hours after stimulation and had not again achieved pre-stimulation levels within 48 hours after stimulation.

A 54 gene expression analysis of cell lines representing a variety of T cells, B cells and monocytic/macrophage cell lines was performed which failed to detect 54 gene expression in non-TH1 cells, demonstrating that 54 gene expression is highly restricted to TH1-like cells. A Northern analysis of 54 gene expression within tissues (FIG. 21), also demonstrated an expression profile consistent with that of a TH1 cell-restricted expression profile. Namely, as shown in FIG. 21, most organs failed to express the 54 gene, while the highest level of 54 gene expression was seen in lymph node tissue, and lowest detectable level of expression was seen in spleen, testis and uterus.

Band 54 nucleotide sequence, which had been obtained from the amplified cDNA produced in the initial differential display analysis in which the 54 gene was identified, was used to isolate seven cDNA clones, designated 54A–G. Each of the clones were of similar size. The 54-C cDNA has been deposited with the NRRL within the *E. coli* clone, 54-C.

FIGS. 22A–22C shows the entire 54 gene coding sequence (SEQ ID NO:11). The derived amino acid sequence of the 54 gene product is also shown in FIGS. 22A–22C (SEQ ID NO:12). Based on database homology searches, the 54 gene appears to encode a novel cysteine protease. Cysteine proteases are enzymes which contribute to intracellular protein degradation and appear to play a role in tissue degradation. It is possible, therefore, that the inhibition of 54 gene expression and/or 54 gene product activity in immune disorders involving TH1-like cells may serve to minimize any tissue damage.

Specifically, the 54 gene sequence exhibits the three thiol protease domains typical of active cysteine protease enzymes. These domains include a CYS domain at approximately amino acid residue 145 to 156 (active site: C, position 151), a HIS domain at approximately amino acid residue 287 to 297 (active site: H, position 289), and an ASN domain at approximately amino acid residue 321 to 340 (active site N, position 326). Interestingly, the typical CYS domain is broken by a K residue at position 149 (this position is usually G or E), perhaps indicating that the 54 gene product cysteine protease is very substrate-specific. Additionally, amino acid sequence analysis indicates probable disulfide bonds between cysteines at 148 and 189, 182 and 224 and 282 and 347. Further, FIGS. 23A–23C depicts the 54 gene product amino acid sequence and points out some of its potential cysteine-protease-like features. For example, the 54 gene product has an amino terminal end which resembles a cysteine protease preproenzyme region, which is cleaved away upon formation of the active cysteine protease. The boxed region, from amino acid residue 56 to 75 represents an "ERFNIN" region which has previously been noted as a feature of several cysteine proteases (Ishidoh, K. et al., 1987) FEBS Lett. 226:33–37). The circled amino acid residues within the boxed region represent conserved amino acid residues. The individual boxed amino acid residues represent residues that, based on homology, are thought to lie within the active site of the enzyme.

9. EXAMPLE

Identification and Characterization of Human 200 Gene

In the Example presented herein, the cloning, identification and characterization of the human 200 gene, corresponding to the human homolog of the murine 200 gene, is described.

9.1 Materials and Methods

Murine 200 gene probe: An approximately 800 bp EcoRI insert containing about 90% of the murine 200 gene cDNA (femt200) ORF was gel purified, $^{32}$P labelled, and used to probe the λgt11 human lymphocyte cDNA library described below.

Human 200 gene probe: The approximately 500 bp insert of the human 200 gene feht200a cDNA clone was $^{32}$P labelled and used to probe the human fetal spleen cDNA library described below.

Screening procedures: Approximately $10^6$ plaques of a λgt11 human lymphocyte cDNA library (Catalog No. HL 1031B; Clontech) were screened with murine 200 gene probe described above in duplicate. The filters were hybridized with probe overnight at 65° C. in Church's buffer (7% SDS, 250 mM NaHPO$_4$, 2 μM EDTA, 1% BSA). The next day, filters were washed in 2×SSC/1% SDS for 30 min at 50° C. The filters were then exposed to Kodak film at −80° C. Positive plaques were rescreened under the same conditions.

A human fetal spleen cDNA library constructed using the Stratagene Uni-Zap cloning System was screened using the human feht200a gene probe described above. Approximately $10^6$ plaques were hybridized in duplicate at 65° C. in Church's buffer overnight. The filters were then washed for 30 min at 65° C. in 0.1×SSC,0.1% SDS and exposed to film. Positives were confirmed by secondary screening under the same conditions.

Subcloning/Sequencing procedures: DNA from the positive clones obtained from the λgt11 cDNA library was generated by a plate lysis method. The purified DNA was digested to obtain cDNA inserts which were subcloned into the pBluescript plasmid (Stratagene).

Positive clones obtained from the human fetal spleen cDNA library were excised with ExAssist helper phage, XL1-Blue cells and SOLR cells as described by Stratagene. Excision products were then plated out on LB/Amp plates and incubated at 37° C. overnight. White colonies were picked and DNA prepared for sequencing.

DNA sequencing was performed according to standard techniques.

Northern blot analysis of human gene 200 expression: Northern blots were carried out as described in Section 6.1, above. 15 µg of total RNA from a variety of human organs were analyzed (Clontech, California). The $^{32}$P labelled probe utilized was the feht200a clone, described above, which contains the 5' ORF of human gene 200.

9.2 Results

The full length sequence of the human 200 gene was successfully cloned and characterized, as described herein.

In order to clone human 200 gene, an 800 bp EcoRI insert containing approximately 90% of the murine 200 gene cDNA (femt200) ORF was gel purified, $^{32}$P labelled, and used to probe a λgt11 human lymphocyte cDNA library. Approximately $10^6$ plaques were screened in duplicate, as described in Section 9.1, above. One positive plaque was obtained and rescreened under the same conditions. Once pure, this clone was used to generate lambda DNA by a plate lysis method, and the lambda DNA was digested to obtain a 500 bp insert (feht 200a) which, upon sequencing, was found to be a human homologue of the murine 200 gene.

To obtain a clone encoding the entire ORF of the human 200 gene, a human 200 gene probe was used to screen a human fetal spleen cDNA library, as described in Section 9.1., above. Three positive clones were obtained, two of which were positive upon secondary screening under the same conditions. The two positive clones were subcloned and their cDNA inserts were sequenced. These two clones labelled feht200b and feht200c were approximately 1.56 kb and 2.0 kb in length, respectively with feht200c containing the entire coding sequence. Clone feht200c was deposited with the ATCC, as described, below, in Section 12.

The nucleotide sequence containing the complete human 200 gene open reading frame is depicted in FIGS. 24A–24D (SEQ ID NO: 23). The derived amino acid sequence of the human 200 gene product is also depicted in FIGS. 24A–24D (SEQ ID NO: 24).

The 301 amino acid residue sequence of the human 200 gene product reveals that it is a cell surface receptor exhibiting distinct domains, including a signal sequence from amino acid residue 1 to approximately 20, an extracellular domain from approximately amino acid residue 21 to 200, a transmembrane domain from approximately amino acid residue 201–224 and a cytoplasmic domain from approximately amino acid 225 to 301. The extracellular domain contains an Ig type variable set domain from approximately amino acid residue 30 to approximately amino acid residue 128, thus placing the 200 gene product within the Ig receptor superfamily.

A Northern analysis of the tissue distribution of 200 gene transcripts was performed. 15 µg RNA from brain, kidney, liver, lung, muscle, prostate, spleen, thymus and trachea were isolated and analyzed for human 200 gene expression. This analysis revealed human 200 gene transcripts of approximately 2.2 kb, in tissues including brain, lung, trachea, spleen and thymus.

In summary, the human 200 gene, corresponding to the human analog of the murine 200 gene, has been successfully cloned and characterized, as described herein. As revealed by its amino acid sequence, the human 200 gene product is a receptor of the Ig superfamily class of molecules.

10. EXAMPLE

Construction and Expression of IgG1 Fusion Proteins

Described in this Example is the construction and expression of IgG1 fusion proteins. Specifically, the construction of human and murine 200 gene and 103 gene IgG1 fusion proteins are discussed.

10.1 Materials and Methods

Recombinant Plasmids Encoding IgG1 Fusion Proteins

Generation of the vector encloding murine 200 gene-hIgG1 fusion protein: The fragment encoding the signal sequence and extracellular domain of murine 200 gene was amplified from a cDNA clone containing the ORF of murine 200 gene using the following oligonucleotides:

Forward oligo: 5'-AAA-TTT-ATT-CTC-GAG-GAC-CCA-CGC-GTC-CGG-ATT-TCC-C-3' (SEQ ID NO: 25);

Reverse oligo: 5'-TTA-ATT-TGG-ATC-CCC-AGT-TCT-GAT-CGT-TTC-TCC-AGA-GTC-3' (SEQ ID NO: 26).

The oligonucleotide primers also introduce XhoI and BamHI restriction sites at the 5' and 3' ends of the PCR products, respectively, to facilitate the subsequent insertion into IgG1 expression vectors (pCD5-CD44-IgG1; see Aruffo, A. et al., 1991, Cell 61:1303–1313). The pCD5-CD44-IgG1 vector encodes a protein containing a CD5 signal sequence, a CD44 extracellular domain and a human IgG1 heavy chain Fc region. For construction of the murine 200 gene-hIgG1 fusion protein vector, the CD5 and CD44 portions of pCD5-CD44-IgG1 were replaced with sequences encoding murine 200 gene product signal sequence and extracellular domain.

The PCR reactions consisted of 25 cycles amplification at an annealing temperature of 60° C. Vent™ thermostable DNA polymerase (New England BioLabs, Inc.; Beverly, Mass.) was used in the amplification. The PCR product (approximately 600 bp) was digested with XhoI and BamHI and inserted into pCD5-CD44-IgG1 previously digested with XhoI and BamHI to remove the sequences encoding the CD5 signal sequence and the CD44 ectodomain.

Generation of the vector encoding human 200 gene-hIgG1 fusion protein: The fragment encoding the signal sequence and extracellular domain of human 200 gene is amplified from a cDNA clone containing the ORF of human 200 gene using the following oligonucleotides:

Forward oligo: 5'-AAA-TTT-ATT-CTC-GAG-CGC-TAA-CAG-AGG-TGT-CC-3' (SEQ ID NO: 27);

Reverse oligo: 5'-TTA-ATT-TGG-ATC-CCC-TCT-GAT-GGT-TGC-TCC-AGA-GTC-CCG-3' (SEQ ID NO: 28).

The amplification and pCD5-CD44-IgG1 subcloning procedures are as described, above, for the murine 200 gene-hIgG1 fusion protein.

Generation of the vector encoding the murine 103 gene-hIg G1 fusion protein: The construction of a vector encoding a soluble Ig-fusion protein (size: approximately 60 kD) containing a murine 103 gene product extracellular domain (but lacking the 103 gene product signal sequence) was constructed as described here. The CD44 portion of the pCD5-CD44-IgG1 vector (described above) was replaced with a nucleotide sequence encoding the 103 gene product extracellular domain. The 103 gene product extracellular domain sequence of the Ig-fusion protein consisted of 103 gene product amino acid residues 27–342 (i.e., the 103 gene product portion ending with amino acid sequence Ile-Val-Ala-Gly-Cys-Ser).

The fragment encoding the 103 gene product extracellular domain was amplified by PCR using synthetic oligonucleotides complementary to the sequences flanking the 103 gene region that would produce the 103 gene product containing amino acid residues 27–342. The oligonucleotides were designed to allow creation of a KpnI site at the 5' end and a BamHI site at the 3' end of each amplified 103 gene fragment to facilitate subsequent insertion into pCD5-CD44-IgG1.

The 5' oligonucleotide was as follows:
5'-CCGCGGGTACCAGTAAATCGTCCTGGGGTGG-3' (SEQ ID NO: 29). The 3'oligonucleotide was as follows: 5'-AAATAAAGGATCCCTACATCCAGCAACTATG TAGTA-3' (SEQ ID NO: 30).

PCR reaction conditions consisted of 15 cycles of 30 seconds at 95° C., 30 seconds at 60° C., and 30 seconds at 72° C., using Vent DNA polymerase (New England Biolabs, Beverly, Mass.) and 103L gene as template.

103 PCR products were digested with KpnI and BamHI, and ligated to KpnI-BamHI sites of CD5-IgG1 vector, thus replacing the CD44 sequences with the 103 gene sequences.

The resulting plasmid, encoding a fusion protein containing CD5-signal sequence, murine 103-extracellular domain and human-IgG1 heavy chain Fc region, was transfected into COS cells using LipofectAMINE™ (GIBCOBRL, Maryland) following manufacturer's suggest. 0.18 µg plasmid DNA and 140 µl LipofectAMINE™ were used for transfection of the cells of a 150 mm plate. Twenty-four hours after transfection, medium was replaced with 10% Ultra-low IgG Fetal Bovine Serum (GIBCOBRL, Maryland)/DMEM(BioWHITTAKER, Maryland), and the transfected cells were allowed to grow for 4–5 days continuously. Supernatants were then harvested, centrifuged to remove nonadherent cells and debris, and stored at −20° C.

For purification, 1 ml of supernatant was precipitated overnight with 10 µl of IPA-300 Immobilized rProteinA (Repligen, Massachusetts) at 4° C. The next day, beads were collected by centrifugation and washed three times with 10 volumes of PBS. For analysis, the beads were suspended in 20 µl of 2×Laemmli Sample Buffer (BIO-RAD, California) and boiled at 100° C. for 10 min. The boiled sample was spun briefly and loaded onto a 10% SDS-PAGE gel (JILEinc. Connecticut).

Metabolic labelling of recombinant fusion proteins: 36 hours after transient transfection of COS-7 cultures, cells were rinsed with replacement growth medium [DMEM methionine and cysteine depleted (ICN, Inc., California)]. After rinsing, 150 µCI/ml medium of a mixture of $^{35}$S-cysteine and $^{35}$S-methionine (Express $^{35}$S$^{35}$S™, Dupont, Massachusetts) was added to the replacement medium and the cells were cultured overnight.

Analysis of recombinant proteins by SDS PAGE: hIgG1 fusion proteins were generated by LipfectAMINE™ (Gibco, Inc., Maryland)-mediated transient transfection of COS-7 cells according to manufacturer's suggestion for 200 gene-hIgG1 fusion proteins, 1 ml of day 5 supernatant was mixed with 20 µl of Protein A Trisacryl bead (Pierce, Inc., Illinois) in the presence of 20 mM HEPES (pH 7.0) overnight at 4° C. with constant agitation. Beads were then washed 3× with PBS prior to the addition to loading buffer. Beads were mixed with either reducing or non-reducing loading buffers (described in, *Molecular Cloning*, Sambrook, Fritsch, and Maniatis, 2nd edition, 1989, with the exception that DTT was replaced with 2.5% β-mercaptoethanol).

10.2. Results

The construction and expression of recombinant IgG fusion proteins is described herein. Specifically, 200 gene product-IgG1 and 103 gene product-IgG1 fusion proteins are described. The murine and human 200 gene product-IgG1 fusion protein contains a 200 gene product signal sequence and extracellular domain fusion to a human IgG1 heavy chain Fc region. The 103 gene product-IgG1 fusion protein contains a CD5 signal sequence and 103 gene product extracellular domain fused to a human IgG1 heavy chain Fc region.

200 gene-hIgG1 fusion proteins were produced by transient transfection of COS-7 cells, as described in Section 10.1, above. Protein A immunoprecipitation of the COS-7 supernatants and their analysis by SDS-PAGE demonstrated, first, that the corect IgG-1 peptide was being produced as part of the fusion (as evidenced by the fusion's protein A immunoprecipitation) and, second, demonstrated substantial expression of the 200 gene-IgG1 fusion protein at a concentration approximately 1 µg per ml of culture supernatant. Further, when the immunoprecipitated supernatants are analyzed and compared under reducing and non-reducing conditions, it is clear that the 200 gene-IgG1 fusion protein undergoes oligomerization, as expected, given the human IgG1 heavy chain peptide sequence present in the fusion protein. Further, the size (i.e., larger than expected from the amino acid sequence alone) and appearance of the fusion proteins as they migrate through the gels (i.e., diffuse, rather than tight bands) indicate that, as expected, the fusion proteins have been glycosylated.

11. EXAMPLE

Production and Characterization of Transgenic Animals

Described herein is the production and characterization of transgenic mice overexpressing either murine 200 gene product or murine 103 gene product.

11.1. Materials and Methods

Construction of 200 gene transgenic clone: A PCR product of the entire 200 gene sequence was used to replace the IL-10 gene in the pCIL-10 plasmid, whose construction is described below.

The pCIL-10 plasmid contained a 5.5 kb BamHI-XbaI genomic fragment, within which human CD2 enhancer was included (Greaves et al., 1989, Cell 56(6):979–86). A 0.5 kb XXXbaI-SmaI fragment containing human immunoglobulin heavy chain promoter, Pµ (Danner and Leder, Proc. Natl. Acad. Sci. U.S.A., 1985, 82:8658–8662), was ligated to the 3'-end of the CD2 fragment. Following the Pµ fragment was a XbaI (blunt-ended)-BamHI fragment containing the IL-10 coding sequence, to which was ligated the 2.1 kb BamHI-EcoRI genomic fragment of human growth hormone (Base 5164 to 7317 of HUMGHCSA (GenBank)) at the 3'-end of the construct.

A 0.8 kb PCR product of the entire murine 200 gene coding sequence was obtained through 25 cycle-reaction using the murine 200 gene cDNA 200-AF as template and oligonucleotides primers with compatible restriction sites SpeI at the 5'-end and BamHI at 3'-end. The 5'-oligo utilized was 5'-GCG CAA TTG ACT AGT GAC CCA CGC GTC CGG ATT TC-3' (SEQ ID NO: 31) and the 3'-oligo, 5'-GAC GCG GAT CCT CAG GAT GGC TGC TGG CTG-3' (SEQ ID NO: 32). After heat denaturation at 95° C. for 2 minutes, 3-step cycling was performed for 30 seconds at 95° C., 30 seconds at 60° C., 60 seconds at 72° C. by Vent™ DNA polymerase (New England Biolabs, Massachusetts). A final step for five minutes, at 72° C., was performed for end-polishing. The PCR product was digested by SpeI and BamHI (New England Biolabs, Beverly, Mass.) and ligated to the fragment of pCIL-10 after removal of SpeI to BamHI of IL-10 gene. MaxEfficient *E. coli* DH5α competent cells (GIBCO BRL, Maryland) were used for transformation following manufacturer's suggestion. Transformants were grown in LB broth containing 0.1 µg/ml ampicillin and the DNA were extracted by Qiagene Plasmid Maxi Kit (Qiagene, California). Restriction analysis was performed for confirmation, and the final construct was sequenced to eliminate any possible PCR introduced mutations. A plasmid designated p200Tr3 was selected from production of transgenic mice.

This final construct contained an approximately 5.5 kb genomic fragment containing the human CD2 enhancer joined to a 0.5 kb fragment of the human IgM promoter immediately upstream of the murine 200 gene coding sequence. A region containing the 3' untranslated sequence of the human growth hormone gene was positioned immediately downstream of the murine 200 gene ORF and contained a polyA splice site.

Construction of 103 gene transgenic clone: A PCR product of the entire 103 gene sequence was used to replace the IL-10 gene in the pCIL-10 plasmid. The pCIL-10 plasmid was as described in this Section, above. A PCR product of the entire murine long form of the 103 gene (Yanagisawa, K. et al., 1993, FEBS 318:83–87) coding sequence was obtained through 35 cycle-reaction using first-strand cDNA from a mouse TH2-type cell line, D10G4 (ATCC, Maryland), as template. Total RNA was extracted from the cell line by RNAzole™ (TEL-TEST, Inc., Texas). Seven micrograms RNA were used in a 20 µl first-strand cDNA synthesis reaction by Superscript Reverse Transcriptase I (GIBCO BRL, Maryland) following manufacturer's suggestion. Two microlitters of cDNA were used in PCR reaction. The 5'-oligo was 5'-GAACACACTAGTACTATCCTGTGCCATTGCCA TAGAGA-3' (SEQ ID NO: 33), and the 3'-oligo, 5'-GGAATATTGGGCCCTTGGATCCCAAGTCTGC ACACCTGCACTCC-3' (SEQ ID NO: 34) with compatible restriction sites SpeI at 5'-end and BamHI at 3' end, respectively. After heat denaturation at 95° C. for 2 minutes, 3-step cycling was performed at 45 seconds at 95° C., 45 seconds at 65° C. and 60 seconds at 72° C. by Vent™ DNA polymerase (New England Biolabs, Beverly, Mass.). A final step for five minutes, at 72° C., was performed for end-polishing. The PCR product was digested by SpeI and BamHI (New England Biolabs) and ligated into the SpeI-BamHI sites of pBSKIIGH vector, containing the human growth hormone fragment from pCIL-10 subcloned into the BamHI-XhoI site of pBSKII (Stratagene), which was named pBS-103L-GH. The pCIL-10 fragment containing human CD2 enhancer and Pµ promoter was then ligated immediately upstream of the 103L gene of pBS-103L-GH. MaxEfficient *E. coli* DH5α competent cells (GIBCO BRL, Maryland) were used for transformation following manufacturer's suggestion. The transformants were grown in LB broth containing 0.1 µg/ml ampicillin and DNA were extracted by Qiagene Plasmid Maxi Kit (Qiagene, California). Restriction analysis was performed for confirmation, and the construct was sequenced to eliminate any possible PCR introduced mutations. A plasmid designated pCD2-103L-GH was selected for production of transgenic mice.

Production of Transgenic Mice: C3H/HEJ and FVB/NJ mice were obtained from the Jackson Laboratory (Bar Harbor, Me.). Females aged 3–4 weeks were induced to ovulate by intraperitoneal injection of pregnant mare's serum (PMS) between 10 a.m. to 2 p.m., followed 46 hours later by intraperitoneal injection of human chorionic gonadotropin (hCG). Following hCG administration, the females were housed overnight with males of the same strain. The following morning females were examined for the presence of a copulation plug and embryos were isolated from those females with plugs, essentially as described in *Manipulating the Mouse Embryo* (Hogan et al., eds., Cold Spring Harbor Laboratory Press, 1994).

DNA for embryo microinjection was prepared by digesting of p200Tr3 and pCD2-103L-GH1 with NotI and XhoI followed by gel electrophoresis. The 9 kb and 10 kb fragments, respectively, were electrophorese onto an NA-45 membrane (Schleicher and Schuell) by cutting a slit into the gel immediately in front of the desired band, inserting the NA-45 membrane and continuing electrophoresis until the DNA band has been transferred to the membrane. The DNA was eluted from the membrane by incubation with 0.4 ml of 1M NaCl/0.05M arginine-free base at 65–70° C. for several hours in a microfuge tube. The eluted DNA was extracted with phenol/chloroform and chloroform, ethanol precipitated and dissolved in 200 µl of 5 mM Tris, pH 7.5/0.1 mM EDTA. The DNA was then re-precipitated with ethanol and re-dissolved in 40 µl of 10 mM Tris, pH 7.5/0.1 mM EDTA. Prior to microinjection, the DNA was diluted to 1–2 µ/ml in 10 mM Tris, pH 7.5/0.1 mM EDTA.

DNA was microinjected into the male pronuclei of strain C3H/HEJ or FVB/NJ embryos and injected embryos were transferred into the oviducts of pseudopregnant females essentially as described in *Manipulating the Mouse Embryo*. The resulting offspring were analyzed for the presence of transgene sequences by Southern blot hybridization of DNA prepared from tail biopsies.

Southern blot analysis of transgenic mice: Approximately ½" piece of tail was clipped and digested in 500 µl proteinase K solution [containing 100 mM Tris HCl, pH 8.0; 5 mM EDTA, pH 8.0; 0.2% SDS; 200 mM NaCl; 100 µg/ml Proteinase K (Boehringer Mannheim, Germany)] at 55° C. overnight. Digests were centrifuged for 15 minutes to remove undigested debris. Supernatants were precipitated with an equal volume of isopropanol at room temperature. Precipitates were centrifuged for 25 minutes and pellets washed in 75% ethanol. Pellets were air dried and resuspended in 100 µl TE; pH 8.0. Restriction digests of tail DNA were performed as follows: 20 µl DNA solution was digested with 80 units BamHI (New England Biolabs) in the presence of 1 mM spermidine overnight at 37° C. Digested samples were analyzed by gel electrophoresis using 0.8% agarose gels. Separated DNA was transferred to Hybond-N+ (Amersham, Inc.) following depurination in 0.25M HCl for 10 minutes followed by 0.5 M NaOH, 1 M NaCl for 30 minutes, and then 2.5M Tris-HCl (pH 7.4), 2.5M NaCl for 30 minutes. Immediately prior to transfer, gels were briefly equilibrated in a 10x SSC transfer buffer. Transfer was carried out overnight in 10x SSC by capillary action. After transfer, the membrane was air dried and UV-crosslinked using a Stratolinker (Stratagene, Inc.). After crosslinking, membranes were rinsed briefly in 2x SSC.

For 200 gene transgenic analysis, radiolabelled probe containing approximately 500 base pairs of the human IgM promoter was produced using the Random Primed DNA Labelling Kit (Boehringer Mannheim). The 500 bp Xba-1/ Spe-1 fragment of human IgM heavy chain promoter was used as probe. Hybridization was carried out using standard hybridization procedures using Rapid-Hyb (Amersham) hybridization solution. $1 \times 10^6$ cpm per ml of hybridization solution was incubated at 65° C. overnight. Membranes were washed twice in 0.5x SSC 0.1% SDS at 65° C. for 30 minutes and were exposed by autoradiography. Transgenic animals were detected by the presence of an approximately 7.0 kb BamHI fragment which hybridizes to a probe containing the 0.5 kb Pμ fragment For 103 gene transgenic animals, a $^{32}$P-radiolabelled PCR fragment of the pCD2-103L-GH construct described above was utilized. The PCR fragment was generated using the following primers: 5' oligo: 5'-GTA-AAT-CGT-CCT-GGG-GTC-TGG-3' (SEQ ID NO:35; 3' oligo: 5'-CCT-TCT-GAT-AAC-ACA-AGC-ATA-AAT-C-3' (SEQ ID NO:36). Using these oligonucleotide primers and the pCD2-103L-GH template, PCR reactions conditions were as follows: 20 cycles of 30 seconds at 94° C., 30 seconds at 60° C. and 30 seconds at 72°, using Vent™ DNA polymerase (New England Biolabs, Beverly Mass.). Upon hybridization to mouse genomic digested with EcoRI and SpeI, the resulting probe hybridized to an endogenous 2.4 kb band and a 0.85 kb transgenic-specific band.

11.2. Results 200 gene transgenic mice (four C3H founder lines, 6 FVB founder lines) and 103 gene transgenic mice (five FVB founder lines) were produced according to the method described above, in Section 11.1. Southern hybridization analysis demonstrated the successful production of both 200 and 103 gene transgenic founder animals.

With respect to the 200 transgenic animals, four lines of transgenic mice were created in the C3H inbred strain of mice. One of these lines was examined for expression of the 200 transgene. As expected, 200 transgene transcripts were detected in the thymus, spleen and lymph nodes, consistent with a predominantly T-cell restricted pattern. At approximately 6 to 7 months of age, three of the founder animals, upon visual examination, appeared sick. One of these founders, designated 130-1.2, was sacrificed at approximately 6 months of age. At the time the sacrifice, it was expected that at the female would not have lived significantly longer. Upon dissection of 130-1.2, it was clear that the spleen and one of the kidneys were grossly abnormal. The spleen was approximately ten-fold normal size and appeared to be filled with pale appearing cells. The splenocyte populations were examined by flow cytometry, and it was determined that the predominant cell population was positive for MAC-1 (a macrophage/granulocyte cell surface marker) expression. These cells also had high side scatter profiles. Spleen sections from this animal were stained with hematoxylin and eosin and viewed by light microscopy. These data suggest that the abnormal cell population was composed of polymorphonuclear neutrophils. The abnormal kidney also appeared to be infiltrated by these same cells.

One of the offspring of 130-1.2 died at approximately 6 months of age while giving birth to her second litter. Upon dissection, it was noted that there appeared to be a bowel obstruction, which may have contributed to the cause of death. In addition, yet another founder animal appeared to be quite sick and was sacrificed. However, in this animal there were no abnormalities observed, either by gross inspection of the organs or by flow cytometric analysis of lymphoid populations. Finally, the remaining founder animal was observed to be exhibiting symptoms of sickness by approximately 6 months of age.

Given that these animals were maintained under SPF (specific pathogen free) conditions, it is highly unlikely that these animals became ill via exposure to an infectious pathogen. Rather, it is most likely that the effect of the transgene is modulating some aspect of the immune system.

Based on the observation of 130-1.2, it is suspected that as a consequence of transgene expression, the line may suffer from an immunodeficiency and is, therefore, susceptible to infection by normally innocuous organisms present in the environment (bacteria, etc.). It is possible, therefore, that this gene product normally functions in some aspect of the immune effector response or in the proper regulation of the immune system.

Two hundred transgenic mouse founder lines generated in the FvB inbred strain exhibited no outward symptoms of illness as they approached 6 months of age.

12. Deposit of Microorganisms

The following microorganisms were deposited with the Agricultural Research Service Culture Collection (NRRL), Peoria, Ill., on Jan. 19, 1995 (10-C, 57-E, 105-A, 106-H, 161-G, 200-O), Mar. 2, 1995 (*E. coli* DH10B(Zip)™ containing 200-P) and Jun. 1, 1995 (200-AF, 10-X, 54-C) and assigned the indicated accession numbers:

| Microorganism | NRRL Accession No. |
| --- | --- |
| 10-C | B-21390 |
| 57-E | B-21391 |
| 105-A | B-21392 |
| 106-H | B-21393 |
| 161-G | B-21394 |
| 200-O | B-21395 |
| *E. coli* DH10B (Zip) ™ containing 200-P cDNA | B-21416 |
| 200-AF | B-21457 |
| 10-X | B-21455 |
| 54-C | B-21456 |

The following microorganisms were deposited with the American Type Culture Collection (ATCC), Rockville, Md., on Dec. 12, 1995 and assigned the indicated accession numbers:

| Microorganism | ATCC Accession No. |
| --- | --- |
| *E. coli*, feht 200C | 69967 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A method for detecting 200 gene expression in a sample comprising: detecting the presence of a 200 gene product or an RNA molecule that encodes the 200 gene product, wherein the 200 gene product comprises:
   (a) the amino acid sequence depicted in SEQ ID NO:24;
   (b) the amino acid sequence encoded by the mammalian nucleotide sequence contained within E. coli clone feht 200C (ATCC accession No. 69967);
   (c) amino acid residues 1–20 shown in SEQ ID NO:24;
   (d) amino acid residues 1–200 shown in SEQ ID NO:24;
   (e) amino acid residues 1–224 shown in SEQ ID NO:24;
   (f) amino acid residues 30–128 shown in SEQ ID NO:24;
   (g) amino acid residues 21–200 shown in SEQ ID NO:24;
   (h) amino acid residues 21–224 shown in SEQ ID NO:24;
   (i) amino acid residues 21–301 shown in SEQ ID NO:24;
   (j) amino acid residues 201–224 shown in SEQ ID NO:24;
   (k) amino acid residues 201–301 shown in SEQ ID NO:24;
   (l) amino acid residues 224–301 shown in SEQ ID NO:24; or
   (m) an amino acid sequence encoded by a nucleotide sequence which hybridizes to the complement of the nucleotide sequence shown in SEQ ID NO:23, or a portion thereof which encodes the amino acid residues of (a) through (l), at 65° C. in 0.5 M NaHPO$_4$, 7% SDS, and 1 mM EDTA, followed by washing in 0.1×SSC/ 0.1% SDS at 68° C.

2. A method for detecting 200 gene expression in a sample comprising: detecting the presence of a 200 gene product or an RNA molecule that encodes the 200 gene product, wherein the 200 gene product comprises:
   (a) the amino acid sequence depicted in SEQ ID NO:10;
   (b) the amino acid sequence encoded by the mammalian nucleotide sequence contained within E. coli clone 200-O (NRRL accession No. B-21395);
   (c) the amino acid sequence encoded by the mammalian nucleotide sequence contained within E. coli clone 200-P (NRRL accession No. B-21415);
   (d) the amino acid sequence encoded by the mammalian nucleotide sequence contained within E. coli clone 200-AF (NRRL accession No. B-21457);
   (e) amino acid residues 1–20 shown in SEQ ID NO:10;
   (f) amino acid residues 1–192 shown in SEQ ID NO:10;
   (g) amino acid residues 1–214 shown in SEQ ID NO:10;
   (h) amino acid residues 21–192 shown in SEQ ID NO:10;
   (i) amino acid residues 21–214 shown in SEQ ID NO:10;
   (j) amino acid residues 21–281 shown in SEQ ID NO:10;
   (k) amino acid residues 193–214 shown in SEQ ID NO:10;
   (l) amino acid residues 193–281 shown in SEQ ID NO:10;
   (m) amino acid residues 215–281 shown in SEQ ID NO:10; or
   (n) an amino acid sequence encoded by a nucleotide sequence which hybridizes to the complement of the nucleotide sequence shown in SEQ ID NO:8, or a portion thereof which encodes the amino acid residues of (a) through (m), at 65° C. in 0.5 M NaHPO$_4$, 7% SDS, and 1 mM EDTA, followed by washing in 0.1× SSC/0.1% SDS at 68° C.

3. The method of claim 1 or 2, wherein the method detects the presence of a 200 gene product in the sample.

4. The method of claim 3, wherein the sample is immobilized on a solid phase support.

5. The method of claim 3, wherein the 200 gene product is detected in the sample by binding the gene product to an antibody directed against the 200 gene product.

6. The method of claim 5, wherein the antibody is directly or indirectly labeled.

7. The method of claim 1 or 2, wherein the method detects in the sample the presence of an RNA molecule that encodes a 200 gene product.

8. The method of claim 7, wherein the sample comprises RNA molecules and the method further comprises:
   (a) annealing nucleic acid molecule primers to RNA molecules in the sample under conditions that selectively anneal the primers to RNA molecules that encode the 200 gene product and result in reverse transcription of the RNA molecules into cDNA molecules; and
   (b) determining whether the cDNA molecules have been amplified.

9. The method of claim 7, wherein the sample comprises RNA molecules and the method further comprises:
   (a) hybridizing nucleic acid molecule probes to the RNA molecules in the sample under conditions that selectively hybridize the probes to nucleic acid molecules that encode the 200 gene product;
   (b) separating non-hybridized nucleic acid probes from the RNA molecules in the sample; and
   (c) detecting the presence of nucleic acid probes hybridized to the RNA molecules of the sample.

10. A method for diagnosing a TH cell subpopulation-related immune disorder comprising detecting, in a sample from a patient suspected of having the disorder, the level of a 200 gene product or an RNA molecule that encodes the 200 gene product so that if the level detected differs from that in a control sample, a TH cell subpopulation-related immune disorder is diagnosed, wherein the 200 gene product is
   (a) the amino acid sequence depicted in SEQ ID NO:24;
   (b) the amino acid sequence encoded by the mammalian nucleotide sequence contained within *E. coli* clone feht 200C (ATCC accession No. 69967);
   (c) amino acid residues 1–20 shown in SEQ ID NO:24;
   (d) amino acid residues 1–200 shown in SEQ ID NO:24;
   (e) amino acid residues 1–224 shown in SEQ ID NO:24;
   (f) amino acid residues 30–128 shown in SEQ ID NO:24;
   (g) amino acid residues 21–200 shown in SEQ ID NO:24;
   (h) amino acid residues 21–224 shown in SEQ ID NO:24;
   (i) amino acid residues 21–301 shown in SEQ ID NO:24;
   (j) amino acid residues 201–224 shown in SEQ ID NO:24;
   (k) amino acid residues 201–301 shown in SEQ ID NO:24;
   (l) amino acid residues 224–301 shown in SEQ ID NO:24; or
   (m) an amino acid sequence encoded by a nucleotide sequence which hybridizes to the complement of the nucleotide sequence shown in SEQ ID NO:23, or a portion thereof which encodes the amino acid residues of (a) through (l), at 65° C. in 0.5 M NaHPO$_4$, 7% SDS, and 1 mM EDTA, followed by washing in 0.1×SSC/0.1% SDS at 68° C.

11. The method of claim 10, wherein the TH cell subpopulation-related immune disorder is a TH1 cell subpopulation-related immune disorder.

12. The method of claim 11, wherein the TH1 cell subpopulation-related immune disorder is multiple sclerosis, psoriasis or insulin dependent diabetes.

13. The method of claim 10, wherein the method detects the level of a 200 gene product in the patient sample.

14. The method of claim 13, wherein the level of the 200 gene product is detected in the patient sample by binding the gene product to an antibody directed against the 200 gene product.

15. The method of claim 14, wherein the antibody is directly or indirectly labeled.

16. The method of claim 10, wherein the method detects the level in the patient sample of an RNA molecule that encodes the 200 gene product.

17. The method of claim 16, wherein the patient sample comprises RNA molecules and the method further comprises:
   (a) annealing nucleic acid molecule primers to RNA molecules in the sample under conditions that selectively anneal the primers to RNA molecules that encode the 200 gene product and result in reverse transcription of the RNA molecules into cDNA molecules;
   (b) annealing the nucleic acid molecule primers to the cDNA molecules under conditions that selectively amplify the cDNA molecules; and
   (c) detecting the level of cDNA molecules encoding the 200 gene product that have been amplified,
so that if the level of cDNA amplified from the patient sample differs relative to the level amplified from a control sample, a TH cell subpopulation-related immune disorder is diagnosed.

18. The method of claim 17, wherein the sample comprises RNA molecules and the method further comprises:
   (a) hybridizing nucleic acid molecule probes to the RNA molecules in the sample under conditions that selectively hybridize the probes to nucleic acid molecules that encode the 200 gene product; and
   (b) detecting the level of nucleic acid probes hybridized to the RNA molecules of the sample,
so that if the level of RNA in the patient sample differs relative to the level detected in a control sample, a TH cell subpopulation-related immune disorder is diagnosed.

* * * * *

SEQUENCE LISTING (1) GENERAL INFORMATION:

(iii) NUMBER OF SEQUENCES: 37

(2) INFORMATION FOR SEQ ID NO:1:

(i) SEQUENCE CHARACTERISTICS:
       (A) LENGTH: 357 base pairs
       (B) TYPE: nucleic acid
       (C) STRANDEDNESS: single
       (D) TOPOLOGY: unknown (ii) MOLECULE TYPE: DNA (xi) SEQUENCE DESCRIPTION: SEQ ID NO:1:

```
CTGGTGAGGG GGATCTACAA CTTGTTCGGT TAAAGAAAAA AGCAACAGCC AACAGAAATG      60

TGGTTATCCT TCACCTACCT AAAAAGGGAG ATGATGTGAA ACCAGGAACC AGATGCCGAG     120

TAGCAGGATG GGGGAGATTT GGCAATAAGT CAGCTCCCTC TGAAACTCTG AGAGAAGTCA     180

ACATCACTGT CATAGACAGA AAAATCTGCA ATGATGAAAA ACACTATAAT TTTCATCCTG     240

TAATTGGTCT AAACATGATT TGGGCAGGGG ACCTCCCCGG CGGAAAGGAC TCCTGCAATG     300

GGGATTCTGG CAGCCCTCTC CTATGTGATT GGTATTTGGG AAGCATCACC TCCTTTT       357
```

(2) INFORMATION FOR SEQ ID NO:2:

(i) SEQUENCE CHARACTERISTICS:
       (A) LENGTH: 255 base pairs
       (B) TYPE: nucleic acid
       (C) STRANDEDNESS: single
       (D) TOPOLOGY: unknown (ii) MOLECULE TYPE: DNA (xi) SEQUENCE DESCRIPTION: SEQ ID NO:2:

```
TTAGCGCCAT TGCCATAGAG AGACCTCAGC CATCAATCAC TAGCACATGA TTGACAGACA      60

GAGAATGGGA CTTTGGGCTT TGGCAATTCT GACACTTCCC ATGTATTTGA CAGTTACGGA     120

GGGCAGTAAA TCGTCCTGGG GTCTGGAAAA TGAGGCTTTA ATTGTGAGAT GCCCCCAAAG     180

AGGACGCTCG ACTTATCCTG TGGAATGGTA TTACTCAGAT ACAAATGAAA GTATTCCTAC     240

CCAAAAAAAA AAAAA                                                      255
```

(2) INFORMATION FOR SEQ ID NO:3:

(i) SEQUENCE CHARACTERISTICS:
       (A) LENGTH: 2055 base pairs
       (B) TYPE: nucleic acid
       (C) STRANDEDNESS: single
       (D) TOPOLOGY: unknown (ii) MOLECULE TYPE: DNA (ix) FEATURE:
       (A) NAME/KEY: CDS
       (B) LOCATION: 496..1509

(xi) SEQUENCE DESCRIPTION: SEQ ID NO:3:

```
CCGGGTCGAC CCACGCGTCC GAGCCTCCTC AGTCAAGAGA AGCATCCCTC CAGAAACAGG      60

GAAACATGAC ACTTTTGAAA GAATGCCAAA CGGCGTGAAA ATAAAAACAG AGCATTCCCA     120

TTTGCACCGA CCAATCTCCA ATCTCCTGTA AGATTCAAAA GGGCAAGCAA GAGGCGGTGA     180
```

```
CCGTTCACGA AAGCTAAAAT CCCATGCTAT TGAACATGAA GACTTCTGAT GCTTAAATCT    240

CATTAACTGC TTTAAGTCAC TCCCAGGAGC TTGGATCCCA ACTTCTAGCA GTAATAGTCT    300

GTGTAAAAAA AAAAAAAAAA TCAGTCTACA ACCACTCTCT AAATGCATGG ATGAACTCAT    360

CAGAACATCA AAACCCAAGG AAACCCTAAG AGAGAAGAAT TCTAATAAAA AGAATTTTAC    420

ATTGAAAACT TACAAGGCAA GGTCCCTTTC CCTGCTGACA GCCTAAGAAG TGATGTAACT    480

GCCACTGTGA AGACC ATG GCG ATG AAC AGC ATG TGC ATT GAA GAG CAG CGC    531
               Met Ala Met Asn Ser Met Cys Ile Glu Glu Gln Arg
                1               5                  10

CAC CTC GAA CAC TAT TTG TTC CCG GTG GTC TAC ATA ATT GTG TTT ATA    579
His Leu Glu His Tyr Leu Phe Pro Val Val Tyr Ile Ile Val Phe Ile
            15                  20                  25

GTC AGC GTC CCA GCC AAC ATC GGA TCT TTA TGC GTA TCC TTT CTG CAA    627
Val Ser Val Pro Ala Asn Ile Gly Ser Leu Cys Val Ser Phe Leu Gln
        30                  35                  40

GCG AAG AAG GAA AAT GAG CTA GGG ATT TAC CTC TTC AGT CTG TCC CTG    675
Ala Lys Lys Glu Asn Glu Leu Gly Ile Tyr Leu Phe Ser Leu Ser Leu
    45              50                  55                  60

TCA GAC CTG CTG TAT GCG CTG ACT CTG CCC CTC TGG ATC AAT TAC ACT    723
Ser Asp Leu Leu Tyr Ala Leu Thr Leu Pro Leu Trp Ile Asn Tyr Thr
                65                  70                  75

TGG AAT AAA GAC AAC TGG ACT TTC TCT CCC ACC TTG TGC AAA GGA AGC    771
Trp Asn Lys Asp Asn Trp Thr Phe Ser Pro Thr Leu Cys Lys Gly Ser
            80                  85                  90

GTT TTC TTC ACC TAC ATG AAC TTT TAC AGC AGC ACG GCG TTC CTC ACT    819
Val Phe Phe Thr Tyr Met Asn Phe Tyr Ser Ser Thr Ala Phe Leu Thr
        95                  100                 105

TGC ATT GCC CTG GAC CGC TAT TTA GCA GTC GTC TAC CCT CTG AAG TTT    867
Cys Ile Ala Leu Asp Arg Tyr Leu Ala Val Val Tyr Pro Leu Lys Phe
    110                 115                 120

TCC TTC CTA AGA ACG AGA AGA TTC GCG TTT ATT ACC AGC CTC TCC ATC    915
Ser Phe Leu Arg Thr Arg Arg Phe Ala Phe Ile Thr Ser Leu Ser Ile
125                 130                 135                 140

TGG ATA TTA GAG TCC TTC TTT AAC TCT ATG CTT CTG TGG AAA GAT GAA    963
Trp Ile Leu Glu Ser Phe Phe Asn Ser Met Leu Leu Trp Lys Asp Glu
                145                 150                 155

ACG AGT GTT GAA TAT TGT GAC TCG GAC AAA TCT AAT TTC ACT CTC TGC   1011
Thr Ser Val Glu Tyr Cys Asp Ser Asp Lys Ser Asn Phe Thr Leu Cys
            160                 165                 170

TAT GAC AAA TAC CCT CTG GAG AAA TGG CAG ATA AAC CTC AAC CTG TTT   1059
Tyr Asp Lys Tyr Pro Leu Glu Lys Trp Gln Ile Asn Leu Asn Leu Phe
        175                 180                 185

CGG ACG TGC ATG GGC TAC GCA ATA CCC TTG ATC ACC ATC ATG ATC TGC   1107
Arg Thr Cys Met Gly Tyr Ala Ile Pro Leu Ile Thr Ile Met Ile Cys
    190                 195                 200

AAC CAT AAA GTC TAC CGA GCT GTG CGG CAC AAC CAA GCC ACG GAA AAC   1155
Asn His Lys Val Tyr Arg Ala Val Arg His Asn Gln Ala Thr Glu Asn
205                 210                 215                 220

AGC GAG AAG AGA AGG ATC ATA AAG TTG CTT GCT AGC ATC ACG TTG ACT   1203
Ser Glu Lys Arg Arg Ile Ile Lys Leu Leu Ala Ser Ile Thr Leu Thr
                225                 230                 235

TTC GTC CTA TGC TTT ACC CCC TTC CAC GTG ATG GTG CTC ATC CGC TGC   1251
Phe Val Leu Cys Phe Thr Pro Phe His Val Met Val Leu Ile Arg Cys
            240                 245                 250

GTT TTA GAG CGC GAC ATG AAC GTC AAT GAC AAG TCT GGA TGG CAG ACG   1299
Val Leu Glu Arg Asp Met Asn Val Asn Asp Lys Ser Gly Trp Gln Thr
        255                 260                 265

TTT ACG GTG TAC AGA GTC ACA GTA GCC CTG ACG AGT CTA AAC TGT GTT   1347
```

```
Phe Thr Val Tyr Arg Val Thr Val Ala Leu Thr Ser Leu Asn Cys Val
    270                 275                 280

GCC GAT CCC ATT CTG TAC TGC TTT GTG ACT GAG ACG GGG AGA GCT GAT    1395
Ala Asp Pro Ile Leu Tyr Cys Phe Val Thr Glu Thr Gly Arg Ala Asp
285                 290                 295                 300

ATG TGG AAC ATA TTA AAA TTG TGT ACT AGG AAA CAC AAT AGA CAC CAA    1443
Met Trp Asn Ile Leu Lys Leu Cys Thr Arg Lys His Asn Arg His Gln
                305                 310                 315

GGG AAA AAA AGG GAC ATA CTT TCT GTG TCC ACA AGA GAT GCT GTA GAA    1491
Gly Lys Lys Arg Asp Ile Leu Ser Val Ser Thr Arg Asp Ala Val Glu
                320                 325                 330

TTA GAG ATT ATA GAC TAA GAGGTGGAGG CAGGTTAAGT TACATGGTAT            1539
Leu Glu Ile Ile Asp  *
        335

TATTTAATGA AACTTACATT TTGGAAAAGA AATCTGGCAT AGTAGAACCC AGTGGAAATA  1599

GTTTGAAGGT ACATTGTATG ACTCCTATGT TGGCTTTATT AAGTAAGGTA TAGAAATGTA  1659

TTATCTTGTA TGTATTCTAA TGACTAGGCA TCATTGTTTT AGTACCAATT CTCTTTGCCT  1719

CTATGTTATA ACCCCTAAGA AGCACGCGGG ACTGTTCGTC TTTAAATCAG TGGCCATTCT  1779

ATCTGACTAC TATGACTTTT TGTTGTTGTT CTGCTTTGGG TTTTCAGTCT GCCTGCATCA  1839

GTCTTCTCCT CTGTATACGT CTGTCTTCAA CAAATGTAAG GACTAAATAC CCCTCCCGAT  1899

CACATCCATT ATCAAGGATT TGAAGCCACT CCATGTACTG GGTTATAAAA GAAATGTTCT  1959

CATGAACTTT CATGAAGTTT ACATACCTTT GGGGATCTAG TCACCGAGTC ACATAAAGTA  2019

AAAGTAAATG GAAAAAAAAA AAAAAAAAAA AAGGGC                            2055

(2) INFORMATION FOR SEQ ID NO:4:

(i) SEQUENCE CHARACTERISTICS:
        (A) LENGTH: 460 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:4:

CGCCAGTGTG CTGGAATTCG GCTTAGAGCA TTTCTTTCAA ACCACAGGTT AACACACACT    60

TACTAAAAAG CAATGCTGTT AGAGGAGAAG GGCTTGGGAG ACTCGGCCAT TTGAAACANA   120

AGCAAGGCAC TCTCCAGGNN CAGCAAGTGG ATTCCCATTT CCTGCTGAGG GCGGGTTCAC   180

ACTGAGACTG CACTCCAGTC AGCGGGAGGA ATCACCTGCA TTAATGCTTG TCCTCTGCAG   240

AGCTAGTGTG CCTTCCACTC TGGGTACACT TGGGTGTCAA CATTTCAAAA TGATGACCTA   300

AGAGGCTCTC ATAGTTGGTG ATAACTATGG NAGGACAGAA GAACACTGGC TGTATTGTCT   360

TTTTCTTTCA GCACTAGTGT CTTGGCCCTT AACTAAAACG GGTTCCATCA TCCTCCAAAC   420

CAGGAAGATA GATTGTTAGA CAGGTCCTTT CCCCTCAACT                         460

(2) INFORMATION FOR SEQ ID NO:5:

(i) SEQUENCE CHARACTERISTICS:
        (A) LENGTH: 414 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:5:
```

```
TTTTTTTTTT TNGGGAGAGG CTAGCACTGA AATTACAGTT TCAGTGGAAT TTAGAGAAGT      60

AATAACTGCA AAAATTTATT TACACACACA CACACACACA CAGGGCATTT TACCTGTGTA     120

AGTGCAGTTT AATCANCCCC ATTACCTTAT GACCTTGGTT GGCAATGTCT CTAAAGCTTT     180

AAAATTAAAA TAAAATTAAA AAGATGGTTT TCCATCTCAT AAAATCCCCT TTGGGAATGG     240

AAGACTTCCT CTTTGGGGTN TTTTTTAGAG GAACAGGAG  GTAACTGTTA ATTATTTATA     300

CATTCTAATA AACCATGAAT GCACCACATA AAATACTGTA CTCGGGGAGC AAACACTGTN     360

TGGGGGGGTT CTCTCTTACC AGAAGGAACA GGGGGCTTTT CAATGGCTGT GGGC           414

(2) INFORMATION FOR SEQ ID NO:6:

(i) SEQUENCE CHARACTERISTICS:
        (A) LENGTH: 240 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:6:

TTTNNGGGAC AGGGTTTCNC TGTGTATCTC TGGCTGTCCT GGAACTNACT CTGTAGACCA      60

GGTTGGCCTC GANCTCAGAA ATCTACCTGC CTCTCCCTCC ANAGTGCTGG GATTAANGGT     120

GTATGCCACC AATNCCCGGC CTTAATATAT TNNTAAACAA CTTCATTTGA ATGANATATT     180

GACACTACCC TTGGAATAAG AGTNCCCAGA ATGANGTACA GGNTTCANGG AATCATTTAA     240

(2) INFORMATION FOR SEQ ID NO:7:

(i) SEQUENCE CHARACTERISTICS:
        (A) LENGTH: 217 base pairs
        (B) TYPE: nucleic acid
        (C) STRANDEDNESS: single
        (D) TOPOLOGY: unknown (ii) MOLECULE TYPE: DNA (xi) SEQUENCE DESCRIPTION: SEQ ID NO:7:

CTTAGCAGGT GGAGTTGCAG CAGGAAGCCT GGTAGCCACA CTCCAATCAG CAGGGGTCCT      60

TGGACTCTCC ACATCAACAA ATGCCATCCT AGGGGCTGCT GGGGCACTGT TGGAGCCTTG     120

CTCTGAGCTT AGGAGATGAC ACTTCTATCA GCTCAACTCA AAGCCTGTAC AGACTACGCA     180

GGAGATGAAG TTCCAAAAGG CACCTTCAGA ACCCTCA                              217

(2) INFORMATION FOR SEQ ID NO:8:

(i) SEQUENCE CHARACTERISTICS:
        (A) LENGTH: 2710 base pairs
        (B) TYPE: nucleic acid
        (C) STRANDEDNESS: single
        (D) TOPOLOGY: unknown (ii) MOLECULE TYPE: DNA (ix) FEATURE:
        (A) NAME/KEY: CDS
        (B) LOCATION: 40..885

(xi) SEQUENCE DESCRIPTION: SEQ ID NO:8:

NGTCGACCCA CGCGTCCGGA TTTCCCCTCC CAAGTACTC ATG TTT TCA GGT CTT         54
                                            Met Phe Ser Gly Leu
                                             1               5

ACC CTC AAC TGT GTC CTG CTG CTG CAA CTA CTA CTT GCA AGG TCA           102
Thr Leu Asn Cys Val Leu Leu Leu Gln Leu Leu Leu Ala Arg Ser
```

```
                          10                    15                    20
TTG GAA GAT GGT TAT AAG GTT GAG GTT GGT AAA AAT GCC TAT CTG CCC                    150
Leu Glu Asp Gly Tyr Lys Val Glu Val Gly Lys Asn Ala Tyr Leu Pro
                25                    30                    35

TGC AGT TAC ACT CTA CCT ACA TCT GGG ACA CTT GTG CCT ATG TGC TGG                    198
Cys Ser Tyr Thr Leu Pro Thr Ser Gly Thr Leu Val Pro Met Cys Trp
            40                    45                    50

GGC AAG GGA TTC TGT CCT TGG TCA CAG TGT ACC AAT GAG TTG CTC AGA                    246
Gly Lys Gly Phe Cys Pro Trp Ser Gln Cys Thr Asn Glu Leu Leu Arg
        55                    60                    65

ACT GAT GAA AGA AAT GTG ACA TAT CAG AAA TCC AGC AGA TAC CAG CTA                    294
Thr Asp Glu Arg Asn Val Thr Tyr Gln Lys Ser Ser Arg Tyr Gln Leu
    70                    75                    80                    85

AAG GGC GAT CTC AAC AAA GGA GAT GTG TCT CTG ATA ATA AAG AAT GTG                    342
Lys Gly Asp Leu Asn Lys Gly Asp Val Ser Leu Ile Ile Lys Asn Val
                90                    95                    100

ACT CTG GAT GAC CAT GGG ACC TAC TGC TGC AGG ATA CAG TTC CCT GGT                    390
Thr Leu Asp Asp His Gly Thr Tyr Cys Cys Arg Ile Gln Phe Pro Gly
            105                   110                   115

CTT ATG AAT GAT AAA AAA TTA GAA CTG AAA TTA GAC ATC AAA GCA GCC                    438
Leu Met Asn Asp Lys Lys Leu Glu Leu Lys Leu Asp Ile Lys Ala Ala
        120                   125                   130

AAG GTC ACT CCA GCT CAG ACT GCC CAT GGG GAC TCT ACT ACA GCT TCT                    486
Lys Val Thr Pro Ala Gln Thr Ala His Gly Asp Ser Thr Thr Ala Ser
    135                   140                   145

CCA AGA ACC TAC ACG GAG AGA AAT GGT TCA GAG ACA CAG ACA CTG              534
Pro Arg Thr Leu Thr Thr Glu Arg Asn Gly Ser Glu Thr Gln Thr Leu
150                   155                   160                   165

GTG ACC CTC CAT AAT AAC AAT GGA ACA AAA ATT TCC ACA TGG GCT GAT                    582
Val Thr Leu His Asn Asn Asn Gly Thr Lys Ile Ser Thr Trp Ala Asp
                170                   175                   180

GAA ATT AAG GAC TCT GGA GAA ACG ATC AGA ACT GCT ATC CAC ATT GGA                    630
Glu Ile Lys Asp Ser Gly Glu Thr Ile Arg Thr Ala Ile His Ile Gly
            185                   190                   195

GTG GGA GTC TCT GCT GGG TTG ACC CTG GCA CTT ATC ATT GGT GTC TTA                    678
Val Gly Val Ser Ala Gly Leu Thr Leu Ala Leu Ile Ile Gly Val Leu
        200                   205                   210

ATC CTT AAA TGG TAT TCC TGT AAG AAA AAG AAG TTA TCG AGT TTG AGC                    726
Ile Leu Lys Trp Tyr Ser Cys Lys Lys Lys Lys Leu Ser Ser Leu Ser
    215                   220                   225

CTT ATT ACA CTG GCC AAC TTG CCT CCA GGA GGG TTG GCA AAT GCA GGA                    774
Leu Ile Thr Leu Ala Asn Leu Pro Pro Gly Gly Leu Ala Asn Ala Gly
230                   235                   240                   245

GCA GTC AGG ATT CGC TCT GAG GAA AAT ATC TAC ACC ATC GAG GAG AAC                    822
Ala Val Arg Ile Arg Ser Glu Glu Asn Ile Tyr Thr Ile Glu Glu Asn
                250                   255                   260

GTA TAT GAA GTG GAG AAT TCA AAT GAG TAC TAC TGC TAC GTC AAC AGC                    870
Val Tyr Glu Val Glu Asn Ser Asn Glu Tyr Tyr Cys Tyr Val Asn Ser
            265                   270                   275

CAG CAG CCA TCC TGA CCGCCTCTGG ACTGCCACTT TTAAAGGCTC GCCTTCATTT                    925
Gln Gln Pro Ser *
        280

CTGACTTTGG TATTTCCCTT TKTGAAAAC TATGTGATAT GTCACTTGGC AACCTCATTG                    985

GAGGTTCTGA CCACAGCCAC TGAGAAAAGA GTTCCAGTTT TCTGGGATA ATTAACTCAC                   1045

AAGGGGATTC GACTGTAACT CATGCTACAT TGAAATGCTC CATTTTATCC CTGAGTTTCA                  1105

GGGATCGGAT CTCCCACTCC AGAGACTTCA ATCATGCGTG TTGAAGCTCA CTCGTGCTTT                  1165

CATACATTAG GAATGGTTAG TGTGATGTCT TTGAGACATA GAGGTTTGTG GTATATCCGC                  1225
```

-continued

```
AAAGCTCCTG AACAGGTAGG GGGAATAAAG GGCTAAGATA GGAAGGTGCG GTCTTTGTTG      1285

ATGTTGGAAA ATCTTAAAGA AGTTGGTAGC TTTTCTAGAG ATTTCTGACC TTGAAAGATT      1345

AAGAAAAAGC CAGGTGGCAT ATGCTTAACA CGATATAACT TGGGAACCTT AGGCAGGAGG      1405

GTGATAAGTT CAAGGTCAGC CAGGGCTATG CTGGTAAGAC TGTCTCAMCA TCCAAAGACG      1465

AAAATAAACA TAGAGACAGC AGGAGGCTGG AGATGAGGCT CGGACAGTGA GGTGCATTGT      1525

GTACAAGCAC GAGGAATCTA TATTTGATCG TAGACCCCAC ATGAAAAAGC TAGGCCTGGT      1585

AGAGCATGCT TGTAGACTCA AGAGATGGAG AGGTAAAGGC ACAACAGATC CCCGGGGCTT      1645

GCGTGCAGTC AGCTTAGCCT AGGTGCTGAG TTCCAAGTCC ACAAGAGTCC CTGTCTCAMA      1705

GTAAGATGGR CTGAGTATCT GGCGCATGTC CATGGGGGTT GTCCTCTCCT CTCAGAAGAG      1765

ACATGCACAT GWCCCTGCAC ACACACACAC ACACACACAC ACACACACAC ACACACACAC      1825

ACACATGAWA TGAAGGTTCT CTCTGTGCCT GCTACCTCTC TATAACATGT ATCTCTACAG      1885

GACTCTCCTC TGCCTCTGTT AAGACATGAG TGGGAGCATG GCAGAGCAGT CCAGTAATTT      1945

ATTCCAGCAC TCAGAAGGCT GGAGCAGAAG CGTGGAGAGT TCAGGAGCAC TGTGCCCAAC      2005

ACTGCCAGAC TCTTCTTACA CAAGAAAAAG GTTACCCGCA AGCAGCCTGC TGTCTGTAAA      2065

AGGAAACCCT GCGAAAGGCA AACTTTGACT GTTGTGTGCT CAAGGGGAAC TGACTCAGAC      2125

AACTTCTCCA TTCCTGGAGG AAACTGGAGC TGTTTCTGAC AGAAGAACAA CCGGTGACTG      2185

GGACATACGA AGGCAGAGCT CTTGCAGCAA TCTATATAGT CAGCAAAATA TTCTTTGGGA      2245

GGACAGTCGT CACCAAATTG ATTTCCAAGC CGGTGGACCT CAGTTTCATC TGGCTTACAG      2305

CTGCCTGCCC AGTGCCCTTG ATCTGTGCTG GCTCCCATCT ATAACAGAAT CAAATTAAAT      2365

AGACCCCGAG TGAAAATATT AAGTGAGCAG AAAGGTAGCT TTGTTCAAAG ATTTTTTTGC      2425

ATTGGGGAGC AACTGTGTAC ATCAGAGGAC ATCTGTTAGT GAGGACACCA AAACCTGTGG      2485

TACCGTTTTT TCATGTATGA ATTTTGTTGT TTAGGTTGCT TCTAGCTAGC TGTGGAGGTC      2545

CTGGCTTTCT TAGGTGGGTA TGGAAGGGAG ACCATCTAAC AAAATCCATT AGAGATAACA      2605

GCTCTCATGC AGAAGGGAAA ACTAATCTCA AATGTTTTAA AGTAATAAAA CTGTACTGGC      2665

AAAGTACTTT GAGCATAAAA AAAAAAAAAA AAAAAGGGCG GCCGC                      2710
```

(2) INFORMATION FOR SEQ ID NO:9:

(i) SEQUENCE CHARACTERISTICS:
        (A) LENGTH: 337 amino acids
        (B) TYPE: amino acid
        (D) TOPOLOGY: unknown (ii) MOLECULE TYPE: protein (xi) SEQUENCE DESCRIPTION: SEQ ID NO:9:

```
Met Ala Met Asn Ser Met Cys Ile Glu Glu Gln Arg His Leu Glu His
 1               5                  10                  15

Tyr Leu Phe Pro Val Tyr Ile Ile Val Phe Ile Val Ser Val Pro
             20                  25                  30

Ala Asn Ile Gly Ser Leu Cys Val Ser Phe Leu Gln Ala Lys Lys Glu
         35                  40                  45

Asn Glu Leu Gly Ile Tyr Leu Phe Ser Leu Ser Leu Ser Asp Leu Leu
     50                  55                  60

Tyr Ala Leu Thr Leu Pro Leu Trp Ile Asn Tyr Thr Trp Asn Lys Asp
 65                  70                  75                  80

Asn Trp Thr Phe Ser Pro Thr Leu Cys Lys Gly Ser Val Phe Phe Thr
```

```
                     85                  90                  95
Tyr Met Asn Phe Tyr Ser Ser Thr Ala Phe Leu Thr Cys Ile Ala Leu
                100                 105                 110

Asp Arg Tyr Leu Ala Val Val Tyr Pro Leu Lys Phe Ser Phe Leu Arg
            115                 120                 125

Thr Arg Arg Phe Ala Phe Ile Thr Ser Leu Ser Ile Trp Ile Leu Glu
        130                 135                 140

Ser Phe Phe Asn Ser Met Leu Leu Trp Lys Asp Glu Thr Ser Val Glu
145                 150                 155                 160

Tyr Cys Asp Ser Asp Lys Ser Asn Phe Thr Leu Cys Tyr Asp Lys Tyr
                165                 170                 175

Pro Leu Glu Lys Trp Gln Ile Asn Leu Asn Leu Phe Arg Thr Cys Met
            180                 185                 190

Gly Tyr Ala Ile Pro Leu Ile Thr Ile Met Ile Cys Asn His Lys Val
        195                 200                 205

Tyr Arg Ala Val Arg His Asn Gln Ala Thr Glu Asn Ser Glu Lys Arg
    210                 215                 220

Arg Ile Ile Lys Leu Leu Ala Ser Ile Thr Leu Thr Phe Val Leu Cys
225                 230                 235                 240

Phe Thr Pro Phe His Val Met Val Leu Ile Arg Cys Val Leu Glu Arg
                245                 250                 255

Asp Met Asn Val Asn Asp Lys Ser Gly Trp Gln Thr Phe Thr Val Tyr
            260                 265                 270

Arg Val Thr Val Ala Leu Thr Ser Leu Asn Cys Val Ala Asp Pro Ile
        275                 280                 285

Leu Tyr Cys Phe Val Thr Glu Thr Gly Arg Ala Asp Met Trp Asn Ile
    290                 295                 300

Leu Lys Leu Cys Thr Arg Lys His Asn Arg His Gln Gly Lys Lys Arg
305                 310                 315                 320

Asp Ile Leu Ser Val Ser Thr Arg Asp Ala Val Glu Leu Glu Ile Ile
                325                 330                 335

Asp (2) INFORMATION FOR SEQ ID NO:10:

(i) SEQUENCE CHARACTERISTICS:
        (A) LENGTH: 281 amino acids
        (B) TYPE: amino acid
        (D) TOPOLOGY: unknown (ii) MOLECULE TYPE: protein (xi) SEQUENCE DESCRIPTION: SEQ ID NO:10:

Met Phe Ser Gly Leu Thr Leu Asn Cys Val Leu Leu Leu Gln Leu
 1               5                  10                  15

Leu Leu Ala Arg Ser Leu Glu Asp Gly Tyr Lys Val Glu Val Gly Lys
            20                  25                  30

Asn Ala Tyr Leu Pro Cys Ser Tyr Thr Leu Pro Thr Ser Gly Thr Leu
        35                  40                  45

Val Pro Met Cys Trp Gly Lys Gly Phe Cys Pro Trp Ser Gln Cys Thr
    50                  55                  60

Asn Glu Leu Leu Arg Thr Asp Glu Arg Asn Val Thr Tyr Gln Lys Ser
65                  70                  75                  80

Ser Arg Tyr Gln Leu Lys Gly Asp Leu Asn Lys Gly Asp Val Ser Leu
                85                  90                  95
```

```
Ile Ile Lys Asn Val Thr Leu Asp Asp His Gly Thr Tyr Cys Cys Arg
            100                 105                 110

Ile Gln Phe Pro Gly Leu Met Asn Asp Lys Lys Leu Glu Leu Lys Leu
            115                 120                 125

Asp Ile Lys Ala Ala Lys Val Thr Pro Ala Gln Thr Ala His Gly Asp
    130                 135                 140

Ser Thr Thr Ala Ser Pro Arg Thr Leu Thr Thr Glu Arg Asn Gly Ser
145                 150                 155                 160

Glu Thr Gln Thr Leu Val Thr Leu His Asn Asn Asn Gly Thr Lys Ile
                165                 170                 175

Ser Thr Trp Ala Asp Glu Ile Lys Asp Ser Gly Glu Thr Ile Arg Thr
            180                 185                 190

Ala Ile His Ile Gly Val Gly Val Ser Ala Gly Leu Thr Leu Ala Leu
            195                 200                 205

Ile Ile Gly Val Leu Ile Leu Lys Trp Tyr Ser Cys Lys Lys Lys Lys
            210                 215                 220

Leu Ser Ser Leu Ser Leu Ile Thr Leu Ala Asn Leu Pro Pro Gly Gly
225                 230                 235                 240

Leu Ala Asn Ala Gly Ala Val Arg Ile Arg Ser Glu Asn Ile Tyr
                245                 250                 255

Thr Ile Glu Glu Asn Val Tyr Glu Val Glu Asn Ser Asn Glu Tyr Tyr
            260                 265                 270

Cys Tyr Val Asn Ser Gln Gln Pro Ser
            275                 280

(2) INFORMATION FOR SEQ ID NO:11:

(i) SEQUENCE CHARACTERISTICS:
        (A) LENGTH: 1257 base pairs
        (B) TYPE: nucleic acid
        (C) STRANDEDNESS: single
        (D) TOPOLOGY: unknown (ii) MOLECULE TYPE: DNA (ix) FEATURE:
        (A) NAME/KEY: CDS
        (B) LOCATION: 22..1137

(xi) SEQUENCE DESCRIPTION: SEQ ID NO:11:

CCGGGTCGAC CCACGCGTCC G ATG ACA CTG ACT GCC CAC CTC TCC TAC TTT        51
                       Met Thr Leu Thr Ala His Leu Ser Tyr Phe
                        1               5                  10

CTG GTC CTG TTG TTA GCG GGC CAA GGC CTC AGT GAC TCC CTC CTC ACC        99
Leu Val Leu Leu Leu Ala Gly Gln Gly Leu Ser Asp Ser Leu Leu Thr
                15                  20                  25

AAG GAT GCA GGT CCC CGC CCA CTG GAG CTG AAG GAA GTC TTC AAG CTG       147
Lys Asp Ala Gly Pro Arg Pro Leu Glu Leu Lys Glu Val Phe Lys Leu
            30                  35                  40

TTC CAG ATC CGG TTC AAC CGG AGT TAC TGG AAC CCA GCA GAG TAC ACT       195
Phe Gln Ile Arg Phe Asn Arg Ser Tyr Trp Asn Pro Ala Glu Tyr Thr
        45                  50                  55

CGC CGT CTG AGC ATC TTT GCC CAC AAT CTG GCT CAG GCT CAA AGG CTA       243
Arg Arg Leu Ser Ile Phe Ala His Asn Leu Ala Gln Ala Gln Arg Leu
    60                  65                  70

CAG CAA GAA GAC TTG GGT ACA GCT GAG TTT GGA GAG ACT CCA TTC AGT       291
Gln Gln Glu Asp Leu Gly Thr Ala Glu Phe Gly Glu Thr Pro Phe Ser
75                  80                  85                  90

GAC CTC ACA GAG GAG GAG TTT GGC CAG TTA TAC GGG CAG GAG AGG TCA       339
Asp Leu Thr Glu Glu Glu Phe Gly Gln Leu Tyr Gly Gln Glu Arg Ser
```

```
                95                     100                     105
CCA GAA AGG ACC CCC AAC ATG ACC AAA AAG GTA GAG TCT AAC ACG TGG     387
Pro Glu Arg Thr Pro Asn Met Thr Lys Lys Val Glu Ser Asn Thr Trp
            110                 115                 120

GGG GAA TCT GTG CCC CGC ACC TGT GAC TGG CGT AAA GCA AAG AAC ATC     435
Gly Glu Ser Val Pro Arg Thr Cys Asp Trp Arg Lys Ala Lys Asn Ile
            125                 130                 135

ATC TCG TCG GTC AAG AAC CAG GGA AGC TGC AAA TGC TGC TGG GCC ATG     483
Ile Ser Ser Val Lys Asn Gln Gly Ser Cys Lys Cys Cys Trp Ala Met
        140                 145                 150

GCA GCT GCC GAC AAC ATC CAG GCT CTG TGG CGC ATC AAA CAC CAG CAG     531
Ala Ala Ala Asp Asn Ile Gln Ala Leu Trp Arg Ile Lys His Gln Gln
155                 160                 165                 170

TTT GTG GAC GTC TCT GTG CAG GAG CTG CTG GAC TGC GAA CGC TGT GGA     579
Phe Val Asp Val Ser Val Gln Glu Leu Leu Asp Cys Glu Arg Cys Gly
                175                 180                 185

AAT GGT TGC AAT GGT GGC TTC GTG TGG GAC GCA TAT CTA ACT GTC CTC     627
Asn Gly Cys Asn Gly Gly Phe Val Trp Asp Ala Tyr Leu Thr Val Leu
            190                 195                 200

AAC AAC AGT GGC CTG GCC AGT GAA AAG GAT TAT CCA TTC CAG GGG GAC     675
Asn Asn Ser Gly Leu Ala Ser Glu Lys Asp Tyr Pro Phe Gln Gly Asp
            205                 210                 215

AGA AAG CCT CAC AGA TGC CTA GCC AAG AAG TAC AAG AAG GTG GCC TGG     723
Arg Lys Pro His Arg Cys Leu Ala Lys Lys Tyr Lys Lys Val Ala Trp
220                 225                 230

ATC CAG GAT TTC ACC ATG TTG TCC AAT AAT GAG CAG GCA ATT GCC CAC     771
Ile Gln Asp Phe Thr Met Leu Ser Asn Asn Glu Gln Ala Ile Ala His
235                 240                 245                 250

TAC CTG GCC GTG CAT GGA CCT ATC ACC GTG ACC ATC AAC ATG AAA CTA     819
Tyr Leu Ala Val His Gly Pro Ile Thr Val Thr Ile Asn Met Lys Leu
                255                 260                 265

CTC CAG CAT TAC CAG AAG GGT GTC ATC AAG GCT ACA CCC AGC TCC TGT     867
Leu Gln His Tyr Gln Lys Gly Val Ile Lys Ala Thr Pro Ser Ser Cys
            270                 275                 280

GAC CCT CGG CAA GTG GAC CAC TCT GTC TTG CTG GTG GGC TTT GGC AAG     915
Asp Pro Arg Gln Val Asp His Ser Val Leu Leu Val Gly Phe Gly Lys
            285                 290                 295

GAG AAA GAG GGC ATG CAG ACA GGG ACA GTC TTG TCC CAT TCT CGA AAA     963
Glu Lys Glu Gly Met Gln Thr Gly Thr Val Leu Ser His Ser Arg Lys
        300                 305                 310

CGT CGC CAC TCC TCC CCA TAC TGG ATC CTG AAG AAC TCC TGG GGA GCT    1011
Arg Arg His Ser Ser Pro Tyr Trp Ile Leu Lys Asn Ser Trp Gly Ala
315                 320                 325                 330

CAC TGG GGC GAG AAG GGT TAC TTC AGG CTG TAT CGG GGA AAC AAC ACC    1059
His Trp Gly Glu Lys Gly Tyr Phe Arg Leu Tyr Arg Gly Asn Asn Thr
                335                 340                 345

TGT GGA GTC ACC AAG TAT CCC TTC ACA GCT CAA GTG GAC TCA CCA GTA    1107
Cys Gly Val Thr Lys Tyr Pro Phe Thr Ala Gln Val Asp Ser Pro Val
            350                 355                 360

AAG AAG GCA CGG ACC TCT TGT CCT CCC TGA AGGCAGCAGV CACTCTTCTG      1157
Lys Lys Ala Arg Thr Ser Cys Pro Pro *
            365                 370

CTTCTCCCAC ATGGCCACTG CCCCTTGTCA GCCCTGCCCA CATCCTCTCT GTATGGCTTC  1217

ATAAACCAAG ACTGCTCCGT GAAAAAAAAA AAAAAAAAA                         1257
```

(2) INFORMATION FOR SEQ ID NO:12:

(i) SEQUENCE CHARACTERISTICS:
        (A) LENGTH: 371 amino acids (B) TYPE: amino acid
    (D) TOPOLOGY: unknown (ii) MOLECULE TYPE: protein (xi) SEQUENCE DESCRIPTION: SEQ ID NO:12:

Met Thr Leu Thr Ala His Leu Ser Tyr Phe Leu Val Leu Leu Leu Ala
  1               5                  10                  15

Gly Gln Gly Leu Ser Asp Ser Leu Leu Thr Lys Asp Ala Gly Pro Arg
                 20                  25                  30

Pro Leu Glu Leu Lys Glu Val Phe Lys Leu Phe Gln Ile Arg Phe Asn
             35                  40                  45

Arg Ser Tyr Trp Asn Pro Ala Glu Tyr Thr Arg Leu Ser Ile Phe
     50                  55                  60

Ala His Asn Leu Ala Gln Ala Gln Arg Leu Gln Gln Glu Asp Leu Gly
 65                  70                  75                  80

Thr Ala Glu Phe Gly Glu Thr Pro Phe Ser Asp Leu Thr Glu Glu
                 85                  90                  95

Phe Gly Gln Leu Tyr Gly Gln Glu Arg Ser Pro Glu Arg Thr Pro Asn
            100                 105                 110

Met Thr Lys Lys Val Glu Ser Asn Thr Trp Gly Glu Ser Val Pro Arg
            115                 120                 125

Thr Cys Asp Trp Arg Lys Ala Lys Asn Ile Ile Ser Ser Val Lys Asn
130                 135                 140

Gln Gly Ser Cys Lys Cys Cys Trp Ala Met Ala Ala Ala Asp Asn Ile
145                 150                 155                 160

Gln Ala Leu Trp Arg Ile Lys His Gln Gln Phe Val Asp Val Ser Val
                165                 170                 175

Gln Glu Leu Leu Asp Cys Glu Arg Cys Gly Asn Gly Cys Asn Gly Gly
                180                 185                 190

Phe Val Trp Asp Ala Tyr Leu Thr Val Leu Asn Asn Ser Gly Leu Ala
                195                 200                 205

Ser Glu Lys Asp Tyr Pro Phe Gln Gly Asp Arg Lys Pro His Arg Cys
210                 215                 220

Leu Ala Lys Lys Tyr Lys Lys Val Ala Trp Ile Gln Asp Phe Thr Met
225                 230                 235                 240

Leu Ser Asn Asn Glu Gln Ala Ile Ala His Tyr Leu Ala Val His Gly
                245                 250                 255

Pro Ile Thr Val Thr Ile Asn Met Lys Leu Leu Gln His Tyr Gln Lys
                260                 265                 270

Gly Val Ile Lys Ala Thr Pro Ser Ser Cys Asp Pro Arg Gln Val Asp
                275                 280                 285

His Ser Val Leu Leu Val Gly Phe Gly Lys Glu Lys Glu Gly Met Gln
290                 295                 300

Thr Gly Thr Val Leu Ser His Ser Arg Lys Arg Arg His Ser Ser Pro
305                 310                 315                 320

Tyr Trp Ile Leu Lys Asn Ser Trp Gly Ala His Trp Gly Glu Lys Gly
                325                 330                 335

Tyr Phe Arg Leu Tyr Arg Gly Asn Asn Thr Cys Gly Val Thr Lys Tyr
                340                 345                 350

Pro Phe Thr Ala Gln Val Asp Ser Pro Val Lys Lys Ala Arg Thr Ser
            355                 360                 365

Cys Pro Pro
370

(2) INFORMATION FOR SEQ ID NO:13:

(i) SEQUENCE CHARACTERISTICS:
        (A) LENGTH: 130 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:13:

```
Met Arg Gln Lys Ala Val Ser Leu Phe Leu Cys Tyr Leu Leu Leu Phe
1               5                  10                  15

Thr Cys Ser Gly Val Glu Ala Gly Lys Lys Lys Cys Ser Glu Ser Ser
            20                  25                  30

Asp Ser Gly Ser Gly Phe Trp Lys Ala Leu Thr Phe Met Ala Val Gly
        35                  40                  45

Gly Gly Leu Ala Val Ala Gly Leu Pro Ala Leu Gly Phe Thr Gly Ala
    50                  55                  60

Gly Ile Ala Ala Asn Ser Val Ala Ala Ser Leu Met Ser Trp Ser Ala
65                  70                  75                  80

Ile Leu Asn Gly Gly Gly Val Pro Ala Gly Gly Leu Val Ala Thr Leu
                85                  90                  95

Gln Ser Leu Gly Ala Gly Gly Ser Ser Val Ile Thr Gly Asn Ile Gly
            100                 105                 110

Ala Leu Met Gly Tyr Ala Thr His Lys Tyr Leu Asp Ser Glu Glu Asp
                115                 120                 125

Glu Glu
    130
```

(2) INFORMATION FOR SEQ ID NO:14:

(i) SEQUENCE CHARACTERISTICS:
        (A) LENGTH: 130 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:14:

```
Met Arg Gln Lys Ala Val Ser Val Phe Leu Cys Tyr Leu Leu Leu Phe
1               5                  10                  15

Thr Cys Ser Gly Val Glu Ala Gly Lys Lys Lys Cys Ser Glu Ser Ser
            20                  25                  30

Asp Ser Gly Ser Gly Phe Trp Lys Ala Leu Thr Phe Met Ala Val Gly
        35                  40                  45

Gly Gly Leu Ala Val Ala Gly Leu Pro Ala Leu Gly Phe Thr Gly Ala
    50                  55                  60

Gly Ile Ala Ala Asn Ser Val Ala Ala Ser Leu Met Ser Trp Ser Ala
65                  70                  75                  80

Ile Leu Asn Gly Gly Gly Val Pro Ala Gly Gly Leu Val Ala Thr Leu
                85                  90                  95

Gln Ser Leu Gly Ala Gly Gly Ser Ser Val Val Ile Gly Asn Ile Gly
            100                 105                 110

Ala Leu Met Arg Tyr Ala Thr His Lys Tyr Leu Asp Ser Glu Glu Asp
                115                 120                 125

Glu Glu
    130
```

(2) INFORMATION FOR SEQ ID NO:15:

(i) SEQUENCE CHARACTERISTICS:
        (A) LENGTH: 110 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:15:

```
Val Glu Ala Gly Lys Lys Cys Ser Glu Ser Ser Asp Ser Gly Ser
 1               5                  10                  15

Gly Phe Trp Lys Ala Leu Thr Phe Met Ala Val Gly Gly Gly Leu Ala
             20                  25                  30

Val Ala Gly Leu Pro Ala Leu Gly Phe Thr Gly Ala Gly Ile Ala Ala
             35                  40                  45

Asn Ser Val Ala Ala Ser Leu Met Ser Trp Ser Ala Ile Leu Asn Gly
             50                  55                  60

Gly Gly Val Pro Ala Gly Gly Leu Val Ala Thr Leu Gln Ser Leu Gly
 65                  70                  75                  80

Ala Gly Gly Ser Ser Val Val Ile Gly Asn Ile Gly Ala Leu Met Gly
                 85                  90                  95

Tyr Ala Thr His Lys Tyr Leu Asp Ser Glu Glu Asp Glu Glu
                100                 105                 110
```

(2) INFORMATION FOR SEQ ID NO:16:

(i) SEQUENCE CHARACTERISTICS:
        (A) LENGTH: 107 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:16:

```
Gly Lys Lys Lys Cys Ser Glu Ser Ser Asp Ser Gly Ser Gly Phe Trp
 1               5                  10                  15

Lys Ala Leu Thr Phe Met Ala Val Gly Gly Gly Leu Ala Val Ala Gly
             20                  25                  30

Leu Pro Ala Leu Gly Phe Thr Gly Ala Gly Ile Ala Ala Asn Ser Val
             35                  40                  45

Ala Ala Ser Leu Met Ser Trp Ser Ala Ile Leu Asn Gly Gly Gly Val
             50                  55                  60

Pro Ala Gly Gly Leu Val Ala Thr Leu Gln Ser Leu Gly Ala Gly Gly
 65                  70                  75                  80

Ser Ser Val Val Ile Gly Asn Ile Gly Ala Leu Met Gly Tyr Ala Thr
                 85                  90                  95

His Lys Tyr Leu Asp Ser Glu Glu Asp Glu Glu
                100                 105
```

(2) INFORMATION FOR SEQ ID NO:17:

(i) SEQUENCE CHARACTERISTICS:
        (A) LENGTH: 122 amino acids
        (B) TYPE: amino acid
        (C) STRANDEDNESS:
        (D) TOPOLOGY: unknown (ii) MOLECULE TYPE: protein (xi) SEQUENCE DESCRIPTION: SEQ ID NO:17:

Met Glu Ala Ser Ala Leu Thr Ser Ser Ala Val Thr Ser Val Ala Lys
1               5                   10                  15

Val Val Arg Val Ala Ser Gly Ser Ala Val Val Leu Pro Leu Ala Arg
                20                  25                  30

Ile Ala Thr Val Val Ile Gly Gly Val Val Ala Met Ala Ala Val Pro
            35                  40                  45

Met Val Leu Ser Ala Met Gly Phe Thr Ala Ala Gly Ile Ala Ser Ser
        50                  55                  60

Ser Ile Ala Ala Lys Met Met Ser Ala Ala Ile Ala Asn Gly Gly
65                  70                  75                  80

Gly Val Ala Ser Gly Ser Leu Val Gly Thr Leu Gln Ser Leu Gly Ala
                85                  90                  95

Thr Gly Leu Ser Gly Leu Thr Lys Phe Ile Leu Gly Ser Ile Gly Ser
            100                 105                 110

Ala Ile Ala Ala Val Ile Ala Arg Phe Tyr
        115                 120

(2) INFORMATION FOR SEQ ID NO:18:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:18:

TTGCCATAGA GAGACCTC                                            18

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:19:

TGCTGTCCAA TTATACAGG                                          19

(2) INFORMATION FOR SEQ ID NO:20:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:20:

GAACACGGCA TTGTCACTAA CT                                    22

(2) INFORMATION FOR SEQ ID NO:21:

(i) SEQUENCE CHARACTERISTICS:
        (A) LENGTH: 21 base pairs
        (B) TYPE: nucleic acid
        (C) STRANDEDNESS: single (D) TOPOLOGY: linear (ii) MOLECULE TYPE: DNA (xi) SEQUENCE DESCRIPTION: SEQ ID NO:21:

CCTCATAGAT GGGCACTGTG T                                             21

(2) INFORMATION FOR SEQ ID NO:22:

(i) SEQUENCE CHARACTERISTICS:
        (A) LENGTH: 843 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:22:

ATGTTTTCAG GTCTTACCCT CAACTGTGTC CTGCTGCTGC TGCAACTACT ACTTGCAAGG     60

TCATTGGAAG ATGGTTATAA GGTTGAGGTT GGTAAAAATG CCTATCTGCC CTGCAGTTAC    120

ACTCTACCTA CATCTGGGAC ACTTGTGCCT ATGTGCTGGG GCAAGGGATT CTGTCCTTGG    180

TCACAGTGTA CCAATGAGTT GCTCAGAACT GATGAAAGAA ATGTGACATA TCAGAAATCC    240

AGCAGATACC AGCTAAAGGG CGATCTCAAC AAAGGAGATG TGTCTCTGAT CATAAAGAAT    300

GTGACTCTGG ATGACCATGG GACCTACTGC TGCAGGATAC AGTTCCCTGG TCTTATGAAT    360

GATAAAAAAT TAGAACTGAA ATTAGACATC AAAGCAGCCA AGGTCACTCC AGCTCAGACT    420

GCCCATGGGG ACTCTACTAC AGCTTCTCCA AGAACCCTAA CCACGGAGAG AAATGGTTCA    480

GAGACACAGA CACTGGTGAC CCTCCATAAT AACAATGGAA CAAAAATTTC ACATGGGCT     540

GATGAAATTA AGGACTCTGG AGAAACGATC AGAACTGCTA TCCACATTGG AGTGGGAGTC    600

TCTGCTGGGT TGACCCTGGC ACTTATCATT GGTGTCTTAA TCCTTAAATG GTATTCCTGT    660

AAGAAAAAGA AGTTATCGAG TTTGAGCCTT ATTACACTGG CCAACTTGCC TCCAGGAGGG    720

TTGGCAAATG CAGGAGCAGT CAGGATTCGC TCTGAGGAAA ATATCTACAC CATCGAGGAG    780

AACGTATATG AAGTGGAGAA TTCAAATGAG TACTACTGCT ACGTCAACAG CCAGCAGCCA    840

TCC                                                                 843

(2) INFORMATION FOR SEQ ID NO:23:

(i) SEQUENCE CHARACTERISTICS:
        (A) LENGTH: 2236 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Coding Sequence
        (B) LOCATION: 42...944
        (D) OTHER INFORMATION: Human 200 gene nucleotide
            sequence (xi) SEQUENCE DESCRIPTION: SEQ ID NO:23:

CGCTAACAGA GGTGTCCTCT GACTTTTCTT CTGCAAGCTC C ATG TTT TCA CAT CTT     56
                                              Met Phe Ser His Leu
                                               1               5

CCC TTT GAC TGT GTC CTG CTG CTG CTG CTA CTA CTT ACA AGG TCC          104
Pro Phe Asp Cys Val Leu Leu Leu Leu Leu Leu Leu Thr Arg Ser
            10                  15                  20

TCA GAA GTG GAA TAC AGA GCG GAG GTC GGT CAG AAT GCC TAT CTG CCC     152

```
                Ser Glu Val Glu Tyr Arg Ala Glu Val Gly Gln Asn Ala Tyr Leu Pro
                             25                  30                  35

TGC TTC TAC ACC CCA GCC GCC CCA GGG AAC CTC GTG CCC GTC TGC TGG                        200
Cys Phe Tyr Thr Pro Ala Ala Pro Gly Asn Leu Val Pro Val Cys Trp
             40                  45                  50

GGC AAA GGA GCC TGT CCT GTG TTT GAA TGT GGC AAC GTG GTG CTC AGG                        248
Gly Lys Gly Ala Cys Pro Val Phe Glu Cys Gly Asn Val Val Leu Arg
     55                  60                  65

ACT GAT GAA AGG GAT GTG AAT TAT TGG ACA TCC AGA TAC TGG CTA AAT                        296
Thr Asp Glu Arg Asp Val Asn Tyr Trp Thr Ser Arg Tyr Trp Leu Asn
70                  75                  80                  85

GGG GAT TTC CGC AAA GGA GAT GTG TCC CTG ACC ATA GAG AAT GTG ACT                        344
Gly Asp Phe Arg Lys Gly Asp Val Ser Leu Thr Ile Glu Asn Val Thr
                 90                  95                 100

CTA GCA GAC AGT GGG ATC TAC TGC TGC CGG ATC CAA ATC CCA GGC ATA                        392
Leu Ala Asp Ser Gly Ile Tyr Cys Cys Arg Ile Gln Ile Pro Gly Ile
            105                 110                 115

ATG AAT GAT GAA AAA TTT AAC CTG AAG TTG GTC ATC AAA CCA GCC AAG                        440
Met Asn Asp Glu Lys Phe Asn Leu Lys Leu Val Ile Lys Pro Ala Lys
        120                 125                 130

GTC ACC CCT GCA CCG ACT CTG CAG AGA GAC TTC ACT GCA GCC TTT CCA                        488
Val Thr Pro Ala Pro Thr Leu Gln Arg Asp Phe Thr Ala Ala Phe Pro
        135                 140                 145

AGG ATG CTT ACC ACC AGG GGA CAT GGC CCA GCA GAG ACA CAG ACA CTG                        536
Arg Met Leu Thr Thr Arg Gly His Gly Pro Ala Glu Thr Gln Thr Leu
150                 155                 160                 165

GGG AGC CTC CCT GAT ATA AAT CTA ACA CAA ATA TCC ACA TTG GCC AAT                        584
Gly Ser Leu Pro Asp Ile Asn Leu Thr Gln Ile Ser Thr Leu Ala Asn
                170                 175                 180

GAG TTA CGG GAC TCT AGA TTG GCC AAT GAC TTA CGG GAC TCT GGA GCA                        632
Glu Leu Arg Asp Ser Arg Leu Ala Asn Asp Leu Arg Asp Ser Gly Ala
            185                 190                 195

ACC ATC AGA ATA GGC ATC TAC ATC GGA GCA GGG ATC TGT GCT GGG CTG                        680
Thr Ile Arg Ile Gly Ile Tyr Ile Gly Ala Gly Ile Cys Ala Gly Leu
        200                 205                 210

GCT CTG GCT CTT ATC TTC GGC GCT TTA ATT TTC AAA TGG TAT TCT CAT                        728
Ala Leu Ala Leu Ile Phe Gly Ala Leu Ile Phe Lys Trp Tyr Ser His
        215                 220                 225

AGC AAA GAG AAG ATA CAG AAT TTA AGC CTC ATC TCT TTG GCC AAC CTC                        776
Ser Lys Glu Lys Ile Gln Asn Leu Ser Leu Ile Ser Leu Ala Asn Leu
230                 235                 240                 245

CCT CCC TCA GGA TTG GCA AAT GCA GTA GCA GAG GGA ATT CGC TCA GAA                        824
Pro Pro Ser Gly Leu Ala Asn Ala Val Ala Glu Gly Ile Arg Ser Glu
                250                 255                 260

GAA AAC ATC TAT ACC ATT GAA GAG AAC GTA TAT GAA GTG GAG GAG CCC                        872
Glu Asn Ile Tyr Thr Ile Glu Glu Asn Val Tyr Glu Val Glu Glu Pro
            265                 270                 275

AAT GAG TAT TAT TGC TAT GTC AGC AGC AGG CAG CAA CCC TCA CAA CCT                        920
Asn Glu Tyr Tyr Cys Tyr Val Ser Ser Arg Gln Gln Pro Ser Gln Pro
        280                 285                 290

TTG GGT TGT CGC TTT GCA ATG CCA TAGATCCAAC CACCTTATTT TTGAGCTTGG                       974
Leu Gly Cys Arg Phe Ala Met Pro
        295                 300

TGTTTTGTCT TTTTCAGAAA CTATGAGCTG TGTCACCTGA CTGGTTTTGG AGGTTCTGTC                     1034

CACTGCTATG GAGCAGAGTT TTCCCATTTT CAGAAGATAA TGACTCACAT GGGAATTGAA                     1094

CTGGGACCTG CACTGAACTT AAACAGGCAT GTCATTGCCT CTGTATTTAA GCCAACAGAG                     1154

TTACCCAACC CAGAGACTGT TAATCATGGA TGTTAGAGCT CAAACGGGCT TTTATATACA                     1214
```

-continued

```
CTAGGAATTC TTGACGTGGG GTCTCTGGAG CTCCAGGAAA TTCGGGCACA TCATATGTCC    1274

ATGAAACTTC AGATAAACTA GGRAAAACTG GGTGCTGAGG TGAAAGCATA ACTTTTTTGG    1334

CACAGAAAGT CTAAAGGGGC CACTGATTTT CAAAGAGATC TGTGATCCCT TTTTGTTTTT    1394

TGTTTTTGAG ATGGAGTCTT GCTCTGTTGC CCAGGCTGGA GTGCAATGGC ACAATCTCGG    1454

CTCACTGCAA GCTCCGCCTC CTGGGTTCAA GCGATTCTCC TGCCTCAGCC TCCTGAGTGG    1514

CTGGGATTAC AGGCATGCAC CACCATGCCC AGCTAATTTG TTGTATTTTT AGTAGAGACA    1574

GGGTTTCACC ATGTTGGCCA GTGTGGTCTC AAACTCCTGA CCTCATGATT TGCCTGCCTC    1634

GGCCTCCCAA AGCACTGGGA TTACAGGCGT GAGCCACCAC ATCCAGCCAG TGATCCTTAA    1694

AAGATTAAGA GATGACTGGA CTAGGTCTAC CTTGATCTTG AAGATTCCCT TGGAATGTTG    1754

AGATTTAGGC TTATTTGAGC ACTACCTGCC CAACTGTCAG TGCCAGTGCA TAGCCCTTCT    1814

TTTGTCTCCC TTATGAAGAC TGCCCTGCAG GGCTGAGATG TGGCAGGAGC TCCCAGGGAA    1874

AAAGGAAGTG CATTTGATTG GTGTGTATTG GCCAAGTTTT GCTTGTTGTG TGCTTGAAAG    1934

AAAATATCTC TGACCAACTT CTGTATTCGT GGACCAAACT GAAGCTATAT TTTTCACAGA    1994

AGAAGAAGCA GTGACGGGGA CACAAATTCT GTTGCCTGGT GGAAAGAAGG CAAAGGCCTT    2054

CAGCAATCTA TATTACCAGC GCTGGATCCT TTGACAGAGA GTGGTCCCTA AACTTAAATT    2114

TCAAGACGGT ATAGGCTTGA TCTGTCTTGC TTATTGTTGC CCCCTGCGCC TAGCACAATT    2174

CTGACACACA ATTGGAACTT ACTAAAAATT TTTTTTTACT GTTAAAAAAA AAAAAAAAA    2234

AA                                                                  2236
```

(2) INFORMATION FOR SEQ ID NO:24:

(i) SEQUENCE CHARACTERISTICS:
        (A) LENGTH: 301 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:24:

```
Met Phe Ser His Leu Pro Phe Asp Cys Val Leu Leu Leu Leu Leu
 1               5                  10                  15

Leu Leu Thr Arg Ser Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
                35                  40                  45

Val Pro Val Cys Trp Gly Lys Gly Ala Cys Pro Val Phe Glu Cys Gly
    50                  55                  60

Asn Val Val Leu Arg Thr Asp Glu Arg Asp Val Asn Tyr Trp Thr Ser
 65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
               100                 105                 110

Gln Ile Pro Gly Ile Met Asn Asp Glu Lys Phe Asn Leu Lys Leu Val
           115                 120                 125

Ile Lys Pro Ala Lys Val Thr Pro Ala Pro Thr Leu Gln Arg Asp Phe
       130                 135                 140

Thr Ala Ala Phe Pro Arg Met Leu Thr Thr Arg Gly His Gly Pro Ala
```

```
145                 150                 155                 160
Glu Thr Gln Thr Leu Gly Ser Leu Pro Asp Ile Asn Leu Thr Gln Ile
                165                 170                 175
Ser Thr Leu Ala Asn Glu Leu Arg Asp Ser Arg Leu Ala Asn Asp Leu
            180                 185                 190
Arg Asp Ser Gly Ala Thr Ile Arg Ile Gly Ile Tyr Ile Gly Ala Gly
        195                 200                 205
Ile Cys Ala Gly Leu Ala Leu Ala Leu Ile Phe Gly Ala Leu Ile Phe
    210                 215                 220
Lys Trp Tyr Ser His Ser Lys Glu Lys Ile Gln Asn Leu Ser Leu Ile
225                 230                 235                 240
Ser Leu Ala Asn Leu Pro Pro Ser Gly Leu Ala Asn Ala Val Ala Glu
                245                 250                 255
Gly Ile Arg Ser Glu Glu Asn Ile Tyr Thr Ile Glu Glu Asn Val Tyr
            260                 265                 270
Glu Val Glu Glu Pro Asn Glu Tyr Tyr Cys Tyr Val Ser Ser Arg Gln
        275                 280                 285
Gln Pro Ser Gln Pro Leu Gly Cys Arg Phe Ala Met Pro
    290                 295                 300
```

(2) INFORMATION FOR SEQ ID NO:25:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Forward oligonucleotide
        (B) LOCATION: 1...37
        (D) OTHER INFORMATION:

(xi) SEQUENCE DESCRIPTION: SEQ ID NO:25:

AAATTTATTC TCGAGGACCC ACGCGTCCGG ATTTCCC                      37

(2) INFORMATION FOR SEQ ID NO:26:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Reverse oligonucleotide
        (B) LOCATION: 1...39
        (D) OTHER INFORMATION:

(xi) SEQUENCE DESCRIPTION: SEQ ID NO:26:

TTAATTTGGA TCCCCAGTTC TGATCGTTTC TCCAGAGTC                    39

(2) INFORMATION FOR SEQ ID NO:27:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: cDNA (ix) FEATURE:
            (A) NAME/KEY: Forward oligonucleotide
            (B) LOCATION: 1...32
            (D) OTHER INFORMATION:

(xi) SEQUENCE DESCRIPTION: SEQ ID NO:27:

AAATTTATTC TCGAGCGCTA ACAGAGGTGT CC                                    32

(2) INFORMATION FOR SEQ ID NO:28:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Reverse oligonucleotide
        (B) LOCATION: 1...39
        (D) OTHER INFORMATION:

(xi) SEQUENCE DESCRIPTION: SEQ ID NO:28:

TTAATTTGGA TCCCCTCTGA TGGTTGCTCC AGAGTCCCG                             39

(2) INFORMATION FOR SEQ ID NO:29:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: cDNA (ix) FEATURE:

(xi) SEQUENCE DESCRIPTION: SEQ ID NO:29:

CCGCGGGTAC CAGTAAATCG TCCTGGGGTG G                                    31

(2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

AAATAAAGGA TCCCTACATC CAGCAACTAT GTAGTA                                36

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

GCGCAATTGA CTAGTGACCC ACGCGTCCGG ATTTC                                 35

(2) INFORMATION FOR SEQ ID NO:32:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:32:

GACGCGGATC CTCAGGATGG CTGCTGGCTG                                              30

(2) INFORMATION FOR SEQ ID NO:33:

(i) SEQUENCE CHARACTERISTICS:
            (A) LENGTH: 38 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:33:

GAACACACTA GTACTATCCT GTGCCATTGC CATAGAGA                                     38

(2) INFORMATION FOR SEQ ID NO:34:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:34:

GGAATATTGG GCCCTTGGAT CCCAAGTCTG CACACCTGCA CTCC                              44

(2) INFORMATION FOR SEQ ID NO:35:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:35:

GTAAATCGTC CTGGGGTCTG G                                                       21

(2) INFORMATION FOR SEQ ID NO:36:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: cDNA (xi) SEQUENCE DESCRIPTION: SEQ ID NO:36:

CCTTCTGATA ACACAAGCAT AAATC                                                   25

(2) INFORMATION FOR SEQ ID NO:37:

(i) SEQUENCE CHARACTERISTICS:
            (A) LENGTH: 903 base pairs
            (B) TYPE: nucleic acid -continued

```
        (C) STRANDEDNESS: single
        (D) TOPOLOGY: linear (ii) MOLECULE TYPE: DNA (xi) SEQUENCE DESCRIPTION: SEQ ID NO:37:

ATGTTTTCAC ATCTTCCCTT TGACTGTGTC CTGCTGCTGC TGCTGCTACT ACTTACAAGG      60

TCCTCAGAAG TGGAATACAG AGCGGAGGTC GGTCAGAATG CCTATCTGCC CTGCTTCTAC     120

ACCCCAGCCG CCCCAGGGAA CCTCGTGCCC GTCTGCTGGG GCAAAGGAGC CTGTCCTGTG     180

TTTGAATGTG GCAACGTGGT GCTCAGGACT GATGAAAGGG ATGTGAATTA TTGGACATCC     240

AGATACTGGC TAAATGGGGA TTTCCGCAAA GGAGATGTGT CCCTGACCAT AGAGAATGTG     300

ACTCTAGCAG ACAGTGGGAT CTACTGCTGC CGGATCCAAA TCCCAGGCAT AATGAATGAT     360

GAAAAATTTA ACCTGAAGTT GGTCATCAAA CCAGCCAAGG TCACCCCTGC ACCGACTCTG     420

CAGAGAGACT TCACTGCAGC CTTTCCAAGG ATGCTTACCA CCAGGGGACA TGGCCCAGCA     480

GAGACACAGA CACTGGGGAG CCTCCCTGAT ATAAATCTAA CACAAATATC CACATTGGCC     540

AATGAGTTAC GGGACTCTAG ATTGGCCAAT GACTTACGGG ACTCTGGAGC AACCATCAGA     600

ATAGGCATCT ACATCGGAGC AGGGATCTGT GCTGGGCTGG CTCTGGCTCT TATCTTCGGC     660

GCTTTAATTT TCAAATGGTA TTCTCATAGC AAAGAGAAGA TACAGAATTT AAGCCTCATC     720

TCTTTGGCCA ACCTCCCTCC CTCAGGATTG GCAAATGCAG TAGCAGAGGG AATTCGCTCA     780

GAAGAAAACA TCTATACCAT TGAAGAGAAC GTATATGAAG TGGAGGAGCC CAATGAGTAT     840

TATTGCTATG TCAGCAGCAG GCAGCAACCC TCACAACCTT TGGGTTGTCG CTTTGCAATG     900

CCA                                                                  903
```